Figure 3:
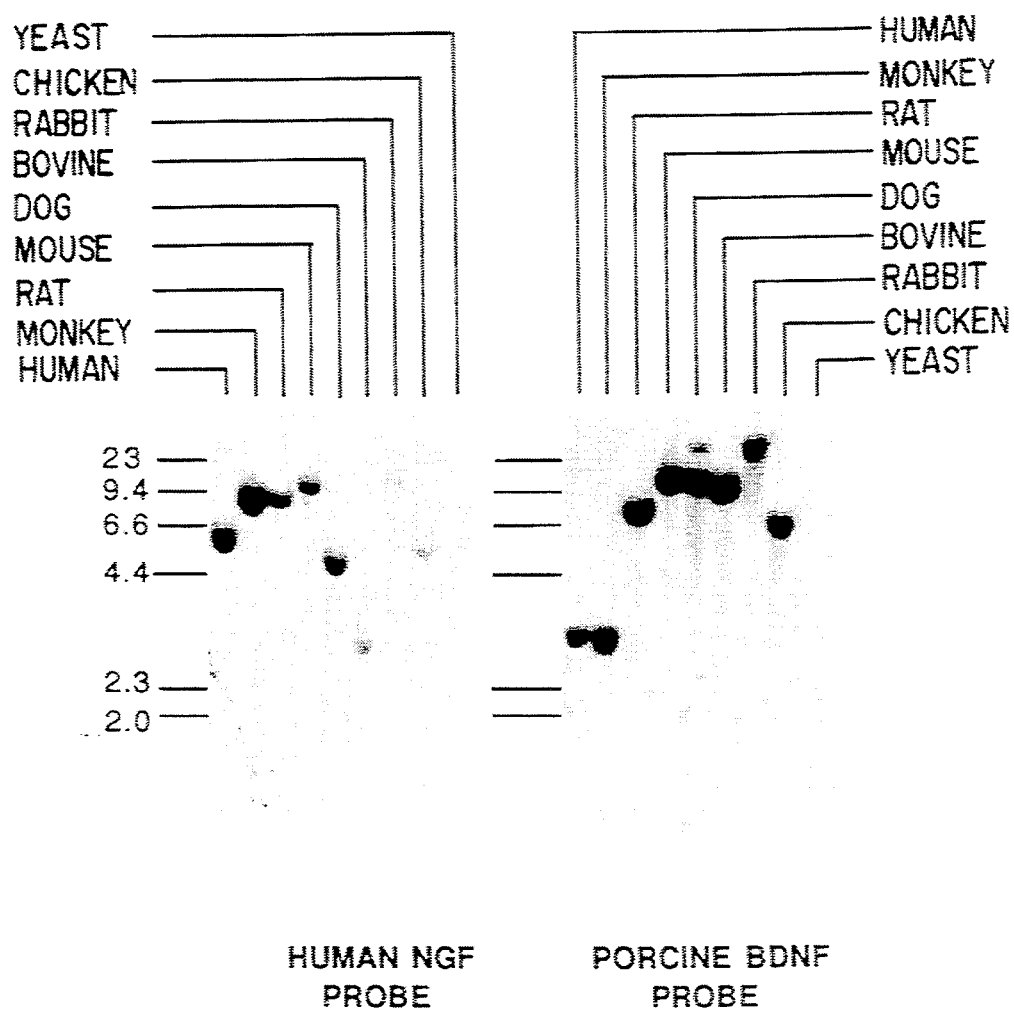

United States Patent [19]

Barde et al.

[11] Patent Number: 5,438,121
[45] Date of Patent: * Aug. 1, 1995

[54] BRAIN DERIVED NEUROTROPHIC FACTOR

[75] Inventors: Yves-Alain Barde, Munich; Joachim Leibrock, Gauting; Friedrich Lottspeich, Neuried, all of Germany; David Edgar, Liverpool, England; George Yancopoulos, New York, N.Y.; Hans Thoenen, Munich, Germany

[73] Assignees: Max-Planck-Gesellschaft Zur Förderung der Wissenschaften e.V., Martinsfried, Germany; Regeneron Pharmaceuticals, Inc., Tarrytown, N.Y.

[*] Notice: The portion of the term of this patent subsequent to Jul. 20, 2010 has been disclaimed.

[21] Appl. No.: 691,612

[22] Filed: Apr. 25, 1991

Related U.S. Application Data

[63] Continuation-in-part of Ser. No. 570,657, Aug. 20, 1990, Pat. No. 5,229,500, which is a continuation-in-part of Ser. No. 400,591, Aug. 30, 1989, Pat. No. 5,180,820.

[51] Int. Cl.[6] .................. A61K 37/24; C07K 3/00; A23J 1/00; C12P 21/06
[52] U.S. Cl. .................... 530/399; 530/350; 530/387.9; 530/389.2; 435/69.1; 536/235.1
[58] Field of Search .............. 435/6, 69.1, 240.2, 435/320.1, 69.3, 252.33; 536/27, 23.51; 530/350, 351, 349, 412, 413.387.9, 389.2; 514/2, 12, 13, 15

[56] References Cited

U.S. PATENT DOCUMENTS

| | | | |
|---|---|---|---|
| 4,935,370 | 6/1990 | Franke | 435/252.33 |
| 4,945,046 | 7/1990 | Horii et al. | 435/69.3 |
| 5,229,500 | 7/1993 | Barde et al. | 530/399 |

FOREIGN PATENT DOCUMENTS

0450386A2 10/1991 European Pat. Off.
3123963A1 10/1983 Germany.
WO9103569 3/1991 WIPO.

OTHER PUBLICATIONS

Hohn et al., 1990 Nature 344:339–341.
Lin et al., 1989, Science 246:1023–1025.
Leibrock et al., 1989, Nature 341:149–152.
Thanos et al., 1989, Eur. J. Neurosci. 1:19–26.
Uchida et al., 1989, Chemical Abstracts 111:203, Abstract No. 229, 882X.
Hallböök et al., 1988, Molecular and Cellular Biology 8(1):452–456.

(List continued on next page.)

Primary Examiner—Robert J. Hill, Jr.
Assistant Examiner—Gian P. Wang
Attorney, Agent, or Firm—Pennie & Edmonds

[57] ABSTRACT

The present invention relates to nucleic acid sequences encoding brain derived neurotrophic factor (BDNF), as well as BDNF protein produced in quantity using these nucleic acid sequences, as well as fragments and derivatives thereof. In addition, the invention relates to pharmacologic compositions and therapeutic uses of BDNF, having provided, for the first time, the means to generate sufficient quantities of substantially pure BDNF for clinical use. In a specific embodiment, BDNF may be used to promote the survival of substantia nigra dopaminergic neurons and basal forebrain cholinergic neurons, thereby providing a method for treating, respectively, Parkinson's disease and Alzheimer's disease. The invention also relates to antibodies directed toward BDNF or fragments thereof, having provided a method for generating sufficient immunogen. Further, by permitting a comparison of the nucleic acid sequences of BDNF and NGF, the present invention provides for the identification of homologous regions of nucleic acid sequence between BDNF and NGF, thereby defining a BDNF/NGF gene family; the invention provides a method for identifying and isolating additional members of this gene family.

11 Claims, 52 Drawing Sheets

OTHER PUBLICATIONS

Hu et al., 1988, Gene 70:57–65.
Erlich et al., 1988, Nature 331:461–462.
Hofer and Barde, 1988 Nature 331:261–262.
Lee et al., 1988, Science 239:1288–91.
Jaenisch, 1988, Science, 240:1468–1474.
Kalcheim and Gendreau, 1988, Develop. Brain Res. 41:79–86.
Lindsay, 1988, J. Neurosci. 8:2394–2405.
Rodriquez-Tébar and Barde, 1988, J. Neurosci. 8(9):3337–3342.
Barde et al. 1987, Prog. Brain Res. 71:185–189.
Kalcheim et al., 1987, EMBO J. 6:2871–2873.
Walz et al., 1987, Biochemical and Biophysical Research Communications 149:755–761.
Davies et al., 1986, J. Neurosci. 6:1897–1904.
Davies et al., 1986, Nature 319:497–499.
Johnson et al., 1986, J. Neurosci. 6:3031–3038.
Kalcheim & LeDouarin, 1986, Develop, Biol. 116:451–466.
Wion et al., 1986, FEBS Letters 203:82–86.
Barde & Thoenen, 1985 in "Hormones and Cell Regulation", vol. 9, Dumont et al., eds., Elsevier Science Publisher, pp. 385–390.
Davies and Lindsay, 1985, Develop. Biol. 111:62–72.
Lindsay et al., 1985, J. Cell. Sci. Supp. 3:115–129.
Lindsay & Rohrer, 1985, Develop. Biol. 112:30–48.
Lindsay et al., 1985, Develop. Biol. 112:319–328.
Appel et al., 1985, Chemical Abstracts 102:401, Abstract No. 43871b.
Appel et al., 1985, Chemical Abstracts 102:418, Abstract No. 147008s.
Lindsay & Peters, 1984, Neurosci. 12:45–51.
Barde et al., 1983, Ann. Rev. Physiol. 45:601–612.
Pearson et al., 1983, Develop. Biol. 96:32–36.
Sarthy et al., 1983, J. Neurosci. 3:2532–2544.
Turner et al., 1983, Dev. Brain Res. 6:77–83.
Barde et al., 1982, EMBO J. 1(5):549–553.
McCaffery et al., 1982, Exp. Brain Res. 48:377–386.
Lindsay et al., 1982, Brain Res. 243;329–343.
Barde et al., 1980, PNAS 77:1199–1203.
Johnson et al., 1980, Science 210:916–918.
Lindsay, 1979, Nature 282:80–82.
Lindsay and Tarbit, 1979, Neurosci. Lett. 12:195–200.
Barde et al., 1978, Nature 274:818.
Levi-Montalcini, 1966, The Harvey Lectures 60:217–259.

FIG. 1

```
                                                              AAACCGGG     8

CACCAAAGATTCCCCCCTACCCCTTCTTTTTGACCAAAGGGAACGTGAAAAAATAATAGAGTCTGGGGATTTCGGGGCC  84

GAAGTCTTCCCCAGAGCAGCTGCCTTGATGTTTACTTTGACAAGTAGTGACTGAAAAGTTCCACCAGGTGAGAAGAGTG  166
 1                  10                                20
Met Thr Ile Leu Phe Leu Thr Met Val Ile Ser Tyr Phe Gly Cys Met Lys Ala Ala Pro
ATG ACC ATC CTT TTC CTT ACT ATG GTT ATT TCA TAC TTC GGT TGC ATG AAG GCT GCC CCC   226
                               30                                40
Met Lys Glu Ala Asn Val Arg Gly Gln Gly Ser Leu Ala Tyr Pro Gly Val Arg Thr His
ATG AAA GAA GCC AAC GTC CGA GGA CAA GGC AGC TTG GCC TAC CCA GGT GTG CGG ACC CAT   286
                               50                                60
Gly Thr Leu Glu Ser Val Asn Gly Pro Lys Ala Gly Ser Arg Gly Leu Thr Ser Ser Ser
GGG ACT CTG GAG AGC GTG AAT GGG CCC AAG GCA GGT TCA AGA GGC CTG ACA TCG TCG TCA   346
                               70                                80
Ser Ser Ser Leu Ala Asp Thr Phe Glu His Val Ile Glu Glu Leu Leu Asp Glu Asp Gln
TCG TCG TCG TTG GCG GAC ACT TTT GAA CAC GTG ATC GAG GAG CTG TTG GAC GAG GAC CAG   406
                               90                                90
Lys Val Arg Pro Asn Glu Glu Asn Asn Lys Asp Ala Asp Met Tyr Thr Ser Arg Val Met
AAA GTT CGG CCC AAT GAG GAA AAC AAT AAG GAC GCG GAC ATG TAT ACG TCC CGA GTC ATG   466
                              110                               120
Leu Ser Ser Gln Val Pro Leu Glu Pro Pro Leu Leu Phe Leu Leu Glu Glu Tyr Lys Asn
CTC AGC AGT CAA GTG CCT TTG GAG CCT CCT CTT CTC TTT CTG CTG GAG GAA TAC AAA AAT   526
                              130                               140
Tyr Leu Asp Ala Ala Asn Met Ser Met Arg Val Arg Arg His Ser Asp Pro Ala Arg Arg
TAC CTG GAT GCT GCA AAC ATG TCC ATG AGG GTC CGG CGC CAC TCG GAC CCC GCC CGC CGC   586
                              150                               160
Gly Glu Leu Ser Val Cys Asp Ser Ile Ser Glu Trp Val Thr Ala Ala Asp Lys Lys Thr
GGG GAG CTG AGC GTG TGC GAC AGC ATT AGC GAG TGG GTG ACG GCG GCG GAT AAA AAG ACG   646
                              170                               180
Ala Val Asp Met Ser Gly Gly Thr Val Thr Val Leu Glu Lys Val Pro Val Ser Lys Gly
GCA GTG GAC ATG TCG GGT GGC ACG GTC ACG GTC CTC GAA AAA GTC CCC GTC TCG AAA GGC   706
                              190                               200
Gln Leu Lys Gln Tyr Phe Tyr Glu Thr Lys Cys Asn Pro Met Gly Tyr Thr Lys Glu Gly
CAA CTG AAG CAG TAC TTC TAC GAG ACC AAG TGC AAT CCT ATG GGG TAC ACA AAG GAG GGC   766
                              210                               220
```

FIG. 1 (cont.)

```
Cys Arg Gly Ile Asp Lys Arg His Trp Asn Ser Gln Cys Arg Thr Thr Gln Ser Tyr Val
TGC AGG GGC ATA GAC AAG AGG CAC TGG AAC TCC CAG TGC CGA ACT ACC CAG TCG TAT GTG    826
                                  230                                      240
Arg Ala Leu Thr Met Asp Ser Lys Lys Arg Ile Gly Trp Arg Phe Ile Arg Ile Asp Thr
CGG GCC CTC ACC ATG GAT AGC AAA AAA CGA ATT GGC TGG CGG TTC ATA AGG ATA GAC ACT    886
                                  250
Ser Cys Val Cys Thr Leu Thr Ile Lys Arg Gly Arg End
TCC TGT GTA TGT ACT TTG ACC ATT AAG AGG GGA AGA TAG TGGCTTTATGTTGTATAGATTATATTG    952

AGACAAAAATTATCTATTTGTATATATACATAACAGGGTAAATTATTCAGTTAAGAAAAAAAATAATTTTATGAACTGC    1031

ATGTATAAATGAAGTTTATACAGTACAGTGGTTCTACAATCTATTTATTGGACATTTCCATGACCAGAGGGAAACAGTC    1110

ATTTTTTGCGCACAACTTTAAAAAAAAAAGTCTGCATTACATTCCTCGATAATGTTGTGGTTTGTTGCCGTTGCT       1184
```

FIG. 2

```
HSDPARRGELSVCDSISEWVTAADKKTAVDMSGGTVTVLEKVPVSKGQLKQYFYETKCNP    pig BDNF
SSSHPIFHRGEFSVCDSVSVWV..GDKTTATDIKGKEVMVLGEVNINNSVFKQYFFETKCRD   human NGF
SSSHPVFHRGEFSVCDSISVWV..GDKTTATDIKGKEVMVLGEVNINNSVFKQYFFETKCRD   bovine NGF
SSTHPVFHMGEFSVCDSVSVWV..ADKTTATDIKGKEVTVLAEVNVNNNVFKQYFFETKCRD   g. pig NGF
SSTHPVFHMGEFSVCDSVSVWV..GDKTTATDIKGKEVTVLAEVNINNSVFRQYFFETKCRA   mouse NGF
TAHPVLHRGEFSVCDSVSMWV..GDKTTATDIKGKEVTVLGEVNINNNVFKQYFFETKCRD    chick NGF
EDHPVHNLGEHSVCDSVSAWV...TKTTATDIKGNTVTVMENVNLDNKVYKQYFFETKCKN    snake NGF MGYTKEGCRGIDKRHVNSQCRTTQSYVRALTMDSKKRIGWRFIRIDTSCVCILTIKRGR     pig BDNF
PNPVDSGCRGIDSKHWNSYCTTTHTFVKALTMDGKQ.AAVRFIRIDTACVCVLSRKAVRRA   human NGF
PNPVDSGCRGIDAKHWNSYCTTTHTFVKALTMDGKQ.AAVRFIRIDTACVCVLSRKTGQRA   bovine NGF
PSPYESGCRGIDSKHWNSYCTTTHTFVKALTTDNKQ.AAVRFIRIDTACVCVLNRKAARRG   g. pig NGF
SNPYESGCRGIDSKHWNSYCTTTHTFVKALTTDEKQ.AAVRFIRIDTACVCVLSRKATRRG   mouse NGF
PRPVSSGCRGIDAKHWNSYCTTTHTFVKALTMCGKQ.AAVRFIRIDTACVCVLSRKSGRP    chick NGF
PNPEPSGCRGIDSSHWNSYCTETDTFIKALTMEGNQ.ASVRFIRIETACVCVITKKKGN     snake NGF
```

FIG. 4B

```
           10         20         30         40         50         60         70         80         90        100        110        120
            .          .          .          .          .          .          .          .          .          .          .          .
HUMAN  AAGCTTGATATCGAATTCCGGAATTCCGTTCCCAACTGCTGTGTTTATTGTGCTATTCATGCCTAGAGACATCACATAGCTAGAAGGCCATCAGAAAGCCCTCAGGCACTGCTGTTCCTGTCACACATTC
       TTCGAACTATAGCTTAAGGCCTTAAGGCAAGGGTTGACGACAAAATAACACGATAAGTACGATCGTAGTGTATCGATCTTCCGGTAGTCTGGGGAGTCTGACGACAAGGACAGTGTGTAAG 130        140        150        160        170        180        190        200        210        220        230        240        250
            .          .          .          .          .          .          .          .          .          .          .          .          .
HUMAN  CTGCAAAGGACCATGTGCTAACTTGAAAAAAATTACTATTAATTACACTTGCAGTTGTGCTTAGTAACATTTATGATTTTGTGTTCTCGTGACAGCATGAGCAGAGATCATTAAAAATTAAACTTA
       GACGTTTCCTGGTACACGATTGAACTTTTTTTAATGATAATTAATGTGAACGTCAACACTGTGTAAATACTAAAAACAAAGAGCACTGTCGTACTCGTCTCTAGTAATTTTAATTTGAAT 260        270        280        290        300        310        320        330        340        350        360        370        380
            .          .          .          .          .          .          .          .          .          .          .          .          .
HUMAN  CAAAGCTGCTAAAGTGGGAAGAAGGAGAAGAACTTGAAGCCACAATTTTTGCACTTGCTTAGAAGCCATCTCAGGTTATATGCTAGATCTCGGTTATATGCTAGATCTTGGGGGCAAACACTGCATGTCTCTGGTTTATATTAAA
       GTTTCGACGATTTCACCCTTCCTCCTCTTGAACTTCGGTGTTAAAAACGTGAACGAATCTTCGGTAGAGTCCAATACGATCTAGAATTAGAGCTACGATACGATCTAGAGACCAAATATAATTT
                                                                                        HBDNF |
           390        400        410        420        430        440        450        460        470        480        490        500        510
            .          .          .          .          .          .          .          .          .          .          .          .          .
HUMAN  CCACATACAGCACACTACTGACACTGATTGTGTCTCGGTGCAGCTGGAGTTGGAGTTTATCACCAAGACTGGAGTTTATCACCAAGACATAAAAAAACCTTGACCCTGCAGAATGCCTGGAATTACAATCAGATGGGCCATGGCATCCCGG
       GGTGTATGTCGTGATGACTGTGACTAACAGACAGAGCCACGTCGACCTCAAATAGTGGTTCTGTATTTTTTGGAACTGGGACGTCTTACCGGACGTCTTACCGGTACGTAGTCTACCGGTGACCGGTACCGGTAGGGCC
                                                                                                                                                    C

RAT   4    ...CA..GGG...G.G..AAAATA.T.GA.T.TG..G....---....A.T....>
PIG  39    ................................G.A.T.T.....-C>
```

HUMAN

|   |   |   |   |   |   |   |   |   |   |   |   |
|---|---|---|---|---|---|---|---|---|---|---|---|
| 520 | 530 | 540 | 550 | 560 | 570 | 580 | 590 | 600 | 610 | 620 | 630 |

————————————————HBDNF₁————————————————

TGAAAGAAGCCCTAACCAGTTTTCTGTCTTGTTTCTGCTTTCCTACAGTTCCACCAGGTGAGAAGAGTG ATG ACC ATC CTT TTC CTT ACT ATG GTT ATT TCA TAC TTT GGT
ACTTCTTTCGGGATTGGTCAAAAGACAGAACAAAGAGGAAAGAGGAAGACAAAGAGAACAAAGAGAACAAAGACGAAAGAAGAGGGAATGTCAAGGTGGTCCACTCTTCTCAC TAC TGG TAG GAA AAG GAA TGA TAC CAA TAA AGT ATG AAA CCA
                                                                Met Thr Ile Leu Phe Leu Thr Met Val Ile Ser Tyr Phe Gly>
                                                    o  o  o  o  PRE-PRO FORM OF BDNF o  o  o  o  o  o  >

RAT 17  CCTTG..C..AG.-C.G.G.A...G.-C.GA.G.GG.-AG.A..T.A.C............................C....>
PIG 99  A..GGAGCT...T.G.--T....A..-.-.GACAAG..AG.GA..-AAA.A..........................C....>

FIG. 4C

FIG. 4D

|HBDNF|

| | 830 | 840 | 850 | 860 | 870 | 880 | 890 | 900 | 910 |
|---|---|---|---|---|---|---|---|---|---|
| HUMAN | CCC AAT GAA AAC AAT AAG GCA GAC TTG TAC ACG TCC AGG GTG ATG CTC AGT AGT CAA GTG CCT TTG GAG CCT CCT CTT CTC TTT CTG CTG GGG TTA CTT CTT TTG TTA TTC CTG CGT CTG AAC ATG TCC AGG TCC CAC GAG TCA GTT CAC GTT CAC GAA CTC GGA GGA AAC GAG GAC Pro Asn Glu Asn Asn Lys Asp Ala Asp Leu Tyr Thr Ser Arg Val Met Leu Ser Ser Gln Val Pro Leu Glu Pro Pro Leu Leu Phe Leu Leu | | | | | | | | |
| | a a a a a a a a a a PRE-PRO FORM OF BDNF a a a a a a a a a a a a a a a a a a a a | | | | | | | | |
| RAT 327 | . . . . . . . C . . . . . . . . . . . . . . . . . . . . . . . . . G . . . . . . . . . . . . . . . . . . . T . . . . C . . . . . . . . . . . . . . . . . . . . . . . . . . . . . . . . . . . . . . . . . . . . . . . . . . . . . . . . . . . . . . . . . . . . . . . . . . . . . . . . | | | | | | | | |
| PIG 416 | . . . . . . . . . . . . . . G . . . . . . . . . . . . . . . . . . . G . . . . . . . . . . . . . A . . . . . . . . C . . . . . . . T . . . . C.A . . . . C . . . . . . . . . . G . . . . . . . . . . . . . . . . . . . . . . . . . . . . . . . . . . . . . . . . . . . . . . . . . | | | | | | | | |

```
                                                          .HBDNF.
          1430      1440      1450      1460      1470      1480      1490      1500      1510      1520      1530      1540      1550
HUMAN     AAAATAATTTATGAACTGCATGTATAAATGAAGTTTATACAGTACAGTGGTTCTACAATCTATTTATTGGACATGTCCATGACCAGAAGGAAACAGTCATTGCGCACAACTTAAAAAGTCTGCATT
          TTTATTAAAATACTTGACGTACATATATTTACTTCAAATATGTCTTGAATAAATAACCTGTAGATAAATAACCTGTAGTGTTAGATAAATAACCTGTCTTGTCAGTAAACGGTGTTGAATTTTTCAGACGTAA

RAT   922 ..G..................................................................A.................A.........................T...........

PIG  1012 ..........................................................................................T................_................TTT    AA
                                                                                                                                    ^     ^
                                                                                                                                   TTTAA

.HBDNF.
          1560      1570      1580      1590      1600      1610
HUMAN     ACATTCCTTGATAATGTTGTGGTTTGTTGCCGTTGCCAAGAACTGAAAACGGAATTCCTGCAG
          TGTAAGGAACTATTACACACCAAACAACGGCAACGGTTCTTGACTTTTGCCTTAAGGACGTC

RAT  1050 ...........C......................................T.....AA..

PIG  1148 ...........C.................................................
```

FIG. 4I

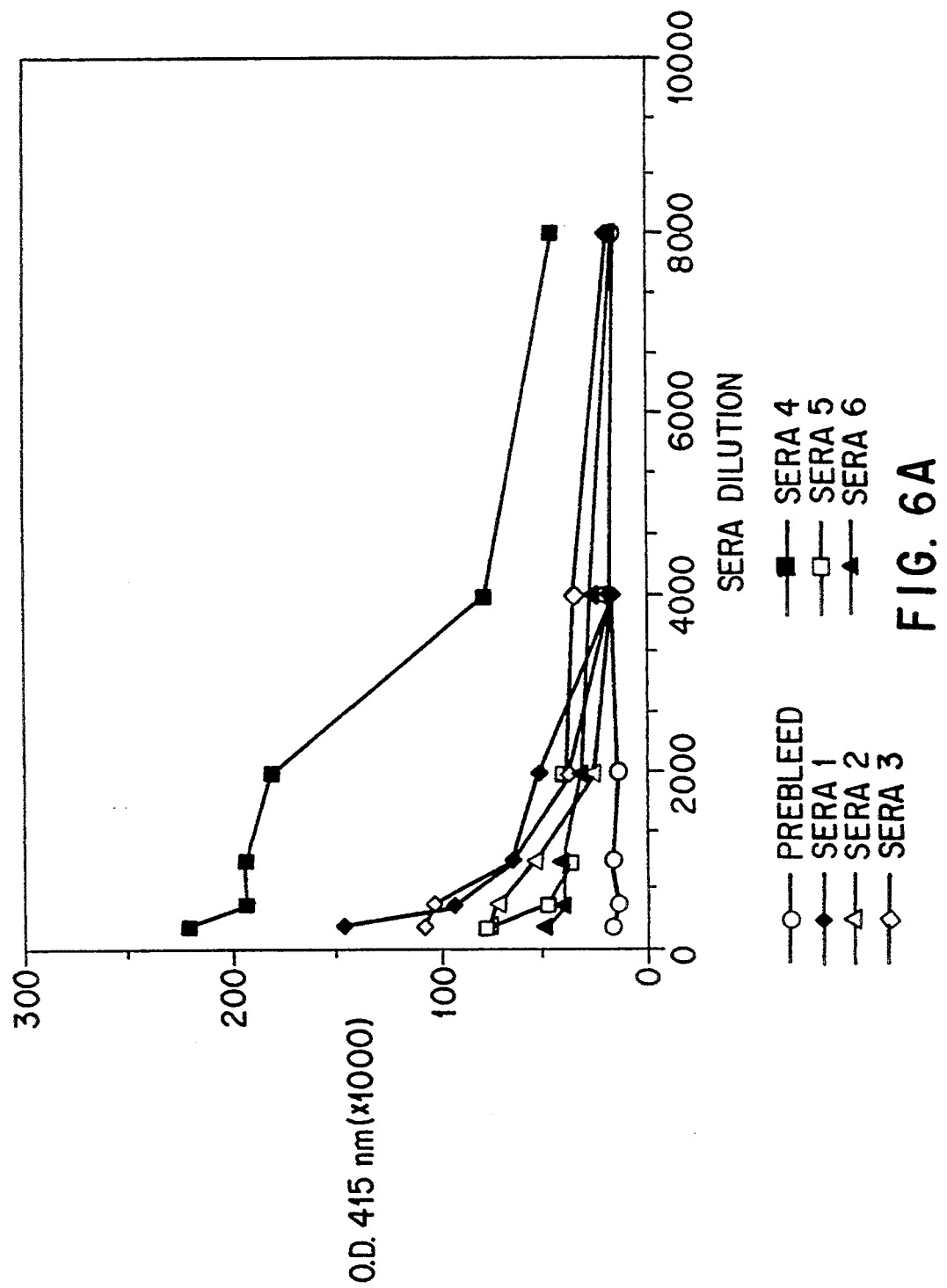

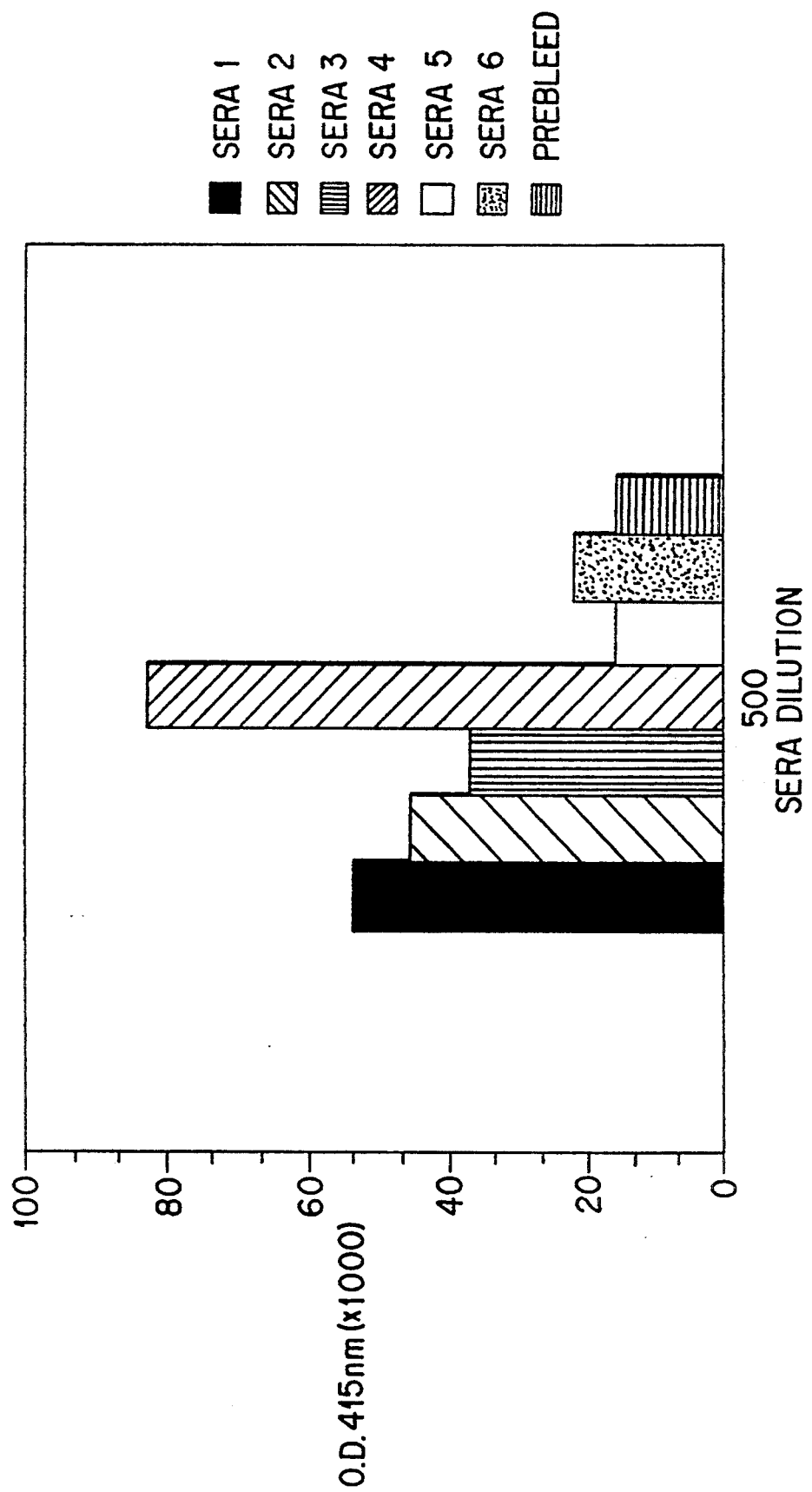

| | | |
|---|---|---|
| M3/4 | GAT GAC AAA CAC TGG AAC TCT CAG TGC AAA ACT TCG CAA ACC<br>Asp Asp Lys His Trp Asn Ser Gln Cys Lys Thr Ser Gln Thr | |
| MuNGF | Asp Ser Lys His Trp Asn Ser Tyr Cys Thr Thr Thr His Thr | |
| HuBDNF | Asp Lys Arg His Trp Asn Ser Gln Cys Arg Thr Thr Gln Ser | |

| | |
|---|---|
| M3/4 | TAT GTC CGA GCA CTG ACT TCA GAA AAC AAC AAA CTC GTA GGC<br>Tyr Val Arg Ala Leu Thr Ser Glu Asn Asn Lys Leu Val Gly |
| MuNGF | Phe Val Lys Ala Leu Thr Thr Asp --- Glu Lys Gln Ala Ala |
| HuBDNF | Tyr Val Arg Ala Leu Thr Met Asp Ser Lys Lys Arg Ile Gly |

| | |
|---|---|
| M3/4 | TGG CGC TGG ATA CGA ATA GAC ACT TCC TGT GTG TGT GCC TTG<br>Trp Arg Trp Ile Arg Ile Asp Thr Ser Cys Val Cys Ala Leu |
| MuNGF | Trp Arg Phe Ile Arg Ile Asp Thr Ala Cys Val Cys Val Leu |
| HuBDNF | Trp Arg Phe Ile Arg Ile Asp Thr Ser Cys Val Cys Thr Leu |

| | |
|---|---|
| M3/4 | TCG AGA AAA ATT GGA AGA ACA TGA ATT GGC ATC TGT CCC CAC<br>Ser Arg Lys Ile Gly Arg Thr End |
| MuNGF | Ser Arg Lys Ala Thr Arg Arg Gly END |
| HuBDNF | Thr Ile Lys Arg Gly Arg END |

| | |
|---|---|
| M3/4 | ATA TAA ATT GAT TGG ACT NNA AAT TAT ATG ATA TGC ATG TAG |
| M3/4 | CAT ATA AAT GTT TAT ATT TTT ATA TAT TAT AAG TTG ACC TCT |
| M3/4 | ATT TAT TAA ACT TCA GCA ACC CTT |

FIG. 13

FIG.31A    FIG.31B
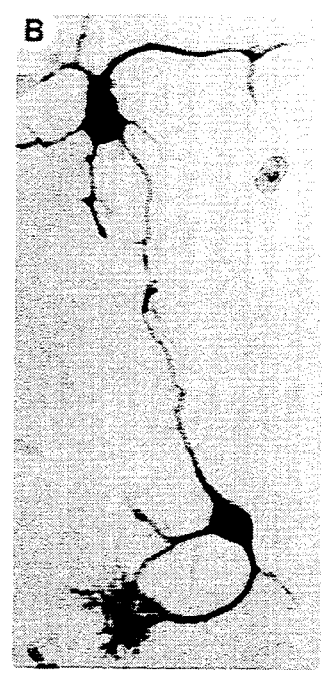
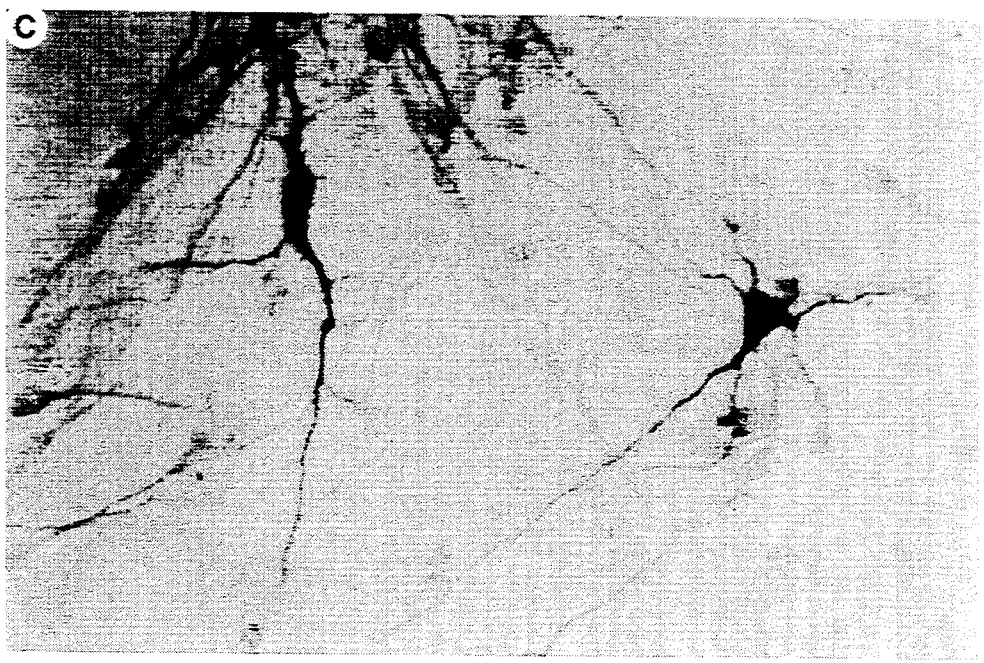
FIG.31C

FIG.32A  FIG.32B
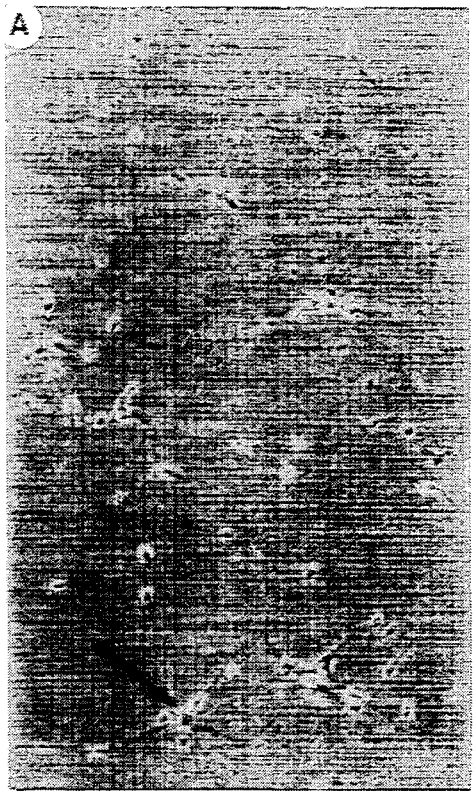
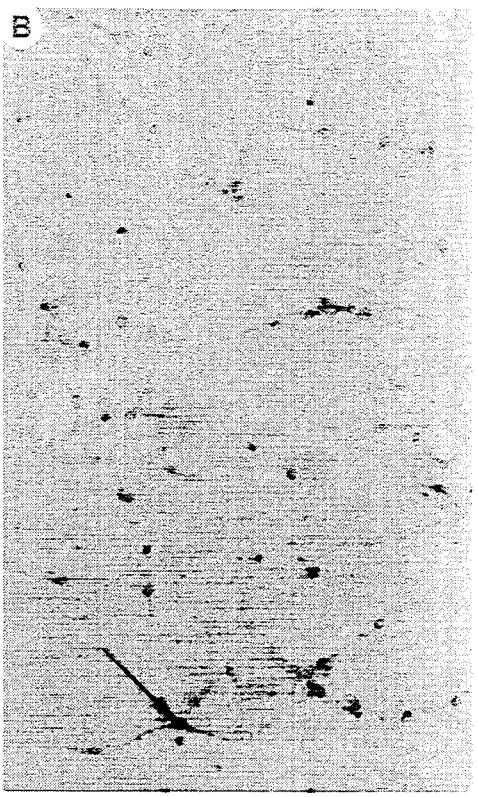
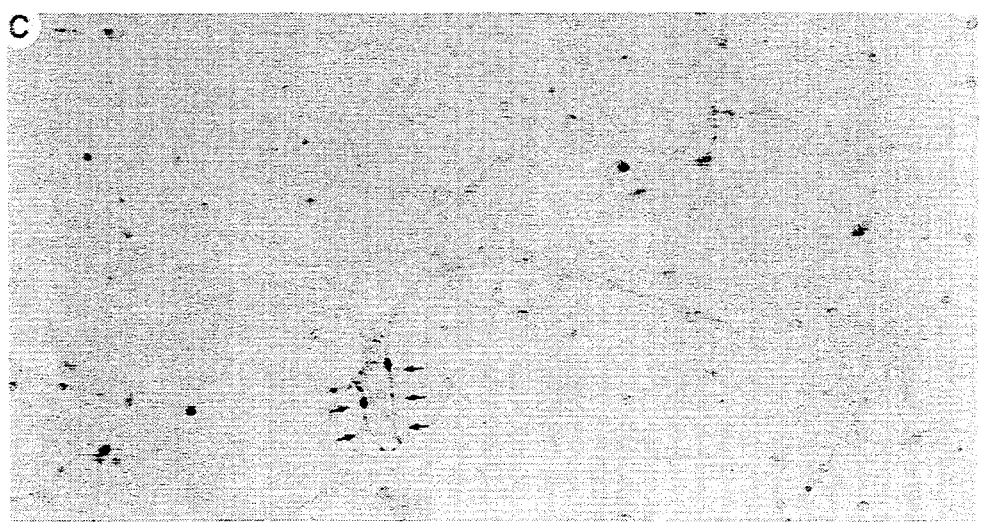
FIG.32C

BRAIN DERIVED NEUROTROPHIC FACTOR

This application is a continuation-in-part of application Ser. No. 07/570,657 filed Aug. 20, 1990, U.S. Pat. No. 5,229,500, which is a continuation-in-part of application Ser. No. 07/400,591, filed Aug. 3, 1989, U.S. Pat. No. 5,180,820, each of which is incorporated by reference herein in its entirety.

TABLE OF CONTENTS

1. Introduction
2. Background of the Invention
 2.1. Neuronal Cell Death And The Role Of Neurotrophic Factors In The Development Of The Nervous System
 2.2. Nerve Growth Factor
 2.3. Other Neurotrophic Factors
  2.3.1. Comparison Of A Brain Derived Neurotrophic Factor (BDNF) And Nerve Growth Factor
  2.3.2. Neuronal Targets of Brain Derived Neurotrophic Factor
Summary of the Invention
 3.1. Abbreviations And Definitions
4. Description of the Figures
5. Detailed Description of the Invention
 5.1. Purification of Brain Derived Neurotrophic Factor
 5.2. Brain Derived Neurotrophic Factor Bioassays
 5.3. Microsequencing Of Brain Derived Neurotrophic Factor Protein
 5.4. Cloning Of Brain Derived Neurotrophic Factor-Encoding DNA
 5.5. Expression Of The Brain Derived Neurotrophic Factor Gene
  5.5.1 Identification And Purification Of The Expressed Gene Product
 5.6. Brain Derived Neurotrophic Factor Genes And Proteins
 5.7. Generation Of Anti-Brain Derived Neurotrophic Factor Antibodies
 5.8. Identification Of Additional Members Of The BDNF/NGF Gene Family
 5.9. Utility Of The Invention
  5.9.1. Diagnostic Applications
  5.9.2. Therapeutic Applications
 5.10. Pharmaceutical Compositions
6. Example: Molecular Cloning and Characterization of Porcine Brain Derived Neurotrophic Factor cDNA
 6.1. Materials And Methods
  6.1.1. Purification of BDNF From Porcine Brain
  6.1.2. Protein Sequencing
  6.1.3. Preparation Of DNA Templates
  6.1.4. Polymerase Chain Reaction
 6.2. Results And Discussion
  6.2.1. Results Of Protein Microsequencing
  6.2.2. Synthesis Of Oligonucleotides And Use Of PCR To Obtain DNA Encoding An Amino Acid Fragment
  6.2.3. Nucleotide Sequence Of cDNA Fragment
  6.2.4. Cloning Of The Entire Porcine BDNF cDNA
  6.2.5. Nucleotide Sequence Of Porcine BDNF cDNA
7. Example: BDNF Gene Is Distinct From The NGF Gene In Diverse Vertebrate Species
 7.1. Materials And Methods
  7.1.1. Preparation Of NGF And BDNF Probes
  7.1.2. Sequencing Of BDNF Genes From Various Species
 7.2. Results And Discussion
8. Example: Expression Of BDNF RNA In Neuronal Versus Non-Neuronal Tissues
 8.1. Materials and Methods
  8.1.1. Preparation Of RNA
  8.1.2. Preparation Of cRNA Probe
 8.2. Results And Discussion
9. Example: Molecular Cloning And Characterization Of Human And Rat BDNF Genes
 9.1 Materials And Methods
  9.1.1. Genomic DNA and cDNA Libraries
  9.1.2. Preparation Of BDNF DNA Probes
  9.1.3. Screening Of Libraries
 9.2 Results and Discussion
10. Example: Expression Of Recombinant BDNF
 10.1. Materials And Methods
  10.1.1. Preparation Of A BDNF Expression Vector
  10.1.2. Expression Of BDNF in COS Cells
 10.2. Results And Discussion
11. Example: Generation Of Antibodies To BDNF
 11.1. Materials And Methods
  11.1.1. Peptide Synthesis And Coupling To Carrier
  11.1.2. Immunization
  11.1.3. Detection Of Antibody Binding To BDNF
 11.2. Results And Discussion
12. Example: Novel Biological Effects Of BDNFF
 12.1. Materials And Methods
  12.1.1. Methods For Culturing Dopaminergic Substantia Nigra Neurons
  12.1.2. Methods For Immunocytochemical Staining Of Ventral Mesencephalon Cultures
  12.1.3. Methods Used in Measuring $^3$H-Dopamine Uptake In Ventral Mesencephalon Cultures
  12.1.4. Methods For Producing Cultures Of Basal Forebrain Cholinergic Neurons
  12.1.5. Choline Acetyl Transferase Assays
  12.1.6. Method Of Generating Purified Astroglial Cell Cultures
 12.2. Results
  12.2.1. The Effect Of BDNF On Tyrosine Hydroxylase Present In Ventral Mesencephalon Cultures
  12.2.2. The Effect Of BDNF On Dopamine Uptake By Ventral Mesencephalon Cultures
  12.2.3. The Effect Of BDNF On Choline Acetyltransferase Expression By Forebrain Cholinergic Neurons
  12.2.4. Effects Of BDNF Or EGF On Astroglial Cell Cultures
 12.3. Discussion
13. Example: Identification of a Novel Gene in the BDNF/NGF Gene Family
 13.1. Materials and Methods
  13.1.1. Polymerase Chain Reaction
 13.2. Results
  13.2.1. Amplification of Both NGF and BDNF Sequences from Genomic DNA
  13.2.2. Detection of Sequences Complementary to the BDNF/NGF Probe in Genomic DNAs of Various Species
  13.2.3. Identification of a Novel Gene Related to BDNF and NGF
  13.2.4. Characterization of a Novel Member of the BDNF/NGF Gene Family 13.3. Discussion
14. Example: Increased Expression of BDNF in Neuroblastoma Cells
    14.1. Materials and Methods
        14.1.1. Cell Lines
        14.1.2. Preparation of RNA
    14.2. Results
15. Example: Activity-Dependent Regulation of BDNF- and NGF-mRNAs in the Rat Hippocampus is Mediated by Non-NMDA-Glutamate Receptors
    15.1. Materials and Methods
        15.1.1. Treatment of Rats with Kainic Acid
        15.1.2. Preparation of Hippocampal Cultures
        15.1.3. Amplification of RNA
    15.2. Results and Discussion
16. Example: Brain-Derived Neurotrophic Factor Increases Survival and Differentiated Functions of Rat Septal Cholinergic Neurons in Culture
    16.1. Materials and Methods
        16.1.1. Preparation of Dissociated Cells and Cell Culture Conditions
        16.1.2. Assay of Choline Acetyltransferase Activity
        16.1.3. Assay of Acetylcholinesterase (AChE) Activity
        16.1.4. Measurement of High Affinity Choline Uptake
        16.1.5. Histochemical Staining for Acetylcholinesterase
        16.1.6. Immunohistochemical Staining for the NGF Receptor
        16.1.7. Purification of BDNF and NGF
    16.2. Results
    16.3. Discussion
17. Example: Enzymatic Conversion of Prepro BDNF to Active, Mature BDNF
    17.1. Materials And Methods
    17.2. Results and Discussion
18. Example: Brain-Derived Neurotrophic Factor Promotes Survival and Maturation of Dopaminergic Neurons of the Rat Ventral Mesencephalon
    18.1. Materials and Methods
        18.1.1. Cell Cultures
        18.1.2. Measurement of Dopamine Uptake
        18.1.3. Transient Expression of BDNF
        18.1.4. Production of hBDNF from Transfected CHO Cells
    18.2. Results and Discussion
19. Example: BDNF Produces A Dose-Dependent Inhibition Of Gamma Aminobutyric Acid Uptake
    19.1. Materials And Methods
        19.1.1. Hippocampal Cell Cultures
        19.1.2. Measurement Of High Affinity Uptake For Gamma-Aminobutyric Acid (GABA)
    19.2. Results And Discussion
20. Example: BDNF Confers A Protective Effect Against Toxic Effects Of MPP+
    20.1. Materials And Methods
        20.1.1. Measurement Of The Effects Of Neurotrophic Factors On MPP+-Treated SH-SY5Y Cells
        20.1.2. Measurement Of The Effects Of Neurotrophic Factors On MPP+-Treated Ventral Mesencephalic Cultures
    20.2. Results And Discussion
21. Example: Pretreatment Of Cells With BDNF Is Protective Against 6-Hydroxydopamine Toxicity
    21.1. Materials and Methods
        21.1.1. Cell Cultures
        21.1.2. Pretreatment Of Ventral Mesencephalon Cultures With BDNF Followed By Exposure To 6-Hydroxydopamine
        21.1.3. Measurement of $^3$H-Dopamine Uptake
        21.1.4. Measurement Of Glutathione Disulfide
    21.2. Results And Discussion
        21.2.1. BDNF Protects Primary Dopaminergic Cultures Against 6-Hydroxydopamine Toxicity
        21.2.2. BDNF Decreases The Oxidation Of Glutathione In 6-Hydroxydopamine Treated Cultures
22. Example: Retrograde Axonal Transport of BDNF In The Peripheral Nervous System
    22.1. Materials And Methods
        22.1.1. Radioiodination of BDNF
        22.1.2. Retrograde Transport Of BDNF In Sensory Neurons
        22.1.3. Results
23. Example: Retrograde Transport of [$^{125}$I]-BDNF In The Central Nervous System
    23.1. Materials and Methods
    23.2. Results
        23.2.1. Transport Of BDNF To The Cholinergic Nuclei Of The Basal Forebrain
        23.2.2. Transport Of BDNF And NGF To The Substantia Nigra
        23.2.3. Transport Of BDNF And NGF To The Other CNS Cell Groups
    23.3. Discussion
24. Deposit Of Microorganisms

1. INTRODUCTION

The present invention relates to nucleic acid sequences encoding brain derived neurotrophic factor (BDNF), to the substantially pure protein, peptide fragments or derivatives produced in quantity therefrom, and to antibodies directed toward BDNF protein, peptide fragments, or derivatives. In addition, the invention relates to genes that are members of a newly defined BDNF/NGF gene family, and to their gene products. The invention also relates to pharmaceutical compositions comprising effective amounts of BDNF gene products or, alternatively, antibodies directed toward BDNF gene products, and to methods of diagnosing and treating a variety of neurological diseases and disorders, including Alzheimer's disease and Parkinson's disease. In particular, the BDNF gene products of the invention have value in the diagnosis and therapy of disorders of dopaminergic neurons, such as Parkinson's disease, as well as disorders of sensory neurons and degenerative diseases of the retina.

2. BACKGROUND OF THE INVENTION

2.1. Neuronal Cell Death and the Role of Neurotrophic Factors in the Development of the Nervous System Throughout many parts of the vertebrate nervous system many more neurons are present during early development than are found in the adult animal. Periods of early development are characterized by waves of naturally occurring neuronal cell death (Carr and Simpson, 1978, J. Comp. Neurol., 182:727-740; Cowan et al., 1984, Science 225:1258-1265). The survival, differentiation and maturation of developing neurons may be regulated by environmental or 'epigenetic' factors rather than by a strict intrinsic genetic program. For example, experimental manipulations of the chick embryo have shown that transplantation or extirpation of peripheral "target fields", such as a limb bud or the eye, at early stages in chick development can result in a corresponding increase or decrease, respectively, in the number of sensory, sympathetic, parasympathetic or motorneurons adjacent to the enlarged or depleted target field (Hamburger, 1934, J. Exp. Zool. 68:449; Hollyday and Hamburger, 1976, J. Comp. Neurol., 170:311–321; Landmesser and Pilar, 1976, J. Cell. Biol., 68:357–374). A target field may only support a limited number of neurons, and a normal part of the developmental process may be the pruning of an excess number of neurons to match the "neurotrophic" capacity of the target tissue. The discovery and isolation of the protein now called nerve growth factor (NGF) has led to a molecular hypothesis of how a target may be able to regulate the number of neurons which survive and innervate that tissue (Levi-Montalcini et al., 1968, Physiol Rev., 48:524–569; Thoenen and Barde, 1980, Physiol Rev., 60:1284–1335).

It is now well established, at least in the peripheral nervous system, that neuronal target tissues synthesize and release limited quantities of various neurotrophic molecules which are critical to the survival of specific types of neurons (Korsching and Thoenen, 1983, Proc. Natl. Acad. Sci. U.S.A. 80:3513–3516; Heumann et al., 1984, EMBO J. 3:3183–3189; Shelton and Reichardt, 1984, Proc. Natl. Acad. Sci U.S.A. 81:7051–7955; Korsching and Thoenen, 1985, Neurosci. Lett. 54:201–205).

2.2. Nerve Growth Factor

Nerve growth factor (NGF) is by far the most fully characterized of these neurotrophic molecules and has been shown, both in vitro and in vivo, to be essential for the survival of sympathetic and neural crest-derived sensory neurons during early development of both chick and rat (Levi-Montalcini and Angeletti, 1963, Develop. Biol. Z:653–659; Levi-Montalcini et al., 1968, Physiol. Rev. 48:524–569). Injections of purified NGF into the developing chick embryo have been found to cause massive hyperplasia and hypertrophy of spinal sensory neurons and sympathetic neurons (Levi-Montalcini and Booker, 1960, Proc. Natl. Acad. Sci. U.S.A. 46:373–384; Hamburger et al., 1981, J. Neurosci. 1:60–71). Conversely, removal or sequestration of endogenous NGF by daily injection of anti-NGF antibodies into neonatal rats has been associated with virtual destruction of the sympathetic nervous system (Levi-Montalcini and Booker, 1960, Proc. Natl. Acad. Sci. U.S.A. 46:384–391; Levi-Montalcini and Angeletti, 1966, Pharmacol. Rev. 18:619–628). Exposure to NGF antibodies even earlier in development either by antibody injections in utero or by passive transplacental transfer of maternal antibodies has been shown to result in a substantial loss of neural crest-derived sensory neurons such as spinal and dorsomedial trigeminal sensory neurons (Goedert et al., 1984, Proc. Natl. Acad. Sci. U.S.A. 81:1580–1584; Gorin and Johnson, 1979, Proc. Natl. Acad. Sci. U.S.A. 76:5382–5386). Until recently, almost all studies of NGF had focused on its role in the peripheral nervous system, but it now appears that NGF also influences the development and maintenance of specific populations of neurons in the central nervous system (Thoenen et al., 1987, Rev. Physiol. Biochem. Pharmacol. 109:145–178; Whittemore and Seiger, 1987, Brain Res. Rev. 12:439–464).

The serendipitous discovery of large amounts of NGF protein in the submandibular gland of the adult male mouse (Cohen, 1960, Proc. Natl. Acad. Sci. U.S.A. 44.:302–311) and an earlier discovery of high levels of NGF in snake venom (Cohen and Levi-Montalcini, 1956, Proc. Natl. Acad. Sci. U.S.A. 42:571–574) fortuitously provided sufficient quantities of NGF to permit studies relating to the physiology, protein chemistry, and, more recently, the molecular biology of NGF (i.e. molecular cloning of NGF and its receptor). The function of large amounts of NGF in the adult male mouse salivary gland remains unknown; however, it appears that this abundant source of NGF may not play any role in development or maintenance of the peripheral or central nervous system. In target tissues innervated by NGF sensitive neurons (neurons which have been shown to depend on NGF for survival, to possess high affinity NGF receptors and to internalize and retrogradely transport NGF with high specificity), the steady state of measurable levels of NGF have been found to be extremely low, in the range of picograms or nanograms per gram of tissue, compared to thousandfold higher levels in adult male mouse salivary gland tissue. NGF has not been found at any appreciable level in serum and therefore does not appear to be a circulating growth factor or hormone (Suda et al., 1978, Proc. Natl. Acad. Sci. U.S.A. 75:4042–4046).

In addition to the important discovery of a major source of NGF protein in the mouse submandibular gland, the development of sensitive, reliable and efficient biological assays has played a major role in elucidating the biology and biochemistry of NGF. Dorsal root ganglia (DRG) of the developing chick embryo were one of the first neuronal types to be shown to be responsive to NGF in vitro. Explant cultures of ES-E12 chick DRG in a plasma clot, and, more recently, dissociated neuron-enriched cultures of chick DRG have proven very useful in bioassays for NGF activity (e.g. during purification) and for in vitro studies of NGF biology (Levi-Montalcini et al., 1954, Cancer Res. 4:49–57; Levi-Montalcini and Angeletti, 1963, Develop. Biol. 1:653–659; Greene, 1977, Develop. Biol. 58:96, ibid 58:106). The fact that more than forty DRG can be dissected from a single chick embryo has led to the widespread use of NGF bioassays in many laboratories.

In addition to the availability of large quantities of NGF protein and efficient NGF assay systems, a third major factor which has greatly contributed to our understanding of the biology of NGF is the relative ease with which antibodies to NGF can be raised in guinea pigs, rabbits, sheep, etc.; it appears that mouse NGF is highly immunogenic. Cohen (1960, Proc. Natl. Acad. Sci. U.S.A. 46:302–311) raised antibodies to the NGF he had purified from mouse submandibular gland and showed, with Levi-Montalcini and Booker (1960, Proc. Natl. Acad. Sci. U.S.A. 46:384–391) that these antibodies caused destruction of sympathetic ganglia, or "immunosympathectomy," when administered daily to newborn rats (Levi-Montalcini and Angeletti, 1966, Pharmacol. Rev. 18:619–628).

The abundance of NGF protein allowed the primary sequence to be determined by relatively conventional protein chemistry (Angeletti and Bradshaw, 1971, Proc. Natl. Acad. Sci. 68:2417–2420). The NGF gene has now been cloned from many species, including mouse (Scott et al., 1983, Nature 302:538–540), human (Ullrich et al., 1983, Nature 303:821–825), cow and chick (Meier et al., 1986, EMBO J. 5:1489–1493), and rat (Whittemore et al., 1988, J. Neurosci. Res., 20:402–410) using essentially conventional molecular biology based on the availability of the protein sequence of mouse NGF to design suitable oligonucleotide probes. The availability of abundant NGF has also greatly facilitated studies on the NGF receptor, which have ultimately led to the molecular cloning of the NGF receptor from human and rat (Johnson et al., 1986, Cell, 47:545–554; Radeke et al., 1987, Nature 325:593–597).

It is now well established that NGF is not a ubiquitous neurotrophic factor. Within the peripheral nervous system, NGF appears not to be a survival factor for parasympathetic neurons, neural placode-derived sensory neurons or enteric neurons, as determined both from studies in vitro and in vivo. Furthermore, NGF does not appear to be a survival factor for developing motorneurons (Oppenheim, 1982, J. Comp. Neurol. 210:174–189), although these neurons do appear to express at least a low affinity form of the NGF receptor during development (Raivich et al., 1985, EMBO J. 4:637–644). The lack of effects of NGF on these neuronal types has prompted the search for other neurotrophic factors, especially factors that would sustain the survival of spinal cord motorneurons and/or parasympathetic neurons of the ciliary ganglion.

2.3. Other Neurotrophic Factors

In the past decade there have been numerous reports of neurotrophic activity in extracts of a great variety of tissues and in the conditioned culture medium of many different cell types. In almost all cases, however, progress in purifying and characterizing these activities has been hampered by the fact that such activities are present in extremely small amounts, in the range of picograms to nanograms per gram of tissue.

Furthermore, whereas adequate bioassays have been established for peripheral neurons, designing reliable, reproducible and specific assays for central nervous system neurons has proved problematic. While individual types of peripheral neurons are found as discrete, easily dissectable ganglia, central nervous system (CNS) neurons are invariably highly heterogenous in their distribution. Thus, specific markers are required for either identification or enrichment of particular classes of CNS neurons. Progress in producing such markers, for example, antibodies directed toward cell surface or cytoskeletal components, or specific histological stains, has been very limited. Accordingly, characterization of neurotrophic factors which are (i) not as abundant as NGF, (ii) difficult to assay, and (iii) not available in sufficient quantities to elicit antibody production, has proved to be an exceedingly difficult process.

2.3.1. Comparison of a Brain Derived Neurotrophic Factor and Nerve Growth Factor Neurotrophic activity capable of sustaining the survival of embryonic chick dorsal root ganglion neurons in vitro was identified in the "conditioned medium" in which rat C-6 glioma cells had been cultured (Barde et al., 1978, Nature 274:818). The activity was not neutralized by antibodies to mouse NGF, suggesting the presence of another neurotrophic factor in the conditioned medium. Similar activities that could not be blocked by NGF antibodies were subsequently reported in cultures of normal adult rat brain astroglial cells (Lindsay, 1979, Nature 282:80–82; Lindsay et al., 1982, Brain Res. 243:329–343) and in extracts of developing and adult rat brain (Barde et al., 1980, Proc. Natl. Acad. Sci. U.S.A. 77:1199–1203) and developing and mature chick spinal cord (Lindsay and Peters, 1984, Neurosci. 12:45–51). However, in no case was the active factor(s) isolated or identified, and it remains questionable as to whether the observed activities were due to the same or different factor(s).

Using pig brain as a starting material, Barde et al. (1982, EMBO J. 1:549–553) reported a factor, now termed brain-derived neurotrophic factor (BDNF), which appeared to promote the survival of dorsal root ganglion neurons from E10/E11 chick embryos. The neurotrophic activity was found to reside in a highly basic protein (isoelectric point, pI > 10.1) which migrated during sodium dodecyl sulfate (SDS) gel electrophoresis as a single band of 12.3 kD molecular weight. The purification factor was estimated to be $1.4 \times 10^6$, but the yield was very low, with only approximately 1 μg of BDNF purified from 1.5 kg of pig brain. Furthermore, because the last step in the purification process was preparative gel electrophoresis, the activity of BDNF could not be fully renatured secondary to the presence of residual SDS (Barde and Thoenen, 1985, in "Hormones and Cell Regulation," Vol 9 Dumont et al., eds Elsevier Science Publishers, pp. 385–390). It was noted that the highly basic nature and molecular size of BDNF were very similar to the NGF monomer. However, BDNF appeared to have properties that differed from the known properties of NGF in that (a) in the chick dorsal root ganglion bioassay, antibodies to NGF had no apparent effect on the biological activity of BDNF; (b) the effects of BDNF and NGF appeared to be additive; and (c) unlike NGF, BDNF was found to have no effect on the survival of E12 chick sympathetic neurons. In addition, during early studies with brain extracts, it was observed that the neurotrophic activity in these sources appeared to act upon sensory neurons at later stages of development than were associated with NGF. Using dissociated cultures of chick embryo neurons cultured on a polycationic substrate such as polylysine or polyornithine, BDNF was found to support the survival of more than 30 percent of E10–11 (embryonic day ten or eleven) dorsal root ganglion neurons but seemed to have little effect on the survival of the same neurons at E6 (Barde et al., 1980, Proc. Natl. Acad. U.S.A. 77:1199–1203 supra). Under similar conditions, NGF supported the survival of 30–40 percent of E6 DRG neurons. Interestingly, it was later found that when cultured on a substrate coated with the extracellular matrix glycoprotein laminin, both NGF and BDNF supported the survival of about 50 percent of DRG neurons from chick embryos of ages E6–E12 (Lindsay et al., 1985, Develop. Biol. 112:319–328). In the latter study, the effects of NGF and BDNF were found to be additive when both were present at saturating concentrations.

Early studies by Levi-Montalcini (1966, The Harvey Lectures 60:217–259) on the neuronal specificity of NGF suggested that NGF was not a ubiquitous neurotrophic factor even for sensory neurons, as NGF appeared to have no effect upon neurons of certain cranial sensory ganglia of the chick, especially the nodose ganglion of the tenth cranial nerve. Later in vivo studies (Johnson et al., 1980, Science 210:916–918; Pearson et al., 1983 Develop. Biol. 96:32–36) showed that NGF deprivation during embryogenesis had no effect on the survival of neurons in most cranial sensory ganglia of the rat, while similar treatment greatly depleted the neuronal count in sensory ganglia derived from the neural crest. More detailed in vitro studies (Lindsay and Rohrer, 1985, Develop. Biol. 112:30–48; Davies and Lindsay, 1985, Develop. Biol. 111:62-72; Lindsay et al., 1985, J. Cell. Sci. Suppl. 3:115-129) clearly indicated that NGF supports the survival of most neural crest-derived sensory neurons but has no apparent effect on the survival of cranial sensory neurons derived from neural placodes.

The first demonstration of a neuronal specificity of BDNF distinct from that of NGF was the demonstration in vitro that purified BDNF supports the survival of 40-50% of sensory neurons dissociated from the neural placode-derived nodose ganglion of the chick embryo at E6, E9 or E12 (Lindsay et al., 1985, J. Cell. Sci. Supp. 3:115-129). NGF was without apparent effect on these neurons either by itself or in conjunction with BDNF. It was later shown in explant culture studies that BDNF appeared to support survival and neurite outgrowth from other neural placode-derived sensory ganglia, including the petrosal, geniculate and ventrolateral trigeminal ganglia (Davies et al., 1986, J. Neurosci. 6:1897-1904), none of which have been found to be sensitive to NGF. In all of the above studies antibodies to NGF had no effect upon the observed activity of BDNF. In addition to its effects on cultured neurons from peripheral ganglia, BDNF was found to stimulate survival and neuronal differentiation of cells cultured from quail neural crest (Kalcheim and Gendreau, 1988, Develop. Brain Res. 41:79-86).

Prior to the instant invention, the inability to produce sufficient amounts of BDNF for immunization prevented the production of anti-BDNF antibodies for comparison to anti-NGF antibodies in their effects on neuronal populations, and precluded BDNF/NGF cross-neutralization experiments. Two recent studies with BDNF (Kalcheim et al., 1987, EMBO J. 6:2871-2873; Hofer and Barde, 1988, Nature 331:261-262) have, however, indicated a physiological role of BDNF in avian PNS development. If a mechanical barrier was placed in ovo between E3/E4 DRG (embryonic day 3 or 4 dorsal root ganglia) and their CNS target in the neural tube, many DRG neurons were observed to die (Kalcheim and Le Douarin, 1986, Develop. Biol. 116:451-466). It was postulated that this neuronal death may have been due to deprivation from a CNS (neural tube) derived neurotrophic factor. It was subsequently observed that BDNF attached to a laminin-coated sialastic membrane could prevent this cell death (Kalcheim et al., 1987, EMBO J. 6:2871-2873). Injections of BDNF into developing quail eggs has been found to reduce naturally occurring cell death in the nodose ganglia, an effect not seen with NGF (Hofer and Barde, 1988, Nature 331:261-262). In addition to its effect on peripheral sensory neurons of both neural crest and neural placode origin, BDNF was found to support the survival of developing CNS neurons. Johnson et al. (1986, J. Neurosci. 6:3031-3938) presents data that indicates that BDNF supports the survival of retinal ganglion cells cultured from E17 rat embryos. This was in agreement with previous studies which showed that conditioned media and brain extracts prepared from the target regions of retinal ganglion cells appeared to support the survival of these neurons (McCaffery et al., 1982, Ex. Brain Res. 48:37-386; Sarthy et al., 1983, J. Neurosci. 3:2532-2544; Turner et al., 1983, Dev. Brain Res. 6:77-83).

In addition to its effects on the survival of developing neurons in culture, BDNF has been shown to have effects on cultured adult peripheral and central nervous system neurons. BDNF, as well as NGF, has been shown to stimulate axonal regeneration from adult rat DRG neurons in culture (Lindsay, 1988, J. Neurosci. 8:2394-2405) although adult sensory neurons did not appear to require neurotrophic factors for maintenance in vitro over 3 or 4 weeks. Furthermore, in cultures of adult rat retina, BDNF was observed to promote both survival and axonal elongation from retinal ganglion cells (Thanos et al., 1989, Eur. J. Neurosci. 1:19-26). A comparison of the biological effects of NGF and BDNF is presented in Table I.

TABLE I

COMPARISON OF BIOLOGICAL ACTIVITIES OF BDNF AND NGF*

| | | SURVIVAL** | |
|---|---|---|---|
| | | BDNF | NGF |
| | PERIPHERAL NERVOUS SYSTEM | | |
| (i) | E6 Chick DRG | − | ++ |
| | E10 Chick DRG | − | ++ |
| | E12 Chick Sympathetic neurons | − | ++ |
| (ii) | E6-E12 Chick DRG | ++ | ++ |
| | E6-E12 Chick Nodose | ++ | − |
| | E12 Chick Sympathetic neurons | − | ++ |
| | E12 Chick ciliary (Lindsay et al., 1985, supra) | − | − |
| (iii) | E3-E14 Chick: | | |
| | Jugular | +/++ | ++ |
| | DM-trigeminal | +/++ | ++ |
| | Petrosal | +/++ | − |
| | Geniculate | +/++ | − |
| | VL-trigeminal | ++ | − |
| | Vestibular | − | − |
| | Mesencephalic (Davies et al., 1986, supra) (Barde et al., 1987, Prog. Brain Res., 71:185-189) | ++ | − |
| | CENTRAL NERVOUS SYSTEM | | |
| (i) | E17 Rat Retinal Ganglion Cells (Johnson et al., 1986, J. Neurosci. 63031-3038) | ++ | − |

*in chronological order according to publication date; effects tested in vitro
**no survival: (−); moderate survival (+); good survival (++)

2.3.2. Neuronal Targets of Brain Derived Neurotrophic Factor

Sensory neurons of peripheral nerve ganglia have been found to arise from either of two distinct, transient embryological structures, namely,the neural crest and neural placodes. The neural crest appears to give rise to both neurons and satellite cells of autonomic ganglia and spinal nerve sensory ganglia, i.e. DRG. The contribution of the neural crest and neural placodes to the formation of cranial nerve sensory ganglia has been studied using the quail/chick chimera transplantation system devised by Le Douarin (Le Douarin, 1973, Develop. Biol. 20:217-222; Noden, 1978, Develop. Biol. 67:313-329; Narayanan and Narayanan, 1980, Anat. Rec. 196:71-82; Ayer-Le Lievre and Le Douarin, 1982, Develop. Biol. 94:291-310; D'Amico-Maratel and Nodem, 1983, Am. J. Anat. 166:445-468). As reviewed in Lindsay et al. (1985, J. Cell. Sci. Supp. 3:115-129), it is now believed, at least for birds, that neurons of the distal ganglia of the VIIth, IXth, and Xth cranial nerves (geniculate, petrosal and nodose ganglia, respectively) and neurons of the vestibuloacoustic complex of the VIIIth cranial nerve are exclusively of neural placode origin. The trigeminal ganglion of the Vth cranial nerve contains neurons of both crest and placode origin (with the placode-derived neurons predominant in the ventrolateral pole of the maxillo-mandibular lobe) whereas the satellite cells of all cranial ganglia have been found to be entirely of neural crest origin.

From in vitro experiments using both explant and dissociated, neuron-enriched cultures of spinal and cranial nerve sensory neurons, it has been found that sensory neurons of neural crest origin are responsive to NGF; in contrast, neurons derived from neural placodes (including neurons of the ventrolateral portion of the trigeminal ganglion and the entire neuronal population of the vestibular, geniculate, petrosal and nodose ganglia) have been observed to be largely unresponsive to NGF throughout embryonic development. In contrast to differences in their requirement and responsiveness to NGF, both placode and neural crest derived sensory neurons have been found (Table I) to be responsive to the survival and neurite-promoting activity of BDNF (Lindsay et al., 1985, J. Cell. Sci. Supp. 3:115–129; Lindsay et al., 1985, Develop. Biol. 112:319–328 Kalcheim and Gendreau, 1988, Develop. Brain Res. 41:79–86). Tebar and Barde (1988, J. Neurosci. 8:3337–3342) studied the binding parameters of radioactively labeled BDNF to chick embryo dorsal root ganglion neurons; their results are consistent with the existence of two classes of BDNF receptors, one with high affinity for BDNF, the other with low affinity. No high affinity receptors were observed on sympathetic neurons.

The known neuronal targets of BDNF were further reviewed by Barde et al. (1987, Prog. Brain Res. 71:185–189). Prior to the instant invention, identification of cells synthesizing BDNF has not been feasible due to the lack of nucleic acid or antibody probes specific for BDNF. Attempts to prepare either polyclonal or monoclonal antibodies to BDNF have been unsuccessful. This failure to raise antibodies had hindered the molecular cloning of BDNF, determination of the physiological effect of depriving developing neurons of BDNF in vivo, quantitation of BDNF in tissues using an immunoassay, and localization of BDNF using immunocytochemistry.

TABLE II

SUMMARY OF BDNF RESPONSIVE AND NON-RESPONSIVE NEURONS*

A. Responsive Neurons
  I. Chick sensory neurons of neural crest origin in:
    (a) dorsal root ganglion
    (b) jugular ganglion
    (c) dorsomedial trigeminal ganglion
    (d) mesencephalic trigeminal nucleus**
  II. Chick sensory neurons of ectodermal placode origin in:
    (a) nodose ganglion
    (b) vestibular ganglion
    (c) petrosal ganglion
    (d) geniculate ganglion
    (e) ventrolateral trigeminal ganglion
  III. Rat retinal ganglion cells
B. Non-Responsive Neurons
  I. Chick and rat sympathetic neurons
  II. Chick parasympathetic ciliary neurons

*From Barde et al., 1987, Prog. Brain Res. 71:185–189
**See Davies et al., 1986, Nature 319:497–499

3. SUMMARY OF THE INVENTION

The present invention relates to nucleic acid sequences encoding brain derived neurotrophic factor (BDNF), to the substantially pure protein, peptide fragments or derivatives produced in quantity therefrom, and to antibodies directed toward BDNF protein, peptide fragments, or derivatives. The present invention makes available, for the first time, sufficient quantities of BDNF to enable anti-BDNF antibody production and to support diagnostic and therapeutic applications of BDNF.

In various embodiments of the invention, the BDNF nucleic acids, proteins, peptides, derivatives, or antibodies of the invention may be utilized in methods for the diagnosis and treatment of a variety of neurologic diseases and disorders, and, in particular, in the diagnosis and treatment of sensory neuron disorders and retinal degeneration. Furthermore, in specific embodiments of the invention, BDNF nucleic acids or BDNF gene products may be used in the diagnosis and treatment of neuroblastoma tumor, Parkinson's disease, and Alzheimer's disease. BDNF gene products may also be used to facilitate incorporation of implants into nervous tissue or, alternatively, to promote nerve regeneration following damage by trauma, infarction, infection, or post-operatively, in additional specific embodiments of the invention.

The invention also relates to pharmaceutical compositions comprising effective amounts of BDNF gene products or, alternatively, antibodies directed toward BDNF gene products, which may be utilized in the diagnosis or treatment of a variety of neurological diseases and disorders.

In addition, by providing the full nucleotide sequence of BDNF, the present invention allows for the comparison of BDNF and NGF genes, thereby identifying homologous regions and defining a BDNF/NGF gene family. Accordingly, the present invention relates to a method for identifying additional members of the BDNF/NGF gene family. In a specific embodiment, the method of the invention is used to identify a novel, non-NGF, non-BDNF member of the BDNF/NGF gene family. The invention further provides for additional members of the BDNF/NGF gene family identified according to the disclosed method and to their gene products.

3.1. Abbreviations and Definitions

BDNF brain derived neurotrophic factor
hBDNF human BDNF
CAT choline acetyltransferase
CNS central nervous system
DRG dorsal root ganglia (ganglion)
EDTA ethylene diamine tetraacetic acid
NGF nerve growth factor
PBS phosphate buffered saline
PCR polymerase chain reaction
PNS peripheral nervous system
SDS sodium dodecyl sulfate
Tris tris(hydroxymethyl)aminomethane

4. DESCRIPTION OF THE FIGURES

FIG. 1. Nucleotide sequence and deduced amino-acid sequence of porcine prepro BDNF cDNA. The complete sequence resulting from analysis of two overlapping cDNA clones is shown in this figure. The peptide sequences obtained from microsequencing (Table III) are underlined. The only consensus sequence for N-glycosylation is double underlined. The start of the mature BDNF sequence is marked by a double carat.

FIG. 2. Sequence comparison between NGF and BDNF. Areas with more than two amino acids found at identical positions are indicated. The sequences start with the first amino acids of the mature proteins and end with the last ones before the stop codons. Fifty-one amino acids are common to BDNF and the various NGFs (Schwarz et al., 1989, J. Neurochem. 52:1203–1209), including the 6 cysteine residues.

FIG. 3. Autoradiograph of Southern blots of EcoRI cut human, monkey, rat, mouse, dog, cow, rabbit, chicken, and yeast genomic DNA, hybridized to $^{32}$P-labeled NGF and BDNF probes.

FIGS. 4A through 4I. Sequence of human BDNF cDNA and deduced amino acid sequence, and comparison of DNA sequences from pig, rat, and chicken.

Figure 4A:
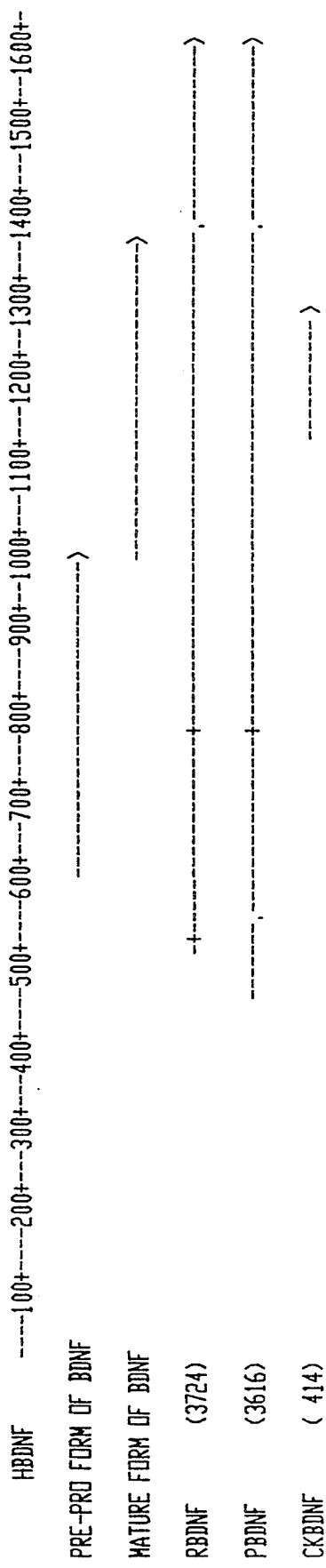
Figure 4D:
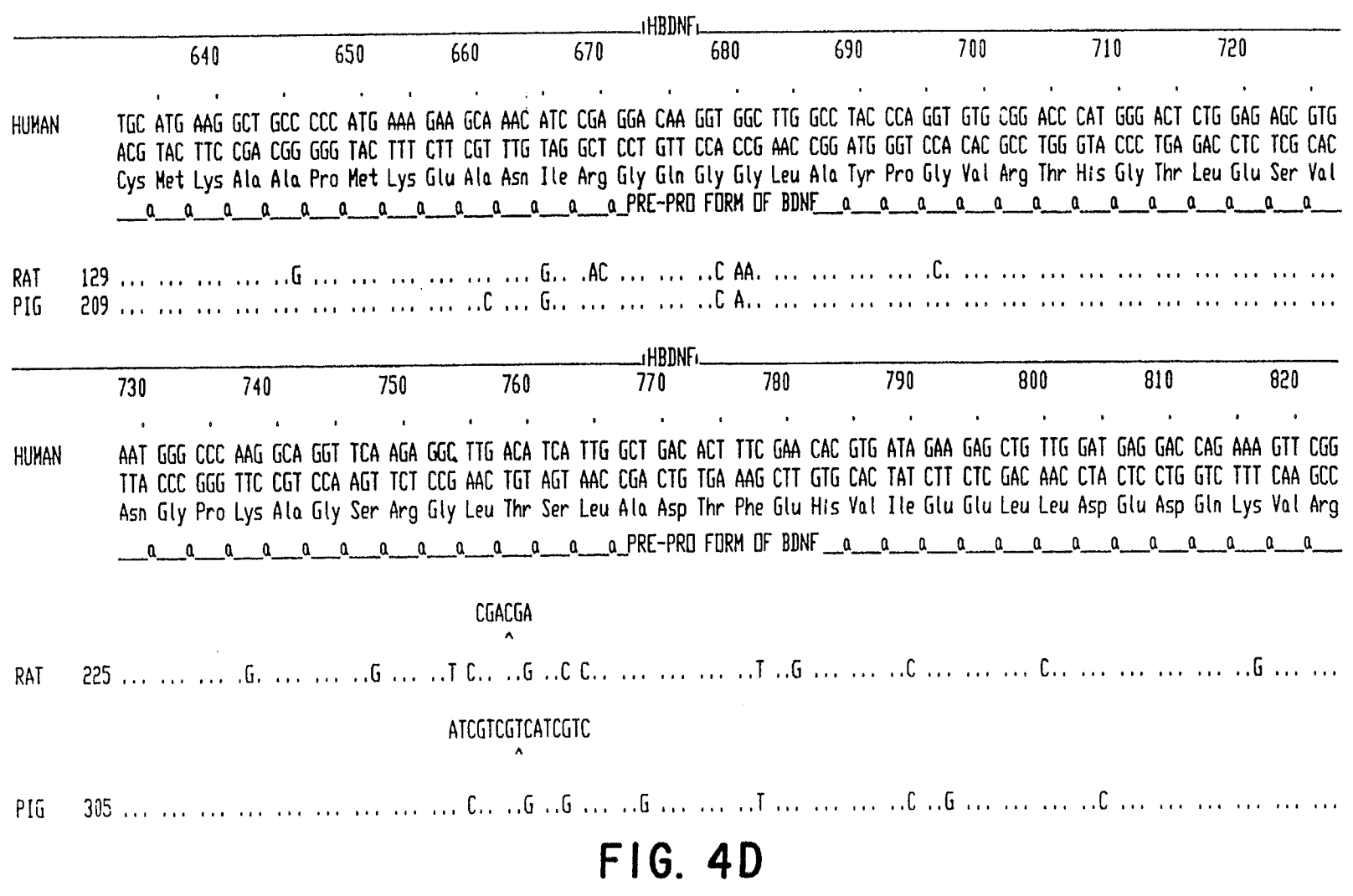
Figure 4F:
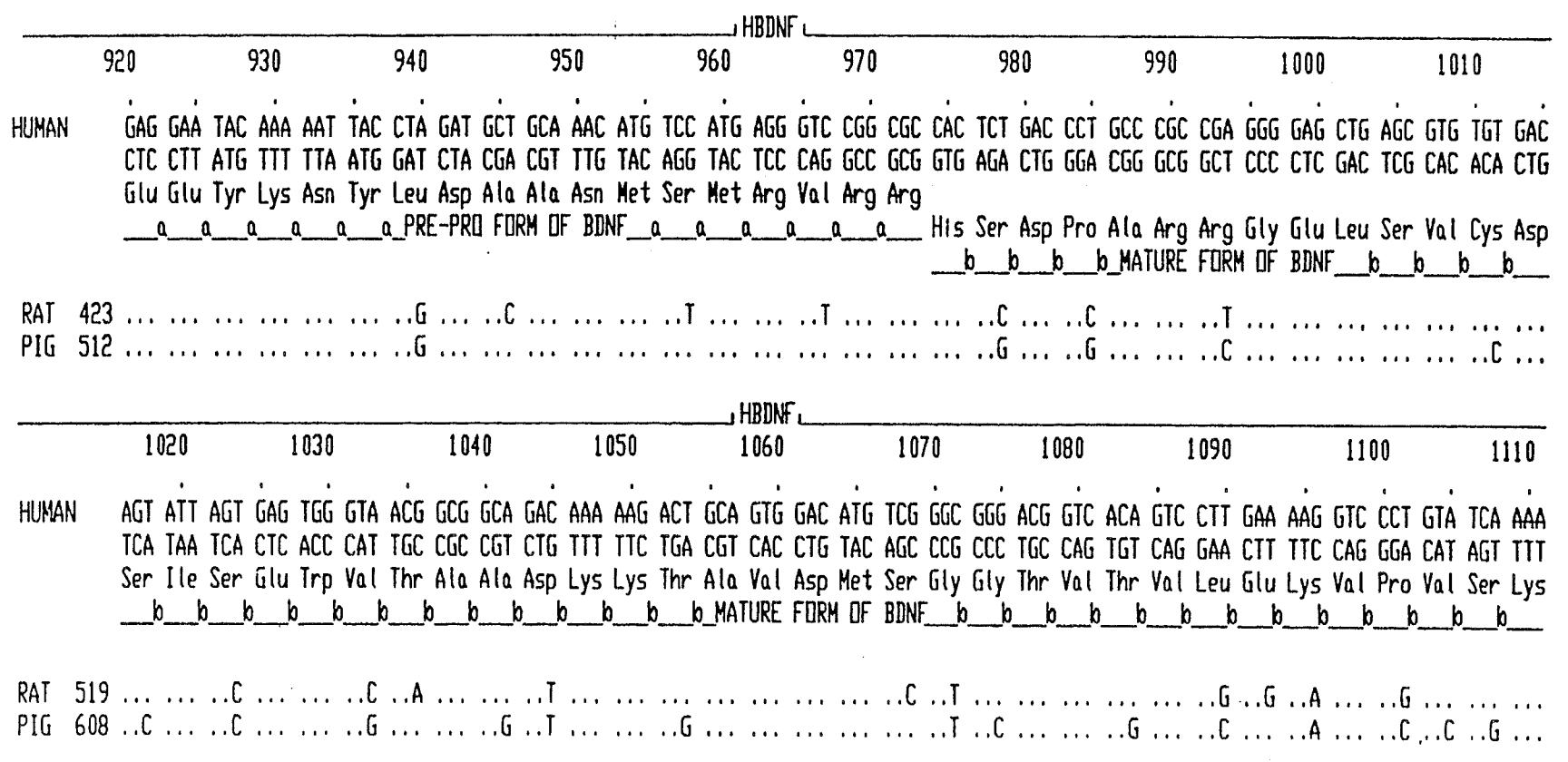
Figure 4G:
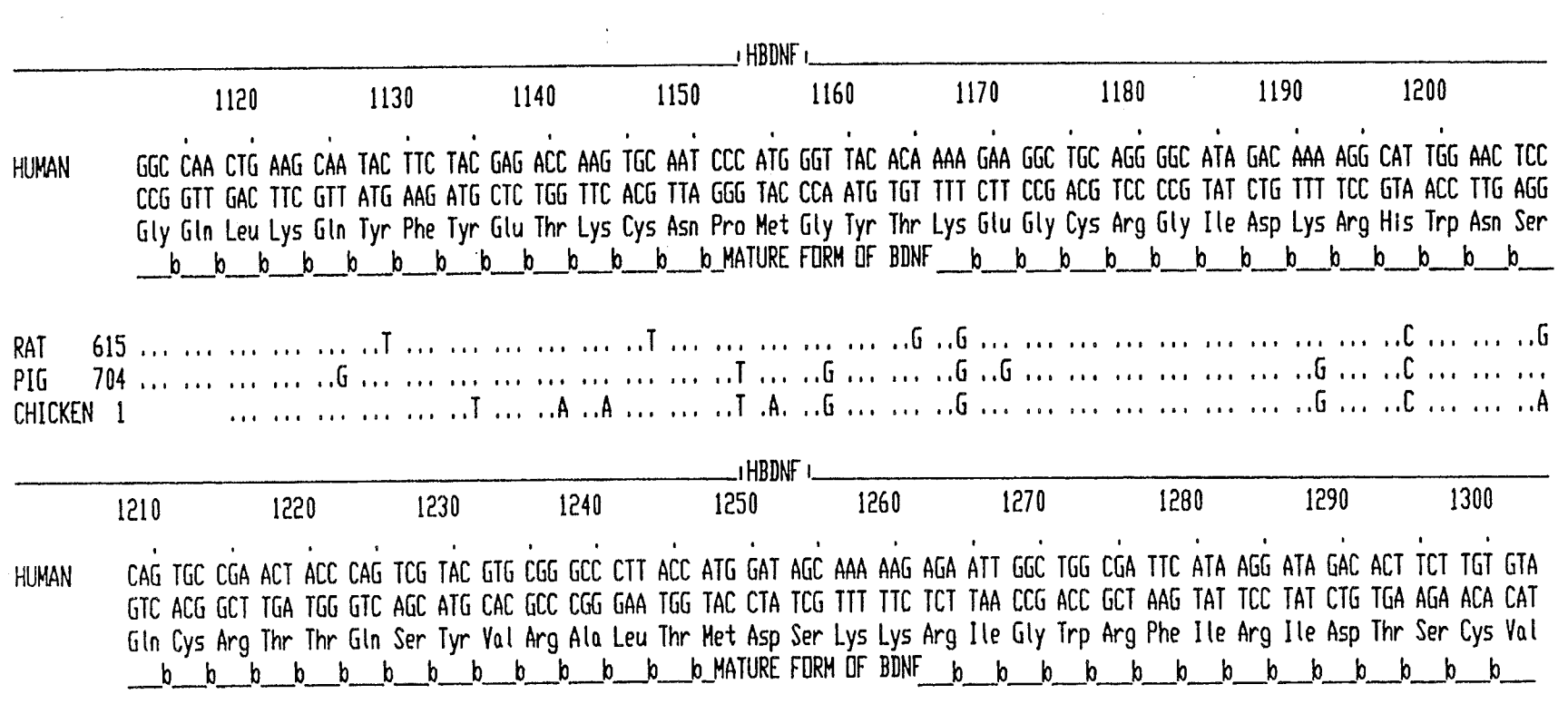
Figure 4H:
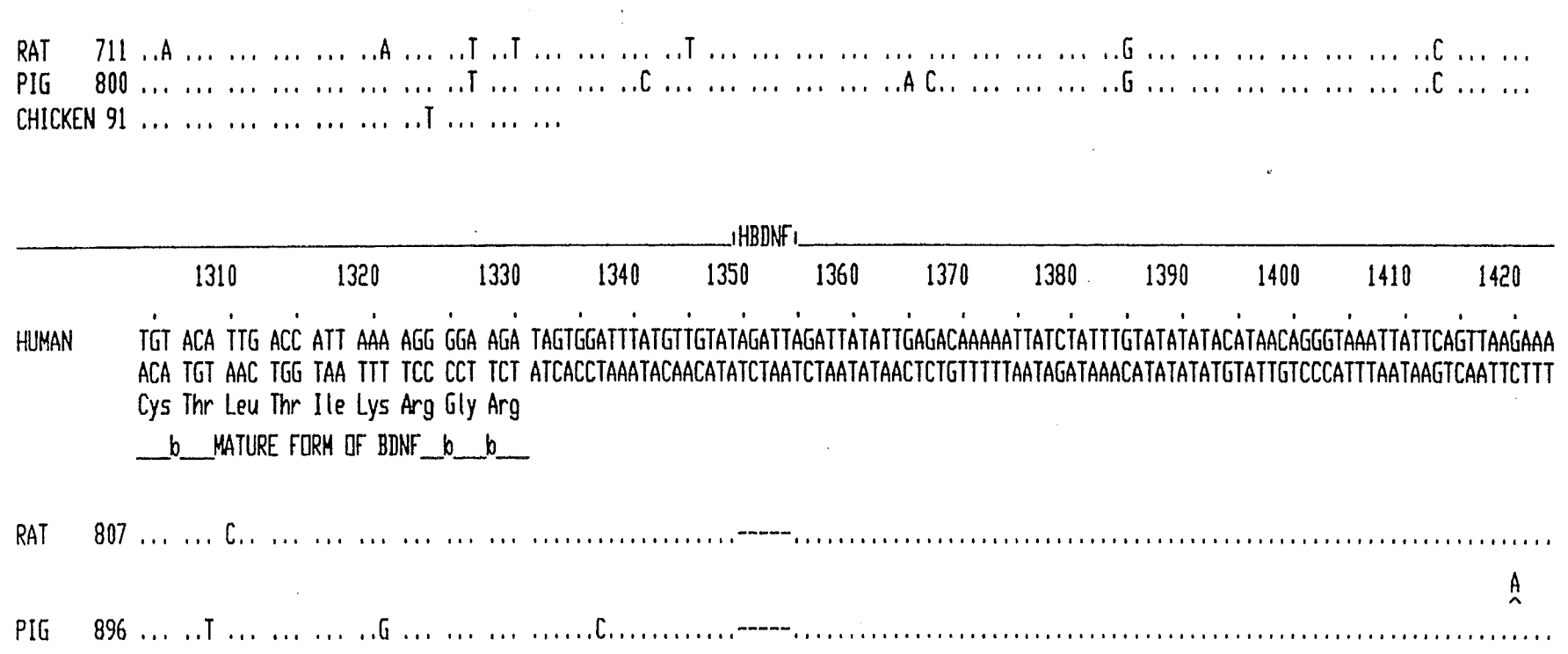

FIG. 4A depicts the cDNAs sequenced for (in descending order) human, rat, pig and chicken BDNF. FIGS. 4B and 4C present noncoding DNA sequence. The DNA sequence encoding pre-pro BDNF, and the corresponding amino acid sequence, begin in FIG. 4C and continue through FIGS. 4D, 4E, and into FIG. 4F. DNA sequence encoding mature BDNF, and the corresponding amino acid sequence, begins in FIG. 4F and continues through FIG. 4G into FIG. 4H. cDNA sequence corresponding to the untranslated region of the BDNF mRNA begins in FIG. 4H and continues through FIG. 4I.

Figure 5:
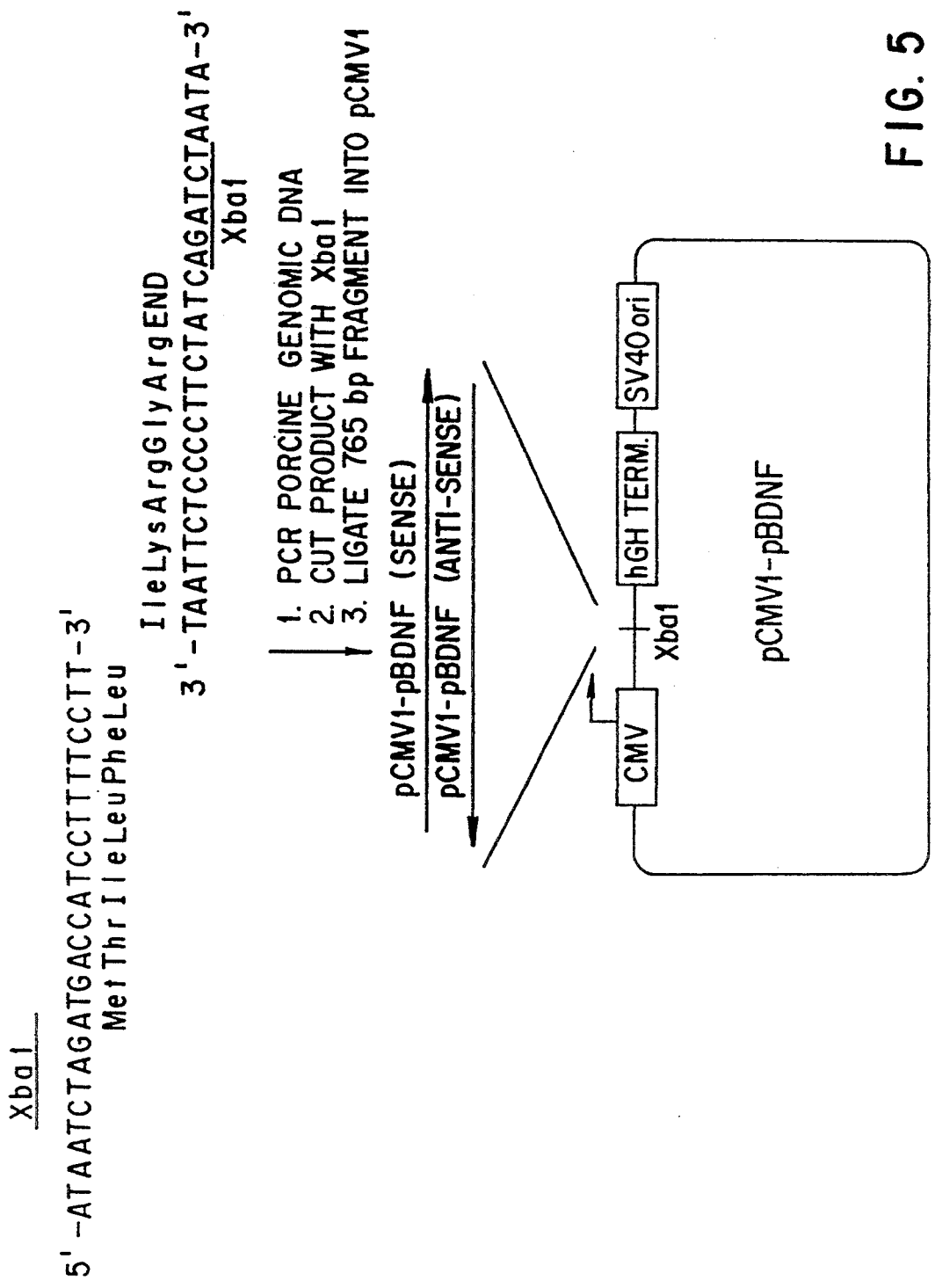

FIG. 5. BDNF expression plasmid PCMV1-pBDNF.

FIG. 6A. Results of ELISA determination of binding of antisera to B5 peptide, using serial dilutions of antisera.

FIG. 6B. Quantitation of binding of 1:500 dilution of various antisera to 50 ng BDNF.

Figure 7:
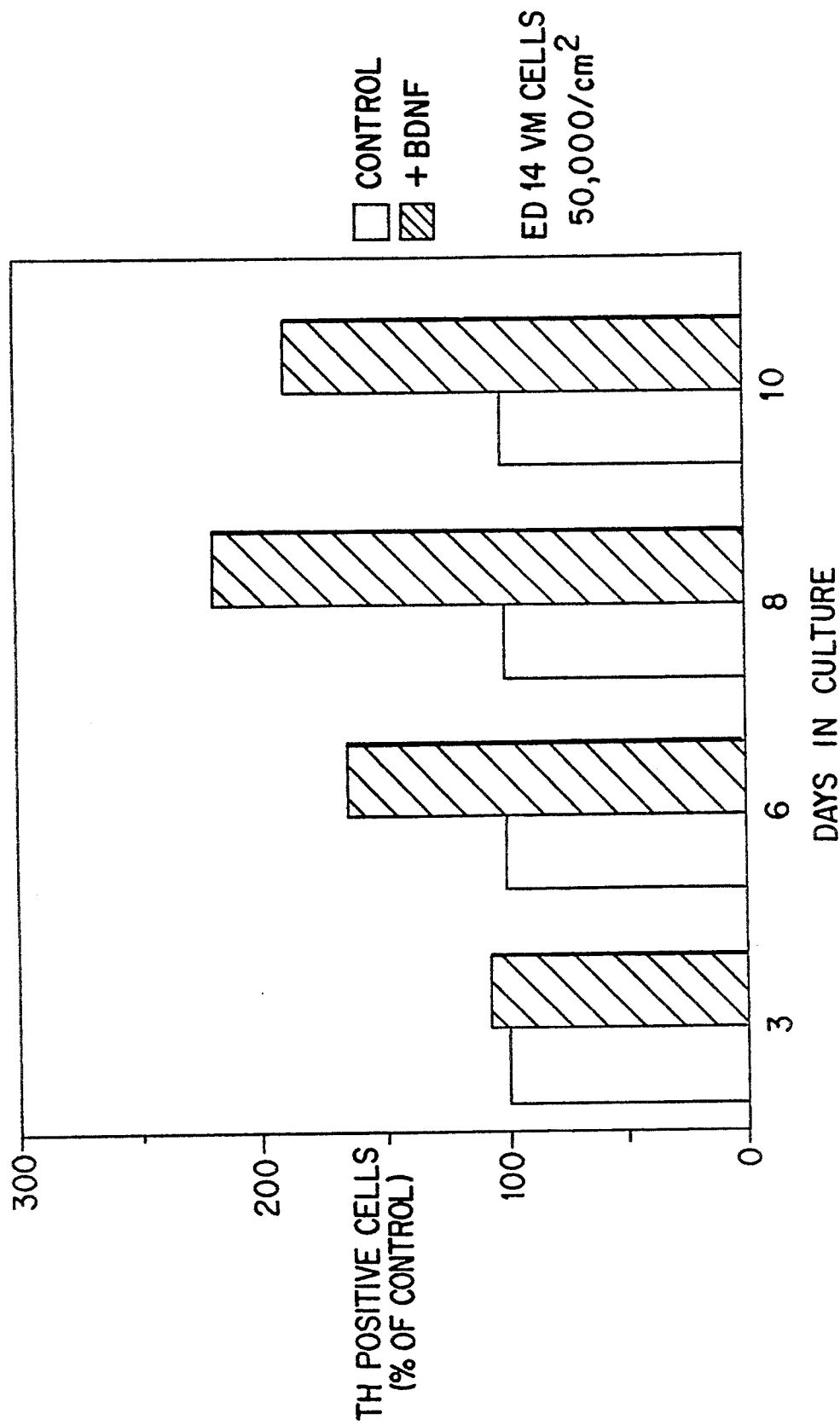

FIG. 7. Results of immunohistochemical staining for tyrosine hydroxylase in BDNF-treated (hatched bars) and control (solid bars) ventral mesencephalon cultures.

Figure 8:
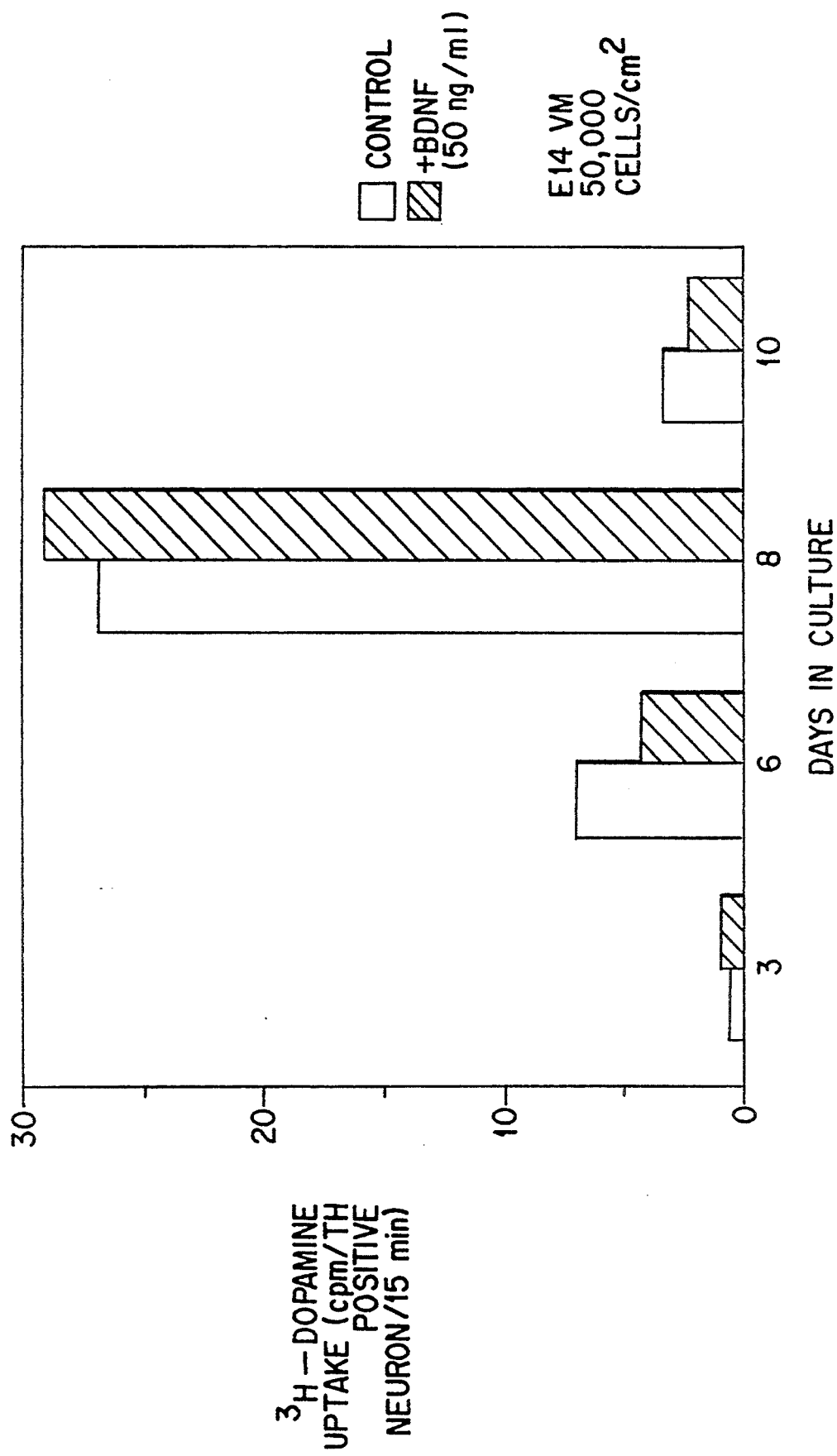

FIG. 8. Dopamine uptake by ventral mesencephalon cultures. Cultures supplemented with BDNF are denoted by hatched bars; control cultures are represented by solid bars.

Figure 9A:
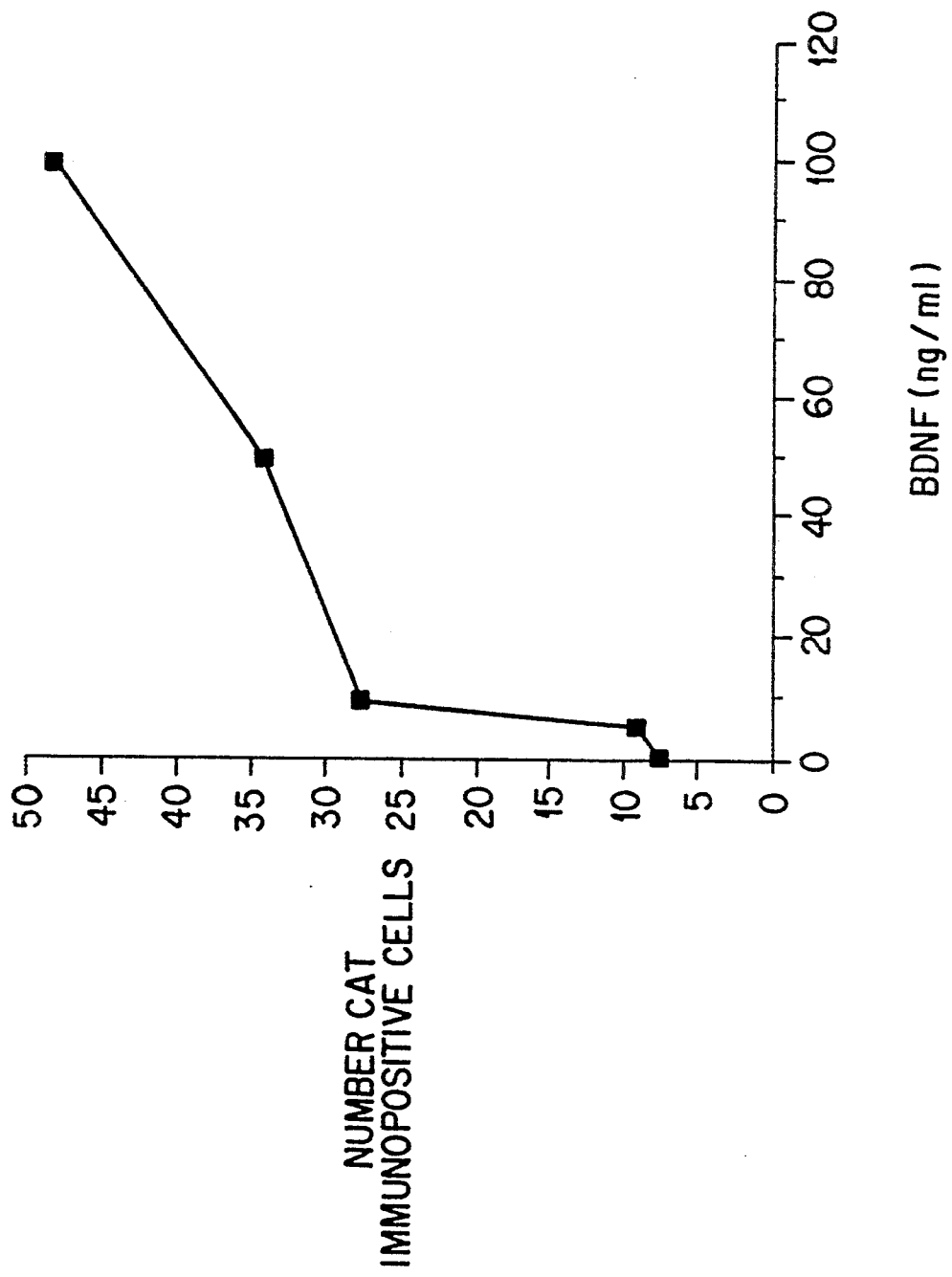

FIG. 9A. The effect of BDNF on the number of CAT positive cells in forebrain cholinergic neuron cultures.

Figure 9B:
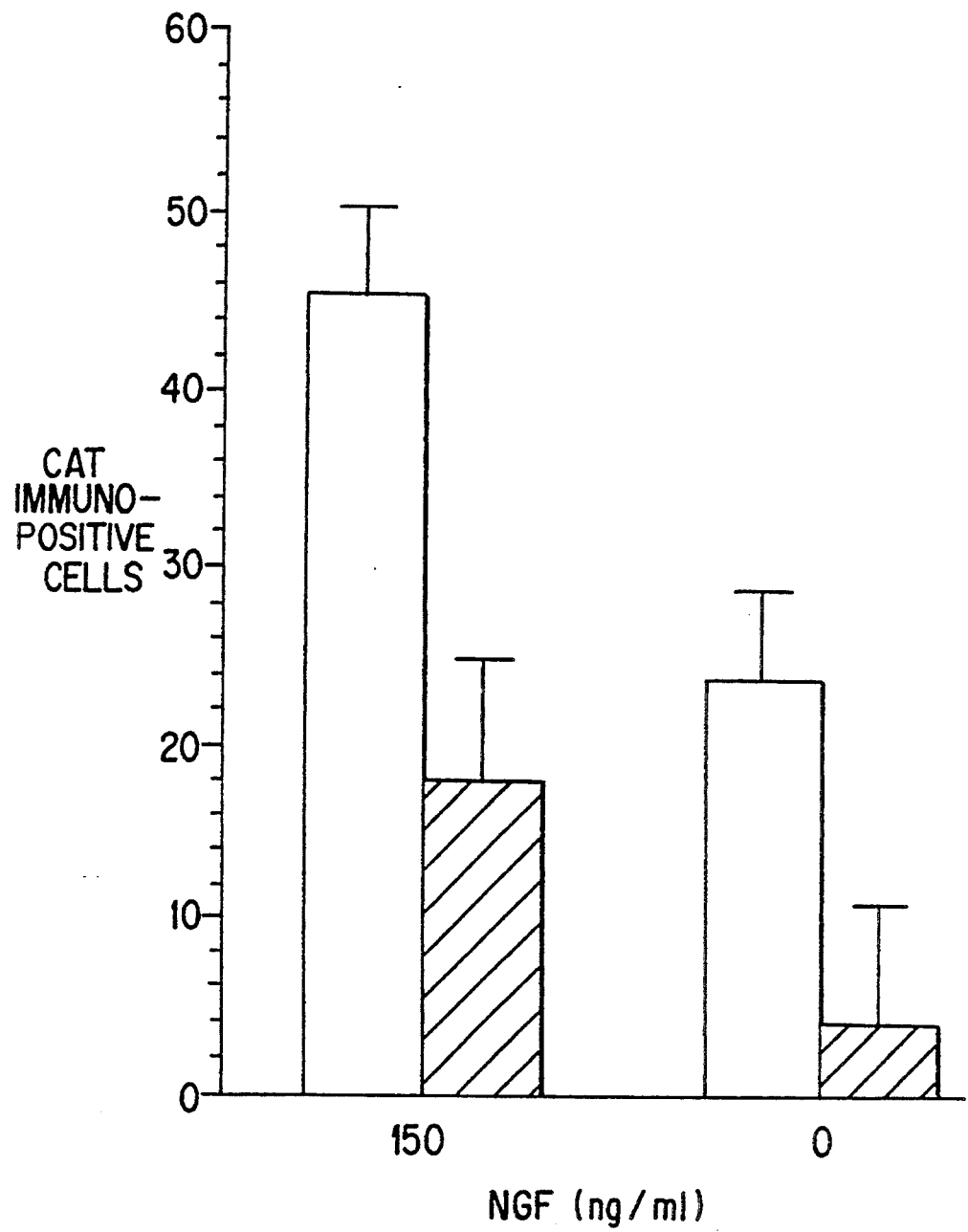

FIG. 9B. Forebrain cholinergic neuron cultures, at densities of 260,000 cells per well (black bar) or 150,000 cells per well (hatched bar), were treated with 150 ng/ml of NGF. The number of CAT immunopositive cells in NGF-treated versus untreated cells was compared.

Figure 10:
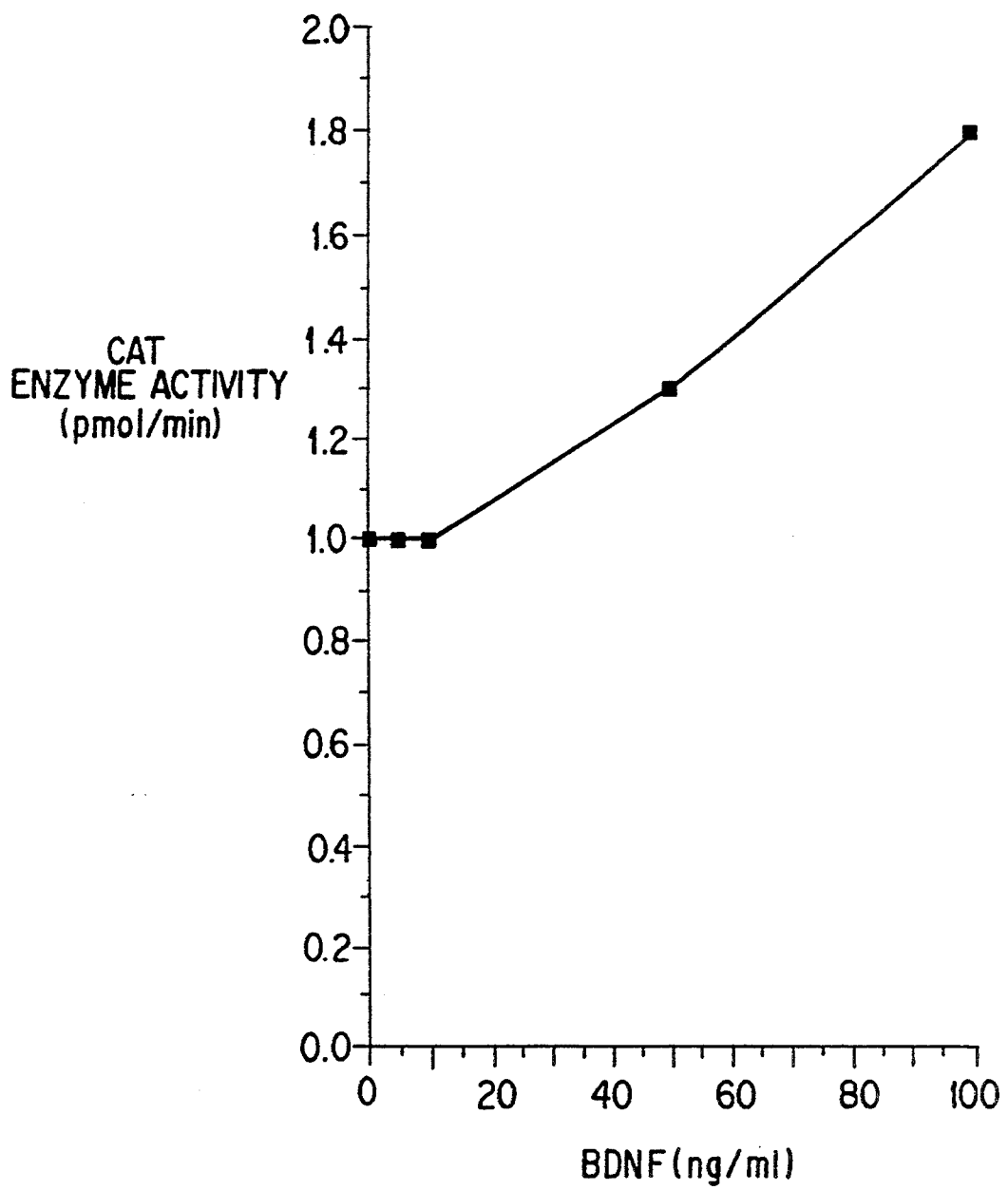

FIG. 10. Changes in the amount of CAT enzyme activity, in picomoles of substrate catalyzed per minute, as a function of BDNF concentration in forebrain cholinergic neuron cultures.

Figure 11A:
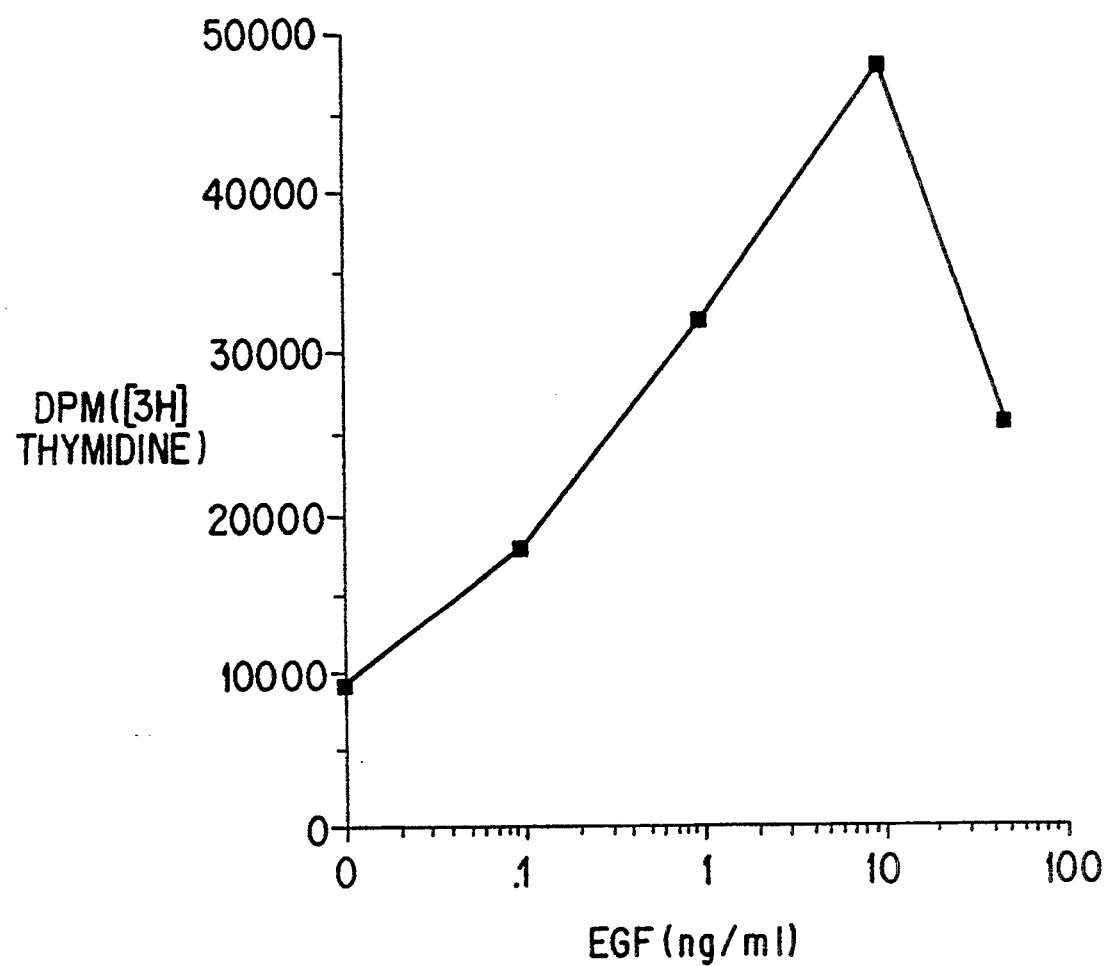

FIG. 11A. Astroglial cell cultures, at approximately 60% confluency, were treated with epidermal growth factor for 42 hours, then incubated with [$^3$H] methylthymidine. Amount of $^3$H incorporated was measured relative to EGF concentration.

Figure 11B:
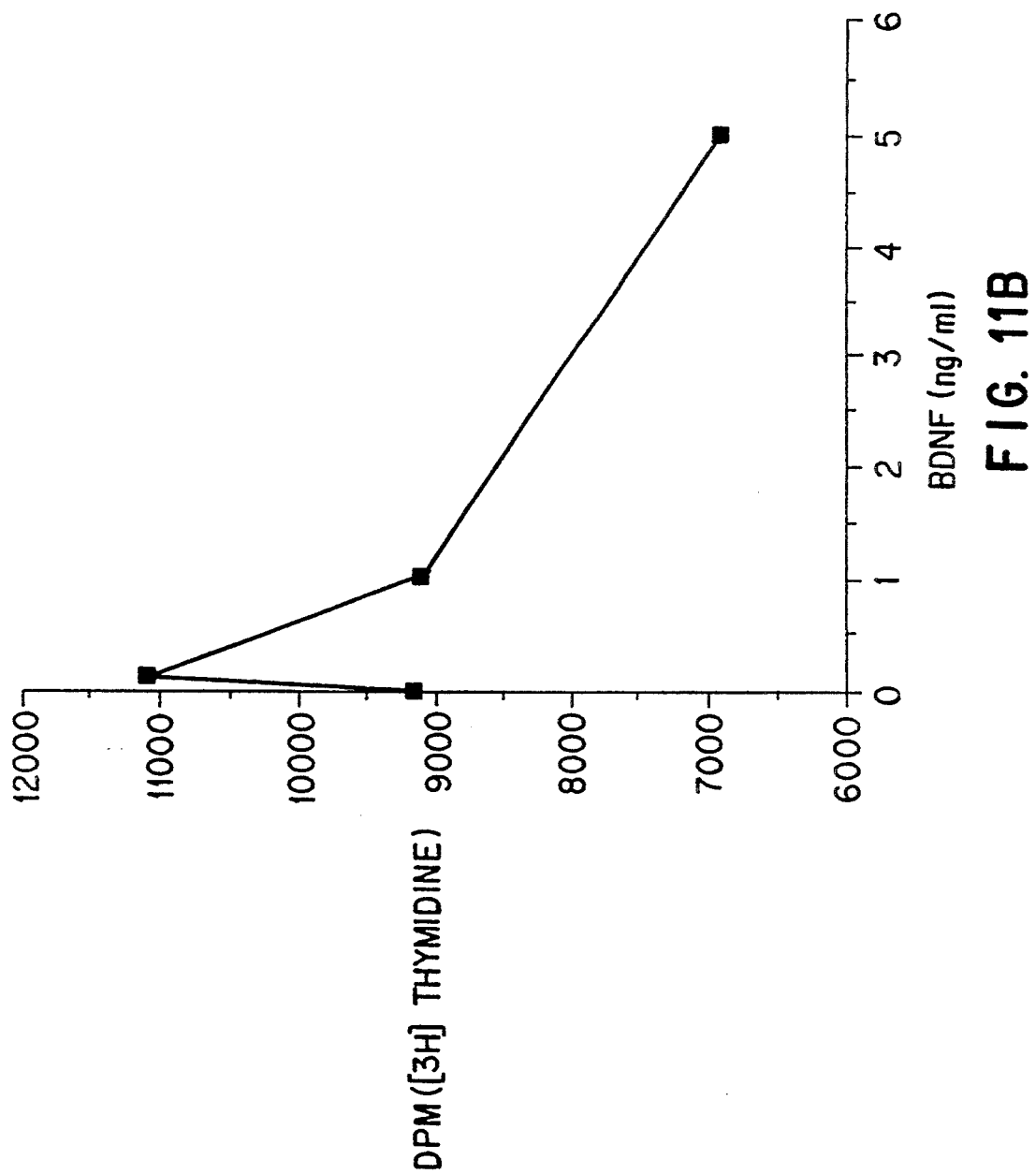

FIG. 11B. Astroglial cell cultures, at approximately 60% confluency, were treated with BDNF for 42 hours, then incubated with [$^3$H] methylthymidine. Amount of $^3$H incorporated was measured relative to BDNF concentration.

Figure 12:
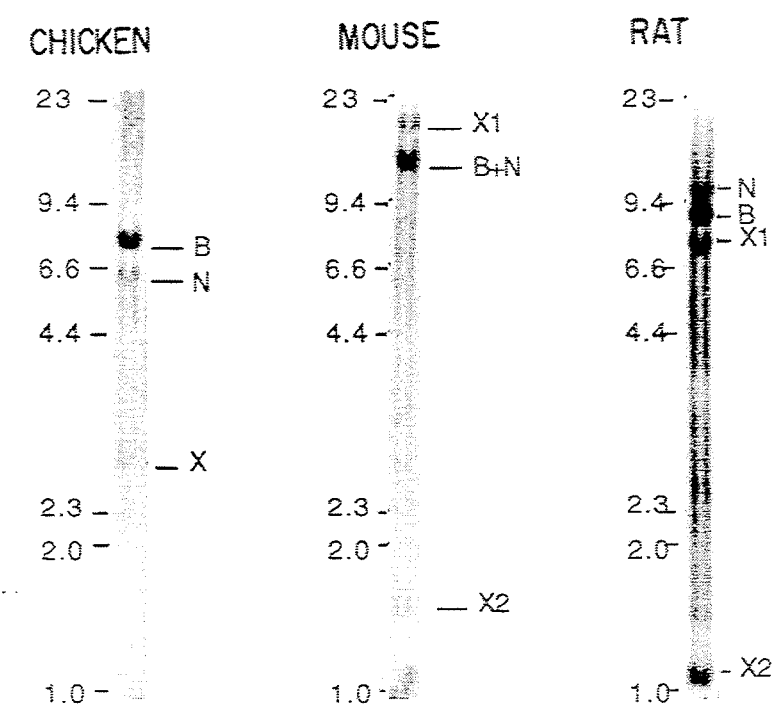

FIG. 12. Southern blot of EcoRI restricted chicken, mouse, rat, hybridized to BDNF/NGF probe R1B/2C. The positions of the NGF and BDNF genomic EcoRI fragments are indicated as N and B, respectively.

FIG. 13. Sequence comparison of NGF and BDNF with novel member of BDNF/NGF family identified by PCR from mouse DNA with Box 3/Box 4 primers: Novel gene [designated here as M3/4], also known as Neurotrophin-3 (NT-3), showing sequence of coding strand only, and deduced amino acid sequence aligned relative to mature mouse NGF and mature pig, rat, mouse, or human BDNF. Dashes indicate a position where a deletion of one codon in NGF is used to optimize alignment relative to BDNF and M3/4. Italics indicate matches in amino acid sequence and/or conservative amino acid substitutions.

Figure 14:
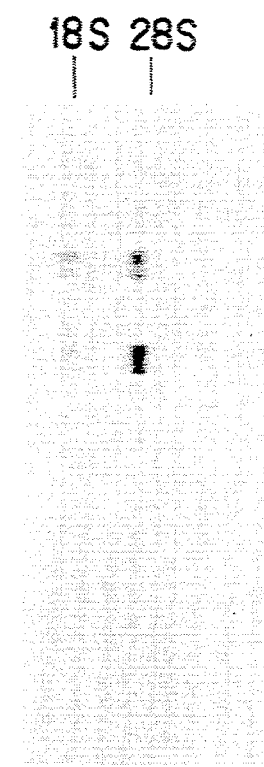

FIG. 14. Northern blots of RNA from a variety of human tumor-derived cell lines hybridized to BDNF human probe.

Figure 15A:
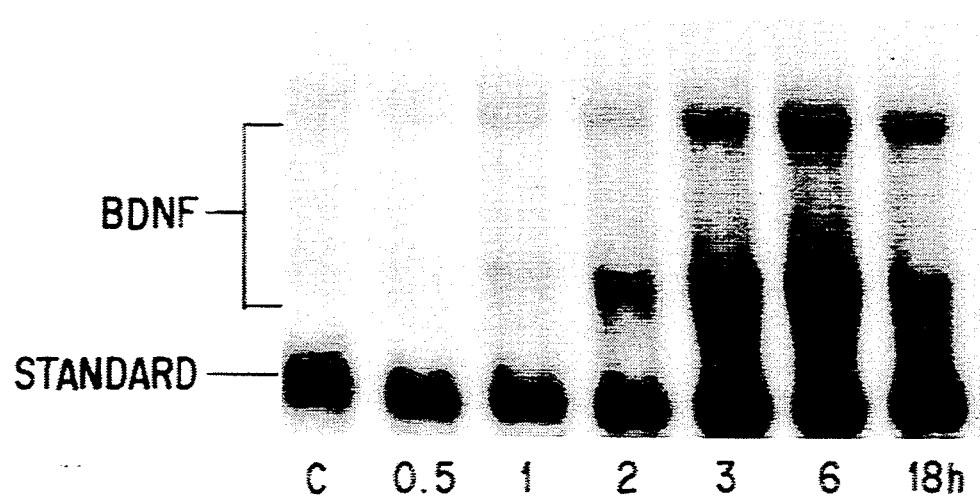

FIG. 15A. Effect of depolarization of BDNF-mRNA levels in hippocampal neurons: time-course of BDNF-mRNA expression in primary cultures of hippocampal neurons in the presence of 50 mM KCl. Total cellular RNA was extracted from $0.5 \times 10^6$ cells, glyoxylated and analyzed by electrophoresis on a 1.3% agarose gel (Biziere, K. and Coyle, T., Neurosci., 1978, Lett. 8:303; McGeer et al., 1978, Brain. Res. 139:381). RNA transferred to Hybond N filters was hybridized with a $^{32}$P-labelled cRNA probe (specific activity, $10^9$ cpm/µg) specific for mouse BDNF and produced by run-off transcription in vitro. The two upper bands (4 and 1.5 kB) correspond to BDNF-mRNA; the two bands for BDNF (4 kb and 1.5 kb) are RNAse A-resistant and represent two different transcripts which seem, however, to be regulated in a similar manner) and the lower (700 bp) to 10 pg of a short BDNF-mRNA recovery standard which was added to samples before extraction of RNA.

Figure 15B:
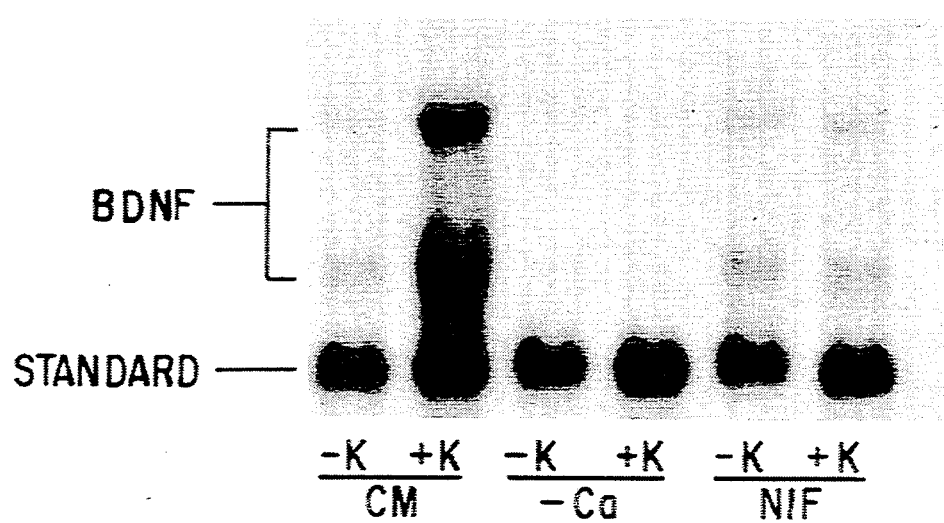

FIG. 15B. Effect of depolarization of BDNF-mRNA levels in hippocampal neurons: calcium dependency. Neurons were incubated for 3 hours in normal culture medium (CM), in a modified medium without calcium (−Ca) or in culture medium with 10M nifedipine (NIF). 50 mM KCl was added where indicated (+K).

Figure 17:
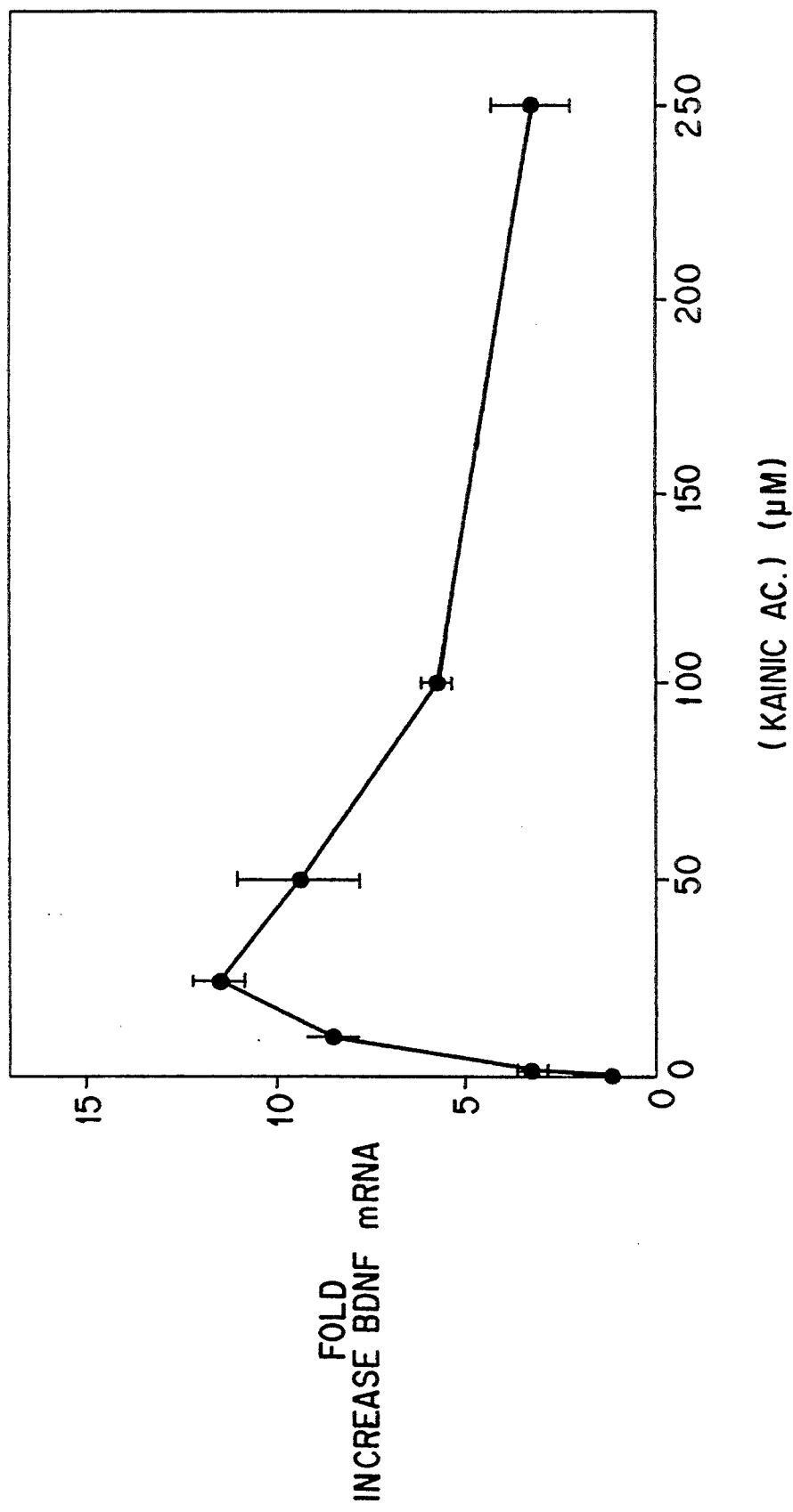

FIG. 17. Increases in NGF-mRNA levels in hippocampal neurons by potassium and kainic acid. Neurons were incubated for 3 hours in control medium (C) or in the presence of 50 mM KCl (K+) or 25 µM kainic acid (KA). RNA was extracted and the NGF-mRNA levels were determined by the quantitative PCR (11). The values are means±SEM (n=6).

FIG. 17. Dose-response curve for the kainic acid effect. Hippocampal neurons were incubated for 3 hours in the presence of various concentrations of kainic acid. RNA was extracted and analyzed as described in FIG. 15A. Values represent means±SEM of three experiments.

Figure 18A:
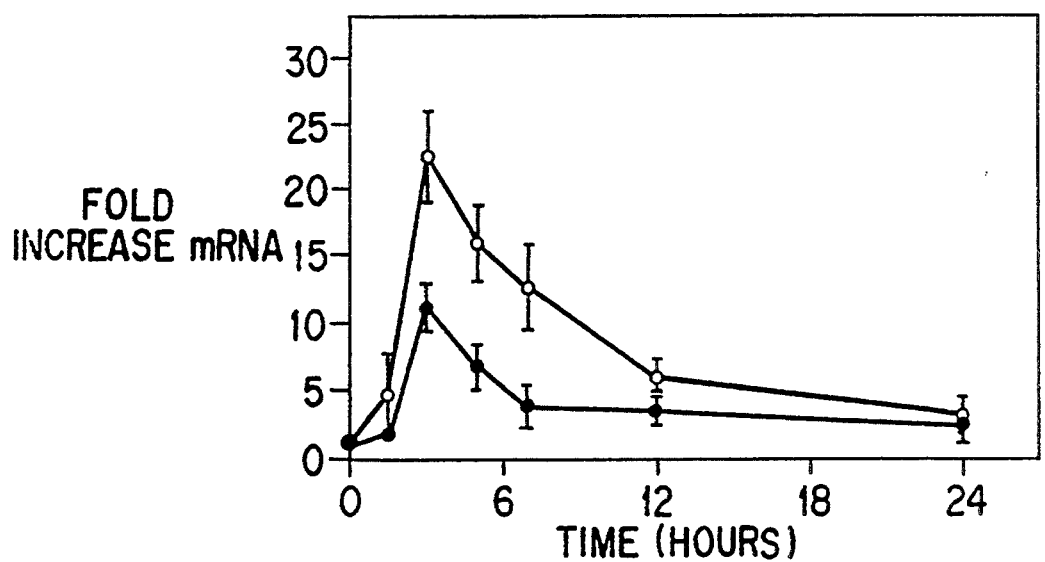

FIG. 18A. Time-course of increases in BDNF- and NGF-mRNA levels by kainic acid treatments. Total cellular RNA was extracted and analyzed as indicated in FIG. 15A from hippocampus at the indicated times (in hours) after intraperitoneal injection of kainic acid (12 mg/kg). One single dose of diazepam (10 mg/kg) was injected 90 minutes after kainic acid (the two bands for BDNF (4 kb and 1.5 kb) are RNAse A-resistant and represent two different transcripts which seem, however, to be regulated in a similar manner). Values corresponding to 1.5 Kb BDNF mRNA (○) and 1.3 Kb NGF-mRNA (○) are shown. Similar increases were observed for the 4 Kb BDNF-mRNA. Values given represent means±S.E.M. of three to four experiments.

Figure 18B:
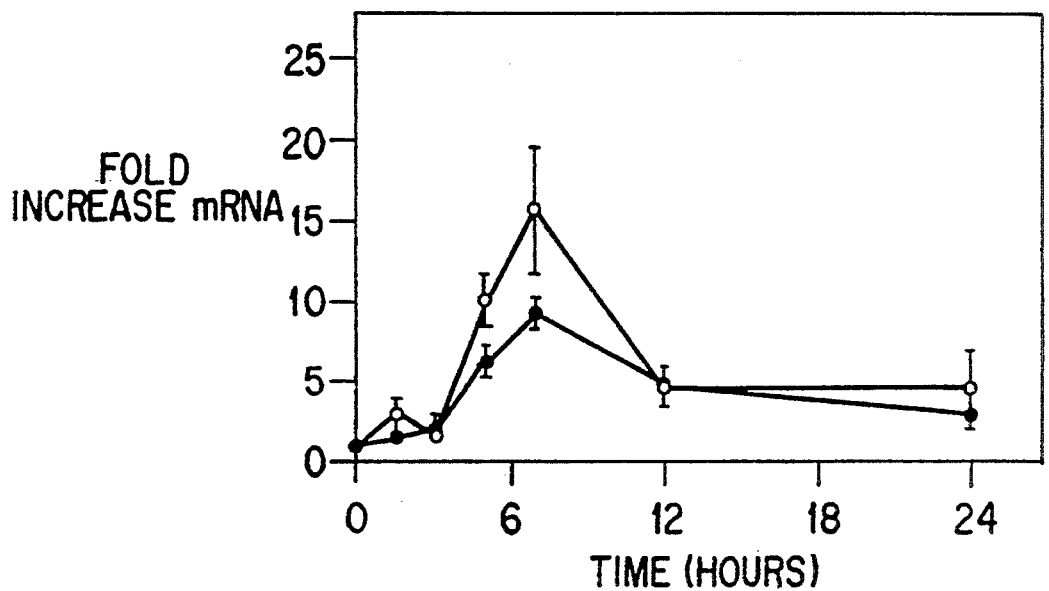

FIG. 18B. Time-course of increases in BDNF- and NGF-mRNA levels by kainic acid treatments. Total cellular RNA was extracted and analyzed as indicated in FIG. 16A from cortex at the indicated times.

Figure 19:
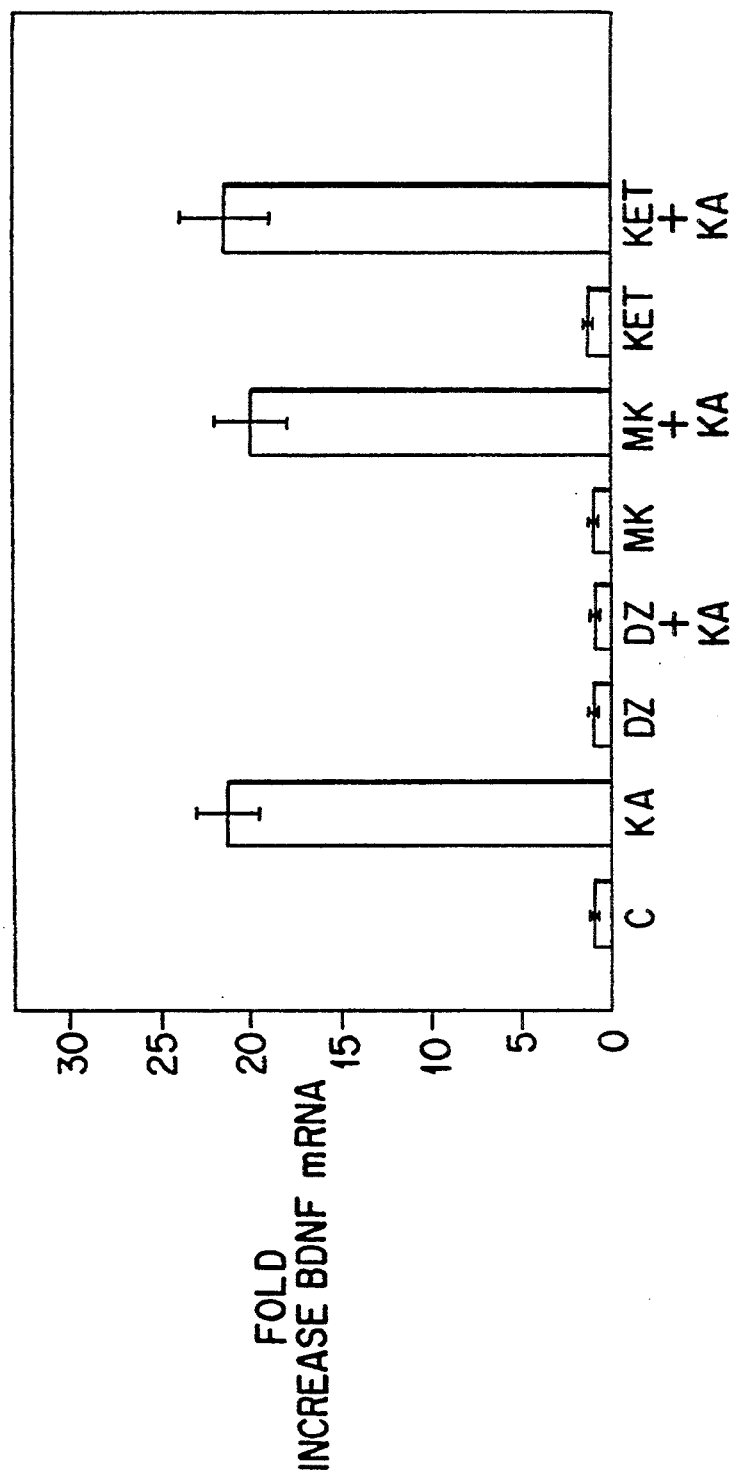

FIG. 19. Effect of anticonvulsants on the kainic acid-induced expression of BDNF-mRNA. Rats were injected intraperitoneally with diazepam (10 mg/kg) (DZ); MK-801 (1 mg/kg (MK) or Ketamine (20 mg/kg) (KET) 15 minutes before injection of kainic acid (12 mg/kg) (+KA) or saline (controls). Three hours later hippocampal tissue was used to prepare total RNA as indicated in FIG. 15A. Values represent means±SEM of three experiments.

Figure 20A:
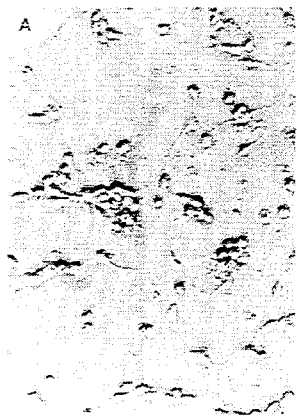

FIGS. 20A through 20I. Septal Cell Cultures. Phase-Contrast Micrograph of the Time Course of Cell Growth in Culture (FIGS. 20A through 20F). The cells were plated at a density of $1.3 \times (10^5)$ cells/cm$^2$ and maintained in 5 HS/NS as described in the text. The time points recorded were 1 (FIGS. 20A and 20B), 2 (FIGS. 20C and 20D), and 4 (FIGS. 20E and 20F) days. Cell type specific markers were used to identify populations of cells, AChE histochemically stained neurons (FIGS. 20G and 20H) and NGF-receptor immunopositive neurons (FIG. 20I). Scale bar=25 μm.

Figure 21A:
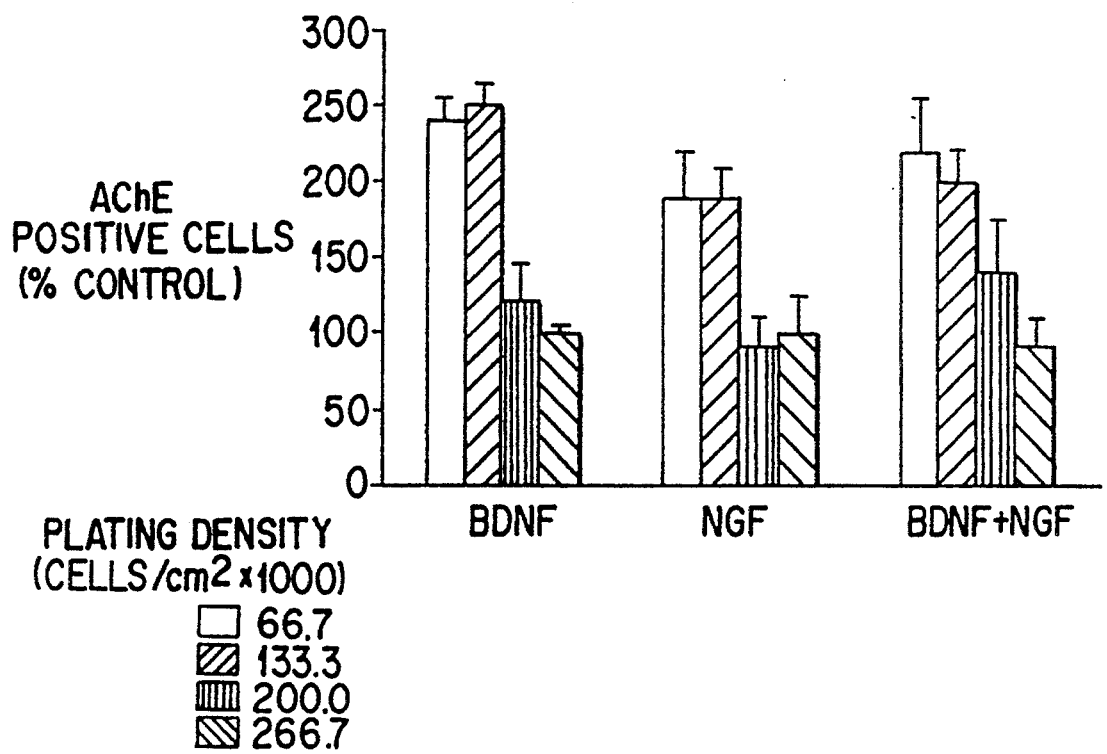

FIG. 21A. Comparison of the response of dissociated septal cells to BDNF or NGF treatment on the basis of AChE cell numbers: comparison of the response to BDNF (25 ng/ml), NGF (50 ng/ml) or the combination of both ligands at different plating densities.

Figure 21B:
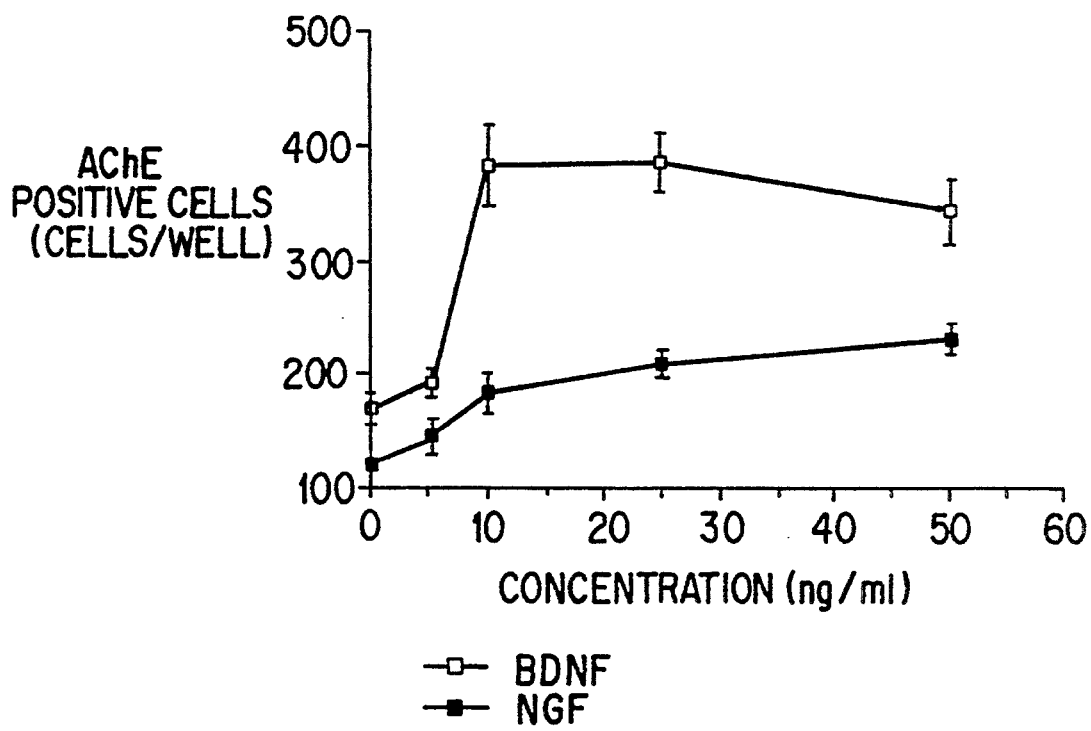

FIG. 21B. Comparison of the response of dissociated septal cells to BDNF or NGF treatment on the basis of AChE cell numbers: comparison of the response of cholinergic neurons to a range of BDNF or NGF concentrations (0–50 ng/ml). The cells for these results were grown for a period of 11–12 days in serum-containing medium. The data points represent the mean±S.E.M. of 6–9 determinations.

Figure 22:
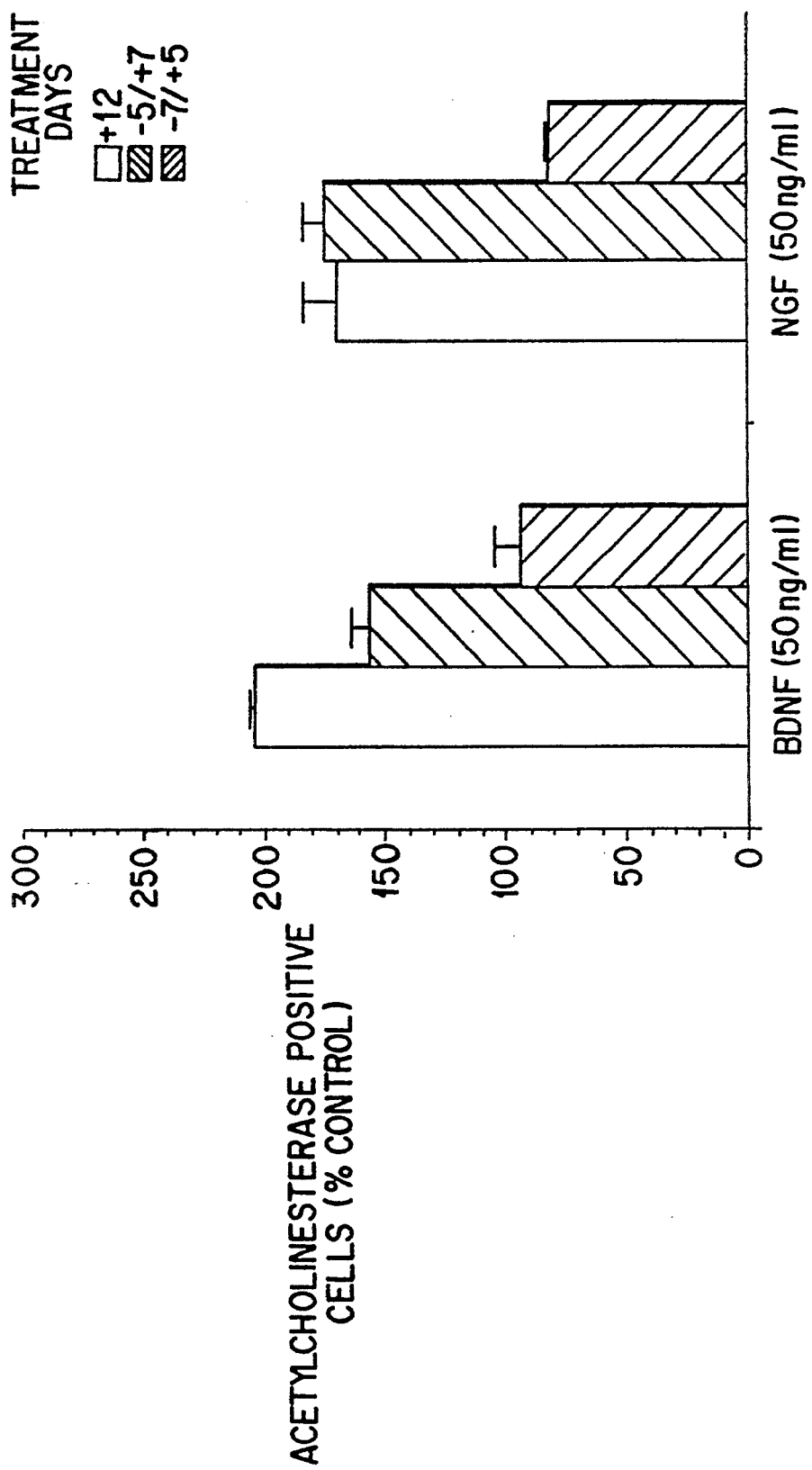

FIG. 22. Bar Graph Depicts the Effect of Delaying the Addition of BDNF or NGF to Dissociated Septal Cultures. BDNF (50 ng/ml) or NGF (50 ng/ml) was added to dissociated cell cultures following a delay of 5–6 hours (+12), 5 days (−5/+7) or 7 days (−7/+5). The cultures were maintained for 12 days. Cells were scored on the basis of AChE positive histochemical staining. The results are expressed as the mean±S.E.M. of 4 to 5 determinations.

Figure 23:
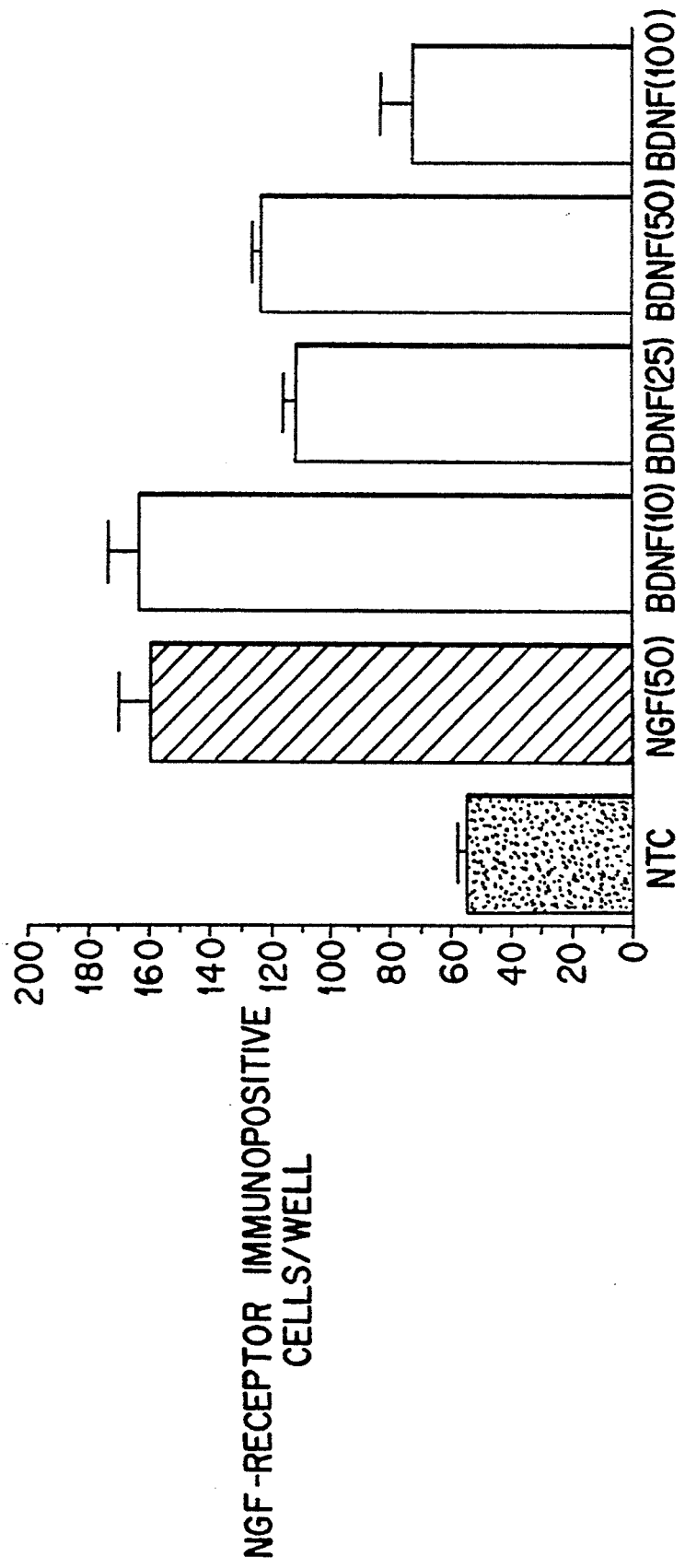

FIG. 23. Bar Graph Depicting the Ability of BDNF or NGF to Regulate the Numbers of NGF-Receptor Immunopositive Cells. The immunoslating for the NGF-receptor was conducted utilizing the monoclonal antibody 192-IgG at a dilution of 1:1000. The dissociated septal cells were plated at a density of $13 \times (10^5)$ cells/cm$^2$, and treated continuously for a period of 12 days. A comparison is made between a saturating dose of NGF and a range of doses of BDNF (0–100 ng/ml). The results depicted are the mean±S.E.M. of an n of 4.

Figure 24A:
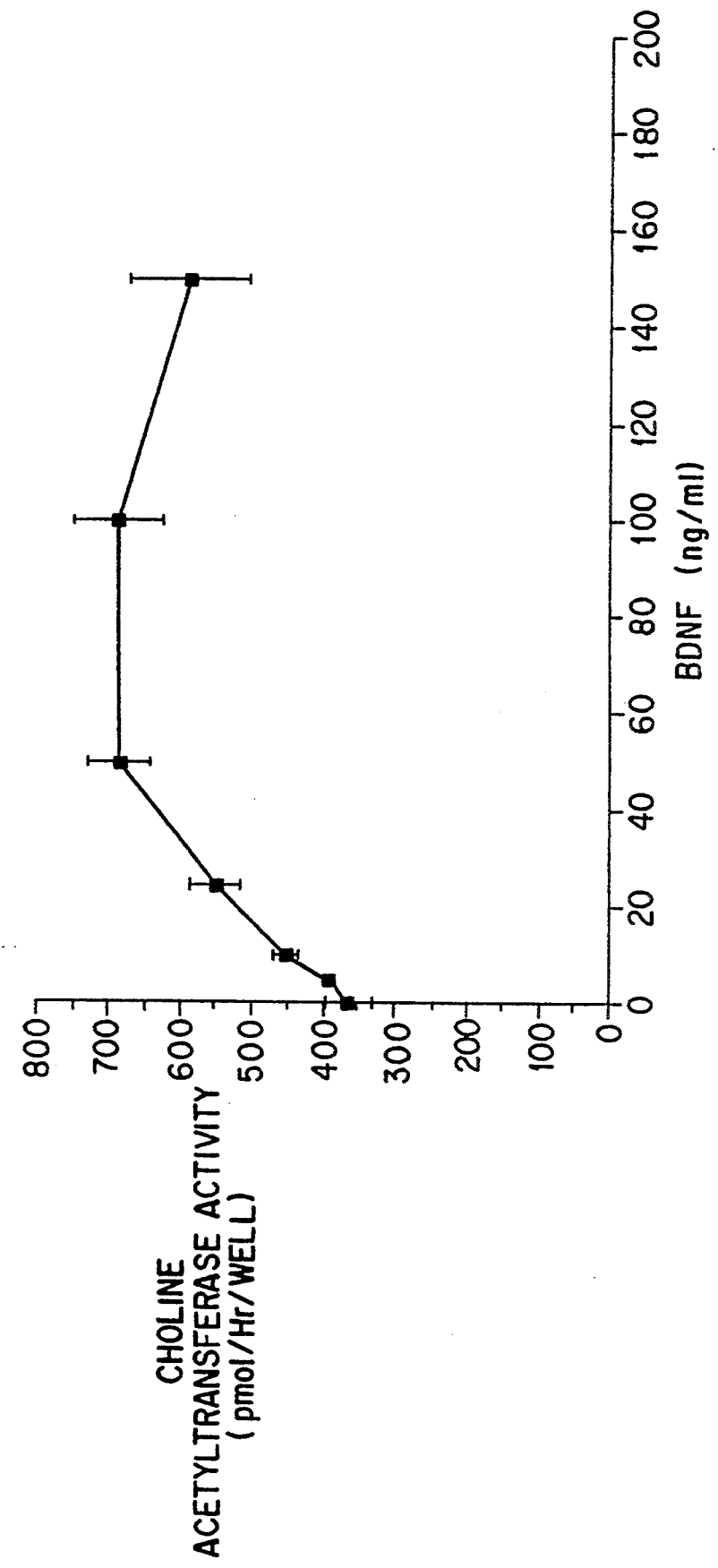

FIG. 24A. Dose Response Curve of Septal Cholinergic Neurons to CAT Inducing Activities of BDNF. Cultures were plated on polyornithine and laminin-coated 6 mm wells and maintained for 12 days in 5 HS/N3. The cells were exposed to BDNF 5–6 hours after plating. The BDNF was replaced every 3 days when the medium was changed. The results shown represent the mean±S.E.M. of an n of 5–6 determinations.

Figure 24B:
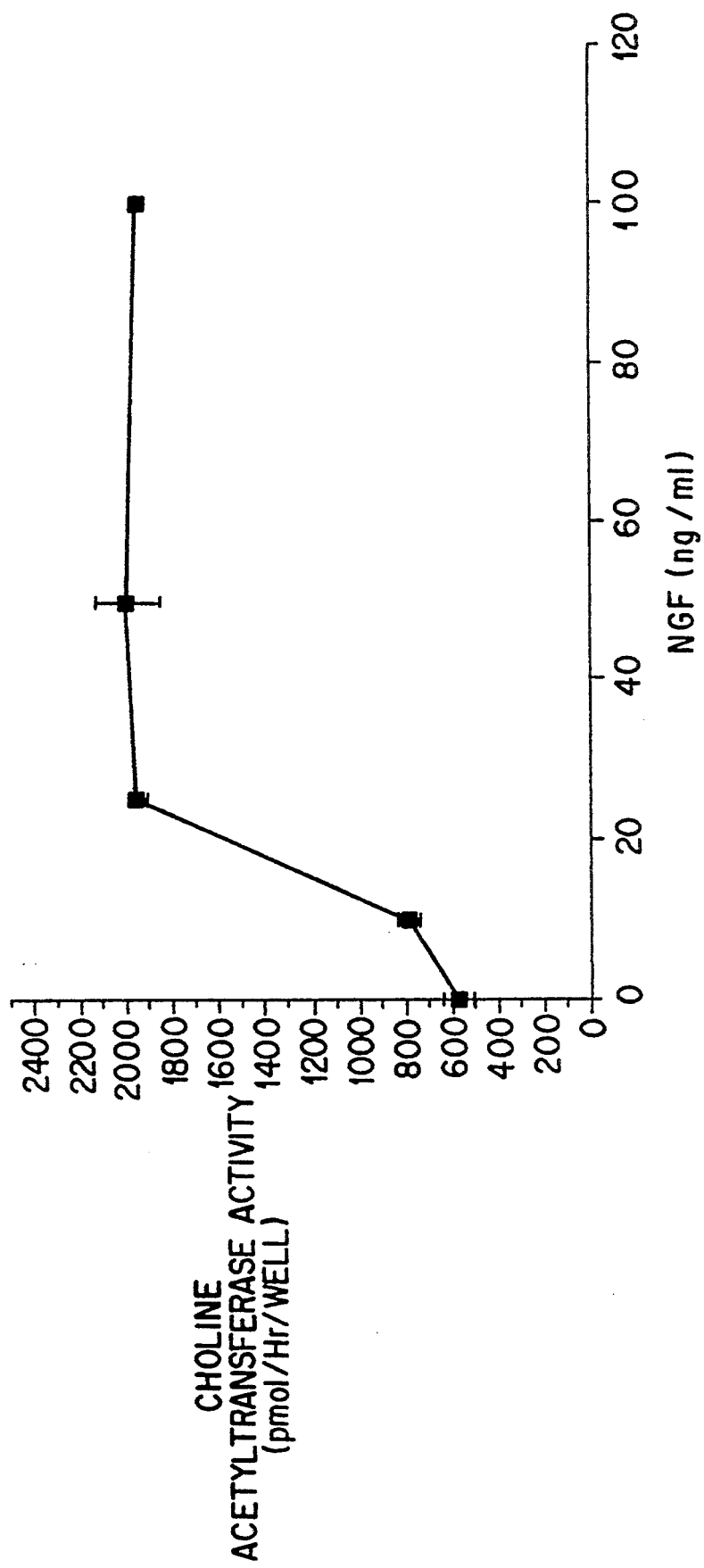

FIG. 24B. Dose Response Curve of Septal Cholinergic Neurons to CAT Inducing Activities of NGF. Cultures were plated on polyornithine and laminin-coated 6 mm wells and maintained for 12 days in 5 HS/N3. The cells were exposed to NGF 5–6 hours after plating. The NGF was replaced every 3 days when the medium was changed. The results shown represent the mean±S.E.M. of an n of 5–6 determinations.

Figure 25:
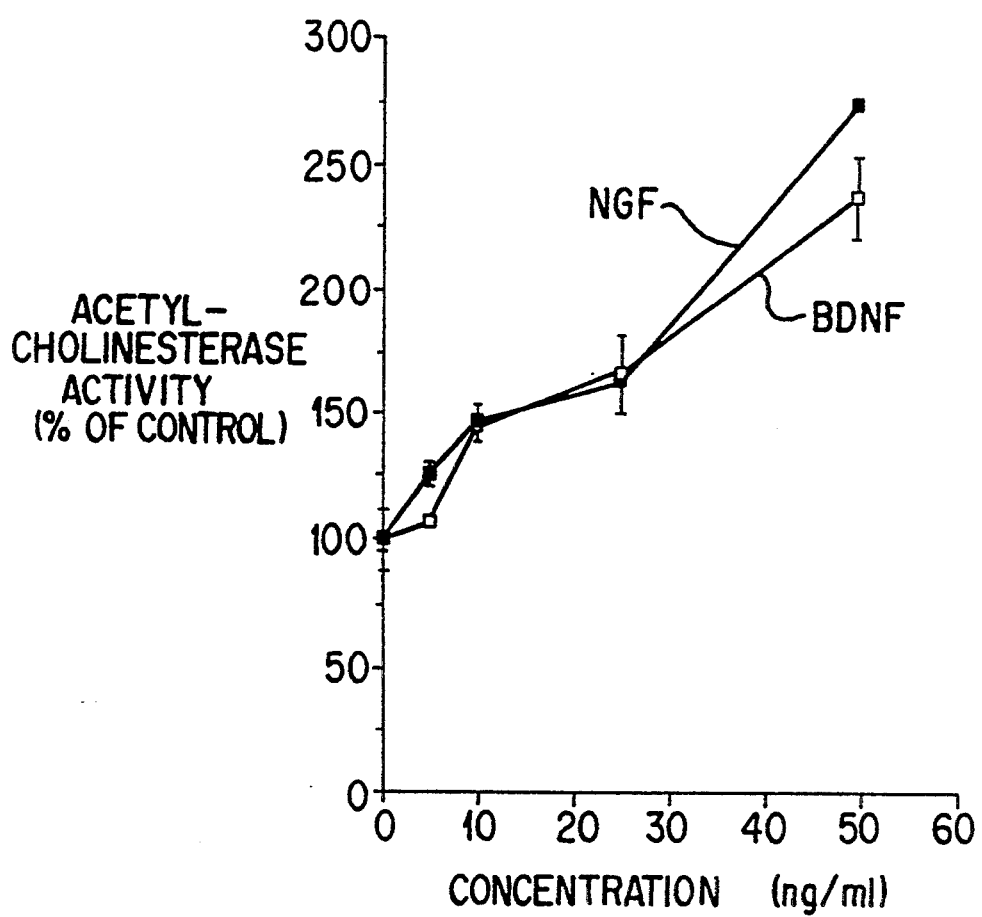

FIG. 25. Dose Response Effect of BDNF and NGF on AChE Enzyme Activity. Rat septal cholinergic neurons were grown for 12 days in serum-containing medium with hormonal supplements. The cells were treated with BDNF (open squares) and NGF (solid squares) as described for FIGS. 24A and 24B. The results are the mean±S.E.M. of an n of 6–9. The AChE activity in the non-treated cultures was 16.4±2 nmol/Hr/Well.

Figure 26:
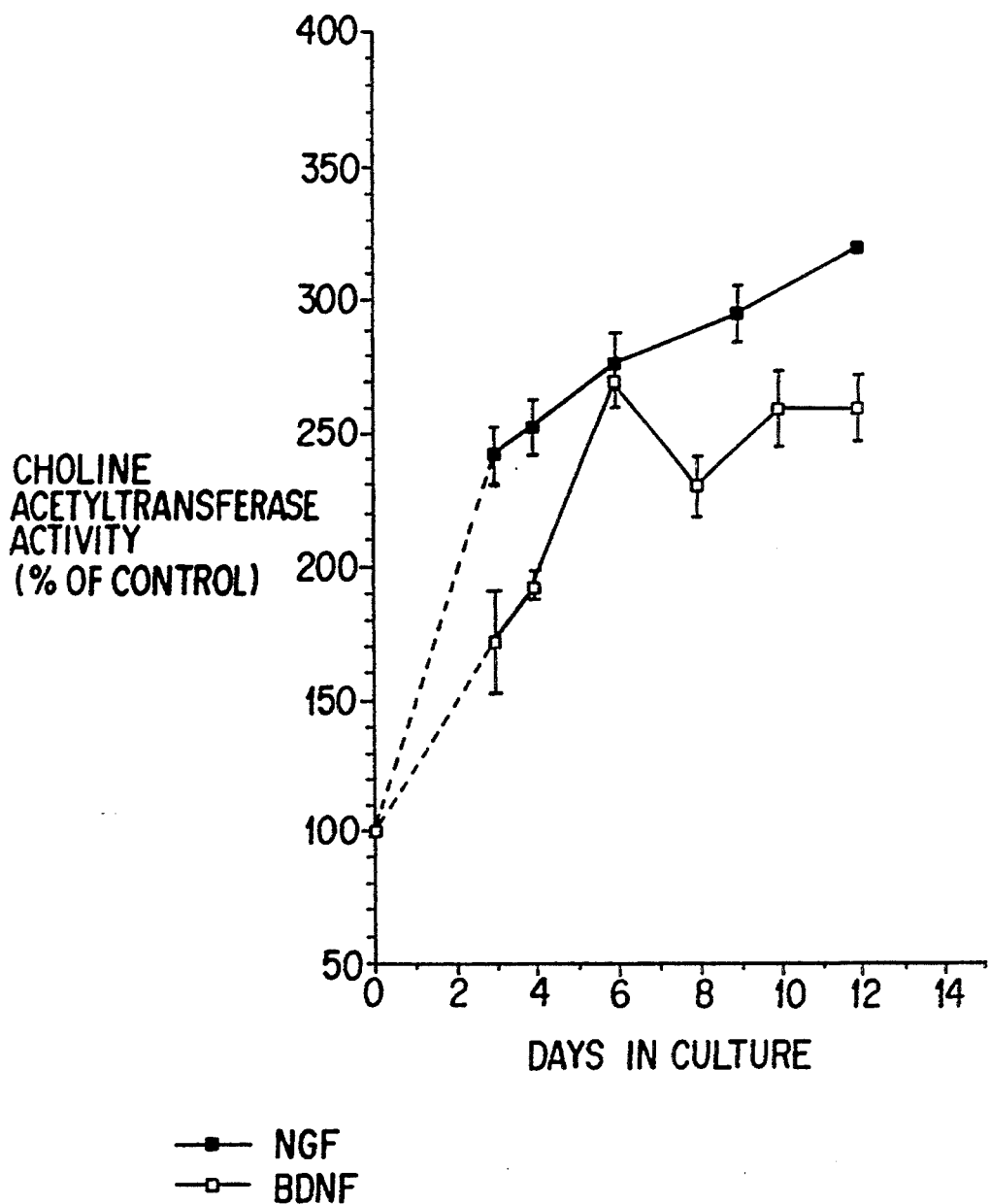

FIG. 26. Time Course of the Increase in CAT Enzyme Activity Induced by BDNF as Compared to NGF. The time requirement for the stimulation of CAT activity was conducted on cells plated at a density of $2.3 \times (10^5)$ cells/cm$^2$ and grown for varying lengths of time in serum-containing medium with hormonal supplements and exogenous factors. The cells were initially exposed to BDNF (open squares) or NGF (solid squares) 5–6 hours after plating. The results represent the percent of the activity determined in the treated cultures versus the non-treated cultures (n=6, BDNF 12 days n=3).

Figure 27:
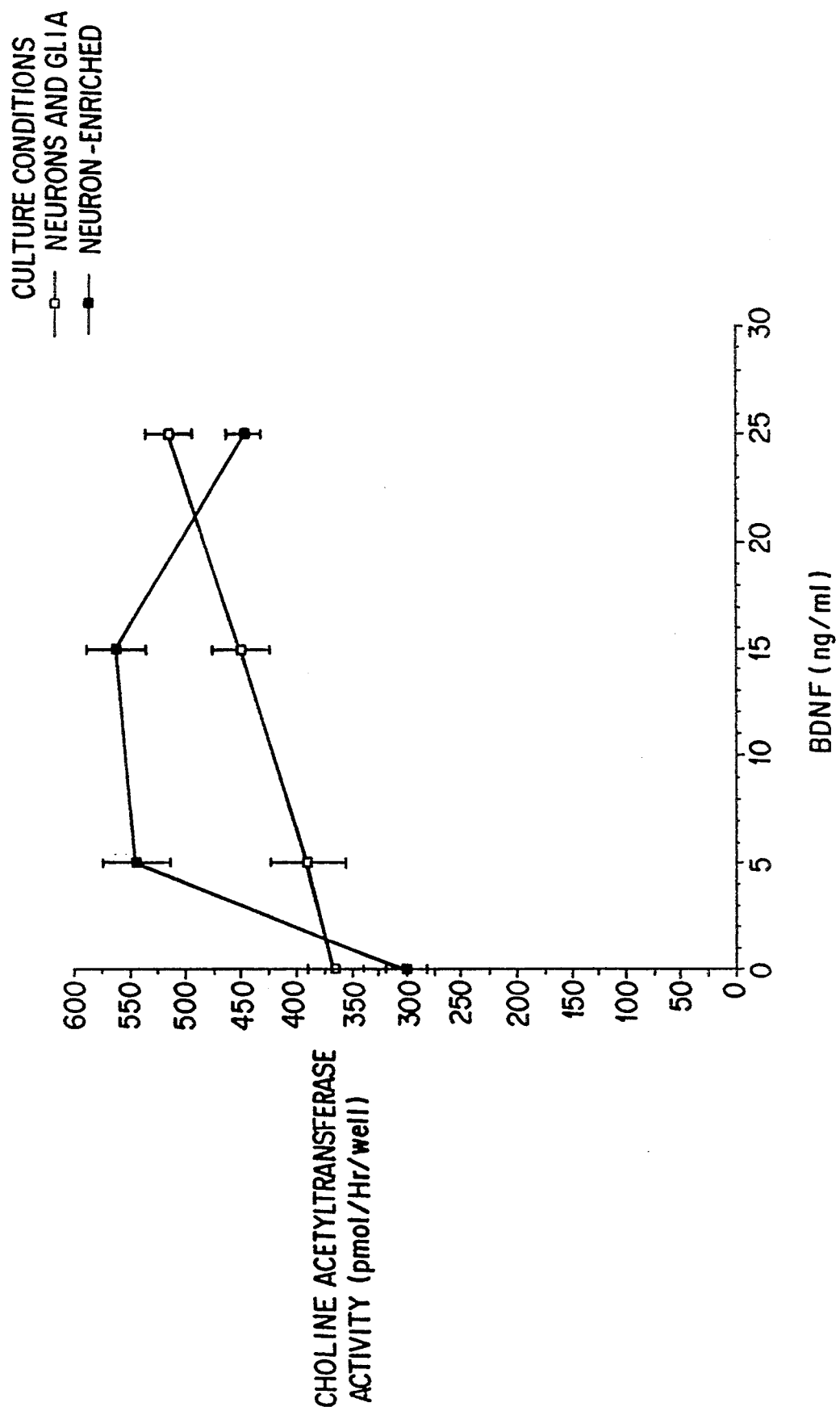

FIG. 27. Comparison of the Effects of Glial Cells on the Ability of BDNF to Induce CAT Enzyme Activity. Septal cells were plated at a density of $2.3 \times (10^5)$ cells/cm$^2$. Following a plating period of 5–6 hours, the medium was changed to either serum-free or a serum-containing medium both supplemented with 1% N3 as detailed in the text. Cytosine arabinoside (1 uM) was added for 24 hours in order to further reduce the numbers of astrocytes. The cultures were then maintained for 12 clays. The results represent the mean±S.E.M. of 4 determinations.

Figure 28:
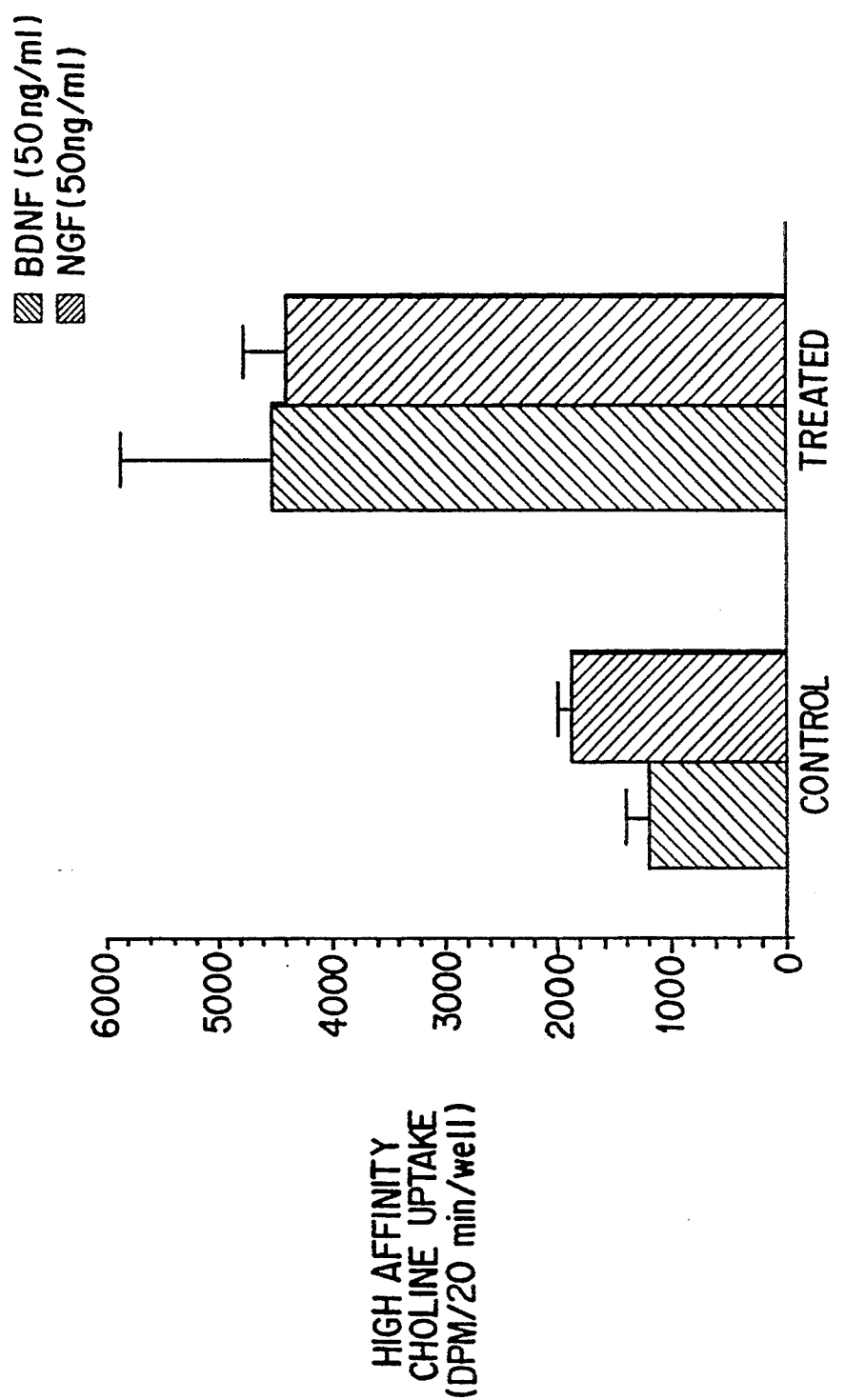

FIG. 28. Bar Graph Depicts the Effect of BDNF or NGF Treatment on the Level of High-Affinity Choline Uptake. The choline uptake was conducted on cells maintained for 11 days, following plating at a density of $1.3 \times (10^5)$ cells/cm$^2$. BDNF (50 ng/ml) or NGF (50 ng/ml) were present during the entire culture period. The data points represent the mean±S.E.M. of 5 determinations for BDNF and 10 for NGF.

Figure 29:
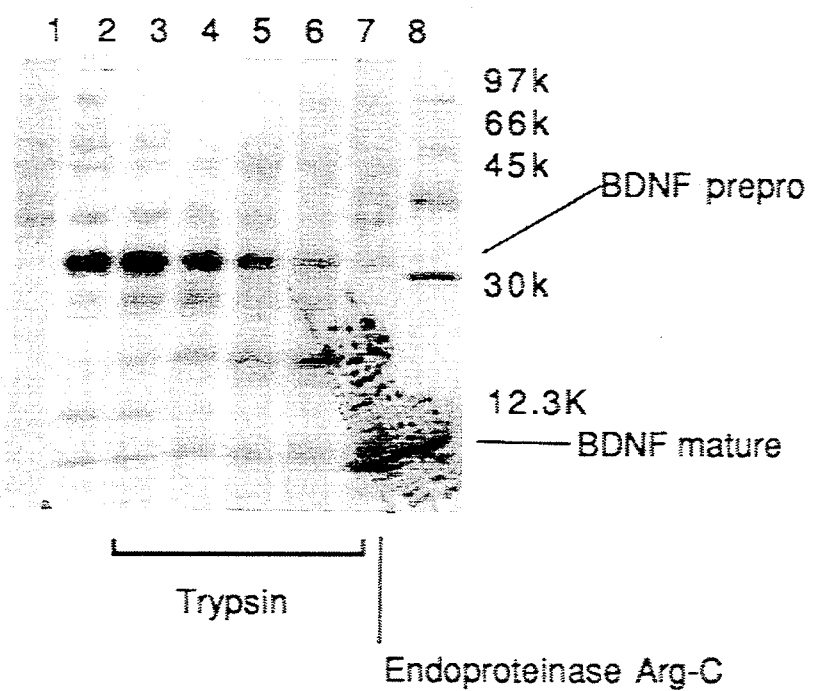

FIG. 29. Resolution by SDS-PAGE of $^{35}$S-labeled reaction products from the enzymatic cleavage of human brain-derived neurotrophic factor by trypsin and endoproteinase Arg-C.

Figure 30:
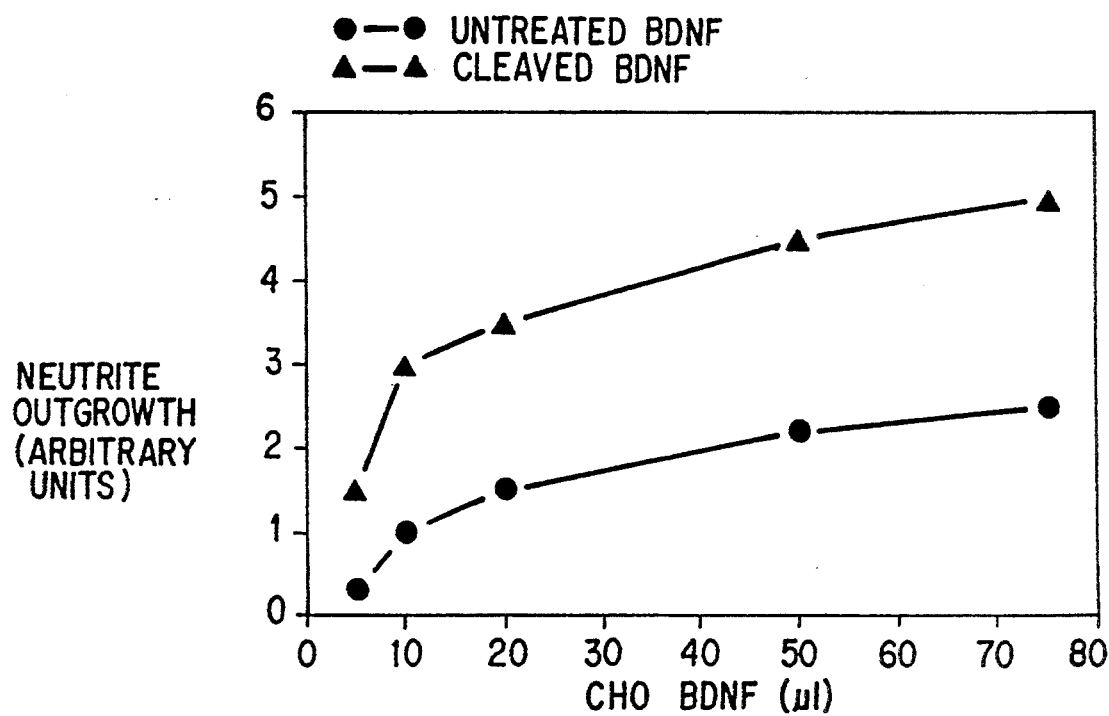

FIG. 30. Graphic representation of the DRG bioassay comparing untreated CHO-hBDNF with endoproteinase-cleaved CHO-hBDNF. Neurite outgrowth is scored between 0 and 5 with a score of 5 representing maximal bioactivity.

FIGS. 31A through 31C. Phase-contrast (FIG. 31A) and bright-field (FIGS. 31B and 31C) photomicrographs of dissociated cultures of E14 rat ventral mesencephalic cells stained after 9 days in culture with monoclonal antibodies to tyrosine hydroxylase (TH). Phase-contrast (FIG. 31A) and bright-field (FIG. 31B) photographs of the same field show the low abundance of TH+ neurons in these cultures. Only a single TH+ neuron (arrows) is seen in a field containing many phase-bright neurons with long neurites. Few nonneuronal cells are evident, by morphology or by staining for GFAP (not shown). Bright field photograph (FIG. 31C) showing two TH+ neurons (small arrows) in a field containing about ~98 phase bright cells of neuronal morphology. Scale bar=100 1M.

FIGS. 32A through 32C. Each of FIGS. 32A, 32B and 32C present high magnification photomicrographs of different views of 6 day culture of E14 rat ventral mesencephalic cells showing varied morphologies of TH+ neurons, some with extensive neuritic growth and extremely elaborate growth cones (FIGS. 32A and 32B). Cultures were established and stained as described in legend to FIGS. 31A through 31C. Scale bar=25

μM. FIG. 33A. BDNF promotes survival of TH+, dopaminergic mesencephalic neurons in culture in dose-dependent manner, evident at culture period longer than 3 days: comparison of the number of TH+ neurons in cultures of E14 rat ventral mesencephalon maintained with (solid bars) or without BDNF (open bars). In treated cultures, BDNF (50 ng/ml) was added once on culture day 2. No difference between control and treated cultures was observed at day 3, but the number of TH+ neurons in BDNF treated cultures was 1.8-fold higher than controls at day 8. Values are the average of duplicate samples.

Figure 33C:
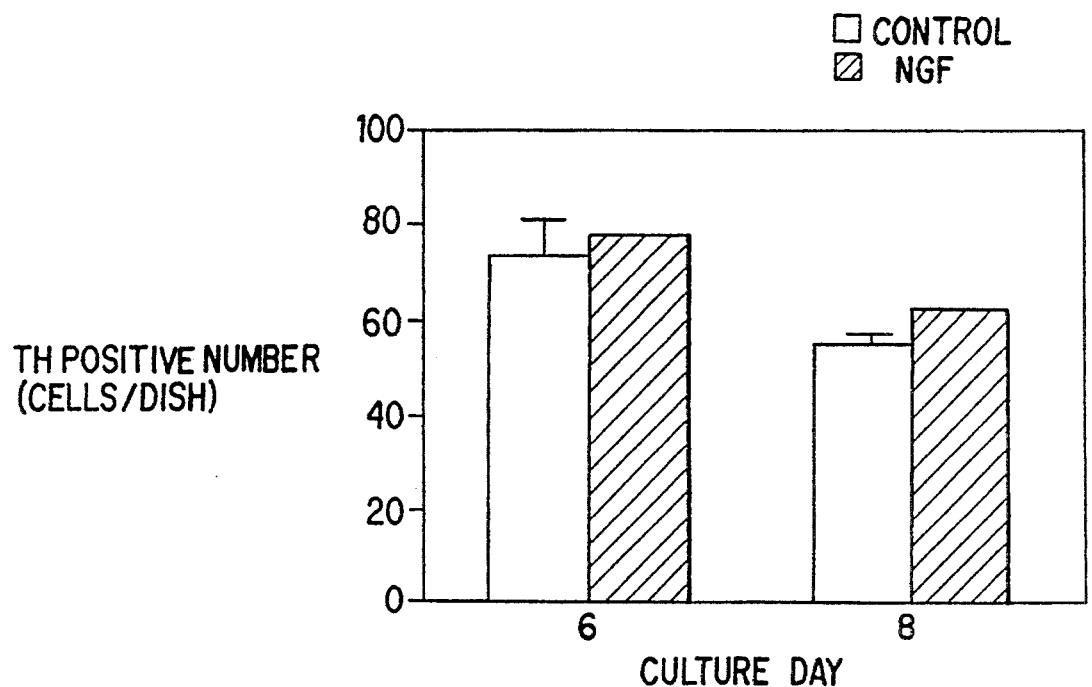
Figure 33A:
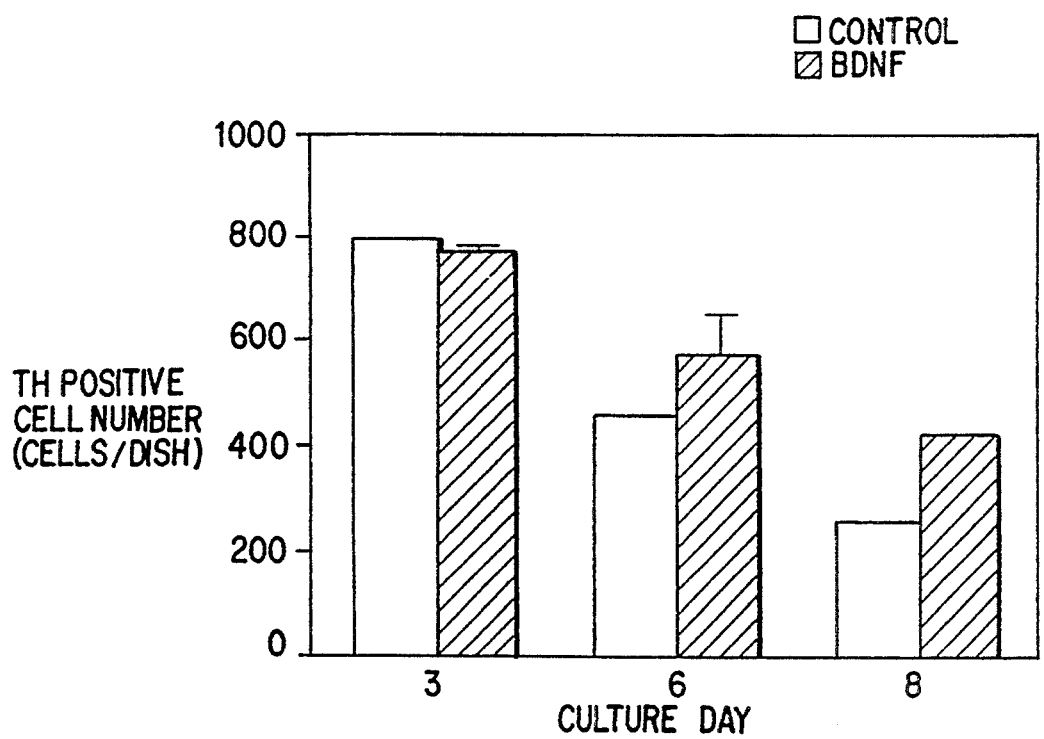
Figure 33B:
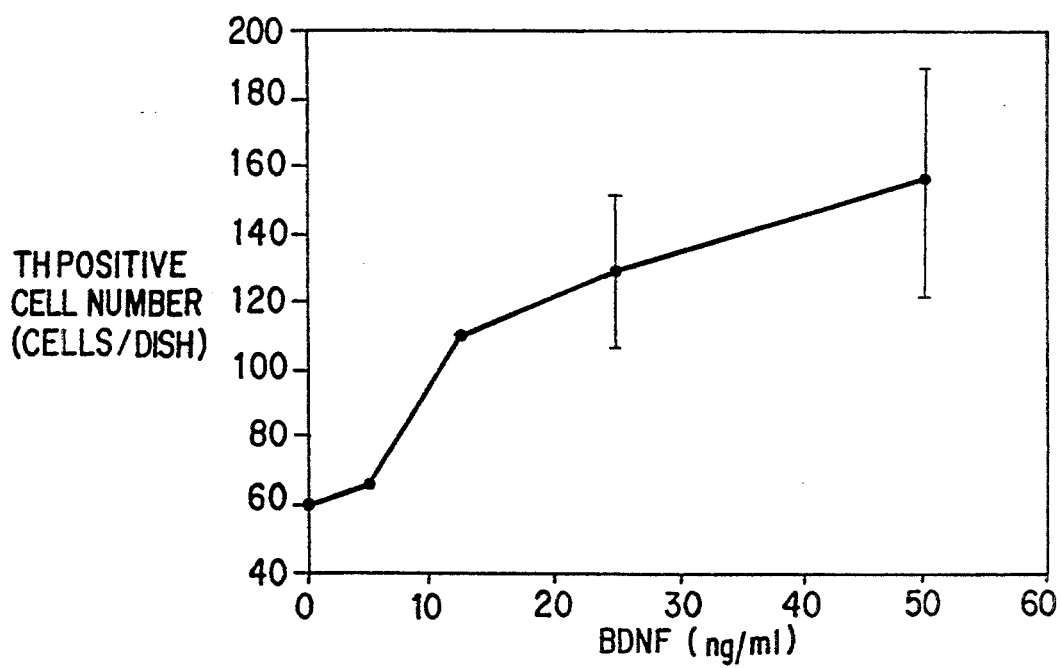

FIG. 33B. BDNF promotes survival of TH+, dopaminergic mesencephalic neurons in culture in dose-dependent manner, evident at culture periods longer than 3 days: effect of BDNF on increasing survival of TH+ neurons is dose-dependent. The number of TH+ neurons was determined in duplicate cultures after 8 days in culture in the absence of BDNF or medium containing increasing concentrations of BDNF added at day 2.

FIG. 33C. NGF has no effect on the survival of TH+ neurons.

Figure 34:
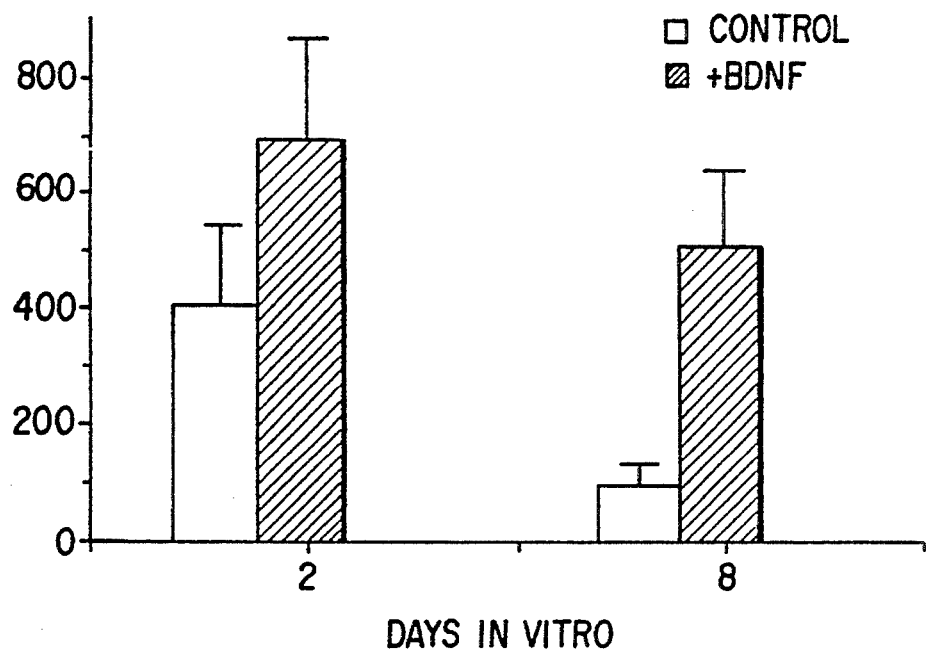

FIG. 34. Repeated doses of BDNF further increase the survival of TH+ neurons when compared to a single addition of BDNF at day 2. Cultures were prepared as described in the text. Recombinant human BDNF was purified from the supernatant of COS M5 cells. Cultures were treated either with a single addition (SA; stipled bars) of BDNF (50 ng/ml) on day 2, or with repeated doses of BDNF (50 ng/ml) on days 1, 2, 4, 6 and 8 (MA-multiple additions; solid bars), or were grown without BDNF (control; open bars). At the times indicated cultures were fixed and stained for TH immunoreactivity. Replenishing BDNF by multiple additions resulted in a 2.7 fold higher number of TH+ neurons at day 11 compared to controls, whereas the maximum increase seen with a single addition of BDNF was a little less than 2-fold after 11 days. Results, typical of several experiments, are the average of duplicate samples.

Figure 35:
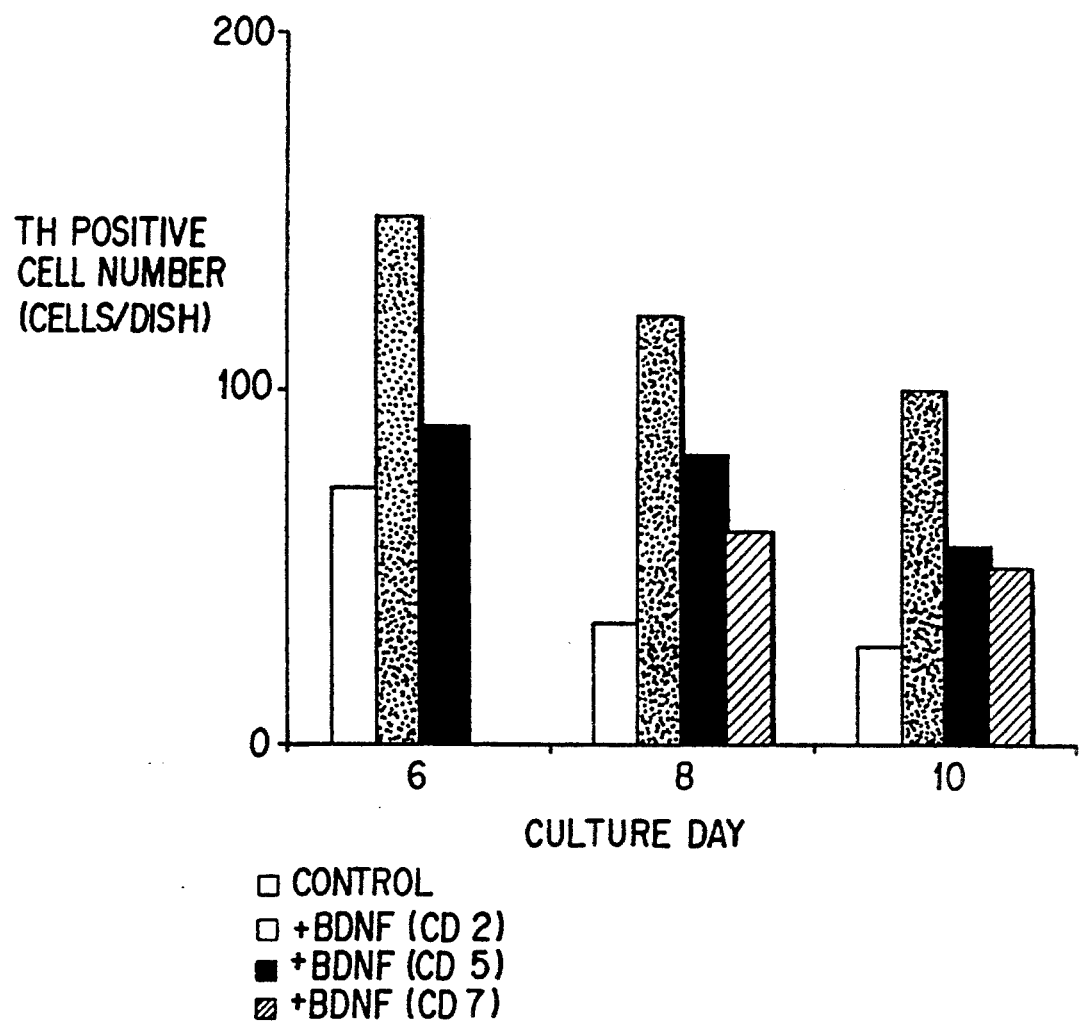

FIG. 35. Delayed addition of BDNF does not increase the number of TH+ neurons to the same extent as seen when BDNF is added at day 2. Cultures were prepared as described in the text, with the exception of the time of addition of exogenous BDNF. All cultures were switched to serum-free medium at day 2, and BDNF (50 ng/ml, pig brain BDNF) was added as a single addition either at day 2, day 5 or day 7 (CD2, CD5, CD7). At culture days six, eight and ten, the number of TH+ neurons was determined in duplicate cultures. In this experiment, a single addition of BDNF at day 2 resulted in a 3-fold higher number of TH+ neurons at day 10. When BDNF was added after a delay, at day 5, an increase in TH+ neurons over controls was seen at day 10, but was less than 2-fold, and this difference in TH+cell number between treated and control cultures did not increase further with longer time in culture. Control, open bars; BDNF addition at day 2, stippled bars; BDNF added at day 5, solid bar; BDNF added at day 7, diagonal-hatched bars.

Figure 36:
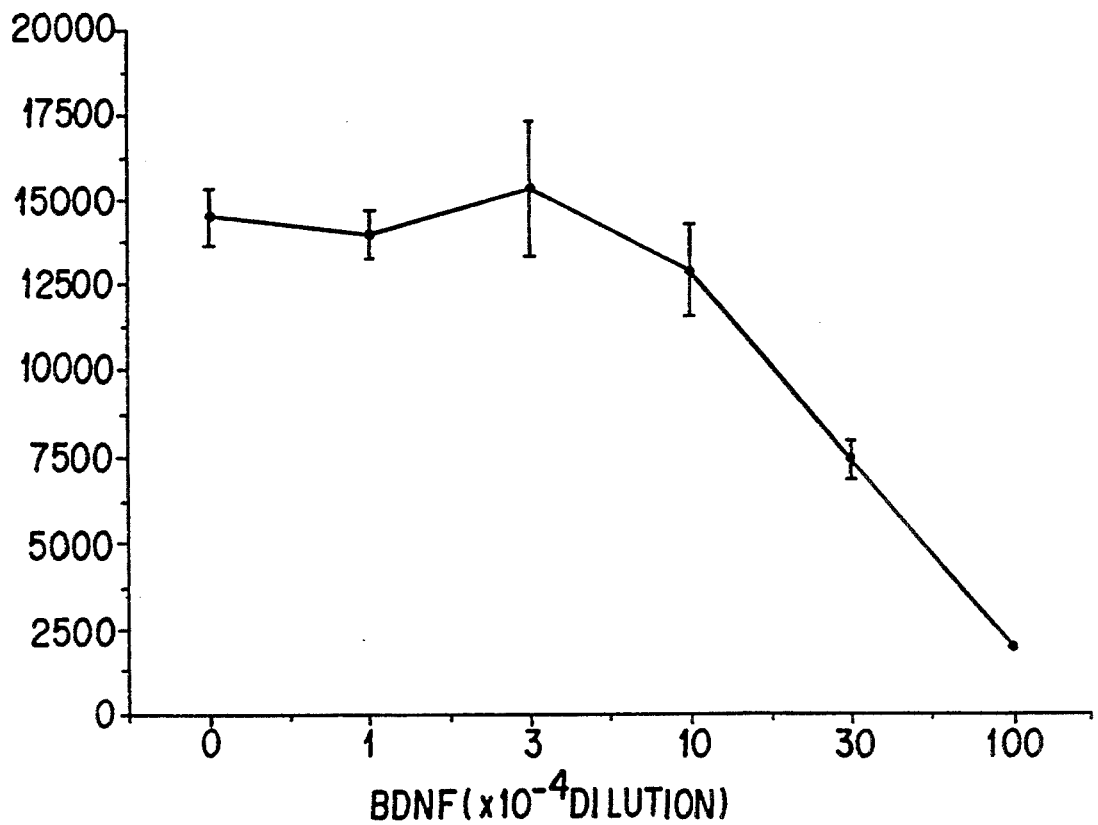

FIG. 36. Dose-dependent response of BDNF on high affinity GABA uptake in hippocampal cultures. Partially-purified nBDNF (rotophor-purified from COS M5 supernatants) was added to the cultures at various dilutions. BDNF at $1 \times 10^{-2}$ dilution was found to have maximal neurite-promoting activity in E8 chick dorsal root ganglion. High affinity $^3$H-GABA uptake was measured following 8 days of BDNF treatment in vitro.

Figure 37:
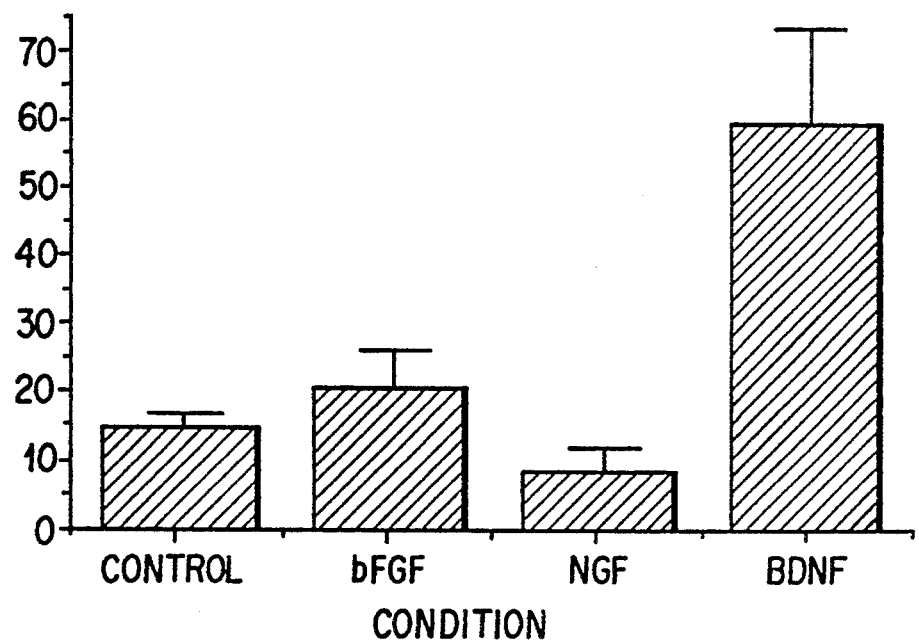

FIG. 37. BDNF protects cultured nigral dopaminergic neurons from the neurotoxic effects of MPP+. Cultures were established from E14 rat embryos as described in FIG. 1. After 24 hours in vitro the culture medium was changed to the serum-free formulation. After 3 days in culture the cultures were divided into four groups of six 35 mm dishes. One group was kept as a control group, and the others received either (i) basic fibroblast growth factor, 10 ng/ml (bovine brain bFGF; Boerhinger-Mannheim); (ii) mouse NGF, 50 ng/ml; or (iii) BDNF, 50 ng/ml. Cultures were kept for a further 24 hours before 3 dishes in each group were exposed to 1 μM MPP+ (Research Biochemicals, Inc., Natick, Mass.) for 48 hours. At the end of the experiment, 6 days in total, all plates were processed for TH immunoreactivity and the number of TH+ cells was determined in each group. The data presented represent the number TH+ neurons after MPP+ treatment calculated as a percentage of the number of TH+ neurons in similar cultures not exposed to MPP+. All values are the mean±s.e.m. of triplicate cultures.

Figure 38:
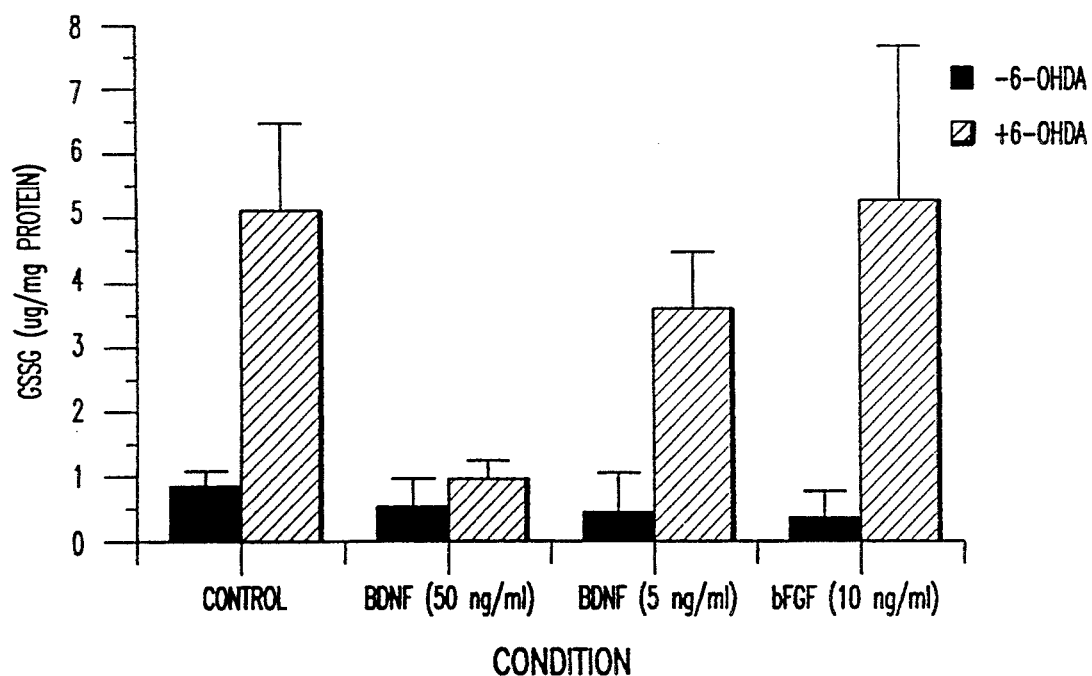
Figure 39:
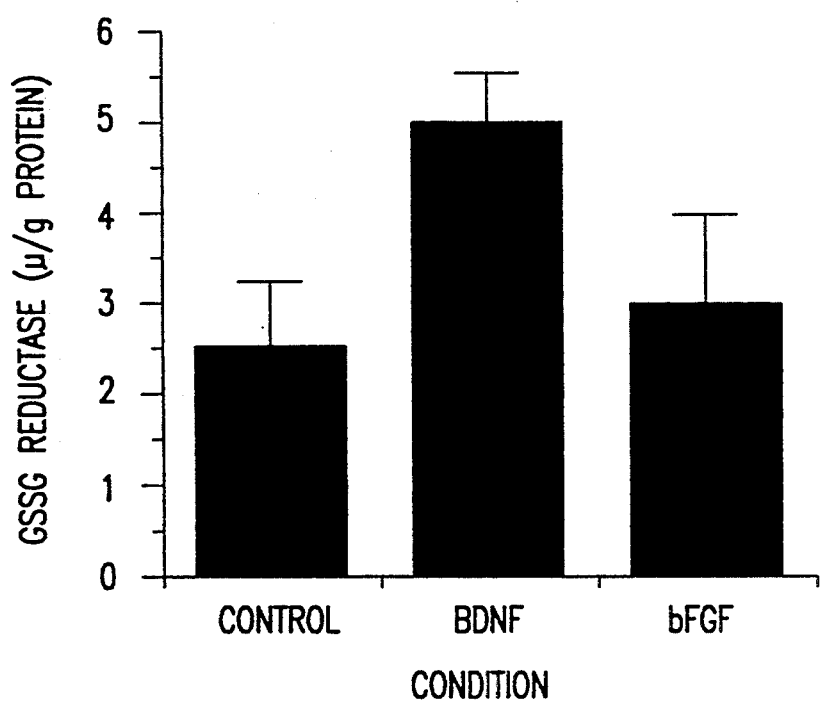

FIG. 38. Glutathione disulfide produced in SH-SY5Y cells in cells exposed (hatched bars) or not exposed (solid bars) to 6-hydroxydopamine, some of which have been pretreated with BDNF (at 50 ng/ml or 5 ng/ml) or bFGF (at 10 ng/ml) prior to 6-hydroxydopamine exposure. FIG. 39. SH-SY5Y cells treated with BDNF or bFGF for 48 hours, and cellular GSSG reductase activity was measured.

5. DETAILED DESCRIPTION OF THE INVENTION

The present invention relates to nucleic acid sequences encoding brain derived neurotrophic factor (BDNF), as well as BDNF protein, peptide fragments and derivatives produced in quantity using these nucleic acid sequences. In addition, the invention relates to pharmacologic compositions and therapeutic uses of BDNF, having provided, for the first time, the means to generate sufficient quantities of substantially pure BDNF for clinical use. The invention also relates to antibodies directed toward BDNF or fragments thereof, having provided a method for generating sufficient immunogen. Further, by permitting a comparison of the nucleic acid sequences of BDNF and NGF, the present invention provides for the identification of homologous regions of nucleic acid sequence between BDNF and NGF, thereby defining a BDNF/NGF gene family; the invention provides a method for identifying and isolating additional members of this gene family.

For purposes of clarity of description, and not by way of limitation, the invention will be described in the following parts:
 (i) purification of BDNF
 (ii) BDNF bioassays
 (iii) microsequencing of BDNF protein
 (iv) cloning of BDNF encoding DNA
 (v) expression of BDNF
 (vi) BDNF genes and proteins
 (vii) generation of anti-BDNF antibodies
 (viii) identification of additional members of the BDNF/NGF gene family
 (ix) utility of the invention
 (X) pharmaceutical compositions

5.1. Purification of Brain Derived Neurotrophic Factor

In order to identify BDNF encoding nucleic acid, microgram amounts of BDNF protein may be obtained from tissue to permit the determination of amino acid sequences which may then be used to design oligonucleotide probes. The extreme rarity of BDNF protein practically limits the amount of amino acid sequence which may be determined. BDNF may be prepared from pig brain by methods described in Barde et al., (1982, EMBO J. 1:549–553), or Hofer and Barde (1988, Nature 331:261–262).

Preferably, BDNF may be prepared, according to the following detailed protocol which is presented by way of example, and not by way of limitation; various modifications are envisioned for use by one skilled in the art. Because of the rarity of BDNF, preferably about six kilograms of brain tissue may be used in a purification procedure. Brain tissue may be homogenized in sodium phosphate buffer at a concentration of about 0.2M sodium phosphate and a pH of approximately 6, containing 1 mM EDTA and 1 mM freshly added phenylmethanesulphonyl fluoride, such that the ratio of brain tissue to fluid is approximately 1 kg of brain to 2 liters of buffer. Hydrochloric acid may then be used to adjust the pH of the mixture to approximately 4, and the mixture may then be stirred for about 2 hours at 4° C. The mixture can then be centrifuged for 25 minutes at 20,000 g. After centrifugation, the supernatant is collected, adjusted to a pH of about 6.0 using sodium hydroxide, and then stirred with about 1 liter of preswollen carboxymethylcellulose (per 6 kg of brain tissue) which has been equilibrated with 0.1M sodium phosphate at a pH of 6. After several washes with a total of about 20 liters of 0.1M sodium phosphate, pH 6, the slurry may be poured into a column and washed with the same buffer containing 0.13M NaCl, preferably overnight. Active fractions, identified by a BDNF sensitive bioassay (see Section 5.2, infra) may then be eluted with phosphate buffer containing 0.5M NaCl and subsequently dialyzed against several changes of about 5 liters of 5 mM potassium phosphate at a pH of 6.8. The dialyzed fractions may then be applied to a hydroxyapatite column having a bed volume of about 20 ml for each kilogram of brain tissue processed; the hydroxyapatite column should be pre-equilibrated with 5 mM potassium phosphate at a pH of 6.8 prior to application of sample. The column may then be eluted with a linear gradient composed of 500 ml of 5 mM potassium phosphate and 500 ml of 700 mM potassium phosphate, both at a pH of about 6.8. The BDNF activity should optimally be eluted at approximately 500 mM potassium phosphate. Pooled active fractions may then be adjusted to a final molarity of about 700 mM potassium phosphate and applied to a phenyl-sepharose column (having a volume of about 5 ml for every 6 kg of brain tissue processed) equilibrated with a solution of 700 mM potassium phosphate having a pH of 6.8. After washing with approximately 40 ml of the same buffer, BDNF activity may be eluted with 0.1M potassium phosphate, pH 6.8, and subsequently the BDNF activity may be dialyzed against distilled water, and then lyophilized. The lyophilized material may then be taken up in an SDS-gel electrophoresis sample buffer containing 0.1% SDS but preferably containing no mercaptoethanol, and applied to an SDS gel comprised of a linear gradient of 10–25% acrylamide. After completion of electrophoretic separation, the gel may be stained for about 10 minutes with Coomassie blue, and destained for about 20 minutes. A band migrating at the level of a cytochrome c marker may be cut out and electrophoretically eluted from the gel. SDS may be largely removed as described by Weber and Kuter (1971, J. Biol. Chem. 246:4504–4509). It should be noted that removal of SDS is generally not complete. A purification procedure for microsequencing of BDNF was modified according to Hofer and Barde (1988, Nature 331:261–262), and does not make use of a gel electrophoresis as the last step of purification.

5.2. Brain Derived Neurotrophic Factor Bioassays

Any system which qualitatively or quantitatively indicates BDNF activity may be used according to the present invention. Such bioassays may be useful in identifying and/or measuring natural or recombinant BDNF activity.

Any BDNF bioassay known in the art may be used. For example, chick embryo dorsal root ganglion (DRG) neurons may be utilized in a BDNF assay, as described in Barde et al. (1980, Proc. Natl. Acad. Sci. U.S.A. 77:1199–1203).

By way of example, dorsal root ganglia from 6 to 14 day chick embryos, and preferably 10 to 12 day chick embryos, may be collected, using dissection techniques known in the art, and immediately placed in a small volume of F14 medium (made from GIBCO F-12 powder, supplemented as in Vogel et al., 1972, Proc. Natl. Acad. Sci. U.S.A. 69:3180–3184), which should be replaced at the end of the dissection by $Ca^{2+}$ and $Mg^{2+}$-free phosphate buffered saline (PBS) containing about 0.1 percent trypsin. After about 20 minutes of incubation at 37° C., the ganglia may be centrifuged and washed twice with F14 medium containing about 10 percent (vol/vol) heat-inactivated horse serum. The ganglia may then be dissociated by gentle trituration (about 10–15 aspirations) using a small (about 1 mm) diameter siliconized pasteur pipette. Remaining lumps of tissue may then, preferably, be removed by passing the cell suspension through a nylon mesh, having about 40 μm sized pores. The cell suspension may then be preplated for about 210 minutes on a plastic tissue culture dish; during this period, most of the nonneuronal cells should adhere to the plastic surface, leaving a neuron-enriched cell population in suspension. Cells may then be diluted to a concentration of about $5 \times 10^3$ cells per milliliter of plating medium (preferably F14 medium supplemented with 10 percent vol/vol heat inactivated horse serum together with antibiotics) and placed in polyornithine or, preferably, polyornithine/-laminin coated tissue culture dishes (see infra).

Alternatively, and not by way of limitation, BDNF bioassays which are relatively insensitive to NGF may, in some circumstances, be preferable to systems, such as the DRG system described supra, which may, under certain conditions, respond to both BDNF and NGF. Such relatively BDNF-specific systems would include retinal ganglion cultures as well as cultures of neurons derived from neural placodes.

Perinatal retinal cells may be cultured according to the methods described in Johnson et al. (1986, J. Neurosci. 6:3031–3038). For example, retinas may be removed from perinatal animals (in the rat the term "perinatal" here refers to embryonic day 17 through postnatal pups within 48 hours after birth), washed in calcium and magnesium free phosphate buffered saline (PBS), then incubated in PBS containing about 0.05% to 0.1% trypsin for approximately 15 minutes at about 37° C. After proteolytic digestion, retinas may be washed in F14 culture medium containing about 10 percent (vol/vol) heat-inactivated horse serum (F14-HS). The retinas may then be dissociated by gentle pipetting in a small volume (about 1-10 ml) of fresh F14-HS. Undissociated tissue may be allowed to settle, and the remaining cells and medium pipetted off for culture.

Alternatively, BDNF bioassays which comprise neural placode derived cells may be used according to the invention. Embryonic cranial nerve explants of, for example, the ventrolateral portion of the trigeminal ganglion, or the vestibular, geniculate, petrosal, or nodose ganglion may be cultured in collagen-gel overlaid with culture medium, as described in Davies et al. (1986, J. Neurosci. 6:1897-1904) or dissociated according to Barde et al. (1980, Proc. Natl. Acad. Sci. 77:1199-1203).

Because it has been observed that responsiveness to BDNF may be increased ten-fold by changing the growth substrate from polyornithine to laminin-polyornithine, (Barde et al., 1987, Prog. Brain Res. 71:185-189), BDNF assays are preferably performed on laminin-containing substrates. Culture surfaces may be prepared, for example, by (i) coating the culture surface for about 8-10 hours with a sterile solution of polyornithine; (ii) washing several times with sterile water; and (iii) coating the culture surface for about two hours with laminin at a concentration of approximately 25 μg/ml in PBS (Johnson et al., 1986, J. Neurosci. 6:3031-3038).

In any bioassay system used according to the invention, a BDNF dose-response curve may be established using methods known in the art. Using a dissociated chick sensory ganglion assay, half-maximal survival was observed with a concentration of about 5 ng/ml purified BDNF, and maximal survival was observed with a concentration of between about ten and 20 ng/ml purified BDNF (Barde et al., 1987, Prog. Brain Res. 71:185-189).

5.3. Microsequencing of Brain Derived Neurotrophic Factor Protein

BDNF protein prepared from brain may be sequenced; however, it must be emphasized that the extreme rarity of the protein makes it unlikely that a substantial portion of BDNF protein sequence may be reliably obtained. The protein may be sequenced directly or initially cleaved by any protease or other compound known in the art, including, but not limited to, *Staphylococcus aureus* V8, trypsin, and cyanogen bromide. Peptides may be sequenced by automated Edman degradation on a gas phase microsequencer according to the method of Hewick et al. (1981, J. Biol. Chem. 256:7990-7997) and Hunkapillar et al. (1983, Methods Enzymol. 91:227-236). Detection of phenylthiohydantoin amino acids may then be performed according to Lottspeich (1985, Chromatography 326:321-327). Overlapping fragments of amino acid sequence may be determined and used to deduce longer stretches of contiguous sequence.

5.4. Cloning of Brain Derived Neurotrophic Factor-Encoding DNA

The rarity of BDNF effectively precludes the use of standard strategies for cloning the BDNF gene. For example, if available protein sequence were used to generate a complementary labeled oligonucleotide probe, and this probe were used to screen cDNA libraries generated from tissue presumed to synthesize BDNF, the number of positive clones would be likely to be vanishingly small. The instant invention provides for the cloning of the BDNF gene by a combination of procedures, comprising the purification of suitable amounts of BDNF protein, microsequencing of the BDNF protein, derivation of an oligonucleotide probe, construction of a cDNA library, amplification based on the derived BDNF amino acid sequence, and finally, selection for the BDNF gene. In this method of the invention, the preferred procedure for amplification utilizes the amplification of tissue nucleic acid sequences by polymerase chain reaction (PCR) (Saiki et al., 1985, Science 230:1350-1354), in order to expand the number of BDNF sequences available for cloning. A detailed description of the preferred method follows:

Firstly, the amino acid sequence derived from purified BDNF protein may be used to deduce oligonucleotide primers for use in polymerase chain reaction. Because of the degeneracy of the genetic code, in which several nucleic acid triplets may specify the same amino acid, several oligonucleotides should be synthesized for a given amino acid sequence, in order to provide for multiple potential nucleotide sequence combinations; the resulting oligonucleotides are referred to as degenerate primers.

The polymerase chain reaction (PCR) requires sense strand as well as anti-sense strand primers. Accordingly, a degenerate oligonucleotide primer corresponding to BDNF amino acid sequence may be used as primer for one DNA strand, and a second primer, homologous to a commonly occurring DNA sequence, such as a stretch of thymidine residues resulting from reverse transcription of the polyadenosine tail of mRNAs, may be used as primer for the second DNA strand. These primers may then be used in polymerase chain reaction with nucleic acid template presumed to contain BDNF encoding sequences, such as genomic DNA or, preferably, cDNA prepared from mRNA collected from tissue presumed to synthesize BDNF. The DNA reaction products may then be analyzed by electrophoresis to determine whether the DNA reaction product has a molecular size similar to the expected size of the BDNF gene and, preferably, by nucleotide sequence analysis.

However, because the use of two degenerate primers in PCR increases the likelihood of amplifying nucleic acid sequences which do not encode BDNF, a preferred method provides for the use of only one degenerate primer, the other primer corresponding to exact BDNF sequence. In order to identify exact BDNF sequence, the amino acid sequence determined using purified BDNF protein may be used to design both degenerate sense and anti-sense oligonucleotide primers. The DNA reaction product resulting from the use of these primers in PCR reaction, using BDNF encoding nucleic acid as a template, should be a nucleic acid fragment encoding the stretch of amino acids used to design the primers, and may be of a predictable size (e.g. at minimum, the number of amino acid residues, multiplied by a factor of three, base pairs in length). Sequence analysis of the DNA reaction product may be compared to the ascertained amino acid sequence to corroborate that the amplified nucleic acid sequence may, in fact, encode the BDNF peptide fragment. Although any method of nucleic acid sequencing known in the art may be utilized, it is preferable to use the dideoxynucleotide chain termination method (Sanger et al., 1979, Proc. Natl. Acad. Sci. U.S.A. 72:3918–3921). Sequencing may be accomplished using gel purified or, preferably, cloned DNA reaction product. The sequence of the DNA reaction product may then be used toward designing an oligonucleotide primer corresponding to exact BDNF-encoding sequence. This primer may then be used together with a second primer, which may be degenerate, to extend the amount of BDNF-sequence beyond that represented by the fragment of exact sequence initially determined. For example, and not by way of limitation, the sense strand primer may correspond to exact BDNF nucleotide sequence, whereas the anti-sense primer may be a degenerate primer homologous to a region of sequence likely to be found downstream of the sequenced fragment, e.g. the polyadenosine tail of mRNA, as reverse transcribed in the cDNA. It may then be necessary to use a similar method to retrieve sequence upstream of the sequenced fragment; for example, the anti-sense strand primer may correspond to exact BDNF nucleotide sequence and the sense strand primer may be a degenerate primer homologous to a region of BDNF sequence upstream of the sequenced fragment, e.g. a 5' polyadenosine tail added at the 5' end of cDNA using terminal deoxynucleotide transferase. Accordingly, the sequence of the entire BDNF gene or mRNA may be assembled.

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

The BDNF gene is inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and BDNF gene may be modified by homopolymeric tailing.

In specific embodiments, transformation of host cells with recombinant DNA molecules that incorporate an isolated BDNF gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

According to a preferred embodiment of the invention, once a cDNA-derived clone encoding BDNF has been generated, a genomic clone encoding BDNF may be isolated using standard techniques known in the art. For example, a labeled nucleic acid probe may be derived from the BDNF clone, and used to screen genomic DNA libraries by nucleic acid hybridization, using, for example, the method set forth in Benton and Davis (1977, Science 196:180) for bacteriophage libraries and Grunstein and Hogness (1975, Proc. Natl. Acad. Sci. U.S.A. 72:3961–3965) for plasmid libraries. Retrieved clones may then be analyzed by restriction-fragment mapping and sequencing techniques according to methods well known in the art.

Furthermore, additional cDNA clones may be identified from a cDNA library using the sequences obtained according to the invention.

5.5. Expression of the Brain Derived Neurotrophic Gene

The nucleotide sequence coding for a BDNF protein, or a portion thereof, can be inserted into an appropriate expression vector, i.e., a vector which contains the necessary elements for the transcription and translation of the inserted protein-coding sequence. The necessary transcriptional and translation signals can also be supplied by the native BDNF gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding BDNF protein or peptide fragment may be regulated by a second nucleic acid sequence so that BDNF protein or peptide is expressed in a host transformed with the recombinant DNA moleucle. For example, expression of BDNF may be controlled by any promoter/enhancer element known in the art. Promoters which may be used to control BDNF expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci.

U.S.A. 80:21-25), see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the bran (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

Expression vectors containing BDNF gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted BDNF gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the BDNF gene is inserted within the marker gene sequence of the vector, recombinants containing the BDNF insert can be identified by the absence of the marker gene function. In the third approach, recombinant expression vectors can be identified by assaying the foreign gene product expressed by the recombinant. Such assays can be based, for example, on the physical or functional properties of the BDNF gene product in bioassay systems as described supra, in Section 5.2.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered BDNF protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous BDNF protein. Furthermore, different vector/host expression systems may effect processing reactions such as proteolytic cleavages to different extents.

In a specific embodiment of the invention, DNA encoding preproBDNF may be cloned into pCMV plasmid, amplified, and then used to transfect COS cells by the calcium phosphate method (Chen and Okayama, 1987, Mol. Cell. Biol. 7:2745-2752); BDNF activity may then be collected from cell culture medium (see Example Section 10, infra).

5.5.1. Identification and Purification of the Expressed Gene Product

Once a recombinant which expresses the BDNF gene is identified, the gene product should be analyzed. This can be achieved by assays based on the physical or functional properties of the product.

Once the BDNF protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any known BDNF assay, including, but not limited to, chick embryo dorsal root ganglia, perinatal rat retinal cells, or neural placode-derived neurons.

Importantly, methods used to prepare BDNF from brain tissue, because they involve, as a final step, preparative gel electrophoresis, would produce BDNF which was not fully active due to the presence of residual SDS (Barde and Thoenen, 1985, in "Hormones and Cell Regulation," Vol. 9, Dumont et al., eds., Elsevier Science Publishers, pp. 385-390). In contrast, the present invention permits the isolation of BDNF which is produced from recombinant nucleic acid molecules and which is free of SDS and therefore possesses full activity. For example, and not by way of limitation, the anti-BDNF antibodies of the invention (such as antibody directed toward the B5-33 amino acid fragment of porcine BDNF, described in Section 11, infra) may be used to collect recombinant BDNF by immunoprecipitation or affinity chromatography, thereby producing detergent-free, fully active BDNF.

In a further embodiment of the invention, prepro BDNF may be converted to active mature BDNF enzymatically, using, for example, endoproteinase Arg-C (see Example Section 17, infra).

5.6. Brain Derived Neurotrophic Factor Genes and Proteins

Using the methods detailed supra and in Example Sections 6 and 9, infra, the following nucleic acid sequences were determined, and their corresponding amino acid sequences deduced. The porcine BDNF cDNA sequence was determined, and is depicted in FIG. 1. The human genomic cDNA BDNF sequence was determined, and is depicted in FIGS. 4A through 4I which also present DNA sequences from pig, rat, and chicken. Each of these sequences, as well as the sequences contained in phBDNF-C-1 and λhBDNF-G-1, deposited with the ATCC and assigned accession numbers 40648 and 40649, respectively, or their functional equivalents, can be used in accordance with the invention. Additionally, the invention relates to BDNF genes and proteins isolated from porcine, bovine, feline, avian, equine, or canine, as well as primate sources and any other species in which BDNF activity exists. The invention is further directed to subsequences of BDNF nucleic acids comprising at least ten nucleotides, such subsequences comprising hybridizable portions of the BDNF sequence which have use, e.g., in nucleic acid hybridization assays, Southern and Northern blot analyses, etc. The invention also provides for BDNF protein, and fragments and derivatives thereof, according to the amino acid sequences set forth in FIGS. 1 and 4A through 4I or their functional equivalents. The invention also provides fragments or derivatives of BDNF proteins which comprise antigenic determinant(s) or which are functionally active. As used herein, functionally active shall mean having positive activity in assays for known BDNF function, e.g. chick embryo DRG assays.

For example, the nucleic acid sequences depicted in FIGS. 1 and 4A through 4I can be altered by substitutions, additions or deletions that provide for functionally equivalent molecules. Due to the degeneracy of nucleotide coding sequences, other DNA sequences which encode substantially the same amino acid sequence as depicted in FIGS. 1 and 4A through 4I may be used in the practice of the present invention. These include but are not limited to nucleotide sequences comprising all or portions of the BDNF genes depicted in FIGS. 1 and 4A through 4I which are altered by the substitution of different codons that encode a functionally equivalent amino acid residue within the sequence, thus producing a silent change. Likewise, the BDNF proteins, or fragments or derivatives thereof, of the invention include, but are not limited to, those containing, as a primary amino acid sequence, all or part of the amino acid sequence substantially as depicted in FIGS. 1 and 4A through 4I including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are BDNF proteins or fragments or derivatives thereof which are differentially modified during or after translation, e.g., by glycosylation, proteolytic cleavage, linkage to an antibody molecule or other cellular ligand, etc.

Additionally, a given BDNF can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB® linkers (Pharmacia), etc.

5.7. Generation of Anti-Brain Derived Neurotrophic Factor Antibodies

According to the invention, BDNF protein, or fragments or derivatives thereof, may be used as immunogen to generate anti-BDNF antibodies. Previous attempts to produce an anti-BDNF immune response have been unsuccessful, possibly because of the small quantities of purified BDNF available. By providing for the production of relatively abundant amounts of BDNF protein using recombinant techniques for protein synthesis (based upon the BDNF nucleic acid sequences of the invention), the problem of insufficient quantities of BDNF has been obviated.

To further improve the likelihood of producing an anti-BDNF immune response, the amino acid sequence of BDNF may be analyzed in order to identify portions of the molecule which may be associated with increased immunogenicity. For example, the amino acid sequence may be subjected to computer analysis to identify surface epitopes, according to the method of Hopp and Woods (1981, Proc. Natl. Acad. Sci. U.S.A. 78:3824–3828) which has been successfully used to identify antigenic peptides of Hepatitis B surface antigen. Alternatively, the deduced amino acid sequences of BDNF from different species could be compared, and relatively non-homologous regions identified; these non-homologous regions would be more likely to be immunogenic across various species.

For preparation of monoclonal antibodies directed toward BDNF, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of BDNF. For the production of antibody, various host animals can be immunized by injection with BDNF protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a BDNF epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')₂ fragment which can be produced by pepsin digestion of the antibody molecule; the Fab' fragments which can be generated by reducing the disulfide bridges of the F(ab')₂ fragment, and the 2 Fab or Fab fragments which can be generated by treating the antibody molecule with papain and a reducing agent.

Example Section 11 describes the preparation of polyclonal antisera directed toward the B5-33 peptide fragment of BDNF protein.

5.8. Identification of Additional Members of the BDNF/NGF Gene Family

Sequence analysis of the gene encoding BDNF and deduction of its amino acid sequence revealed that this protein has many structural similarities to NGF (FIG. 2). The primary sequence of mature BDNF, as well as the general structure and probable mode of processing from a precursor protein, suggest strongly that the NGF and BDNF genes may have evolved from a common ancestral gene. Within the region of the mature polypeptides, if only three gaps are introduced in the NGF sequences to optimize matching, a total of 51 amino acid identities are common to the previously known NGFs from many species and to porcine and human BDNF. These identities include all six cysteine residues, suggesting that the NGFs and BDNF share very similar secondary structure. Furthermore, four segments of six or more amino acids can be seen in which NGFs from all of the species listed above and from porcine BDNF are either identical, or differ by no more than about one conservative amino acid substitution. Thus, it is reasonable to conclude that NGF and BDNF appear to be closely related members of a gene family.

A rational search for additional members of the BDNF/NGF gene family may be carried out using an approach that takes advantage of the unanticipated existence of the conserved segments of strong homology between NGF and BDNF. For example, additional members of the BDNF gene family may be identified by selecting, from among a diversity of nucleic acid sequences, those sequences that are homologous to BDNF and NGF, and further identifying, from among the selected sequences, those that also contain nucleic acid sequences which are non-homologous to NGF and BDNF. The term "non-homologous" may be construed to mean a region which contains at least about 6 contiguous nucleotides in which at least about two nucleotides differ from NGF and BDNF sequence.

A preferred embodiment of the invention provides the following method. Corresponding to each of the four conserved segments ("boxes") described above and set forth in Table III, infra, sets of degenerate oligonucleotide probes of at least 18 nucleotides may be synthesized, representing all of the possible coding sequences for the amino acids found in either NGF or BDNF over six contiguous codons. Numbering with respect to the amino terminus of the mature polypeptides (so that His134 of preproBDNF is treated as His1 in the mature protein), the four boxes may be characterized as follows (numbered relative to human mature proteins; DNA sequence as depicted in FIG. 1).

TABLE III

|        |      |              | DNA Sequence |
|--------|------|--------------|--------------|
| Box 1: | NGF  | Gly10—Ser19  | 587–616      |
|        | BDNF | Gly8—Ser17   |              |
| Box 2: | NGF  | Lys50—Cys58  | 713–739      |
|        | BDNF | Lys50—Cys58  |              |
| Box 3: | NGF  | Gly67—Asp72  | 764–781      |
|        | BDNF | Gly67—Asp72  |              |
| Box 4: | NGF  | Trp99—Cys110 | 863–898      |
|        | BDNF | Trp100—Cys111|              |

Synthetic oligonucleotides derived from sequence pairs from the boxes set forth in Table III may be utilized as primers to amplify by PCR sequences from a source (RNA or DNA) of potential interest. This might include mRNA or cDNA or genomic DNA from any eukaryotic species that could express a polypeptide closely related to BDNF or NGF. By carrying out as few as six PCR reactions (namely: a primer from Box 1 with a primer from Box 2; Box 1 with Box 3; Box 1 with Box 4; Box 2 with Box 3; Box 2 with Box 4; Box 3 with Box 4), it may be possible to detect a gene or gene product sharing any two of the four above segments of conserved sequence between NGF and BDNF. If one chooses to synthesize several different degenerate primers for each box, it may still be possible to carry out a complete search with a reasonably small number of PCR reactions. It is also possible to vary the stringency of hybridization conditions used in priming the PCR reactions, to allow for greater or lesser degrees of nucleotide sequence similarity between the unknown gene and NGF or BDNF. If a segment of a previously unknown member of the BDNF/NGF gene family is amplified successfully, that segment may be molecularly cloned and sequenced, and utilized as a probe to isolate a complete cDNA or genomic clone. This, in turn, will permit the determination of the unknown gene's complete nucleotide sequence, the analysis of its expression, and the production of its protein product for functional analysis.

The approach described above has been used to identify a novel gene related to both BDNF and NGF, and described in Example Section 13, infra.

In addition, the present invention provides for the use of the BDNF/NGF sequence homologies in the design of novel recombinant molecules which are members of the BDNF/NGF gene family but which may not occur in nature. For example, and not by way of limitation, a recombinant molecule can be constructed according to the invention, comprising portions of both NGF and BDNF genes. Such a molecule could exhibit properties associated with both BDNF and NGF and portray a novel profile of biological activities, including agonists as well as antagonists. Primary sequence of BDNF and NGF may also be used to predict tertiary structure of the molecules using computer simulation (Hopp and Woods, 1981, Proc. Natl. Acad. Sci. U.S.A. 78:3824–3828); BDNF/NGF chimetic recombinant genes could be designed in light of correlations between tertiary structure and biological function. Likewise, chimeric genes comprising portions of any one or more members of BDNF/NGF gene family, including the novel member described in Section 13 may be constructed.

5.9. Utility of the Invention

The present invention relates to the nucleic acid sequence of BDNF and to the substantially pure protein, peptide fragments, or derivatives produced therefrom. BDNF may be produced, for the first time, in quantities sufficient for diagnostic and therapeutic applications. Likewise, anti-BDNF antibodies, also available for the first time as a consequence of the invention, and BDNF nucleic acid probes, may be utilized in diagnostic and therapeutic applications. For most purposes, it is preferable to use BDNF genes or gene products from the same species for diagnostic or therapeutic purposes, although cross-species utility of BDNF may be useful in specific embodiments of the invention.

5.9.1. Diagnostic Applications

The present invention, which relates to nucleic acids encoding BDNF and to proteins, peptide fragments, or derivatives produced therefrom, as well as antibodies directed against BDNF protein, peptides, or derivatives, may be utilized to diagnose diseases and disorders of the nervous system which may be associated with alterations in the pattern of BDNF expression.

In various embodiments of the invention, BDNF genes and related nucleic acid sequences and subsequences, including complementary sequences, may be used in diagnostic hybridization assays. The BDNF nucleic acid sequences, or subsequences thereof comprising about 15 nucleotides, can be used as hybridization probes. Hybridization assays can be used to detect, prognose, diagnose, or monitor conditions, disorders, or disease states associated with changes in BDNF expression, including, in particular, conditions resulting in sensory neuron damage and degeneration of retinal neurons. Such diseases and conditions include but are not limited to CNS trauma, infarction, infection, degenerative nerve disease, malignancy, or post-operative changes including but not limited to Alzheimer's Disease, Parkinson's Disease, Huntington's Chorea, and degenerative diseases of the retina. For example, total RNA in a tissue sample from a patient can be assayed for the presence of BDNF mRNA, wherein the decrease in the amount of BDNF mRNA is indicative of neuronal degeneration. Relatively high levels of BDNF mRNA have been identified in neuroblastoma tumor cells (see Section 14, infra, for details); accordingly, in a specific embodiment of the invention, detection of increased levels of mRNA using BDNF nucleic acid probes can be utilized to diagnose neuroblastoma tumor. The extremely low levels of BDNF synthesized by most tissues render BDNF mRNA a particularly useful tumor marker.

In alternate embodiments of the invention, antibodies directed toward BDNF protein, peptide fragments, or derivatives can be used to diagnose diseases and disorders of the nervous system, including, in particular, sensory disorders and degenerative diseases of the retina, as well as those disorders and diseases listed supra. The antibodies of the invention can be used, for example, in in situ hybridization techniques using tissue samples obtained from a patient in need of such evaluation. In a further example, the antibodies of the invention can be used in ELISA procedures to detect and/or measure amounts of BDNF present in tissue or fluid samples; similarly, the antibodies of the invention can be used in Western blot analysis to detect and/or measure BDNF present in tissue or fluid samples. An antibody of the invention which binds to BDNF in ELISA and Western blots is described in Section 11, infra.

In further embodiments of the invention, BDNF protein, peptide fragments or derivatives can be used to diagnose diseases and disorders of the nervous system. In a particular embodiment and not by way of limitation, labeled BDNF protein or peptide fragments can be used to identify tissues or cells which express the BDNF receptor in order to identify aberrancies of BDNF receptor expression and consequently, potential abnormalities in the tissue or cellular response to BDNF.

As shown in Sections 22 and 23, infra, retrograde axonal transport of BDNF has been observed in the peripheral and central nervous systems, respectively. The specific retrograde transport of BDNF maybe used to indicate whether neurons are responsive to BDNF in normal or diseased states. Accordingly, the present invention provides for a method of diagnosing a BDNF-related peripheral nervous system disorder comprising injecting detectably labeled BDNF into a peripheral nerve and determining whether the labeled BDNF is retrogradely transported, in which a failure to be retrogradely transported positively correlates with lack of responsiveness to BDNF and indicates that the peripheral nervous system disorder is BDNF-related. Analogous methods may be used to diagnose a central nervous system disorder. Evaluation of retrograde transport may be performed by any method known in the art, including but not limited to MRI, CAT, or scintillation scanning. Such methods may be used to identify the location of a nervous system lesion, as retrograde transport should substantially diminish upon reaching the lesion. Examples of peripheral nervous system disorders that may be diagnosed in this manner include, but are not limited to, acute neurapraxia, neurtomesis, axotmesis, diabetic neuropathy, amyotrophic lateral sclerosis and compression. Examples of central nervous system disorders that may be diagnosed in this manner include, but are not limited to, tumor, abscess, trauma, Alzheimer's disease, and Parkinson's disease. These same methods maybe applied to diagnostic studies involving other members of the neurotrophin family.

5.9.2. Therapeutic Applications

The present invention, which relates to nucleic acids encoding BDNF, and to proteins, peptide fragments, or derivatives produced therefrom, as well as to antibodies directed against BDNF protein, peptides, or derivatives, may be utilized to treat diseases and disorders of the nervous system which may be associated with alterations in the pattern of BDNF expression or which may benefit from exposure to BDNF or anti-BDNF antibodies.

In various embodiments of the invention, BDNF protein, peptide fragments or derivatives can be administered to patients in whom the nervous system has been damaged by trauma, surgery, ischemia, infection, metabolic disease, nutritional deficiency, malignancy, or toxic agents. The invention in particular can be used to treat conditions in which damage has occurred to sensory neurons or retinal ganglion cells by administering effective therapeutic amounts of BDNF protein or peptide fragments or derivatives. In various specific embodiments of the invention, BDNF can be locally administered to sensory neurons which have been severed, including, but not limited to, neurons in dorsal root ganglia or in any of the following tissues: the geniculate, petrosal, and nodose ganglia; the vestibuloacoustic complex of the VIIIth cranial nerve; the ventrolateral pole of the maxillo-mandibular lobe of the trigeminal ganglion; and the mesencephalic trigeminal nucleus. It may be desirable to administer the BDNF-related peptides or BDNF protein by adsorption onto a membrane, e.g. a silastic membrane, that could be implanted in the proximity of the severed nerve. The present invention can also be used for example in hastening the recovery of patients suffering from diabetic neuropathies, e.g. mononeuropathy multiplex. In further embodiments of the invention, BDNF protein or peptide fragments or derivatives derived therefrom, can be used to treat congenital conditions or neurodegenerative disorders, including, but not limited to, Alzheimer's disease, Parkinson's disease, Parkinson-Plus syndromes (in which Parkinsonian symptoms result from degeneration of dopaminergic neurons), such as Progressive Supranuclear Palsy (Steele-Richardson-Olszewski Syndrome), Olivopontocerebellar Atrophy (OPCA), Shy-Drager Syndrome (multiple systems atrophy), and Guamanian Parkinsonism dementia complex, and Huntington's chorea; in particular, the invention can be used to treat congenital or neurodegenerative disorders associated with sensory nerve dysfunction and degenerative diseases of the retina. For example, the BDNF protein, or peptide fragments, or derivatives of the invention can be used in the treatment of hereditary spastic paraplegia with retinal degeneration (Kjellin and Barnard-Scholz syndromes), retinitis pigmentosa, Stargardt disease, Usher syndrome (retinitis pigmentosa with congenital hearing loss), and Refsum syndrome (retinitis pigmentosa, hereditary hearing loss, and polyneuropathy), to name but a few. It is possible that a defect in BDNF synthesis or responsiveness may be the underlying etiology for syndromes characterized by a combination of retinal degeneration and other sensory dysfunction.

In a specific embodiment of the invention, administration of BDNF protein, or peptide fragments or derivatives derived therefrom, can be used in conjunction with surgical implantation of tissue in the treatment of Alzheimer's disease and/or Parkinson's disease. As discussed in Sections 12 and 18, infra, BDNF may be used to promote the survival of dopaminergic substantia nigra neurons in a dose-dependent manner (FIGS. 33A through 33C), supporting the use of BDNF in the treatment of disorders of CNS dopaminergic neurons, including, but not limited to, Parkinson's disease [particularly in light of data presented in Section 20, infra, which shows that BDNF may be used to prevent neurotoxicity caused by MPP, a toxin which is associated with the induction of a Parkinson's disease-like syndrome or in Section 21, infra, which shows that pretreatment of dopaminergic neurons with BDNF is protective against the toxic effects of agents such as 6-hydroxydopamine which results in superoxide radical formation.]. In addition, BDNF has been observed to sustain the survival of CNS cholinergic neurons (Sections 12 and 16, infra) and, in particular, basal forebrain cholinergic neurons, indicating that BDNF may be useful in the treatment of disorders involving cholinergic neurons, including, but not limited to, Alzheimer's disease. It has been shown that approximately 35 percent of patients with Parkinson's disease suffer from Alzheimer-type dementia; BDNF produced according to the invention may prove to be useful single agent therapy for this disease complex. Similarly, BDNF produced according to the invention may be used therapeutically to treat Alzheimer's disease in conjunction with Down's Syndrome. BDNF produced according to the invention can be used in the treatment of a variety of dementias as well as congenital learning disorders. It has also been found that BDNF appears to suppress the proliferation of astroglial cells, supporting the use of BDNF for diminishing scar formation in the CNS (for example, following surgery, trauma, or infarct) as well as the use of BDNF in the treatment of astroglial derived CNS tumors. In yet another embodiment of the invention, BDNF may be used to upregulate the expression of NGF receptor, and thereby may be advantageously administered prior to or concurrently with NGF to a patient in need of such treatment.

As exemplified in Section 15, infra, administration of kainic acid may be used to induce an increase in BDNF expression (and, to a lesser extent, NGF expression) in neurons, including hippocampal as well as cortical neurons. It has been observed (Section 15, infra) that inhibition of non-NMDA receptors blocked this kainic acid-mediated increase in BDNF expression. Accordingly, expression of BDNF and BDNF related peptides of the invention may be induced in vitro or in vivo by the administration of kainic acid or related compounds or carbachol, histamine, or bradykinin, or related compounds thereof, which are found to have similar effects in vitro or in vivo or by agonists of non-NMDA glutamate receptors or other drugs which augment or mimic the action of acethycholine, histamine, or bradykinin. Induction of NGF expression may also be accomplished by administering kainic acid or related molecules or agonists of non-NMDA receptors.

In further embodiments of the invention, BDNF protein, fragments or derivatives can be used in conjunction with other cytokines to achieve a desired neurotrophic effect. For example, and not by way of limitation, according to the invention BDNF can be used together with NGF or with skeletal muscle extract to achieve a synergistic stimulatory effect on growth of sensory neurons wherein synergistic is construed to mean that the effect of the combination of BDNF protein, peptide fragment, or derivative and a second agent achieves an effect greater than the same amount of either substance used individually. It is envisioned that BDNF may function synergistically with other CNS-derived peptide factors yet to be fully characterized, in the growth, development, and survival of a wide array of neuronal subpopulations in the central nervous system.

It is further envisioned that, based on the full characterization of the BDNF molecule, novel peptide fragments, derivatives, or mutants of BDNF may be developed which are capable of acting as antagonists of some, or all of the biological functions of BDNF. Such BDNF antagonists may be useful in the selective ablation of sensory neurons, for example, in the treatment of chronic pain syndromes.

In still further embodiments of the invention, antibodies directed toward BDNF protein, or peptide fragments or derivatives thereof, can be administered to patients suffering from a variety of neurologic disorders and diseases and who are in need of such treatment. For example, patients who suffer from excessive production of BDNF may be in need of such treatment. Anti-BDNF antibodies can be used in prevention of aberrant regeneration of sensory neurons (e.g. post-operatively), or, as discussed supra, in the treatment of chronic pain syndromes. In light of the high levels of BDNF mRNA found in neuroblastoma tissue, it is possible that BDNF serves as an autocrine tumor growth factor for neuroblastoma; accordingly, anti-BDNF antibodies can be administered therapeutically to achieve tumor regression in a specific embodiment of the invention.

5.10. Pharmaceutical Compositions

The active compositions of the invention, which may comprise all or portions of the BDNF gene product, including protein, peptide fragments or derivatives produced therefrom, or antibodies (or antibody fragments) directed toward BDNF protein, peptide fragments, or derivatives, or a combination of BDNF and a second agent, such as NGF or skeletal muscle extract, may be administered in any sterile biocompatible pharmaceutical carrier, including, but not limited to, saline, buffered saline, dextrose, and water.

BDNF protein, peptide fragment or derivative may comprise an amino acid sequence or subsequence thereof substantially as depicted in FIG. 1 or FIGS. 4A through 4I; it may be preferable to use BDNF protein comprising, in particular, all or a portion of the amino acid sequence from about amino acid 134 to about amino acid 252, as depicted in FIG. 1, or a functionally equivalent sequence, as this subsequence is believed to comprise the functional portion of the BDNF molecule. BDNF may be derived from sequences corresponding to the BDNF genes of any suitable species, including, but not limited to, human, pig, rat, chicken, cow, dog, sheep, goat, cat, rabbit, etc.

The amount of BDNF protein, peptide fragment, derivative, or antibody which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, e.g. in the BDNF bioassay systems described supra, and then in useful animal model systems prior to testing in humans. Based on in vitro data, in a specific embodiment of the invention, a pharmaceutical composition effective in promoting the survival of sensory neurons may provide a local BDNF protein concentration of between about 5 and 25 ng/ml, and, preferably, between 10 and 20 ng/ml of BDNF. In an additional specific embodiment of the invention, a pharmaceutical composition effective in promoting the growth and survival of dopaminergic or cholinergic neurons may provide a local BDNF protein concentration of between about 10 ng/ml and 100 ng/ml.

Methods of introduction include but are not limited to intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

Further, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions comprising BDNF proteins, peptide fragments, or derivatives administered via liposomes, microparticles, or microcapsules. In various embodiments of the invention, it may be useful to use such compositions to achieve sustained release of BDNF and BDNF-related products.

It is envisioned that it may be possible to introduce cells actively producing BDNF, BDNF related substances, BDNF antagonists, or anti-BDNF antibodies into areas in need of increased or decreased concentrations of BDNF.

6. EXAMPLE: MOLECULAR CLONING AND CHARACTERIZATION OF PORCINE BRAIN DERIVED NEUROTROPHIC FACTOR cDNA

The extreme rarity of BDNF protein in tissues precluded the use of standard strategies toward cloning the BDNF gene. Instead, a limited amount of protein sequence data was expanded, utilizing DNA amplification technology, as follows:

(i) Microgram quantities of BDNF were purified from kilogram quantities of porcine brain.
(ii) Purified BDNF was analyzed by protein microsequencing techniques, and the amino acid sequence of a stretch of 36 amino acid residues was determined.
(iii) Based on the amino acid sequence determined in (ii), oligonucleotides were synthesized and then used as primers in polymerase chain reaction, using porcine superior colliculus cDNA as template in order to amplify DNA encoding the defined amino acid fragment.

(iv) The DNA reaction product of (iii) was sequenced, and (v) Corresponding oligonucleotide primers were synthesized and utilized in polymerase chain reaction with porcine superior colliculus cDNA to generate overlapping fragments of DNA representing BDNF mRNA upstream as well as downstream of sequences encoding the original 36 amino acid fragment. Thus, the complete coding region for porcine BDNF was molecularly cloned in two overlapping fragments.

The details of each of these steps, as well as further characterization of the BDNF gene, are set forth below.

6.1. Materials and Methods

6.1.1. Purification of BDNF from Porcine Brain

Purification of BDNF from porcine brain was performed by the procedure essentially as set forth in Hofer and Barde (1988, Nature 331:261–262).

Six kg of pig brain was homogenized with an Ultra-Turrax homogenizer in 0.2M sodium phosphate buffer, pH 6.0, containing 1 mM EDTA and freshly added phenylmethanesulphonyl fluoride (1 mM) at a ratio of 1 kg of brain to 2 liters of buffer. The pH of the supernatant was brought to pH 4.0 with 1N HCl and stirred for 2 hr at 4° C. After centrifugation for 25 min at 20,000×g the combined supernatants (adjusted to pH 6.0 with 1N NaOH), corresponding to 3 kg of brain, were stirred for 2 hr with 1 liter of preswollen carboxymethyl-cellulose which had been equilibrated with 0.1M sodium phosphate, pH 6.0. After two washes with a total of 20 liter of 0.1M sodium phosphate, pH 6.0, the slurry was poured into a column and washed overnight in the same buffer containing 0.13M NaCl. Active fractions were eluted with phosphate buffer containing 0.5M NaCl and subsequently dialyzed against 2×5 liter of 5 mM potassium phosphate, pH 6.8. The dialyzed fractions resulting from processing 2×3 kg of starting material were applied to a 130 ml bed volume hydroxyapatite column which had been previously equilibrated with 5 mM potassium phosphate, pH 6.8. The column was then eluted with a linear gradient composed of 500 ml of 5 mM and 500 ml of 700 mM potassium phosphate, both pH 6.8, whereby the BDNF activity was eluted at approximately 500 mM potassium phosphate (see Barde et al., 1982, EMBO J. 1:549–553). By addition of 1.0M potassium phosphate, the pooled active fractions were adjusted to a final molarity of 700 mM potassium phosphate and applied to a 5 ml phenyl-sepharose column equilibrated with 700 mM potassium phosphate, pH 6.8. After washing with 40 ml of the same buffer, BDNF activity was eluted with 0.1M potassium phosphate, pH 6.8 dialyzed against distilled water, and lyophilized. The lyophilized material was taken up in an SDS-gel electrophoresis sample buffer containing 0.1% SDS and no mercaptoethanol as described in Barde et al. (1982, EMBO J., 1:549–553), before being applied to an SDS-gel comprised of a linear (rather than exponential) gradient of 10–25% acrylamide. After completion of electrophoretic separation, the gel was briefly stained (10 min) with Coomassie blue, destained for 20 min, and a band migrating at the level of cytochrome c was cut out and electrophoretically eluted from the gel. SDS was removed as described Barde et al. (1982, EMBO J., 1:549–553). The purification procedure that eventually led to the microsequencing of BDNF was modified (according to Hofer and Barde, 1988, Nature 331:261–262) and does not make use of gel electrophoresis as the last step of purification.

6.1.2. Protein Sequencing

BDNF was either sequenced directly (55 pmole as determined by amino acid analysis, with an initial yield of 40 pmole for the amino terminal histidine) or cleaved as follows: 5 to 10 μg BDNF (from 5 different preparations) were cleaved according to the following procedures. V8:1 μg S. aureus V8 (Miles) was added to 5 μg BDNF in 0.2M NH4CO3, pH 8.0 containing 10% acetonitrile (total volume: 50 μl) and incubated overnight at room temperature. Trypsin: 1 μg TPCK-treated trypsin (bovine pancreas, Sigma Type XIII) was added to 8 μg BDNF in Tris-HCl (0.1M, pH 8.0) containing 10 mM CaCl2 (total volume: 40 μl) and incubated overnight at 37° C. Cyanogen bromide (CNBr): 10 μg BDNF were incubated for 3 hours at room temperature (total volume: 60 μl) with 10% (w/v) CNBr in 70% (v/v) formic acid (final concentrations). After addition of 500 μl H2O at the end of the reaction, the sample was concentrated to 50 μl in a speed-vac. 50 μl Tris-HCl (1.0M, pH 8.0) were added together with 5 μl β-mercaptoethanol and the sample was incubated overnight at 37° C. After addition of 5 μl iodomethane, the sample was evaporated to dryness on a speed-vac. Reduction and alkylation of BDNF after CNBr cleavage were found to be necessary: no fragments were obtained without reduction, as revealed by HPLC and Swank-Munkres SDS-gel electrophoresis (Swank and Munkres, 1971, Anal. Biochem. 39:462–477). This indicates that disulfide bridges are present in BDNF, and arranged in such a way that none of the cleavages can give rise to free peptides. After all cleavages, the dried samples were resuspended in 0.1% trifluoroacetic acid (TFA) and applied onto a reverse phase C8 microbore HPLC column (Applied Biosystems) and the peptides eluted at 0.1 ml/min, using a 60 min linear gradient of 0–60% acetonitrile in 0.1% TFA. Detection was at 214 nm with a Waters 441 UV detector. The peptides were sequenced by automated Edman degradation on a gas phase microsequencer (model 470A Applied Biosystems), according to Hewick (1981, J. Biol. Chem. 256:7990–7997) and Hunkapillar (1983, Methods Enzymol. 91:227–236). Detection of the PTH amino acids was as described by Lottspeich (1985, J. Chromatogr. 326:321–327).

6.1.3. Preparation of DNA Templates

Pig genomic DNA was isolated according to the method of Herrmann and Frischauf (1987, Methods Enzymol. 152:180–183).

For preparation of cDNA, total RNA was obtained from a 6 gram sample of superior colliculus of pig brain. The tissue specimen was obtained, dissected and frozen in liquid nitrogen at a local slaughterhouse. Standard methods (Okayama et al., 1987, Methods Enzymol. 154:3–28) were utilized to extract the RNA. Eighty μg total RNA was transcribed with the reverse transcriptase of the Moloney murine leukemia virus (BRL, according to the manufacturer's instructions except for the addition of 1 μl RNasin and the omission of actinomycin D), using the primer mixture CGGATCCGAATTCTGCAGTTTTTTTTTTTT with A, C or G as terminal 3' nucleotide (oligo3, designed to match a 3' poly-A stretch and containing recognition sites for BamHI, EcoRI and PstI).

6.1.4. Polymerase Chain Reaction

Polymerase chain reaction (PCR) was performed according to the method described in Saiki et al., (1985, Science 230:1350–1354).

TABLE IV

6.2. RESULTS AND DISCUSSION
6.2.1. RESULTS OF PROTEIN MICROSEQUENCING
The results of protein microsequencing are presented in Table IV.
EXPERIMENTALLY DETERMINED PEPTIDE SEQUENCE OF BDNF

| | |
|---|---|
| N-terminal | HSDPARRGELSV |
| V8 | XVTAADKKTAVD |
| V8 | KVPVSKGQLKQYFYE |
| CNBr | XGGTVTVLEKVP(V) (S) |
| CNBr | GYTKEGXRGIXRGI |
| Trypsin | (T)AVDMSGGTVTVLEK |
| Trypsin | ALTMDSK |

Combined sequence VTAADKKTAVDMSGGTVTVLEKVPVSKGQL-KQYFYE underlined amino acids represent sequences encoded by oligonucleotide primers used in PCR; see Section 6.1.2.

Four contiguous segments of amino acid sequences were determined using Edman degradation, which could, in turn, be used to deduce a sequence of 36 amino acids representing approximately one-third of the entire amino acid sequence.

6.2.2. Synthesis of Oligonucleotides and Use of PCR to Obtain DNA Encoding an Amino Acid Fragment

Two fully degenerate 17-mer oligonucleotide primers were chemically synthesized, based on the coding sequences for segments of six amino acids near the amino-terminal and carboxyl-terminal ends, respectively, of the 36 amino acid residue fragment described in Section 6.2.1., supra. In particular, two separate mixtures of 17-mer oligonucleotides (corresponding to all possible codons and designated oligo1 and oligo2) based on the sequence AADKKT (sense) and KQYFYE (antisense) (underlined in Table III) were chemically synthesized, and 150 pmole of each primer were added to 1 μg pig genomic DNA template. Thirty-Five amplification cycles were performed using the polymerase chain reaction (PCR) according to the instructions of the manufacturers (GeneAmp TM, Perkin-Elmer Cetus) Denaturation was at 94° C. for one minute, primer annealing at 45° C. for 2 min. and primer extension at 72° C. for 2 min. A DNA band of the predicted size (101 bp) was cut out from a 3% agarose gel (stained with ethidium bromide) and asymmetrically amplified as described by Innis et al. (1988, Proc. Natl. Acad. Sci. U.S.A. 85:9436-9440) with a 100-fold excess of either oligo1 or oligo2.

6.2.3. Nucleotide Sequence of cDNA Fragment

The resulting sense and antisense DNA fragments were sequenced by the dideoxynucleotide chain termination method (Sanger et al., 1979, Proc. Natl. Acad. Sci. U.S.A. 72:3918-3921) using the $^{32}P$ end-labelled oligonucleotides 1 and 2 as primers. The observed nucleotide sequence contained only one open reading frame uninterrupted by a chain termination codon. The deduced amino acid sequence for this open reading frame was completely consistent with the actual amino acid sequence determined for this region of porcine BDNF.

6.2.4. Cloning of the Entire Porcine BDNF cDNA

The complete coding region for porcine BDNF was molecularly cloned in two overlapping segments. In order to obtain the 3' portion (relative to the sense strand) of the BDNF cDNA, a 30-mer oligonucleotide primer containing 21 bases of exact sense strand BDNF sequence, from within the region described above, was synthesized to serve as a "sense primer". The nucleotide sequence of this primer was oligo 4, (5')AAACTAGT-CGACGGCATGGACATGTCGGG(3') [underlining indicates the sequence corresponding to sense strand of BDNF, from positions 643 to 663 on FIG. 1, encoding the amino acid sequence Thr-Ala-Val-Asp-Met-Ser-Gly (first two bases of Gly codon)]. The additional 9 nucleotides at the 5' end of this primer were included to provide convenient restriction endonuclease cleavage sites for Spe I and Sal I for use in molecular cloning. A three-fold degenerate 31-mer oligonucleotide primer was designed to be complementary to a stretch of poly-A preceded by any nucleotide (T, G, or C) on the sense strand of cDNA, and to contain recognition sites for the restriction endonucleases BamHI, EcoRI, and PstI. The sequence of this "antisense" primer (oligo 3) was (5')CGGATCCGAATTCT-GCAGTTTTTTTTTTTTX(3'), where X=A, C, or G. The synthetic oligonucleotide primers were utilized to amplify sequences from the porcine superior colliculus cDNA preparation described above, by PCR. Specifically, the 3' amplified DNA was obtained by using 10 μl of the reverse transcription reaction, 150 pmole of the sense primer (oligo 4) and 150 pmole of oligo3 as antisense primer in a PCR reaction. A Southern blot analysis was performed on the amplified DNA products and the band giving a hybridization signal with the $^{32}P$-end-labelled oligonucleotide AAGGATCCT-GCAGTTGGCCTTTCGAGACGG (oligo5, used as antisense primer in the 5' reaction described below and containing recognition sequences for BamHI and PstI) was cut out, extracted by the glassmilk method (gene clean TM) digested with EcoRI and SalI, cloned into a Bluescript SK+ plasmid (Stratagene) and sequenced.

In order to obtain the remainder (upstream or 5' portion) of the BDNF coding sequence, cDNA was prepared as described above, and poly-A tails were added at the 5' ends using terminal deoxynucleotide transferase. The same mixture of three 31-mer oligonucleotides each containing a stretch of 12 consecutive T residues, described above, was used to give a primer complementary to these added poly-A tails. A unique 30-mer oligonucleotide primer containing 17 bases corresponding to the complementary strand of the BDNF coding sequence, and with recognition sites for restriction endonucleases BamHI and PstI was synthesized. The sequence of this primer was (5')AAGGATCCT-GCAGTTGGCCTTTCGAGACGG(3') (oligo5, supra; underlining indicates the region complementary to the sense strand of the coding sequence of BDNF, from positions 709 to 693 on FIG. 1); this corresponds to the segment encoding the amino acid sequence Pro(last two bases of codon)-Val-Ser-Lys-Gly-Gln. The primers were added to the poly-A-tailed cDNA, and amplification by PCR was carried out as above. The reaction products were cut with PstI and cloned into Bluescript vector and the nucleotide sequence was determined by the dideoxynucleotide chain termination method.

6.2.5. Nucleotide Sequence of Porcine BDNF cDNA

The combined nucleotide sequence determined from the overlapping porcine BDNF cDNA clones is shown in FIG. 1 together with the deduced amino acid sequence. The sequence comprises an open reading frame for a polypeptide of 252 amino acids. The identification of the initiator Met codon (ATG) is based on the presence of two adjacent chain termination codohs (TAG-TGA) in the same reading frame, beginning 36 base-pairs upstream. The amino terminus of porcine BDNF, determined by direct sequence analysis on purified protein corresponds to residue His134 of this polypeptide. Thus, the sequencing data show that mature BDNF is derived by processing from a precursor polypeptide. The residue His134 is preceded immediately by the sequence Arg-Val-Arg-Arg. Such sequences of one basic amino acid residue followed by a neutral residue and then two more basic residues have been implicated as target sites for proteolytic processing of precursor polypeptides. The deduced amino acid sequence of mature BDNF predicts a protein of 119 amino acids (molecular weight 13,511 daltons) with basic charge (pI=9.99), properties consistent with previous characterization of BDNF by evaluation of biologically active factor after fractionation by two-dimensional gel electrophoresis. The amino acid sequence of portions of BDNF determined by protein microsequencing (a total of 64 amino acid residues) is in complete agreement with the amino acid sequence deduced from the nucleotide sequence of cDNA clones (underlined in FIG. 1). The sequence of the precursor polypeptide is consistent with processing of BDNF in at least two steps: first, a signal peptide of perhaps 18 residues would be cleaved from the amino terminus, followed by cleavage between Arg133 and His134 to liberate the mature polypeptide. If this model is correct, then the precursor could be designated preproBDNF.

7. EXAMPLE: BDNF GENE IS DISTINCT FROM THE NGF GENE IN DIVERSE VERTEBRATE SPECIES

7.1. Materials and Methods

7.1.1. Preparation of NGF and BDNF DNA Probes

A plasmid containing a synthetic gene encoding mature human NGF, incorporating the normal human NGF coding sequence with a few conservative codon substitutions to introduce convenient restriction endonuclease cleavage sites, was purchased from British Biotechnologies Limited. A pair of 18-mer oligonucleotide primers were synthesized to permit amplification of a 270 base pair segment of this gene, corresponding to the coding region for amino acid residues 9 to 111, by PCR. In order to obtain a labeled DNA probe, a PCR reaction of 10 cycles was carried out with $^{32}$P-dCTP. A BDNF probe was obtained by similar procedures, except that amplification was carried out using porcine genomic DNA as the original template, and the segment amplified corresponded to the coding region for amino acids 28 to 111 of mature BDNF. A complementary strand ("antisense") primer corresponding to the region of amino acids 106 to 111 was synthesized, and had the sequence (5')ACATACACAGGAAGTGTC(3'). A sense strand oligonucleotide primer was prepared for the region of amino acid residues 28-33 [(5')GCAGTGGACATGTCGGGT(3')]. Southern blot hybridization (Southern, 1975, J. Mol. Biol. 98:503-517) with these two probes was carried out under stringent conditions in 2×SSC at 68° C.

7.1.2. Sequencing of BDNF Genes from Various Species

The same two 18-mer oligonucleotides bracketing the coding region for amino acids 28 to 111 of mature porcine BDNF, described above, were used as primers to amplify, under standard PCR conditions, 252 base pair segments of genomic DNA of pig, rat, chicken, and human, and the resulting DNA reaction products were sequenced by the dideoxynucleotide chain termination method (Sanger et al., 1979, Proc. Natl. Acad. Sci. U.S.A. 72:3918-3921). In some cases the band of amplified DNA was cut out and extracted after agarose gel electrophoresis, and reamplified prior to sequencing. In other cases reamplification was not essential.

7.2. Results and Discussion

Prior to the instant invention, BDNF protein had been purified only from pig. It was of paramount importance to demonstrate unequivocally that BDNF is not simply the porcine nerve growth factor beta subunit (beta-NGF, or simply referred to herein as NGF), the purification and molecular cloning of which has not been reported to date. This was especially critical because the previously reported physical properties of porcine BDNF are virtually identical to those of the β-NGF monomer from a variety of species. The lack of a neutralizing antibody against porcine BDNF, and the previous lack of amino acid or nucleotide sequence information on porcine BDNF made it impossible to determine the exact relationship between BDNF and NGF. It was conceivable that the observed differences in biological activity between BDNF and NGF might, for example, simply reflect differences in NGF between pig and certain other species (e.g. mouse), or might result from differential modification of the NGF protein molecule in different tissues (e.g. pig brain versus mouse salivary gland), or from modifications inadvertently introduced into the protein at some step(s) during purification from pig brain.

If BDNF were found to be clearly distinct from NGF, it was of great interest to determine whether the BDNF gene is present in other species, notably man. Prior to the instant invention, no information was available concerning this point, because BDNF was purified from only one species. The presence of neurotrophic activity apparently distinct from NGF in a variety of crude extracts and conditioned media did not imply the existence of a substance identical or substantially equivalent to porcine BDNF.

Comparison of the predicted amino acid sequence of porcine BDNF with the known sequences of NGF from a number of species (human, bovine, guinea pig, mouse, chicken, and snake) indicated that BDNF is significantly less closely related to any vertebrate NGF than the NGF's are to each other (FIG. 2). A striking feature of the primary structure of mature BDNF is its similarity to that of NGF; with only 3 gaps introduced in the NGF sequences to optimize matching, 51 identities are common to the various NGFs (from snake to man) and BDNF (FIG. 2). Importantly, those identities include all 6 cysteine residues. Though the exact arrangement of BDNF's disulfide bridges are not yet known, it is clear that such bridges are present (Table III, legend). The 3 tryptophan and 2 phenylalanine residues found in BDNF are found at identical positions in NGF. We also note that 6 aspartic acid residues (out of 7 in BDNF) and 7 valine (out of 9) are present at identical positions in mammalian NGFs and BDNF. These 5 amino acids account for about half of the amino acid identities between the 2 proteins. Conversely, there are some striking differences between BDNF and all NGFs: in addition to the 3 gaps already mentioned, there are also 21 positions at which the amino acids are identical in all NGFs, but different in BDNF.

Most of BDNF's precursor sequence is unrelated to that of NGF, with 2 exceptions: the putative secretory signal sequence of BDNF shows 5 amino acid identities (out of 18 amino acids) and an overall striking relatedness with the signal sequence of mouse NGF, where cleavage has been demonstrated to occur after an alanine residue found in position 18 after the translation initiation methionine (Edwards et al., 1988, Mol. Cell Biol. 8:2456–2464). It seems likely that the alanine also found in position 18 in BDNF represents a potential cleavage site for the removal of BDNF's signal sequence. The other similarity with NGF starts at the only N-glycosylation consensus sequence (double underlined in FIG. 1), corresponding to asparagine 126. This asparagine is located 8 amino acids before the cleavage site giving rise to mature BDNF. The same arrangement is found in several NGFs, as well as the sequence Arg-X-Basic-Arg as the last 4 amino acids of the precursor (Schwarz et al., 1989, J. Neurochem. 52:1203–1209)

Proof that NGF and BDNF are encoded by distinct genes in a variety of vertebrate species was obtained by preparing DNA probes from molecularly cloned human NGF and porcine BDNF, and carrying out Southern blot hybridization with genomic DNA digested with restriction endonuclease EcoRI. Genomic DNAs were analyzed from the following sources: human, monkey, rat, mouse, dog, bovine, rabbit, chicken, and yeast. DNA was digested with EcoRI, and analyzed by Southern blotting, on duplicate filters, with a $^{32}$P-labeled human NGF probe and a porcine BDNF probe. Single bands were observed with each probe in all organisms tested except yeast. In most cases the bands hybridizing with the NGF and BDNF probes in any one organism were of different electrophoretic mobility, although in some cases (e.g. mouse DNA), the EcoRI fragments hybridizing to NGF and BDNF probes were of approximately the same size, and could not be resolved under the electrophoretic conditions used (FIG. 3).

A portion of the coding sequences for mature BDNF was amplified by PCR from genomic DNA of pig, rat, chicken, and human, and the nucleotide sequences determined. DNA sequence analysis of the amplified region from porcine genomic DNA exactly confirmed the sequence results obtained with molecular clones from porcine brain cDNA. The genomic sequences of rat, human, and chicken BDNF for this 252 base pair segment were also determined (FIGS. 4A through 4I). Remarkably, in rat and human the deduced amino acid sequence for the region of at least amino acids 28 to 111 was identical to that of porcine BDNF, although a number of nucleotide differences (e.g. conservative changes in the third position of a codon) were observed among the various species. In chicken a single amino acid substitution was observed in this region; residue 61 of the mature protein is a lysine in chicken compared to a methionine in mammalian BDNFs. The sequence data, together with the Southern blot hybridization experiment described above, provided unequivocal proof that BDNF is encoded by a highly conserved gene distinct from that encoding NGF.

8. EXAMPLE: PREPARATION OF RNA

Total RNA was extracted from adult female mice tissues according to Okayama et al. (1987, Methods Enzymol. 154:3–28). Briefly, frozen tissue was homogenized in 5.5M guanidinium thiocyanate, the lysate centrifuged to remove debris, and the supernatant overlaid onto a cushion of cesium trifluoroacetate adjusted to a density of 1.51 g/ml. After a 24 hour centrifugation at 125,000×g in a SW 27 swinging bucket rotor (Beckmann), the RNA was resuspended and precipitated with ethanol and 8M ammonium acetate and stored at −70° C. Electrophoresis was according to Lehrach et al. (1977, Biochemistry 16:4743–4751) on 1.3% agarose-formaldehyde gels. The RNA was transferred to nylon membranes (Hybond-N, Amersham) and hybridized overnight at 62° C. in 1 ml 2×SSC containing 50% formamide with a $^{32}$P-cRNA mouse BDNF probe ($10^7$ cpm, see below). Washing was for 60 min at 65° C. in 0.1×SSC. After washing, the blot was incubated for 60 min at room temperature with 0.1 μg/ml RNAse A (Pharmacia) and the film exposed at −70° C. (with intensifying screen) for 48 hours.

9. EXAMPLE: MOLECULAR CLONING AND CHARACTERIZATION OF HUMAN AND RAT BDNF GENES

9.1. Materials and Methods

9.1.1. Genomic DNA and cDNA Libraries

An adult human retina cDNA library, in lambda-ZAPII was obtained from Stratagene. A human placenta genomic DNA library in EMBL3/SP6/T7 was obtained from Clontech. A rat fetal brain cDNA library in λgt11 was obtained from Clontech. A rat genomic DNA library in EMBL3/SP6/T7 was obtained from Clontech. Both genomic libraries were prepared by partial digestion of genomic DNA with Sau 3A restriction endonuclease and ligation into the BamHI site of the vector. A rat brain cDNA library in lambda-ZAPII was obtained from Stratagene.

9.1.2. Preparation of BDNF DNA Probes $^{32}$P-labeled BDNF DNA probes were prepared using the same oligonucleotide primers described in Section 7.1.1., supra in PCR reaction with human genomic DNA in order to amplify the coding region for residues 28–111 of human BDNF. In parallel, a rat BDNF-specific $^{32}$P-labeled probe was obtained, using rat genomic DNA as a template for PCR.

9.1.3. Screening of Libraries

Lambda phage libraries were screened according to standard methods (Benton and Davis, 1977, Science 196:180–182; Maniatis et al., 1978, Cell. 15:687–701), hybridizing in 50% formaldehyde with dextran sulfate and Denhardt's solution at 42° C. Filters were prehybridized at 42° C. in 50% formamide, 5×SSCPE, 10% Denhardt's, 0.5 mg/ml Salmon sperm DNA, 0.1% SDS, and 10% dextran sulfate. Hybridization was carried out in the same buffer except that Denhardt's solution was at 2%, Salmon sperm DNA was at 0.1 mg/ml, and SDS and dextran sulfate were omitted. After hybridization filters were washed at 68° C. Human BDNF probe was used to screen human genomic DNA and retina cDNA libraries; rat BDNF probe was used to screen rat genomic DNA and brain cDNA libraries. Libraries were also screened with human and rat NGF probes, prepared as described in Section 7.1.1. supra.

9.2. Results and Discussion

At least 670,000 plaques were screened from each library. Positive human clones were considered to be those which hybridized with the human BDNF probe, but not with the human NGF probe described above. BDNF genomic clones were obtained from both the human and rat libraries at a frequency consistent with representation of the BDNF gene at one copy per haploid genome. For both rat and human genomic libraries, approximately one million plaques were screened. Three positives were obtained from the rat genomic library and one was obtained from the human genomic library. Positive clones from the human retinal and rat brain cDNA libraries were obtained at a frequency consistent with a gene expressed at very low levels; in rat brain cDNA, 2 positives were identified in 670,000; in human retinal cDNA library, one in 670,000 clones were identified. No positive clones were detected among 670,000 from the commercial cDNA library prepared from human fetal brain. Nucleotide sequencing was carried out on human BDNF cDNA and genomic clones, using synthetic oligonucleotide primers representing exact sequences from within the human and rat BDNF coding region, as determined in Section 7.1.2., supra. The longest human cDNA clone obtained, phBDNF-C-1, had an insert of approximately 1.6 to 1.8 kbp, and, as expected, contained the exact sequence of the portion of human BDNF determined after direct amplification from human genomic DNA, as described in Section 7.2., supra. Detailed sequence analysis of this cDNA (FIGS. 4A through 4I) clone revealed an open reading frame encoding a polypeptide of 247 amino acids, similar but not identical to the full-length precursor to porcine BDNF. Within the region corresponding to the mature BDNF polypeptide (e.g. from the codon for His134 to the chain termination codon) no differences in deduced amino acid sequence were found; all nucleotide substitutions between pig and man were conservative with respect to coding specificity. The remainder of the putative BDNF precursor polypeptide showed some amino acid sequence differences between human and pig, most notably the absence in the human BDNF gene of 5 of 6 consecutive Ser codohs seen in pig, resulting in a slightly shorter polypeptide (247 versus 252 amino acids).

Libraries prepared in vector EMBL3 have inserts of between 10 to 23 kbp of foreign DNA. The exact insert size in the human genomic BDNF clone analyzed in detail, λhBDNF-G-1, was not determined. However, the clone contained a single EcoRI restriction endonuclease fragment of approximately 4 kbp that hybridized with the labeled BDNF probe used to screen the library. This fragment is the expected size, based on the results of Southern blot hybridization of human genomic DNA with the porcine BDNF probe described above. Sequence analysis was carried out on the human clone, using synthetic oligonucleotides representing cDNA sequence to prime DNA synthesis from the bacteriophage DNA template. The sequence of the coding sequence for the putative human BDNF precursor was found to be identical to that in the human cDNA clone, with the exception of a single nucleotide substitution in the prepro region, corresponding to an amino acid substitution of methionine (ATG) for Valine (GTG), at nucleotide 785, in FIGS. 4A through 4I. This change may reflect a polymorphism in the human genome. As in the case of the human NGF gene, no intervening sequences were detected within the coding sequence for the putative human preproBDNF. Rat cDNA sequence data is also presented in FIGS. 4A through 4I.

10. EXAMPLE: EXPRESSION OF RECOMBINANT BDNF

10.1. Materials and Methods 10.1.1. Preparation of a BDNF Expression Vector

The sequence corresponding to pig preproBDNF was obtained by using the oligonucleotide primers (150 pmole each) ATAATCTAGATGAC-CATCCTTTTCCTT (sense) ATAATCTAGAC-TATCTTCCCCTCTTAAT (antisense) in a PCR reaction using 1 μg of pig genomic template (each primer has an added XbaI site). The amplification reaction was as described, except that the annealing temperature was 50° C. After digestion with XbaI, the amplified DNA was ligated in the XbaI site of the plasmid pCMV1 to produce pCMV1-pBDNF−1 (−1 denotes sense orientation in FIG. 5 and corresponds to COS+ in Table V), and the plasmid was introduced into XL-1 bacteria by electropotation.

10.1.2. Expression of BDNF in COS Cells pCMV1-pBDNF plasmid DNA from positive clones (checked by hybridization with oligo5, FIG. 2) was cut with both XbaI and PstI. The size of the resulting products allowed us to determine the orientation of the inserts, and both plasmids were used to transfect COS cells by the calcium phosphate method (Chen et al., 1987, Mol. Cell Biol. 7:2745-2752), and the growth medium collected after 24 h. BDNF activity was tested in the chick embryo dorsal root ganglion bioassay discussed in detail supra.

10.2. Results and Discussion

E8 chick spinal sensory neurons were plated (6,000 per well), incubated for 24 h and counted after 24 h (Lindsay et al., 1985, Develop. Biol. 112: 319-328). The values are the means of triplicate determinations±standard deviation. BDNF and NGF were used at 1 ng/ml, concentrations at which maximal survival is observed with either factor. COS+ refers to cells transfected with plasmids containing the BDNF insert in the sense orientation, COS− to cells transfected with plasmids containing the BDNF inserts in the reverse orientation. COS refers to non-transfected cells. At dilutions higher than 1:20, no survival above control was seen with either COS− or COS conditioned medium. In all experiments without NGF, a monoclonal anti-NGF antibody (Korsching et al., 1988, Proc. Natl. Acad. Sci. U.S.A. 80:3513-3516) was used at 1 μg/ml.

As shown in Table V, only the medium obtained from cultures of COS cells bearing pCMV1-pBDNF plasmid in the sense orientation was associated with chick sensory neuron survival above control values. Therefore, the recombinant BDNF is biologically active. Further, addition of BDNF isolated from pig brain did not increase the survival of sensory neurons significantly above survival levels resulting from recombinant BDNF alone, indicating that the recombinant BDNF is capable of saturating BDNF receptors. Recombinant BDNF was also observed to have an additive or synergistic effect toward promoting chick sensory neuron survival when used together with NGF.

TABLE V

| SURVIVAL OF CULTURED CHICK SENSORY NEURONS | | | |
|---|---|---|---|
| COS medium (final dilution) | 1:20 | 1:50 | 1:200 |
| COS+ | | 2,510 ± 263 | 2,833 ± 171 |
| COS− | 211 ± 16 | | |
| COS | 250 ± 87 | | |
| BDNF + COS+ | | 2,516 ± 209 | |
| NGF + COS+ | | 5,770 ± 72 | |
| BDNF alone | | 2,718 ± 424 | |

11. EXAMPLE: GENERATION OF ANTIBODIES TO BDNF

11.1. Materials and Methods

A polyclonal antiserum specific for BDNF, designated sera 4, was generated in a NZ white rabbit by immunization with a synthetic peptide.

11.1.1. Peptide Synthesis and Coupling to Carrier

A peptide consisting of 34 amino acid residues, designated B5, was synthesized by conventional methods. It has the following amino acid sequence, corresponding to 33 residues of mature BDNF (residues 153 to 185 of the complete porcine preproBDNF sequence shown in FIG. 1) with an additional cysteine residue at the amino-terminus (shown in italics) to permit coupling to a carrier protein using m-maleimidobenzoic acid-N-hydroxysuccinimide (MBS), if desired:

*Cys*-Val-Thr-Ala-Ala-Asp-Lys-Lys-Thr-Ala-Val-
Asp-Met-Ser-Gly-Gly-Thr-Val-Thr-Val-Leu-Glu-
Lys-Val-Pro-Val-Ser-Lys-Gly-Gln-Leu-Lys-Gln-
Tyr

The B5 peptide was coupled to bovine serum albumin (BSA) using bis-diazo benzidine (BDB). Fresh BDB was prepared by dissolving 46 mg benzidine-HCl (p-diaminodiphenyl-HCl, obtained from Sigma) in 9.0 ml of 0.2 N HCl. 35 mg $NaNO^2$ was dissolved in 1.0 ml $H_2O$ and added to the benzidine solution, and stirred for 1 hour at 4° C. 21 mg of BSA was dissolved in 3.0 ml of 0.16M borate, 0.13 M NaCl, pH 9.0. Approximately 15 mg of B5 peptide was dissolved in 1.5 ml borate-NaCl buffer, pH 0.0. The peptide solution was added to the BSA solution, and placed in ice. 1.0 ml of BDB was added to the BSA-peptide solution, and the reaction mixture was incubated with stirring for 2 hours at 4° C.; the pH was monitored and maintained in the range of 9.0 by the addition of small amounts of 0.5M NAOH, as required. The reaction was terminated by addition of 0.2 ml of 1% phenol-buffered solution. Excess reagents were removed by dialysis against phosphate buffered saline (PBS).

11.1.2. Immunization

A total of six-rabbits were immunized according to the following protocol:
Rabbits 1 and 4—peptide B5 coupled at its C-terminus to BSA, using BDB;
Rabbits 2 and 3—peptide B5 coupled at its N-terminus to BSA, using MBS;
Rabbits 5 and 6-peptide B5 mixed with powdered nitrocellulose.

In all cases the first immunization used 1 mg of immunogen (100 μg B5/500 μg nitrocellulose for rabbits 5 and 6) in 0.5 ml PBS plus 0.5 ml ml complete Freund's adjuvant. This mixture was injected subcutaneously into multiple sites on the back. The second immunization was carried out three weeks later, and was identical to the first except that incomplete Freund's adjuvant was used in place of complete Freund's adjuvant. Subsequent boosts occurred at intervals of 4–6 weeks. Rabbits were bled 1 week after immunization, and the antisera routinely checked for binding to the pure B5 peptide by enzyme-linked immunosorbent assay (ELISA).

11.1.3. Detection of Antibody Binding to BDNF

100 μg of antigen (B5 peptide) in $H_2O$ was added to wells on a microtiter plate and allowed to dry overnight, then washed briefly with $H_2O$ and blocked with 100 μg 1% gelatin for 30 minutes at room temperature. Wells were washed three times with distilled water, and then 100 μg of antisera was added and allowed to incubate at 4° C. overnight. Wells were then washed three times in PBS/0.05% triton X-100, after which 100 μg peroxidase labeled anti-rabbit immunoassay (1/1000 dilution) was added to wells and incubated at room temperature for three hours. Wells were washed twice, and 100 μg ABTS solution (10 mg ABTS (Sigma) dissolved in 10 ml 0.1M NaCitrate pH 4.0 plus 10 μg $H_2O_2$) was added and incubated for about 5 minutes, until color developed. The reaction was stopped by the addition of 10 μg 1% $NaN_3$. Samples were diluted 1:5 with $H_2O$ and optical density was measured at 415 nm.

11.2. Results and Discussion

The antiserum from rabbit 4 (sera 4) showed the highest titer, (FIG. 6A) and was utilized in subsequent experiments. Antibodies from sera 4 were partially purified by precipitation with ammonium sulphate; to a portion of antiserum an equal volume of saturated ammonium sulfate was added slowly, with stirring, and the solution was stirred for a further 15 minutes, then centrifuged at 2,000×g. The pellet was washed twice in 50% saturated ammonium sulphate, then redissolved in PBS in a volume corresponding to the original volume of serum. Ammonium sulphate was removed by dialysis against several changes of PBS. The dialyzed solution was aliquoted in 1.0 ml volumes and subjected to lyophilization using a speed-vac. A sample of sera 4 antibody was resuspended in 0.5 ml $H_2O$ and tested for reactivity with peptide B5 by ELISA, and was found to react to a dilution of 1:4000.

Polyclonal antibodies to a synthetic peptide (B5) corresponding to a 33 amino acid fragment of porcine BDNF were generated by immunizing rabbits as described above. Sera 4, which showed the highest titer against the synthetic peptide, showed reactivity with purified BDNF from porcine brain by ELISA (FIG. 6B). Weak reactivity was also detected by immunoblotting (DATA NOT SHOWN). However, the antiserum was unable to block the activity of BDNF in a biological assay on chick embryo dorsal root ganglion sensory neurons.

12. EXAMPLE: NOVEL BIOLOGICAL EFFECTS OF BDNF

The following observations indicate that BDNF is capable of (i) sustaining the survival and inducing the fully differentiated state of CNS dopaminergic neurons; (ii) sustaining the survival of CNS cholinergic neurons; and (iii) suppressing the proliferation of astroglial cells. These biological effects of BDNF have not been described previously. As dopaminergic neurons, cholinergic neurons, and astroglial cells may each be associated with neurological diseases or disorders, BDNF may prove to be useful in the treatment of neuropathologies involving these cell populations.

12.1. Materials and Methods

12.1.1. Methods for Culturing Dopaminergic Substantia Nigra Neurons

Ventral mesencephalon was dissected from brains of rat embryos varying in age from embryonic day 13 to embryonic day 15. Typically, two litters were used in each experiment. The dissection solution had the following composition: NaCl, 136.8 mM, KCl, 2.7 mM, $Na_2HPO_4.7H_2O$, 8.0 mM, $KH_2PO_4$, 1.5 mM, glucose, 6 mg/ml, and BSA, 0.1 mg/ml, pH 7.4. This solution was prepared and subsequently filter sterilized through a 0.2 μM pore filter. The dissection was performed under non-sterile conditions. Once the tissue was dissected from all the brains, the rest of the procedure was carried out under sterile conditions. The tissue fragments were placed in a 35 mm culture dish and minced using a fine scissors. Two ml of F-12 nutrient media containing 0.125% trypsin was then added to the tissue, and incubated at 37° C. At the end of this incubation period, DNAseI was added to the slurry such that the final concentration was 80 ng/ml. Another identical incubation was carried out, and the tissue slurry was subsequently added to 8.0 ml of growth medium consisting of Minimal Essential Medium (MEM) supplemented with 2 mM glutamine, 6 mg/ml glucose, 5 units/ml penicillin, 5 mg/ml streptomycin, and 7.5% fetal calf serum (FCS). The sample was centrifuged in a tabletop centrifuge at room temperature at 500 rpm for a period of 5 minutes. The medium was aspirated, and 2 ml growth medium was added to the cell pellet. A fire polished pipette with an opening of 1 mm was used to triturate the cells eight times. The remaining tissue fragments were allowed to settle by gravity, and a small aliquot of the supernatant was taken to assess cell number by counting in a hemocytometer. After cell density was determined, the cells were plated into tissue culture plates at a density of $50,000/cm^2$.

The culture plates were prepared on the day prior to dissection. Tissue plates (24 well, $2 cm^2$/well) were precoated with polyornithine (molecular weight 30,000–70,000 g/mol), 0.5 mg/ml, at room temperature for 3 hours. The plates were extensively washed with water, and subsequently treated with mouse laminin, 5 μg/ml, at room temperature for 3 hours. The plates were then washed with water as above, and incubated overnight at 37° C. in a humidified atmosphere consisting of 5% $CO_2$, 95% air, in the presence of growth medium. The medium in the plates was removed the following day and replaced with fresh growth medium.

Once the cells were plated onto the culture plates, the cells were placed in an incubator set at 37° C. and 5% $CO_2/95\%$ air for a period of 24 hours. The culture medium was changed to a serum-free formulation (SFM) having the following composition: a 1:1 (vol:vol) mixture of Basal Eagle Medium (BEM) and nutrient mixture F-12 with glucose (33 mM), glutamine (2 mM), $NaHCO_3$ (15 mM), HEPES (10 mM), supplemented with insulin (25 μg/ml), transferrin (100 μg/ml), putrescine (60 μM), progesterone (20 nM), sodium selenite (30 nM), penicillin (5 U/ml), streptomycin (5 mg/ml), and $T_3$ (30 nM). In some experiments, purified BDNF was added to the cultures after the media change to SFM on culture day 2.

The solutions used for culturing dopaminergic neurons were prepared using water taken from a Milli-Q reagent water system. The tissue culture media formulations were obtained through Gibco Laboratories (Santa Clara, Calif.), as was the fetal calf serum (lot number 43N1086) and the mouse laminin. All other media components were purchased from Sigma Chemical (St. Louis, Mo.), and were cell culture tested grade. The polyornithine and DNAseI were also obtained from Sigma. Trypsin was obtained from Worthington (Freehold, N.J.), lot number 3667. Commercial chemicals were of analytical grade, purchased from Baker Chemical (Phillipsburg, N.J.). The BDNF used in these experiments was purified from pig brain by Dr. Y.-A. Barde, according to the procedure of Barde et al., 1982 (supra).

12.1.2. Methods for Immunocytochemical Staining of Ventral Mesencephalon Cultures Fixative solutions were prepared fresh for each experiment. For the staining of tyrosine hydroxylase (TH), the fixative was 4.0% paraformaldehyde in Sorenson's phosphate buffer. The Sorenson buffer was prepared by adding a 0.2M solution of $KH_2PO_4$ to a stock of 0.2M $Na_2HPO_4$ until the pH reached 7.3. The paraformaldehyde was subsequently added to the solution and briefly heated, to allow it to be dissolved, and cooled to room temperature before use.

To begin the procedure, culture medium was removed from the culture dishes by gentle suction, and the proper fixative solution was gently added to the dish. A room temperature incubation of 20 minutes was carried out. Three washes in Sorenson's phosphate buffer, for 5 minutes each, with gentle rotation, followed. The cells were then incubated in a quench solution for 30 minutes at room temperature with gentle rotation. The quench solution for the cultures to be stained for TH consisted of Sorenson's phosphate buffer containing 2% normal horse serum. Next, the cultures were incubated in permeabilization buffer at room temperature for 30 minutes with gentle rotation. The solution consisted of Sorenson's buffer containing 0.2% saponin, and 1.5% of normal horse serum for the cultures to be stained for TH. Following the permeabilization step, the cultures were incubated in the presence of primary antibody overnight at 4° C. The antibody against rat TH was a mouse monoclonal antibody of isotype IgG2a. It was used at 40 μg/ml in a solution of 10 mM $NaPO_4$, 50 mM NaCl, 0.2% saponin pH 7.5. Following the primary antibody incubation, the cultures were washed 5 times for 15 minutes each in the appropriate permeabilization buffer. Next, the cultures were incubated with secondary antibody conjugated to biotin, that is biotinylated horse anti-mouse IgG. This incubation was carried out at room temperature for two hours with gentle rotation. Washes identical to those described above followed, and the cultures were then incubated in the presence of a preformed avidin-biotinylated horseradishperoxidase complex (ABC reagent, Vector Laboratories, Burlingame, Calif.) prepared according to manufacturer's protocol. After a 30 min. incubation at room temperature with gentle rotation, the cultures were washed as described above. The cultures were subsequently incubated with 55 mM Tris-Cl pH 7.3 containing 0.5 mg/ml diaminobenzidine and 0.01% hydrogen peroxide. The development of reaction product was allowed to proceed for 2–5 min. after which the solution was removed and the cultures were washed several times with ice cold PBS. The number of positive cells/$cm^2$ was then ascertained.

The paraformaldehyde and the glutaraldehyde were obtained from Fluka Chemical. Vectastain kits containing normal serum (used as a blocking agent), biotinylated, affinity-purified anti-immunoglobulin, avidin DH, and biotinylated HRP-H were purchased from Vector Laboratories. The diaminobenzidine was obtained from BRL (Gaithersberg, Md.).

12.1.3. Methods Used in Measuring $^3$H-Dopamine Uptake in Ventral Mesencephalon Cultures $^3$H-dopamine ($^3$H-DA) uptake was performed as described by Dal Toso et al. (1988, J. Neurosci. 8:733–745) with minor modifications. The uptake buffer had the following composition: NaCl, 136.8 mM, KCl, 2.7 mM, $Na_2HPO_4.7H_2O$, 8.0 mM, $KH_2PO_4$, 1.5 mM, glucose, 5.0 mM, $caCl_22$, 1.0 mM, $MgSO_4$, 1.0 mM, ascorbic acid, 0.1 mM, pargyline, 0.1 mM, pH 7.4 When necessary, 5.0 μM benztropine mesylate (BZT) was added to the uptake buffer.

The cells were washed once with prewarmed (37° C.) uptake buffer, and replaced with 0.4 ml uptake buffer/2 cm$^2$ well. The cultures were then preincubated for 5 min. at 37° C. At the end of this preincubation 0.1 ml $^3$H-DA, in uptake buffer (250 nM, 40 Ci/mMol), was added such that the final concentration of $^3$H-DA in the buffer was 50 nM. The cultures were incubated at 37° C. for 15 min., followed by four washes at 4° C., 0.5 ml each, with uptake buffer. Two additional washes with ice cold PBS (10 mM NaPO$_4$, 150 mM NaCl, pH 7.6) were carried out as well. After the last wash was completed, 0.2 ml/2 cm$^2$ well 0.5N NaOH was added to the cells, and allowed to stand at room temperature for two hours. The NaOH extract was subsequently collected, and counted in a scintillation counter (Packard, LS 500TD) with 10 ml "ultimagold" scintillation fluid. Specific uptake was defined as that uptake which was abolished in the presence of 5 μM BZT. Typically, this represented 70-90% of the total uptake observed.

$^3$H-DA was obtained from NEN (Boston, Mass.). Ascorbate, pargyline, BZT, and glucose were obtained from Sigma (St. Louis, Mo.). The ultimagold scintillation fluid was purchased from Packard (Sterling, Va.).

12.1.4. Methods for Producing Cultures of Basal Forebrain Cholinergic Neurons

Primary cultures of basal forebrain cholinergic cells were produced from embryonic day 17 rats. Specifically, the cholinergic neurons used in this study were derived from the medial septal nucleus and the nucleus of the diagonal band of Broca. This neuronal population projects primarily to the hippocampus. The dissociated mixed cultures (neurons and glia) were produced by the following procedure. The septal region was dissected free from the surrounding tissue, and removed from the fetal brain. The tissue pieces were then pooled, minced with scissors, and treated for 20 minutes at 37° C. with 12.5% trypsin. The trypsin was inactivated by dilution in the plating medium (Dulbecco's modified Eagle medium (DMEM) containing 1% penicillin and streptomycin, 5% horse serum, and 1% N3, a hormone supplement). A single cell suspension was produced by trituration of the digested tissue fragments with a fire polished pasteur pipette. The dissociated cells were counted on a hemocytometer and plated at the appropriate density in the plating medium. Test ligands were added to the cultures five to six hours after plating and the cells were then grown in vitro for ten days with medium changes being made every three days.

12.1.5. Choline Acetyl Transferase Assays

Following the treatment period the cells were either used for choline acetyltransferase (CAT) enzyme assays or processed for immunohistochemical staining for CAT by the following protocol. The monoclonal antibody to CAT was purchased from Boehringer Mannheim Biochemical Co. and has been characterized elsewhere. At the end of the experimental period the cells were rinsed twice with DMEM. The cultures were fixed by a two step procedure; 50 μl of 4% paraformaldehyde was added to 50 μl of DMEM for a 10 minute incubation period. This solution was removed and replaced with 100 μl of 4% paraformaldehyde and the incubation was continued for 30 minutes at room temperature. Following the fixation, the cells were rinsed three times with phosphate buffered saline (PBS) and permeabilized by a 30 minute incubation with saponin (0.5 mg/ml). The detergent was removed with three washes of PBS, and a blocking solution of 5% normal rabbit serum was added for 30 minutes. The primary antibody was added at a dilution of 1:3 in 1% normal rabbit serum, subsequent to the removal of the blocking solution, and the cultures were incubated overnight at 4° C. The solution containing the primary antibody was removed with a PBS wash. The bound immunoglobulin was detected by the Vectastain "ABC" method. Diaminobenzidene tetrahydrochloride (DAB) was used as the substrate for the peroxidase reaction which was usually carried out for one to five minutes. The reaction was stopped by rinsing the cultures two times with 0.1M tris-HCl pH 7.2. The cultures were stored in 50 mM tris, pH 7.6 containing 0.15M NaCl, 42% glycerol, and 0.15% Zephiran (Pierce Chemical Co., Rockville, Ill.) at 4° C.

12.1.6. Method of Generating Purified Astroglial Cell Cultures

Purified glial cultures were prepared essentially by the method of McCarthy and DeVellis (McCarthy, K. D., and DeVellis, J., 1980, J. Cell Biol. 85:890-902) from postnatal day 1-2 rat hippocampus. Hippocampi were removed from five pups and minced with scissors. The tissue pieces were then digested in 2 mls of 0.125% trypsin for 20 minutes at 37° C. The protease was inactivated by dilution, with plating medium (10% fetal bovine serum Gibco, DMEM, 0.5% penicillin (5000 mcg/ml) and 0.5% glutamine). A single cell suspension was produced by passing the digested tissue fragments through a constricted pasteur pipette. The cells were pelleted by centrifugation at 900 rpm for five minutes, resuspended in plating medium, and then counted on a hemocytometer. The single cell suspension was divided into three, 75 cm$^2$ tissue culture flasks and the cells were-grown to approximately 80% of confluency. The cells were then subcultured by a trypsinization protocol similar to that just described. The glial cells were counted and plated at a density of 10,000 cells/0.9cm$^2$.

12.2. Results 12.2.1. The Effect of BDNF on Tyrosine Hydroxylase Present in Ventral Mesencephalon Cultures Immunocytochemical staining, as described in section 12.1.2, supra, was used to measure the effect of BDNF on the number of tyrosine hydroxylase (TH) positive cells (FIG. 7). A maximal increase of more than 200 percent of control was observed by day 8 in BDNF stimulated cultures of ventral mesencephalon cells. A very slight increase was observed as early as culture day 3 in BDNF-stimulated cultures.

12.2.2. The Effect of BDNF on Dopamine Uptake by Ventral Mesencephalon Cultures $^3$H-dopamine ($^3$H-DA) uptake was measured according to the method of Dal Taso et al. (1988, J. Neurosci. 8:733-745) with minor modifications, as described in section 12.1.3, supra. A slight increase in dopamine uptake was observed in BDNF stimulated ventral mesencephalon cultures by day 8 in culture (FIG. 8). 12.2.3. The Effect of BDNF on Choline Acetyltransferase Expression by Forebrain Cholinergic Neurons FIG. 9A depicts the effect of BDNF on the number of CAT positive cells following a growth period of 12 days in vitro. A 5.9 fold increase in CAT cell number was observed with the addition of 100 ng/ml of BDNF, while the EC50 was calculated to be 10 ng/ml. As a positive control, cultures at 260,000 (Black bar) or 150,000 (hatched bar) cells per well were treated in an identical manner with NGF (FIG. 9B). The 260,000 cell per well density corresponds to that used for the BDNF study. This increase in the number of CAT immunopositive cells is similar to that which has been reported previously. The potential for BDNF to act on cholinergic neurons was also examined by measuring CAT enzyme activity (F. Fonnum; J. Neurochemistry, 1975, 24:407–409). FIG. 10 depicts the changes in CAT produced with a BDNF treatment. In this case, a 1.8 fold increase was achieved with 100 ng/ml of BDNF and the EC50 was calculated to be 61 ng/ml.

12.2.4. Effects of BDNF or EGF on Astroglial Cell Cultures

Type II astrocytes have been demonstrated to have high affinity receptors for a variety of neurotransmitters and neuropeptides. Thus astrocytes are capable of responding to neuronally derived signals. For this reason and because the type II astrocytes represent a cellular component in the primary cultures, a possible direct effect of BDNF on glial cells was tested. The cells were kept in vitro for four days prior to the addition of growth factors to allow them to reach approximately 60% of confluency and were then treated for 42 hours with EGF or BDNF. For the last 18 hours of the incubation [$^3$H]methylthymidine was present in the medium. The effect of EGF is shown in FIG. 11A. As has been previously reported, EGF was found to be mitogenic for the astrocytes. The maximal response was observed with 10 ng/ml of EGF which produced a 5.2-fold increase in [$^3$H]methylthymidine incorporation. FIG. 11B depicts the effect of BDNF on [$^3$H]methylthymidine incorporation. The response to BDNF appears to be biphasic: very low doses (0.1 ng/ml) produced a slight increase in thymidine incorporation; while doses greater than 1 ng/ml BDNF inhibited the incorporation of [$^2$H]methylthymidine. BDNF at a dosage of 5 ng/ml produced an inhibition of 24% suggesting a decrease in the rate of glial cell proliferation over the treatment period.

12.3. Discussion

These in vitro experiments clearly show that BDNF sustains the survival or induces the fully differentiated state of dopaminergic neurons of the developing rat substantia nigra, as shown by staining for tyrosine hydroxylase and dopamine uptake in cultures of these neurons derived from embryonic rat mesencephalon. As these are the neurons which degenerate in Parkinson's disease, it is highly probable that BDNF has therapeutic potential in Parkinson' disease either by reducing loss of neurons or by increasing the levels of tyrosine hydroxylase (the rate limiting enzyme in dopamine synthesis) or possibly both.

Furthermore, like nerve growth (NGF), BDNF appears to have an effect on the survival of cholinergic neurons of the rat basal forebrain as shown by increased choline acetyltransferase (CAT) staining, increased CAT activity and increased acetylcholinesterase staining in cultures of rat embryo medial septal nucleus and nucleus of the diagonal band of Broca. Accordingly, BDNF alone or in conjunction with NGF may be useful in the treatment of diseases or disorders that affect the cholinergic neurons of the basal forebrain, including, for example, Alzheimer's disease.

13. EXAMPLE: IDENTIFICATION OF A NOVEL GENE IN THE BDNF/NGF GENE FAMILY

The approach of identifying novel members of the NGF/BDNF gene family by utilizing PCR with degenerate oligonucleotides, based on the segments of amino acid sequence conservation between NGF and BDNF (Boxes 1–4, see section 5.8), was first tested by determining whether pairs of such primers could be utilized to amplify both NGF and BDNF gene sequences from genomic DNA of several species. This method was then used to identify a novel gene which shares homology with NGF and BDNF in all four boxes of homology noted.

13.1. Materials and Methods 13.1.1. Polymerase Chain Reaction

PCR was performed essentially as described in Section 6, supra.

13.2. Results 13.2.1. Amplification of Both NGF and BDNF Sequences from Genomic DNA Degenerate synthetic oligonucleotide primers were synthesized corresponding to portions of Box 1 and Box 2 of amino acid sequence conservation between NGF and BDNF (see section 5.8 above), and utilized in a PCR reaction with rat genomic DNA as template. The exact primer sequences were as follows (positions of degeneracy, with mixture of two or more bases included in oligonucleotide synthesis step, shown in parentheses; underlining italics indicate tails with multiple restriction endonuclease cleavage sites provided to facilitate ligation to vector in a subsequent cloning step; A=adenine, G=guanine, C=cytosine, T=thymine, M=mixture of A,G,C,T):

Box 1 (sense), primer 1B:

5'-*GACTCGAGTCGACTCGG*TGTG(C,T-)GACAG(C,T)(A,G)T(C,T,A)AG-3'

Box 2 (antisense), primer 2C:

5'-*CCAAGCTTCTAGAATT*CCA(C,T)TT(N)GT(C,T)TC(A,G)(A,T)A(A,G-)AA(A,G),TA(C,T)TG-3'

300 ng of each degenerate primer mixture was added to 500 ng of rat genomic DNA in 100 microliters of the standard reaction mixture for PCR. 35 cycles were carried out, each consisting of incubation for 1 minute at 94° C., 2 minutes at 43° C., and 2 minutes at 72° C. The anticipated size of the product of PCR amplification of either the BDNF or NGF gene using these primers would be 175 base pairs, including the two 17-mer "tails" (underlined) included for convenience in subsequent cloning steps. Electrophoresis of the reaction mixture on an 8% polyacrylamide/5% glycerol gel yielded a major band of amplified DNA of the anticipated size, 175 bp.

13.2.2. Detection of Sequences Complementary to the BDNF/NGF Probe in Genomic DNAs of Various Species The 175 bp band was removed from the acrylamide gel by electroelution, and amplified further in a second PCR reaction of seven cycles, under identical reaction conditions to the first except that the concentrations of dGTP, dATP, and TTP were lowered to 50 μM each, and alpha-$^{32}$P-dCTP tracer wets utilized in place of unlabeled dCTP. The radiolabeled DNA product was separated from reaction components by chromatography on a sizing column. This probe, designated "R1B/2C" (for rat DNA amplified from primers 1B and 2C), was then utilized to detect complementary sequences in genomic DNAs of various vertebrate species (results with rat, mouse, and chicken are shown in FIG. 12), after digestion with EcoRI restriction endonuclease and blotting to nitrocellulose by the method of Southern hybridization on EcoRI-digested genomic DNAs, as shown in FIG. 12.

The sizes of the EcoRI fragments of genomic DNA containing NGF and BDNF sequences were determined in controls on parallel blots using radiolabeled human NGF and BDNF probes, prepared by PCR from cloned genes. The positions of the NGF and BDNF genomic EcoRI fragments are indicated in FIG. 12 as N and B, respectively. The results of a similar analysis were presented in FIG. 3, and equivalent results were obtained using a human BDNF probe as with the porcine BDNF probe shown in FIG. 3. As noted above, NGF and BDNF probes each hybridized to single EcoRI fragments in a variety of vertebrate genomic DNAs. For example in rat DNA the BDNF probe detected a band of approximately 8.8 kb, while the NGF probe detected a band of approximately 10.4 kb.

As seen in FIG. 12, in every species tested (data shown for chicken, mouse and rat) the R1B/2C probe hybridized to a DNA band indistinguishable from that identified by the NGF probe as well as to a band indistinguishable from that identified by the BDNF probe (in mouse, the NGF and BDNF genomic EcoRI fragments have the same electrophoretic mobility, corresponding to approximately 11.5–12.0 kb). This demonstrates that the degenerate oligonucleotide primers 1B and 2C can be utilized to amplify sequences from both the NGF and BDNF genes. It was noteworthy that in some cases additional bands were observed in the genomic Southern blot hybridized with the R1B/2C probe. For example, in EcoRI-digested mouse genomic DNA at least two additional bands (labeled X1 and X2, of approximately 19.0 kb and 1.5 kb, respectively), corresponding to neither NGF nor BDNF were observed. Similarly, at least two additional bands were observed in hybridization to rat DNA (X1, X2, of approximately 7.3 and 1.2 kb, respectively), and at least one in chicken DNA (X, approximately 2.6 kb). Additional bands, not labeled explicitly in this figure, were also observed in some cases. The presence of bands not attributable to NGF or BDNF suggested the possible existence of additional member(s) of the gene family. Similarly, bands clearly distinct from those known to contain the BDNF and NGF gene sequences were found utilizing other sets of primer pairs and genomic DNA templates (data not shown).

13.2.3. Identification of a Novel Gene Related to BDNF and NGF

A specific test of the hypothesis that novel genes related to NGF and BDNF could be identified by PCR using degenerate oligonucleotide primers was carried out using primers for Box 3 and Box 4 (see section 5.8 above), and mouse genomic DNA as template. Degenerate primers were synthesized of the sequences:

Box 3 (sense):

5'-GGGGATCCGCGGITG(T,C)(C,A)GIG-GIAT(T,C,A,)GA-3'

Box 4 (anti-sense):

5'-TCGAATTCTAGATIC(T,G)IAT(AG-)AAIC(T,G)LCCA-3'

(G=guanine, A=adenine, C-cytosine, T=thymine, I=inosine; mixtures of more than one base at a single position in the oligonucleotide shown in parentheses). Note that inosine was utilized at some positions corresponding to the third ("wobble") base of a codon, to allow for the degeneracy of the genetic code. It is also possible to utilize a mixture of the four conventional DNA bases rather than inosine, and essentially identical results have been obtained with such primers.

With the degenerate Box 3/Box 4 primer pair, PCR from the genomic NGF and BDNF sequences in mouse DNA would be expected to amplify a segment of approximately 90 bp. Utilizing the primers shown above, PCR was carried out for four cycles with an annealing temperature of 45° C., followed by 31 cycles with an annealing temperature of 49° C. The products were analyzed by gel electrophoresis, and a major band of the expected size was observed. In the mouse the NGF gene contains a HindII restriction endonuclease cleavage site in the region between Box 3 and Box 4, while the BDNF gene contains a site of cleavage for the enzyme ApaI in this region. Therefore, digestion of the product of PCR amplification with HindII and ApaI would be expected to eliminate NGF and BDNF sequences from the major product band. However, when the PCR product was digested to apparent completion with these two restriction enzymes, a digestion-resistant band was found to persist in the amplified DNA. This suggests that, in addition to NGF and BDNF genes, at least one novel gene had been amplified.

13.2.4. Characterization of A Novel Member of the BDNF Gene Family

The digestion-resistant PCR product was eluted from a gel, and utilized as template in asymmetric PCR reactions in which either one of the original degenerate primers was present in 100-fold molar excess over the other primer. This asymmetric amplification permitted the production of single-stranded DNA templates suitable for sequencing by the chain termination method. The sequence analysis of the novel gene (designated here as "M3/4" but also referred to as Neurotrophin-3) was extended further by PCR amplification of sequences between an exact primer located between Boxes 3 and 4 and the polyA sequence at the 3' end of the gene's transcript, using the strategy for "rapid amplification of cDNA ends" (RACE) described by M. A. Frohman, M. K. Dush, and G. R. Martin, Proc. Natl. Acad. Sci. USA, 85:8998–9002 (1988). The results of DNA sequencing revealed that a novel gene had been amplified, comprising an open reading frame capable of encoding a polypeptide distinct from both NGF and BDNF but closely related in amino acid sequence to both (FIG. 13).

Preliminary evidence that this new gene encodes a neurotrophic factor was obtained by determining its pattern of expression in rat tissues by northern blot hybridization. This analysis indicated that the novel gene is expressed much more strongly in brain tissue than in any other tissue examined.

13.3. Discussion

As shown above (FIG. 12), the DNA probe obtained by PCR amplification using primers for Boxes 1 and 2 with rat genomic DNA as template (R1B/2C) hybridized to novel bands in addition to those known to contain NGF and BDNF gene sequences in EcoRI-digested DNA of every species tested. A similar analysis was carried out using a radioactively labeled probe for the novel gene amplified using Box 3 and 4 primers on mouse genomic DNA (M3/4). In each case, the M3/4 probe hybridized to a single major band of EcoRI-digested genomic DNA, that was distinct from the bands known to contain BDNF and NGF sequences. It should e noted that the EcoRI fragments of genomic mouse, rat, and chicken DNA observed by hybridization with the M3/4 probe are in every case coincident with one of the novel bands obtained by hybridization with the R1B/2C probe. These are the 19.0 kb EcoRI fragment in mouse DNA (X1 in FIG. 13), the 7.3 kb fragment in rat DNA (X1 in FIG. 13), and the 2.6 kb band in chicken DNA (X in FIG. 13). This suggests that portions of the same gene were amplified from rat DNA using the 1B/2C primer pair, and from mouse DNA using the 3/4 primer pair. Thus, at least one novel gene apparently shares homology with NGF and BDNF genes in all four of the boxes of homology noted above.

The concept of the homology boxes between NGF, BDNF, and additional members of the gene family (e.g. "M3/4" also known as NT-3) has been expressed here primarily in terms of primary amino acid sequence, and methods for the identification of novel genes in the family. However, it is important to note that there are likely to be additional implications for the secondary and tertiary structure of these neurotrophic factors, their interactions with specific receptors, and rational design of novel molecules with potential therapeutic value.

For example, there are 6 Cys residues in NGF, and all have been shown to be involved in disulfide bonds. Numbering them from most N-terminal to most C-terminal as Cys1–Cys6, it is known that the disulfide bridges involve Cys1–Cys4, Cys2–Cys5, Cys3–Cys6. The positions of all 6 Cys residues are conserved between NGF and BDNF, and the positions of 3 Cys residues in the portion of "M3/4" sequenced to date line up exactly with Cys4, Cys5, Cys6, of NGF and BDNF. This suggests that the secondary structure of all members of the gene family may be closely related, and largely determined by the conserved Cys residues. It should be noted that the homology boxes pointed out for BDNF and NGF cover 5 of the 6 Cys residues (Cys1 in Box 1, Cys2 in Box 2, Cys3 and Box 3, Cys5 and Cys6 in Box 4). This supports the idea that these Cys residues and their immediate neighbors play an important role in determining the general structure of these neurotrophic factors. The structural determinants for specific interaction with high affinity receptors for each of the neurotrophic factors presumably reside in unique portions of each molecule.

Accordingly, novel chimetic genes may be produced by recombination between family members (e.g. by in vitro recombination, or by direct gene synthesis) at any of the four homology boxes already described, or elsewhere in the molecule. Such chimeric proteins are likely to have similar secondary structure, because of conservation of Cys residues, and other amino acid residues, but may have novel biological properties. For example, a BDNF/NGF chimeric protein may be bifunctional in terms of interaction with both BDNF and NGF receptors. Chimetic proteins may also differ from parent molecule(s) in terms of dimerization, and other physio-chemical properties. Chimeric proteins might also be able to function as antagonists of either parent molecule.

Active fragments of BDNF/NGF may be used to design other family members based on knowledge of critical "core" regions for appropriate folding, plus information regarding which regions are required for type-specific interaction with receptors.

Comparison of new family members (e.g. "M3/4") with already known family members may be used to reveal new boxes of homology that can help guide the search for additional members of the BDNF/NGF gene family. For example, "M3/4" comparison with BDNF reveals some useful homology boxes. One of particular interest involves the fourth conserved Cys residue, the only one not in the previously noted Boxes 1–4. There is actually a rather long segment of identity or conserved amino acid substitution shared by BDNF and "M3/4", which includes this Cys residue, namely: His-Trp-Asn-Ser-Gln-Cys-(Arg or Lys)-Thr(Thr or Ser)-Gln-(Ser or Thr)-Tyr-Val-Arg-Ala-Leu-Thr. Within this region one could choose at least two homology boxes for the synthesis of useful degenerate oligonucleotide primers (e.g. His-Trp-Asn-Ser-Gln-Cys requires only 96-fold degeneracy for an 18-mer primer, or 48-fold degeneracy for a 17-mer; Tyr-Val-Arg-Ala-Leu-Thr would also be a useful box).

14. EXAMPLE: INCREASED EXPRESSION OF BDNF IN NEUROBLASTOMA CELLS

14.1. Materials and Methods

14.1.1. Cell Lines

CHP100, CHP126, CHP134, CHP234, LAN1, LAN5, NB9, SY5Y, Y79, FO1, BU2, HO1, HL60, and COL320 are cell lines maintained in the laboratory of Dr. Fred Alt, who provided RNA for the Northern blot used in FIG. 15. All cell lines were human tumor cell lines. CHP100 is a neuroepithelioma cell line; CHP126, CHP134, CHP234, LAN1, LAN5, NB9, and SY5Y are neuroblastoma cell lines; Y79 is a retinoblastoma cell line; FO1, BU2, HO1 are melanoma cell lines, HL60 is a promyelocytic leukemia cell line, COL320 is a neuroendocrine colon carcinoma cell line.

14.1.2. Preparation of RNA

RNA was prepared and Northern blots performed essentially as described in Section 8 supra, using a full-length human cDNA probe. 10 μg of total RNA was in each lane of the gel used to produce the Northern blot of FIG. 14, except that the RNA in LAN1 was less heavily loaded and for SY5Y one microgram of poly(A)+ RNA was used.

14.2. Results

FIG. 14 depicts the results of Northern blot analysis of BDNF probe hybridized to a panel of RNA samples obtained from a variety of human cell lines. An abundance of RNA which hybridized to BDNF probe was detected in CHP234 and LAN5 cell lines, and lower amounts were found in CHP126 and CHP134. All of the positive lines were derived from human neuroblastoma tumors.

15. EXAMPLE: ACTIVITY-DEPENDENT REGULATION OF BDNF- and NGF-mRNAs IN THE RAT HIPPOCAMPUS IS MEDIATED BY NON-NMDA-GLUTAMATE RECEPTORS

15.1. Materials and Methods

15.1.1. Treatment of Rats with Kainic Acid

The rats usually received diazepam (Valium) 90 minutes after intraperitoneal injection of kainic acid 12 mg/kg to suppress extensive seizure activity. As shown in FIGS. 18A through 18B, Valium given after kainic acid did not interfere with the further increase in BDNF- and NGF-mRNA levels. Rats which did not receive Valium showed similar increases of BDNF- and NGF-mRNA levels in hippocampus 3 hours after kainic acid, compared with animals given kainic acid followed by Valium.

15.1.2. Preparation of Hippocampal Cultures

Hippocampi were prepared from E17-day old rat embryos, dissected and incubated for 20 minutes at 37° C. in phosphate buffered saline (PBS) without calcium or magnesium ions, but containing 10 mM glucose, 1 mg/ml albumin, 6 µg/ml DNAase and 1 mg/ml papain. After washing with the solution without papain, the hippocampal cells were carefully dissociated with a fire polished pasteur pipette. Cells were collected by centrifugation at low speed, resuspended in DMEM, supplemented with 10% fetal calf serum and plated on plastic culture dishes ($0.5 \times 10^6$ cells per 35 mm) which were precoated with poly-DL-ornithine (0.5 mg/ml) and laminin (5 µg/ml). Three hours after plating, the medium was changed to a serum-free one, which contained the supplements as described by Brewer and Cotman (Brain Res. 497:65, 1989), but lacking glutamate. Neurons remained viable up to three weeks in culture and were usually used for the experiments at day 7 after plating.

15.1.3. Amplification of RNA

Total cellular RNA was extracted as described by Chomcynski and Sacci (Anal. Biochem., 1987, 162:156–159) from $0.5 \times 10^6$ cells after the addition of a shortened NGF cRNA recovery standard (30 fg). NGF mRNA and cRNA were coamplified in a combined one tube reverse transcription/polymerase chain reaction (RT/PCR) containing 1/5 of the extracted RNA, $1 \times$ RT/PCR buffer (10 mM Tris-HCl pH 8.3, 50 mM KCl, 1.5 mM $MgCl_2$, 0.1 mg/ml gelatin, 0.1% Triton X-100), 0.25 mM dNTP, 0.1 µM each 5' and 3' primer, 5 U RNasin (Promega), 3.2 U AMV-reverse transcriptase (Life Science) and 2 U Taq Polymerase (Genofit) in a total volume of 25 µl. The mixture was overlaid with mineral oil, incubated at 41° C. for 30 minutes, heated to 92° C. for 60 seconds, followed by primer annealing at 55° C. for 60 seconds and primer extension at 72° C. for 60 seconds). The amplification products (203 bp for NGF mRNA and 153 bp for recovery standard) were separated on a 3% NuSieve/Agarose 3:1 gel (FMC Bioproducts), alkali-blotted to a Hybond N plus membrane (Amersham) and hybridized as described (Heumann, R. and Thoenen, H., 1986, J. Biol. Chem. 261:9246; Lindhold et al., 1988, J. Biol. Chem. 263:16348). For absolute quantification, known amounts of in vitro transcribed NGF mRNA and recovery standard were coamplified in parallel reactions. Recently, a similar method was described by Wang et al. (PNAS 86:9717–9721, 1989).

15.2. Results and Discussion

BDNF and NGF are members of a gene family with about 50% amino acid identity (Leibrock et al., 1989, Nature 341:149). The molecules exhibit strictly conserved domains. Contained within these domains are the 6 cysteine residues most probably involved in the stabilization of the three dimensional structure of these molecules, which is necessary for their biological activity. However, there are also variable domains in BDNF and NGF which determine their different neuronal specificity (Lindsay et al., 1985, Dev. Biol 112:319; Johnson et al., 1986, J. Neurosci. 6:3031; Hofer, M. and Barde, Y. 1988, Nature 331:261; Rodriguez-Tebar et al., 1989, Dev. Biol. 136:296). Moreover, the difference between these two neurotrophic molecules is also indicated by their sites of synthesis. NGF is expressed both in the periphery (Korsching, S. and Thoenen, H., 1983, Proc. Natl. Acad. Sci. U.S.A. 80:3513; Ebendal et al., 1983, Exp. Cell Res. 148:311; Heumann et al., 1984, EMBO J. 3:3183; Shelton, D. L. and Reichardt, L. F., 1984, Proc. Natl. Acad. Sci. U.S.A. 81:7951) and in the central nervous system (CNS) (Korsching et al., 1985, EMBO J. 4:1389; Shelton, D. L. and Reichardt, L. F., 1986, Proc. Natl. Acad. Sci. U.S.A. 83:2714; Whittemore et al., 1986, Proc. Natl. Acad. Sci. U.S.A. 83:817; Large et al., 1986, Science 234:352). The densities of innervation by NGF-responsive neurons reflect the levels of NGF in the corresponding target tissues (Korsching, S. and Thoenen, H., 1983, Proc. Natl. Acad. Sci. U.S.A. 80:3513; Ebendal et al., 1983, Exp. Cell Res. 148:311; Heumann et al., 1984, EMBO J. 3:3183; Shelton, D. L. and Reichardt, L. F., 1984, Proc. Natl. Acad. Sci. U.S.A. 81:7951; Korsching et al., 1985, EMBO J. 4:1389; Shelton, D. L. and Reichardt, L. F., 1986, Proc. Natl. Acad. Sci. U.S.A. 83:2714; Whittemore et al., 1986, Proc. Natl. Acad. Sci. U.S.A. 83:817; Large et al., 1986, Science 234:352). In contrast to NGF, BDNF is predominantly expressed in the CNS in neurons, and the levels of BDNF-mRNA are considerably higher than those of NGF-mRNA, e.g. about 50-fold in the hippocampus. In the peripheral nervous system, NGF is synthesized by various non-neuronal cell types (Bandtlow et al., 1987, EMBO J. 6:891), whereas in the brain it is mainly localized in neurons, as demonstrated by in-situ hybridization (Rennert, P. D. and Heinrich, G., 1986, Biochem. Biophys. Res. Commun. 138:813; Ayer-LeLievre et al., 1988, Science 240:1339; Whittemore et al., 1988, J. Neurosci. Res. 20:403). However, cultured type-1 astrocytes have also been shown to produce substantial quantities of NGF (Lindsay, R. M., 1979, Nature 282:80; Furukawa et al., 1987, Biochem. Biophys. Res. Commun. 142:395). The relative contribution of neurons and astrocytes to the NGF synthesized in brain is not yet known.

In view of the predominant expression of both BDNF- and NGF-mRNAs in central nervous system neurons, we investigated whether the levels of these two mRNAs are influenced by neuronal activity and if so, which transmitter(s) could possibly be involved in the regulation. In a first series of experiments, we prepared neuronal cultures from embryonic (E17) rat hippocampus. As shown in FIG. 15A, depolarization of the hippocampal neurons with high (50 mM) potassium resulted in an increase in BDNF-mRNA. Maximal levels were reached between 3 and 6 hours after increasing the potassium concentration. The potassium-mediated increase in BDNF-mRNA could be inhibited by omitting calcium ions from the medium and it was also reduced by inhibiting calcium influx by the calcium channel blocker nifedipine (FIG. 15B).

Figure 16:
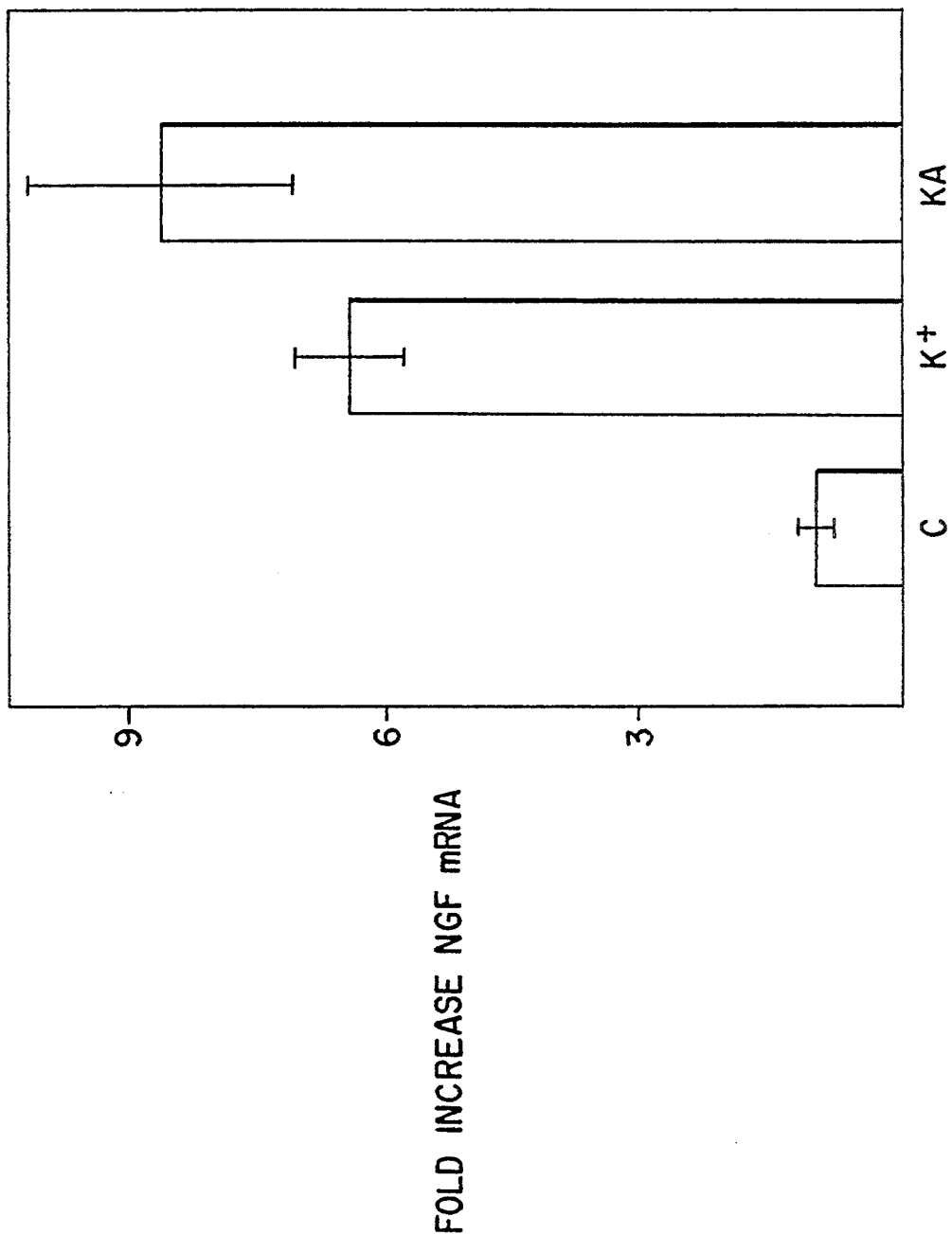

Because the hippocampal cultures used consisted of a mixed population of neurons exhibiting different patterns of transmitter and receptor expression, we studied the effect of various physiological and synthetic receptor agonists on BDNF- and NGF-mRNA expression. The results presented in Table VI show that of all the substances tested, kainic acid, a glutamate receptor agonist (Monaghan et al., 1989, Annu. Rev. Pharmacol. Toxicol. 29:365), produced by far the largest increase in BDNF-mRNA in hippocampal neurons. In contrast, other molecules, such as carbachol (a muscarinic receptor agonist) and to a lesser extent histamine and bradykinin, elevated slightly, but significantly, BDNF-mRNA (Table VI). Because the levels of NGF-mRNA in the hippocampal neurons were very low, we established a quantitative polymerase chain reaction (PCR) method suitable for determining changes in NGF-mRNA. Using this method we found that, like BDNF-mRNA, NGF-mRNA levels were also increased by potassium and kainic acid in hippocampal neurons (FIG. 16).

As shown in FIG. 17, the maximal increase in BDNF-mRNA in the hippocampal neurons was obtained with about 25 µM kainic acid. A further increase in the kainic acid concentration resulted in a decrease of the BDNF-mRNA levels, which most probably reflects toxic effects of the high concentrations or kainic acid on hippocampal neurons (FIG. 17). A glutamate receptor-mediated neurotoxicity has previously been reported (Choi et al., 1987, J. Neurosci. 7:357; Rothman, S. M. and Olney, J. W., 1987, Trends Neurosci. 10:299; Choi, D. W., 1988, Neuron 1:623) for various central neurons following the application of analogues of the excitatory amino acid glutamate. However, the concentrations of kainic acid necessary to enhance the expression of BDNF- and NGF-mRNA in the hippocampal neurons could clearly be separated from the concentrations resulting in neurotoxicity.

To investigate the effects of kainic acid in more detail, we studied whether the increase in BDNF-mRNA could be blocked by any of the known glutamate receptor antagonists (Monaghan et al., 1989, Annu. Rev. Pharmacol. Toxicol. 29:365). Kynurenic acid, a broad spectrum glutamate receptor antagonist, as well as CNQX, a competitive inhibitor of non-NMDA receptors (Monaghan et al., 1989, Annu. Rev. Pharmacol. Toxicol. 29:365), completely blocked the kainic acid-mediated increase in BDNF-mRNA in hippocampal neurons (Table VII). On the other hand, MK 801, which specifically blocks NMDA receptors, was ineffective in blocking the rise of BDNF-mRNA in these neurons. Moreover, NMDA itself did not change BDNF-mRNA levels (Table VI). This shows that kainic acid acts directly via its receptors and that the effect is not due to the release of endogenous glutamate (which also acts on NMDA receptors). It can thus be concluded that kainic acid in vitro elevates BDNF-mRNA levels via non-NMDA glutamate receptors.

TABLE VI

EFFECT OF VARIOUS RECEPTOR AGONISTS ON BDNF-MRNA EXPRESSION IN CULTURED NEURONS

| Addition | % of Control |
| --- | --- |
| none | 100 ± 5 |

TABLE VI-continued

EFFECT OF VARIOUS RECEPTOR AGONISTS ON BDNF-MRNA EXPRESSION IN CULTURED NEURONS

| Addition | % of Control |
| --- | --- |
| carbachol (50 mM) | 220 ± 25 |
| carbachol (50 mM) + atropine 10 (µM) | 85 ± 15 |
| nicotin (100 µM) | 110 ± 7 |
| histamine (50 µM) | 150 ± 12 |
| serotonin (100 µm) | 95 ± 6 |
| dopamine (100 µM) | 115 ± 7 |
| norepinephrine (25 µM) | 75 ± 10 |
| substance P (1 mM) | 85 ± 9 |
| somatostatin (1 mM) | 110 ± 8 |
| bradykinin (1 µM) | 155 ± 15 |
| kainic acid (25 µM) | 1365 ± 70 |
| NMDA (25 mM) | 105 ± 10 |

TABLE VII

EFFECT OF ANTAGONISTS TO THE DIFFERENT GLUTAMATE RECEPTORS ON THE KAINIC ACID INDUCED EXPRESSION OF BDNF-mRNA

| Addition | % of Control |
| --- | --- |
| none | 100 ± 60 |
| Kainic acid (25 µM) | 1250 ± 60 |
| Kynurenic acid (1 mM) | 70 ± 6 |
| Kynurenic acid (1 mM) + Kainic acid (25 µM) | 84 ± 7 |
| CNQX (10 µM) | 109 ± 6 |
| CNQX (10 µM) + Kainic acid (25 µM) | 105 ± 7 |
| MK-801 (5 µM) | 96 ± 5 |
| MK-801 (5 µM) + Kainic acid (25 µM) | 1130 ± 80 |

To evaluate the physiological significance of our in vitro observations, we studied whether similar mechanisms were also operating in vivo. We treated adult Wistar rats of both sexes weighing 180–200 g with 12 mg/kg of kainic acid. After various time periods, we determined the changes in BDNF- and NGF-mRNAs in the hippocampus and cortex by Northern blot analysis. FIGS. 18A and 18B show that kainic acid elicited an increase in the levels of BDNF- and NGF-mRNAs in both brain regions. The increase in BDNF-mRNA was substantially larger than that of NGF-mRNA. Moreover, for as long as 24 hours after administration of kainic acid, the mRNA levels remained elevated. The time-course of BDNF- and NGF-mRNAs changes showed that the maximal increase in the hippocampus was reached approximately 3 hours after the administration of kainic acid (FIGS. 18A and 18B). It is interesting to note that the increase in BDNF- and NGF-mRNAs in the hippocampus was preceded by an increase in c-fos-mRNA; the two phenomena may be causally related, as was recently shown to be the case for sciatic nerve after lesion (Hengerer et al., 1990, Proc. Natl. Acad. Sci. U.S.A. 87:3899). Moreover, there is a delay in the increase of both BDNF- and NGF-mRNAs in the cerebral cortex compared with the increase in the hippocampus, which indicates that the signals leading to an enhanced expression of BDNF and NGF spread from the hippocampus to other brain regions. This observation is in keeping with previous reports (Morgan et al., 1987, Science 237:192) showing that the increase in c-fos elicited by the convulsant metrazole occurred first in the hippocampus and then in the cortex.

After previous studies had provided evidence that NMDA receptors are involved in the regulation of hippocampal mRNAs, such as NGFI-A (Cole et al., 1989, Nature 340:474), we then studied whether or not the NMDA receptor antagonists MK 801 and ketamine could block the increase in BDNF- and NGF-mRNAs in vivo. However, confirming our results in vitro, MK 801 did not inhibit the kainic acid-mediated increase in hippocampal BDNF-mRNA, although it effectively suppressed seizures resulting from NMDA receptor activation (FIG. 19). Most probably this NMDA receptor activation results from endogenous glutamate released by kainic acid (Biziere, K. and Coyle, T., Neurosci., 1978, Lett. 8:303; McGeer et al., 1978, Brain. Res. 139:381). Likewise, the increase in NGF-mRNA in hippocampus after kainic acid treatment was neither prevented by MK 801 nor by ketamine. In a previous study (Gall, C. M. and Isackson, P. J., 1989, Science 245:758), it was shown that electrolytical lesions causing limbic seizures elevate NGF-mRNA in rat hippocampus. However, the present results obtained with MK 801 and kainic acid showed a clear dissociation between induction of seizures and increases in BDNF and NGF expression. Diazepam (Valium) treatment of rats prior to kainic acid injections completely blocked the increase in BDNF- and NGF-mRNAs in the rat hippocampus (FIG. 19). The blocking effect of diazepam on the increase of BDNF- and NGF-mRNA most probably resulted from the suppression of neuronal activity via the inhibitory GABAergic system. However, 90 minutes after the administration of kainic acid (i.e., approximately 30 minutes after the start of convulsion), the increase in BDNF- and NGF-mRNA could no longer be blocked by diazepam, indicating that a relatively short period of augmented activity may be sufficient to initiate the cascade of events leading to an augmented expression of the mRNAs of the two neurotrophic factors.

The present investigation showed that non-NMDA receptors may be involved in the regulation of BDNF- and NGF-mRNA in hippocampus, thus distinguishing this regulatory mechanism from that previously described by Cole et al. (Cole et al., 1989, Nature 340:474) which concluded that hippocampal mRNAs encoding early genes seemed to be regulated via the NMDA-subtype of glutamate receptors. It has been reported that some of the effects of kainic acid on neurons can also be mediated by the quisqualate type of glutamate receptors (Monaghan et al., 1989, Annu. Rev. Pharmacol. Toxicol. 29:365).

In conclusion, the present study showed that neuronal activity regulates the levels of mRNAs encoding the neurotrophic factors BDNF and NGF in the rat hippocampus and cortex. Of all the substances tested, kainic acid, acting via the non-NMDA glutamate receptors, elevated BDNF- and NGF-mRNAs both in vivo and in hippocampal neuronal cultures. In contrast, in the periphery there is no evidence that NGF synthesis in non-neuronal cells is regulated by conventional transmitter substances or neuropeptides released by innervating (NGF responsive) neurons (Barth et al., 1984, J. Cell Biol. 99:839; Hellweg et al., 1988, Exp. Cell Res. 179:18). BDNF is predominantly expressed in the CNS and there is at least a partial overlap between the central pathways using glutamate as a neurotransmitter and regions shown to be relatively rich in BDNF- and NGF-mRNA (Hofer et al., EMBO J., in press; Monaghan et al., 1989, Annu. Rev. Pharmacol. Toxicol. 29:365). In particular, there are striking similarities between the distribution of NGF-mRNA as demonstrated by in situ hybridization (Hofer et al., EMBO J., in press) and kainic acid receptors visualized by autoradiography in hippocampus, cerebral cortex, and cerebellum (Monaghan et al., 1989, Annu. Rev. Pharmacol. Toxicol. 29:365). The observations are compatible with the interpretation that glutamate represents the physiological transmitter regulating BDNF- and NGF-mRNAs in the CNS.

16. EXAMPLE: BRAIN-DERIVED NEUROTROPHIC FACTOR INCREASES SURVIVAL AND DIFFERENTIATED FUNCTIONS OF RAT SEPTAL CHOLINERGIC NEURONS IN CULTURE

16.1. Materials and Methods 16.1.1. Preparation of Dissociated Cells and Cell Culture Conditions The septal region from rats (Sprague-Dawley) after 17 days of gestation was dissected free from the surrounding tissue. Tissue fragments were pooled, washed three times with Ham's F-10, and then transferred to a 35 mm tissue culture dish and minced. A single cell suspension was made by incubating the tissue with 0.25% trypsin for 20 minutes at 37° C. Following the inactivation of the trypsin by a five minute incubation at room temperature in growth medium (infra), containing 50 ug/ml deoxyribonuclease type 1 (Sigma), the cells were dissociated by passing the fragments repeatedly through the constricted tip of a Pasteur pipet. The dissociated cells were then centrifuged at 500×g for 45 seconds. The supernatant was removed and recentrifuged. The loose cell pellets were resuspended and combined in growth medium, and the cell yield was determined by use of a hemocytometer. Finally, the cells were plated into 6 mm wells which had been coated with polyornithine (10 μg/ml) and laminin (10 μg/ml). The cell viability was checked, after 24 hours in culture, by the ability of the cells to exclude trypan blue.

The normal growth medium, 5HS/N3, for cultures composed of neurons and glia contained: 5% (v/v) horse serum (Gibco), 1% N3 additives (v/v) (Romijn et al., 1982, Dev. Brain Res. 2:583–589), 0.5% (v/v) glutamine (200 mM, Gibco), and 0.25% (v/v) penicillin-streptomycin (10,000 units/ml, 10,000 mcg/ml respectively, Gibco) in Dulbecco's modified Eagle's medium (DMEM). Neuronal-enriched cultures were prepared by replacing the growth medium, five to six hours after plating, with DMEM containing: 1% N3 additives, 0.5% glutamine, and 0.25% penicillin and streptomycin. In both conditions, treatment with cytosine arabinoside (1 μM for 24 hours) was used to limit glial cell proliferation.

16.1.2. Assay of Choline Acetyltransferase Activity

The growth medium was removed from the cultures by rinsing the cells twice with 100 μl of PBS. The cells were lysed via one freeze-thaw cycle and a 15 minute incubation at 37° C. in 50 mM $KH_2PO_4$ pH 6.7 containing 200 mM NaCl and 0.25% (v/v) Triton X-100. Two microliters of the cell lysate was removed and assayed for CAT activity according to the micro-Fonnum procedure (Fonnum, F, 1975, J. Neurochem. 24:407–409). The final substrate composition consisted of 0.2 mM [$^{14}$C]Acetyl-CoA (NEN, 54.4, mCi/mmol), 300 mM NaCl, 8 mM choline bromide, 20 mM ethylenediaminetetraacetic acid, and 0.1 mM neostigmine in 50 mM $NaH_2PO_4$ (pH 7.4) buffer. At these enzyme and substrate concentrations, the enzymatic reaction was linear for 90–120 minutes. The specificity of the induction for choline acetyltransferase was tested by the addition of a specific inhibitor of CAT activity, N-hydroxyethyl-4-

(1-napthylvinyl)pyridium (HNP), during the assay (White, H. L. and Cavallito, C. J., 1970, J. Neurochem. 17:1579–1589).

16.1.3. Assay of Acetylcholinesterase (AChE) Activity

The level of AChE present in the lysates was measured by the methods of Potter (Potter, L. T., 1967, J. Pharmacology and Experimental Therapeutics 156:500–506) and Johnson and Russell (Johnson, C. D. and Russell, R. L., 1975, Anal. Biochem. 64:229–238) with several modifications. Lysates prepared in 50 mM $KH_2PO_4$ buffer pH 6.7 containing 200 mM NaCl and 0.25% (v/v) Triton X-100, were combined with [$^3$H] acetylcholine iodide (NEN, NET-113, 73.3 mCi/mmol), ethopropazine (0.1 mM) in 50 mM $KH_2PO_4$ pH 7.0. Following a 15 minute incubation at 37° C., the reaction was terminated by the addition of 100 μl of a stop buffer solution containing: 1M chloroacetic acid, 0.5M NaOH, and 2.0M NaCl. Specific AChE activity was determined in the presence of 1.0 ($10^{-6}$)M neostigmine.

16.1.4. Measurement of High Affinity Choline Uptake

Choline uptake via a high affinity, Na+-dependent mechanism was assayed essentially by the procedure of Vaca and Pilar, 1979 (Vaca, K. and Pilar, G., 1979, J. Gen. Physiol. 73:605–628). The cells were washed once with 100 μl Ham's F-10, followed by a 100 μl rinse with Tyrodes solution. Following a 10 minute depolarization induced by Tyrodes solution containing 25 mM potassium, the cells were incubated for 20 minutes at room temperature with [$^3$H] choline (NEN, NET-109, 0.11 μM, 86.7 Ci/mmol) in normal Na+ or Li+ containing Tyrodes solution. The uptake reaction was stopped by rinsing the cells twice with PBS. The accumulated choline was extracted by incubating the cultures for at least 20 minutes with 100 μl of cold acetone containing 1N formic acid. The soluble fraction was then removed and counted. The specific choline uptake is the difference between the level of total and the Na+-independent choline uptake.

16.1.5. Histochemical Staining for Acetycholinesterase

Cholinergic cells were identified by histochemically staining for acetylcholinesterase by a modification of the staining method of Geneser-Jensen and Blackstadt, (1971, Z. Zellforsch. 114:460–481). Following fixation of the cultures in 4% paraformaldehyde, the cells were incubated 5–6 days at 4° C. in the presence of the AChE substrate solution composed of the following: 4 mM acetylithiocholine iodine, 2 mM copper sulfate, 10 mM glycine and 10 μg/ml gelatine in 50 mM acetate buffer pH 5.0. Visualization of the reaction product was accomplished as previously described (Hartikka, J. and Hefti, F., 1988, J. Neurosci. 8:2967–2985).

16.1.6. Immunohistochemical Staining for the NGF-Receptor

Cultures were washed twice with DMEM and then fixed with 4% paraformaldehyde. The cells were then treated for 3–4 hours with a sodium phosphate buffer pH 7.4 containing 5% bovine serum albumin, 0.02% triton X-100 and 5% sucrose (Hartikka, J. and Hefti, F., 1988, J. Neurosci. 8:2967–2985). The NGF-R was detected utilizing the monoclonal antibody 192-IgG (Taniuchi, M. and Johnson, E., 1985, J. Cell Biol. 101:1100–1106; Chandler et. al., 1984, J. Biol. Chem. 259:6882–6889) and at 1:1000 dilution in buffer containing 5% horse serum. The cultures were incubated with the diluted antibody for 15–18 hours at 4° C. The bound mouse immunoglobulin was detected utilizing biotinylated horse antimouse IgG (1:200 Vector). The immunoreactive cells were identified by using 3',3' diaminobenzidine as the substrate for the bound peroxidase enzyme.

16.1.7. Purification of BDNF and NGF

The purification of BDNF, from porcine brain, and NGF, from male mouse submaxillary gland, was conducted according to previously published protocols (Barde et al., 1982, EMBO J. 1:549–553; Lindsay et al., 1985, Dev. Biol. 112:319–328). The recombinant BDNF, used for a portion of these studies, has been characterized previously (Maisonpierre et al., 1990, Science. 247:1446–141).

16.2. Results

Figure 20B:
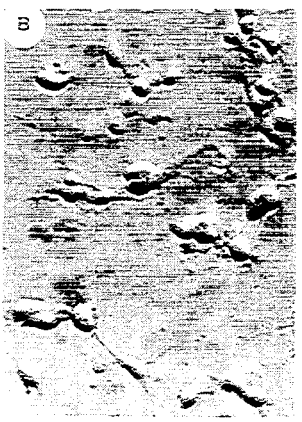
Figure 20C:
Figure 20D:
Figure 20E:
Figure 20F:
Figure 20G:
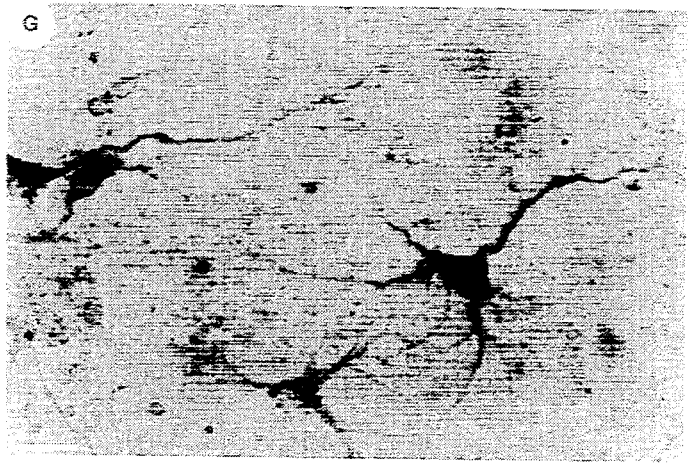
Figure 20H:
Figure 20:
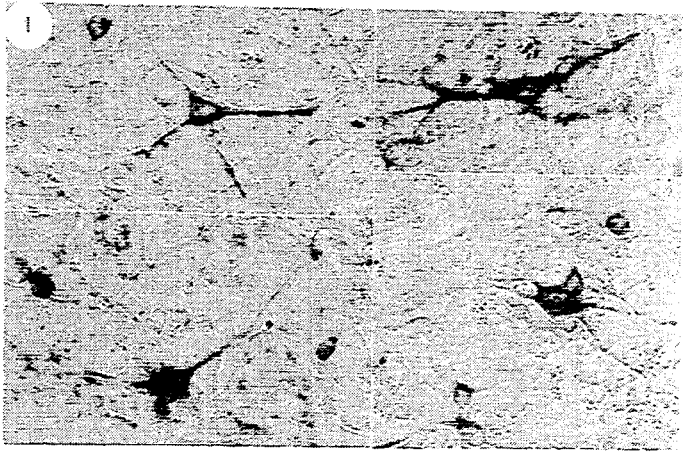

Cultures of septal cells produced elaborate neurite outgrowth on polyornithine-laminin coated wells, with many of the cells displaying a characteristic neuronal phase-bright soma by 24 hours (FIGS. 20A and 20B). Continued neurite outgrowth resulted in a progressive increase in the extent of cell-cell contact at days 2 and 4 in vitro (compare FIGS. 20C and 20D with FIGS. 20E and 20F). There were very few non-neuronal cells in the cultures even after 4 days, as noted by the absence of flattened phase-dark cells. To assess the effects of BDNF on septal cholinergic neuron survival in culture, a histochemical stain for AChE and a immunohistochemical stain for the NGF-receptor was used. Typical morphologies of AChE positive neurons are shown in FIGS. 20G and 20H. Several NGF-receptor positive neurons are shown in FIG. 20I.

BDNF elicited a 2.4-fold increase in the number of AChE positive cells in low density cultures (defined as cell densities between 66,700–133,300 cells/cm$^2$) of embryonic rat septal cells as shown in FIG. 21A. At the same cell densities the effect of NGF was slightly less (1.9-fold). The finding that BDNF as well as NGF can produce an increase in the number of AChE positive neurons in septal cultures prompted us to examine whether these two factors act upon similar or distinct neuronal populations. As shown in the third panel of FIG. 21A, concurrent addition of saturating levels of BDNF and NGF lead to no greater increase in the number of AChE positive neurons than that seen with either factor alone. In terms of neuronal survival, these results suggest that the cholinergic neurons in rat septal cultures which respond to BDNF or NGF must be closely overlapping populations.

The effect of BDNF upon the survival of AChE positive neurons was dependent upon the density at which the cells were grown (FIG. 21A). At high plating densities (200,000–266,000 cells/cm$^2$) neither BDNF alone nor in combination with NGF produced an increase in the number of AChE expressing neurons. This may be due to increased endogenous levels of neurotrophic activity, or alternatively, survival promoting effects of the increased cell-cell contact occurring at the higher cell densities.

At low cell density, the number of AChE positive cells increased as a function of BDNF concentration, with a maximal response observed at a dose of 10 ng/ml, which increased the number of AChE positive cells/well from control values of 169.2±12.9 to 388.0±26.2 (a 2.5 fold increase) in treated cultures. In comparison, a maximal response to NGF was observed at 50 ng/ml and produced an increase in AChE positive cells/well from 121.0±7.6 to 231.7±12.9 (a 1.9 fold increase). The plateau phase in the response curve appeared to be stable for both BDNF and NGF, in that there was no reduction in the number of AChE positive neurons at doses as high as 100 ng/ml.

It is apparent that in low density cultures, both BDNF and NGF are capable of increasing the number of cells detected by AChE histochemistry. It is possible that this increase is due to a rescue of cholinergic cells dying in culture in the absence of growth factor, to recruitment of precursor cells, or to the induction of the cholinergic marker, AChE. To attempt to differentiate among these possibilities, delayed addition experiments were conducted (FIG. 22) in a series of cultures maintained for a total of 12 days. One set of cultures, treated five to six hours after plating, was maintained in the presence of BDNF or NGF for the entire 12 days. A second set of cultures was established without growth factors for 5 days and then treated with BDNF or NGF for the last seven days ($-5/+7$). When comparing these two sets of cultures, the response to NGF or BDNF added after 5 days was much the same as was observed when the cells were grown continuously in the presence of the factors (compare solid and cross hatched bars in FIG. 22). The results were strikingly different, however, in a third set of cultures in which BDNF or NGF was only present for the final 5 days ($-7/+5$) cultures). Under these conditions, neither NGF nor BDNF was capable of enhancing the number of AChE positive cells. In other experiments, it has been established that exposure of septal neurons to either NGF or BDNF for as little as 3-4 days is sufficient to produce a large increase in AChE enzyme activity, and thus detection of cells by AChE staining. Therefore, the lack of a detectable increase in the number of AChE positive neurons in the "$-7/+5$" cultures was not due to the possibility that the time of exposure to growth factor was insufficient to allow for an induction of AChE positive cells.

It has been shown in vivo (Montero, C. and Hefti, F., 1988, J. Neurosci. 8:2986–2999; Higgins et al., 1989, Neuron. 3:247–256) as well as in vitro that NGF is capable of regulating the levels of its own receptor as measured both at the mRNA and protein level. Since BDNF was found to display similar effects to NGF in the induction of cholinergic phenotype and cell survival in septal cultures, the potential that BDNF may regulate the levels of NGF-receptor, as quantitated by the numbers of IgG-192 immunopositive cells, was tested. At 10 ng/ml, BDNF produced a 3-fold increase in the number of NGF-receptor immunopositive cells, as shown in FIG. 23. Interestingly, at higher concentrations (25-100 ng/ml) the effect of BDNF was progressively less marked. Thus, the dose response in this instance was notably different from that observed for the effect of BDNF on other parameters in these cultures, e.g., number of AChE positive cells. As a positive control, the cells were treated with NGF at a concentration of 50 ng/ml, which also resulted in a 3-fold increase in the number of positive cells. Therefore, on the basis of IgG-192 staining, BDNF has an approximately equal effect to NGF on up-regulating the expression of the NGF-receptor.

In addition to effects on cell survival, the possibility that BDNF could promote cholinergic phenotypic traits was investigated. A linear increase in CAT activity was found in septal cultures grown in the presence of increasing levels of BDNF up to 50 ng/ml, where the response saturated at a level of 1.8 fold over control values, as shown in FIG. 24A. Induction of CAT activity in parallel cultures treated with NGF reached a plateau at 25 ng/ml, representing a 3.4 fold increase over control values, as shown in FIG. 24B. The response to either BDNF or NGF showed no significant decline at three times the concentration sufficient to produce a saturating response. The induction of CAT activity with either BDNF or NGF did not effect the level of [N-hydroxyethyl-4-(1-napthylvinyl)pyridium] HNP-independent transferase activity.

In light of the finding that BDNF as well as NGF elicited increased CAT activity in septal cultures, the response to concurrent treatment with both factors was studied (Table VIII). For these experiments, two concentrations of BDNF were used, 5 and 25 ng/ml, which increased CAT activity by 1.4 and 2.6 fold, respectively. When NGF (50 ng/ml), which alone increased enzyme activity by 2.8 fold, was combined with BDNF, the level of CAT activity reflected at least an additive effect (Table VIII). At the concentrations of BDNF used, a purely additive effect to that of NGF would have lead to increases of 4.2 and 5.4 fold, respectively, over control values. The observed values were actually somewhat more than additive.

TABLE VIII

EFFECTS OF CO-ADDITION OF BDNF AND NGF ON CAT ACTIVITY

| Concentration (ng/ml) | CAT Activity (pmol/Hr/Well) | % Control |
|---|---|---|
| Control | 561.3 ± 34.8 | — |
| NGF (50) | 1546.3 ± 89.7 | 280 |
| BDNF (5) | 768.0 ± 25.4 | 140 |
| BDNF (25) | 1470.1 ± 66.2 | 260 |
| NGF (50) ± BDNF (5) | 2767.6 ± 177.2 | 490 |
| NGF (50) ± BDNF (25) | 3742.0 ± 669.3 | 670 |

Septal cells were grown for a period of 12 days in 5HS/N3 in the presence of the indicated concentrations of trophic factors. CAT activity was determined as described. Values represent the means ± S.E.M. of 4–5 determinations.

The possibility that the biological response observed with BDNF treatment was due to a BDNF-dependent release of endogenous NGF was tested. To examine this question, a monoclonal antibody to NGF (antibody 27/21, Korsching and Thoenen, 1983) was used to block any NGF-related response. As shown in Table IX, the effect of NGF on CAT activity was greatly reduced by anti-NGF, while the BDNF-induced response was essentially unaffected. One should note, however, that the basal level of CAT activity was reduced by about 20% in cultures treated with anti-NGF alone, as compared to untreated controls. Nevertheless, the observed increase in CAT activity in septal cultures produced by BDNF appears to be a direct effect and not mediated by an increase in endogenous NGF.

TABLE IX

EFFECT OF ANTI-NGF ON THE ABILITY OF NGF AND BDNF TO INDUCE CAT ENZYME ACTIVITY

| Concentration (ng/ml) | CAT Activity (pmol/HR/Well) | % Control |
|---|---|---|
| Control | 517.53 ± 3.2 | |
| BDNF (25) | 1021.6 ± 106.1 | 197 |
| NGF (50) | 1139.0 ± 99.1 | 220 |
| Control + Anti-NGF | 418.7 ± 27.0 | 81 |
| BDNF + Anti-NGF | 819.2 ± 68.8 | 158 |
| NGF + Anti-NGF | 551.0 ± 27.0 | 107 |

The possibility that AChE activity is coordinately regulated along with CAT activity by BDNF or NGF was also tested (FIG. 25). In contrast to CAT activity, the dose response of AChE to BDNF or NGF appeared quite similar in that the enzyme activity increased linearly up to a concentration of 50 ng/ml. At this concentration, NGF and BDNF increased AChE activity 274% and 234% respectively, as compared to the non-treated control values.

The time course of BDNF or NGF induced increase in CAT activity was investigated (FIG. 26). CAT activity in cultures treated with 50 ng/ml of BDNF increased to 170% of control values by 3 days. This increase continued until day 6, where it plateaued at 2.5-fold above control values throughout the remainder of the period tested. In contrast, the CAT response to NGF (50 ng/ml) administration was more rapid, with the induced level reaching 2.5 fold over control by day 3. The increase in CAT activity continued to rise linearly, reaching a value of 3.2 fold over the controls after 12 days.

Astrocytes, grown in culture for a period of time, have been shown to synthesize a variety of neurotrophic activities, in addition to NGF (Lindsay, R. M., 1979, Nature 282:80-82; Lindsay et al., 1982, Brain Res. 243:329-343; Alderson et al., 1989, Dev. Brain. Res. 48:229-241). Although we have ruled out the possibility that our present observations on BDNF are mediated through an increase in levels of NGF, it is conceivable that BDNF may act indirectly by modulating expression of other neurotrophic factors, especially in glial cells. To assess the possibility that nonneuronal cells might influence the effect of BDNF on CAT activity in septal cultures, we compared the response of cholinergic neurons to BDNF in mixed glial-neuronal cultures and neuron-enriched cultures (FIG. 27). In neuron-enriched cultures, the response of CAT activity to BDNF displayed a bell-shaped curve; a maximal increase was achieved at a dose of 5 ng/ml of BDNF and at a concentration of 25 ng/ml there was a significant decline in enzymatic activity ($p > 0.001$, comparing 15 to 25 ng/ml of BDNF). Similar to the result shown in FIG. 24A, the CAT response to BDNF in the presence of a confluent glial layer was linear, in this case up to 25 ng/ml of BDNF, the highest dose tested. In the presence of nonneuronal cells higher levels of BDNF were required to produce an equivalent increase in CAT activity to that found in similarly treated neuron-enriched cultures. Notwithstanding, the ability of BDNF to maximally stimulate CAT activity in the septal cholinergic neurons was essentially the same in the presence or absence of glial cells.

On the basis of CAT and AChE activity, it is apparent that BDNF can act similarly to NGF in enhancing cholinergic phenotypic markers. To examine this further, the effect of BDNF on the level of Na+-dependent, high-affinity choline uptake was compared to that of NGF (FIG. 28). Cells grown for 12 days in the presence of 50 ng/ml of BDNF accumulated choline to a level 3.8 fold over that of the non-treated controls. In parallel cultures, NGF (25 ng/ml) induced a 2.3 fold increase in choline accumulation.

16.3. Discussion

In comparison to its established effects on peripheral neurons (Barde et al., 1982, EMBO J. 1:549-553; Lindsay et al., 1985, Dev. Biol. 112:319-328; Davies et al., 1986, J. Neurosci. 6:1897-1904; Hofer, M, and Barde, Y., 1988, Nature 331:262-262), the neuronal specificity of BDNF within the central nervous system is less well characterized. To date, the only known responsive CNS neurons are a small subpopulation of Thy-1 positive retinal ganglion cells first identified in cultures of E17 rat retina (Johnson et al., 1986, J. Neurosci. 6:3031-3038). Further studies have also established effects of BDNF upon adult retinal ganglion cells in explant cultures (Thanos et al., 1989, Eur. J. Neuro. 1:19-26). In this study, we have shown that BDNF increases the survival of cultured cholinergic neurons from the embryonic rat septum, as shown by AChE histochemical staining, and increases the expression of various cholinergic phenotypic markers, i.e., enzymatic activity of AChE and CAT and high affinity choline uptake. In addition, BDNF was found to increase expression of the NGF receptor in septal cultures.

In initial experiments, we found that BDNF increased the number of AChE positive neurons in E17 septal cultures by approximately 2 fold. As with NGF (Hartikka, J. and Hefti, F., 1988, J. Neurosci. 8:2967-2985) this effect was most apparent at low cell densities. Interestingly, co-addition of NGF and BDNF were ineffective in further increasing the number of AChE positive cells over the level observed in the presence of either growth factor alone. This observation strongly suggests that BDNF and NGF act largely upon the same population of septal cholinergic neurons.

As initially reported for NGF (Hefti et al., 1985, Neuroscience 1:55-68), BDNF did not enhance cholinergic neuron survival in cultures established at relatively high cell densities. As a proportion of the cells plated, cholinergic neuron survival was found to be higher at high cell density than at low cell density, even in the absence of any neurotrophic factor. There are several possible explanations that may account for this including increased cell-cell contact, beneficial effects of increased numbers of nonneuronal cells or a more than proportional increase in endogenous neurotrophic activity. In terms of the latter possibility, we found no indication of substantially increased levels of endogenous NGF since addition of an excess of anti-NGF to untreated high density cultures only reduced basal CAT activity by 20%. In such cultures, exogenous NGF was able to produce as much as 3.4 fold increase in CAT activity.

As observed both at the level of protein and mRNA, there are now many reports which indicate that NGF can upregulate the expression of its own receptor both on cultured neurons and in vivo. In this study, we used the monoclonal antibody IgG-192 to detect the NGF-receptor. This monoclonal has been characterized on both rat sensory neurons and in rat brain (Taniuchi, M. and Johnson, E., 1985, J. Cell Biol. 101:1100-1106). While confirming the findings of Hartikka and Hefti that NGF can up-regulate the level of its receptor in septal cultures, as noted by an increase in the number of IgG-192 immunopositive neurons, we have additionally found that BDNF increases the number of IgG-192 immunopositive cells by up to 3 fold. The response to BDNF was biphasic in that high concentrations, in the range of 25-100 ng/ml, failed to produce as large an increase in the number of positive cells as was noted with 10 ng/ml. Interestingly, this type of dose response was quite different from that seen for the BDNF induced increase in the number of AChE positive neurons. In the latter, no reduction in the maximal effect of BDNF was seen at high concentrations. It should be noted that the low-affinity NGF receptor has recently been shown to also bind BDNF with similar affinity, suggesting that the NGF and BDNF low-affinity receptors might be identical (Rodriguez-Tebar et al. 1990, Binding of Brain-Derived Neurotrophic Factor to the Nerve Growth Factor Receptor Neuron. 4, 487–492).

Possible similarities in the mechanism of action of BDNF and NGF were suggested by the findings that BDNF was equipotent with NGF in the induction of AChE activity. Although BDNF was also found to promote cholinergic neuron survival to a similar extent to NGF, the effect of BDNF on CAT enzymatic activity was not as great as NGF. Over several experiments maximal CAT induction with BDNF ranged from 1.8–2.6 fold, while values of greater than 3-fold were seen routinely with NGF. Thus, although there may be some similarities in the mechanism of action of BDNF and NGF, it is quite probable that there are subtle differences in the expression and regulation of their respective receptors and the coupling of these receptors to the second messenger pathway(s) necessary to induce CAT activity.

The supposition that differences in the level of induction of CAT activity produced by BDNF or NGF might represent differential regulatory pathways was further supported by results from time course studies. Cultured septal neurons responded to BDNF with a rise in CAT activity until day 6 at which time the response appeared to plateau. In contrast, induction in CAT activity in response to NGF showed a protracted linear rise from 3 to 12 days. The cessation of a rise in the induction of CAT activity at 6 days in BDNF treated cultures may be indicative of a developmental change in the expression of either the BDNF receptor or a required component in the response pathway. Given that the number of cholinergic neurons (AChE positive neurons) found in high density cultures after 12 days appears to be independent of exogenous BDNF or NGF, it seems unlikely that differential neuronal cell death would account for the time course differences found in the induction of CAT activity by these two growth factors.

In the initial experiments involving BDNF treatment of basal forebrain cholinergic cells, no assumption was made as to the primary cell type, neuronal or glial, responsive to this neurotrophic factor. Although studies conducted on highly enriched cultures of peripheral neurons strongly suggest that BDNF has its effects directly on neurons (Lindsay et al., 1985, Dev. Biol. 112:319–328; Lindsay, 1988, J. Neurosci. 7:2394–2405), it is conceivable that the neuronal effects of BDNF seen in the present study could have been mediated through a primary action of BDNF on astroglia or other non-neuronal cells. However, BDNF was found to be equally effective in the induction of CAT activity in the presence ok a confluent monolayer of predominantly astroglial cells or in cultures greatly depleted of glial cells by treatment with the mitotic inhibitor, cytosine arabinoside. An intriguing observation from these experiments was that the shape of the dose response curves to BDNF was distinctly different in the two cases. In the presence of a glial monolayer, the response to BDNF was linear with an increasing concentration of BDNF. In neuron-enriched cultures, the dose response to BDNF was shifted to the left. One possible explanation for these results is that the glia themselves may express the BDNF receptor, thus lowering the effective concentration of the ligand available for the receptor localized on neurons. Alternatively, the suppressive effect of astrocytes could be indirect, unrelated to an effect on ligand concentration or receptor expression, and mediated for example by greatly increased degradation of BDNF. Similar observations have been reported by Hartikka and Hefti (Hartikka, J. and Hefti, F., 1988, J. Neurosci. 8:2967–2985) and Honegger and Lenoir (Honegger, P. and Lenoir, D., 1982, Dev. Brain Res. 3:229–238). It has been demonstrated that glial cells of different brain regions can greatly influence the morphology of neurons associated with them (Prochiantz et al., 1979, Proc. Natl. Acad. Sci. U.S.A. 76:5387–5391; Prochiantz et al., 1981, Nature 293:570–572). Thus, septal glia may have intrinsic properties either of a membranal or secretory nature which may act to suppress the expression of the cholinergic phenotype. The regulatory properties of astrocytes derived from the hippocampus under similar test conditions is now being investigated.

On the basis of the data presented, it is apparent that BDNF and NGF are both capable of increasing septal cholinergic neuronal function. It is interesting to speculate as to the possible physiological relevance of two highly homologous neurotrophic factors apparently acting on a single neuronal population. There has been some suggestion that the actions of BDNF and NGF may initially overlap during early development of peripheral neurons, especially on subpopulations of dorsal root ganglion neurons or their precursors, and then later segregate to act independently on distinct populations (Lindsay et al., 1985, Dev. Biol. 112:319–328; Ersberger, U. and Rohrer, H., 1988, Dev. Biol. 126:420–432); Barde, Y. A. 1989, Neuron. 2:1525–1534). This has not, however, been definitively established using appropriate markers to define subpopulations of sensory neurons. Since the present study focused on embryonic septal neurons established in culture at a single time-point in development, E17, it is possible that a similar sort of segregative phenomenon may occur at later development stages in the septum. Thus, there may prove to be interesting temporal and spatial differences in the responsiveness of septal cholinergic neurons to BDNF or NGF.

It will now be interesting to examine the effects of BDNF on basal forebrain cholinergic neurons in vivo, where there is now evidence that hippocampal-derived NGF may be involved in the normal development and maintenance of basal forebrain cholinergic neurons in vivo. It will be interesting to establish whether or not BDNF has a similar role in vivo. The recent finding that BDNF mRNA is particularly abundant in the hippocampus supports such a role.

17. EXAMPLE: ENZYMATIC CONVERSION OF PREPRO BDNF TO ACTIVE, MATURE BDNF

17.1. Materials and Methods

Commercially available endoproteinase Arg-C (purified from mouse submaxillary glands) was used to enzymatically convert the large precursor form of hBDNF (preproBDNF) to the biologically active mature protein. This enzymatic cleavage was accomplished in an in vitro reaction. The substrate in the enzymatic reaction was preprohBDNF synthesized in CHO-DG44 cells which was secreted into the cell culture media and harvested. The culture media consisted of Ham's F12 media (nucleoside-free) with 1% fetal bovine serum (FBS) and 1% each of penicillin and streptomycin. The reaction was carried out at 37° C. for 5 minutes using 5 units of enzyme and 50 $\mu$l of CHO-DG44 cell supernatant containing prepro hBDNF. Cleavage of preprohBDNF to mature hBDNF was complete under these conditions.

17.2. Results and Discussion

The prepro form of recombinant hBDNF (approximately 31,000 daltons) was completely processed to the mature bioactive form of hBDNF (approximately 12,000 daltons) in vitro using endoproteinase Arg-C. Recombinant human brain derived neurotrophic factor has been successfully produced in mammalian cells (CHO-DG44 cells). The hBDNF gene has been stably integrated into the CHO cell genome and the hBDNF gene amplified using a methotrexate amplification strategy. The recombinant hBDNF was secreted into the medium and found to be biologically active. Metabolic labeling followed by SDS polyacrylamide gel electrophoresis (15% gel) demonstrates that most of the synthesized [$^{35}$S]-labeled hBDNF product secreted into the culture medium migrated as the prepro form with an apparent molecular weight of 31,000 (FIG. 29, lane 2). [$^{35}$S]-labeled proteins secreted from wild type CHO-DG44 cells are shown in FIG. 30, lane 1. In order to generate predominately the mature form of hBDNF (apparent molecular weight of 12,000), we designed an in vitro strategy to enzymatically cleave the prepro form of hBDNF.

Trypsin digestion products are shown in FIG. 30, lanes 3–6. Bovine pancreas trypsin (purchased from Worthington; chymotryps in-free) was dissolved in phosphate buffered saline and added to 50 ul aliquots of [$^{35}$S]-labeled CHO cell hBDNF. Trypsin concentrations used were 25, 50, 75, and 100 ug/ml. The [$^{35}$S]-labeled reaction products are shown in lanes 3–6, respectively. The enzymatic cleavage reaction was carried out at 37° C. for 5 minutes. A gradual decrease in the labeling intensity of the 31,000 prepro-hBDNF was observed with a corresponding increase in an 18,500 molecular weight product. The mature form of hBDNF (molecular weight 12,000) was not generated under these conditions. FIG. 29, lane 7 shows the [$^{35}$S]-labeled reaction products following enzymatic digestion of CHO cell hBDNF with endoproteinase Arg-C isolated from mouse submaxillary gland from Boehringer Mannheim Biochemicals, Inc. 100 units of this enzyme were reconstituted from a lyophilized preparation with 100 ul of Milli-Q water and stored at −20° C. For the enzymatic digestion of CHO cell hBDNF, we used 5 units (5 ul) of enzyme and 50 ul of $^{35}$S-labeled protein from CHO cell supernatants containing preprohBDNF (FIG. 30, lane 2). As seen in FIG. 29, lane 7, 5 units of endoproteinase Arg-C was able to convert the prepro form of hBDNF (31,000 molecular weight) to the mature form of hBDNF (12,000 molecular weight) in 5 minutes at 37° C.

Enzymatic treatment with endoproteinase Arg-C of the supernatants of CHO cells expressing hBDNF increased the level of BDNF biological activity relative to unprocessed supernatants. Supernatants from CHO-DG44 cells expressing hBDNF were treated for 5 minutes with endoproteinase Arg-C at 37° C. 200 ul of supernatant were treated with 20 units of enzyme and both the treated and untreated hBDNF were assayed for biological activity using explants of E8 chick dorsal root ganglia. Twenty-four hours after the addition of hBDNF, neurite outgrowth was qualitatively scored. We consistently observed that the endoproteinase-treated BDNF samples were significantly more bioactive than the control (untreated) hBDNF samples. A concentration curve of this data is plotted in FIG. 30.

In conclusion, purified endoproteinase Arg-C can be used in an in vitro enzymatic reaction to generate the mature bioactive form of recombinant human brain derived neurotrophic factor from incompletely processed precursor molecules (i.e., pro BDNF). This novel method will allow for an efficient large scale production of bioactive human BDNF from mammalian cell culture systems. For example, it may be possible to immobilize the endoproteinase Arg-C to a solid matrix and establish an efficient column chromatography step.

18. EXAMPLE: BRAIN-DERIVED NEUROTROPHIC FACTOR PROMOTES SURVIVAL AND MATURATION OF DOPAMINERGIC NEURONS OF THE RAT VENTRAL MESENCEPHALON

18.1. Materials and Methods

18.1.1. Cell Cultures

Dissociated cultures were established by enzymatic and mechanical dissociation of ventral mesencephalon tissue dissected from E14–E15 rat embryos. Typically, pooled tissue from two or three litters of rat embryos from time-mated Sprague-Dawley rats were trypsinized (0.125%; Worthington) in F12 medium (Gibco) for 20 minutes at 37° C. After washing in growth medium (MEM containing the following supplements: glutamine, 2 mM, glucose, 6 mg/ml, penicillin G, 0.5 U/ml, streptomycin 5 μg/ml, fetal calf serum, 7.5%) the tissue was briefly centrifuged at low speed for 5 minutes and the pellet was dissociated by trituration. After allowing 1–2 minutes for nondispersed cell clumps to settle, the single cell suspension was seeded onto 35 mm dishes (precoated with polyornithine and laminin; Lindsay et al., 1985, Dev. Biol. 112:319) containing growth medium to give a density of $5 \times 10^4$ cells per cm$^2$. After an overnight incubation in growth medium to allow cell attachment, cells were cultured in the presence or absence of BDNF in a serum-free, defined medium as described by Bottenstein and Sato (Bottenstein and Sato, 1979, Proc. Natl. Acad. Sci. USA 76:514), except that insulin was included at 20 ng/ml. To visualize dopaminergic cells, cultures were fixed with 4% paraformaldehyde, washed extensively, permeabilized with 0.02% Saponin in Sorensen's buffer with 1.5% horse serum and stained with a mouse monoclonal antibody to rat TH (Boehringer-Mannheim). Primary antibody binding was visualized using a Vectastain ABC kit (Vector Labs).

18.1.2. Measurement of Dopamine Uptake

Cultures were prepared as described in 18.1.1., supra, and were grown for the number of days indicated, either in the presence or absence of porcine BDNF, 50 ng/ml. Dopamine uptake was determined in triplicate cultures at the time points indicated. Cells were prewashed in uptake-buffer of the following composition: 136.8 mM NaCl, 2.7 mM KCl, 8 mM Na$_2$HPO$_4$7H$_2$O, 1.5 mM KH$_2$PO$_4$, 5 mM glucose, 1 mM CaCl$_2$, 1 mM MgSO$_4$, 0.1 mM ascorbate and 0.1 mM pargyline, pH 7.4. Those samples to be measured for nonneuronal $^3$H-dopamine uptake had benztropine included (BZT) in the uptake buffer, at a concentration of 5 μM. After washing, the cells were prewarmed to 37° C. for five minutes in fresh uptake buffer at which point $^3$H-dopamine (NEN, 40 Ci/mmol) was added to a final concentration of 50nM. The cultures were incubated at 37° C.

for 15 minutes, the uptake solution was removed and the cells were placed on ice, and washed four times with ice-cold uptake buffer. Cells were harvested by addition of 0.5N NaOH to the culture dishes, and the NaOH extract was counted in a Beckman scintillation counter with 15 mls Ultima Gold scintillation fluid (Packard Instruments). Specific neuronal dopamine uptake is defined as that uptake (cpm) observed in the absence of BZT less that observed in the presence of BZT. Routinely, between 70–90% of the total uptake was inhibitable by BZT. In replicate cultures at each time point the number of TH+ neurons was determined by immunocytochemical staining and the results shown represent uptake normalized on a per TH+ basis.

18.1.3. Transient Expression of BDNF

Cos M5 cells were transfected with the vector CDM8 containing the sequence encoding human BNDF. At 72 hours post transfection, 50 ml of culture supernatant was collected and dialyzed against 6M urea. The dialyzed supernatant was then combined with ampholines (pH 3.5–10, BioRad) for 4½ hours. Fractions were collected, dialyzed against 25 mM NaPO4 buffer pH 7.6 using dialysis tubing which had been prewashed in BSA (0.5 mg/ml) to prevent nonspecific absorption. Fractions were assayed for neurite outgrowth promoting activity in cultures of E8 chick dorsal root ganglion explants. Active fractions were pooled. Analysis of the active pool by SDS PAGE and subsequent silver staining (Wray et al., 1981, Anal. Biochem. 118:197) on an 8–18% gel revealed a faint band at 68 kD corresponding to BSA, and a single band at approximately 12 kD, corresponding to that observed previously for porcine BDNF (Barde et al., 1982, EMBO J. 1:549) (data not shown). In comparative bioassays carried out on chick dorsal root, nodose and sympathetic ganglion explants the specific activity and neuronal specificity of purified recombinant human BDNF was similar to that of purified porcine BDNF.

18.1.4. Production of hBDNF from Transfected CHO Cells

CHO-DG44 cells were a kind gift of Dr. L. Chasin (Columbia University, New York). These cells are deficient in dihydrofolate reductase (dhfr−) (Urlaub and Chasin, 1980, Proc. Natl. Acad. Sci. USA 77:4216–4220). CHO-DG44 cells were maintained in Ham's F12 medium with 10% fetal bovine serum, 1% penicillin and streptomycin, and 2 mM glutamine. Cells were passaged twice a week and were routinely checked for mycoplasma contamination. All plasmid DNA was purified by double cesium chloride banding prior to transfection. The human brain-derived neurotrophic factor gene was subcloned into the mammalian expression vector pCDM8 to generate pC8hB as described previously (Maisonpierre et al., 1990, Science 247:1446–1451). A weakened dihydrofolate reductase gene, p410, was kindly provided by Dr. L. Chasin. These two gene constructs were cotransfected into CHO-DG44 cells by electroporation (reviewed in Shigekawa and Dower, 1988, BioTechniques 6:742–751). Approximately $1 \times 10^6$ cells were transfected with 20 ug of pC8hB and 0.2 ug of p410. 48 hours after transfection, the CHO-DG44 cells were split into selection media consisting of nucleoside-free Ham's F12 (without thymidine and hypoxanthine; −HT) plus 10% dialyzed fetal bovine serum and 1% penicillin and streptomycin. Individual colonies were isolated approximately 10 days after placing the cells in nucleoside-free selection medium. Individually selected colonies resistant to growth in nucleoside-free Ham's F12 (−HT) medium were treated with either 0.02, 0.05, or 0.1 uM methotrexate (MTX) to induce gene amplification (Alt et al., 1978, J. Biol. Chem. 253:1357–1370). MTX-resistant colonies were cultured as pools and were further amplified with either 1.5, 2.0, or 2.5 uM MTX. A single colony resistant to 2.5 uM MTX was isolated and selected for scale-up culture and production of hBDNF. Southern blotting analysis of this clone (DGZ1000-B-3-2.5) indicated an amplification of the BDNF gene relative to wild-type CHO-DG44 cells of approximately 50-fold. Bioassays with explants of embryonic (E8) chick dorsal root ganglia (DRG) were used to estimate that this clone was producing approximately 9.5 ug of hBDNF/ml (not shown). Recombinant hBDNF was produced on a large scale by culturing DGZ1000-B-3-2.5 cells in 480 cm$^2$ roller bottles. Media was harvested approximately four days after these cells reached confluence. Purification of hBDNF from culture supernatant was performed as above for COS supernatant.

18.2. Results and Discussion

Characterization of molecular signals which control neuronal survival and specificity of target innervation is of fundamental interest, not only because it will help to elucidate how the nervous system is shaped but also because it is likely to lead to a better understanding of the mechanisms involved in maintenance and repair of mature neurons in appropriate synaptic configurations. While it is widely recognized that the survival and maintenance of neurons depend upon specific, target cell-derived neurotrophic factors (Levi-Montalcini and Angeletti, 1968, Physiol. Rev. 48:534; Thoenen and Barde, 1980, Physiol. Rev., 60:1284; Purves, D., 1988, in Body and Brain, Harvard University Press, Cambridge, Mass.; Barde, Y. A., 1989, Neuron, 2:1525; Lindsay, R. M. 1988, The Making of the Nervous System, Oxford University Press, Oxford, p. 148) very few such molecules have been fully characterized. To date, only two neurotrophic factors, nerve growth factor (NGF) and brain-derived neurotrophic factor (BDNF), have been shown to selectively support the survival of distinct neuronal populations in vivo (Levi-Montalcini and Angeletti, 1968, Physiol. Rev. 48:534; Barde, Y. A., 1989, Neuron, 2:1525; Leibrock et al., 1989, Nature 341:149).

Neuronal cell culture has been widely used to establish bioassays for the identification of neurotrophic activity in cell and tissue extracts (Levi-Montalcini and Angeletti, 1968, Physiol. Rev. 48:534; Thoenen and Barde, 1980, Physiol. Rev., 60:1284; Lindsay, R. M. 1988, The Making of the Nervous System, Oxford University Press, Oxford, p. 148; Varon and Adler, 1981, Adv. Cell. Neurobiol., 2:118) and to determine the neuronal specificity(ies) of purified neurotrophic factors (Ebendal, T., 1989, in Nerve Growth Factors, John Wiley, London, p. 81; Barbin et al., 1984, J. Neurochem. 43:1468; Barde et al., 1982, EMBO J. 1:549; Davies et al., 1986, J. Neurosci. 6:1897; Lindsay et al., 1985, Dev. Biol. 112:319). To date, most studies have concentrated on the neurotrophic requirements of different classes of neurons of the peripheral nervous system (PNS). The availability of NGF has established it as by far the most well characterized neurotrophic factor: NGF has been shown both in vitro and in vivo to be essential for the survival and maintenance of neuronal subpopulations of both the PNS and CNS (Levi-Montalcini and Angeletti, 1968, Physiol. Rev. 48:534; Thoenen and Barde, 1980, Physiol. Rev., 60:1284; Whittemore and Seiger, 1987, Brain Res. Rev. 12:439; Snider and Johnson, 1989, Ann. Neurol. 26:489; Hefti et al., 1989, Neurobiology of Aging 10:515; Martinez et al., 1987, Brain Res. 412:295; Takei et al., 1988, J. Neurochem. 51:1118; Hartikka and Hefti, 1988, J. Neurosci. 8:2967). Hampering the identification of neurotrophic growth factors for specific CNS neurons has been the limited availability of purified preparations of neurotrophic factors other than NGF, and the difficulty in preparing homogeneous preparations of specific neuronal populations. Two recent observations prompted us to study the effects of BDNF on the survival of CNS (nigral) dopaminergic neurons. Firstly, it is now clear that the BDNF gene is expressed in the CNS, and at comparably or higher levels than the NGF gene (Leibrock et al., 1989, Nature 341:149). Secondly, it has been reported that a protein partially purified from bovine striatum (a target of nigral dopaminergic neurons), with characteristics apparently similar to those of BDNF, can increase the in vitro survival of dopaminergic neurons prepared from the mesencephalon (Dal Toso et al., 1988, J. Neurosci 8:733).

FIG. 31A illustrates the typical appearance of dissociated ventral mesencephalic cells after nine days in culture. Virtually all of the cells had phase bright perikarya and long processes. Few cells of fibroblast morphology were evident and no astroglial cells were detected when cultures were stained with antibodies for the astroglial marker, glial fibrillary acidic protein (GFAP; Bignami et al., 1972 Brain Res. 43:429). To visualize dopaminergic neurons in these culture, immunocytochemical staining was carried out with monoclonal antibodies to TH. As expected, the number of TH+ neurons was small (arrows, FIGS. 31B and 31C) and varied, depending on the time in culture, between 0.1–0.5% of the cells plated. Various neuronal morphologies were noted among the TH+ cells, as shown in FIGS. 32A through 32C.

In all cultures, there was invariably a gradual decline in the number of TH+ cells (FIGS. 33A and 34) after the first 3–4 days in vitro. By 8 days in culture, for example, the number of TH+ cells in control cultures was only 25% of that found in similar cultures at day 2 (FIG. 34). However, in cultures treated with BDNF, the loss of TH+ cells was greatly reduced when compared to controls. At all times examined after 8 days in vitro the number of TH+ cells in BDNF treated cultures was greater than in the untreated controls, e.g. 1.8-fold higher after a single addition of BDNF (FIG. 33A) and 5-fold higher after multiple additions (FIG. 34). Even when added only once to cultures maintained for 8 days, the effect of BDNF was found to be dose dependent (FIG. 33B). In agreement with previous reports (Dal Toso et al., 1988, J. Neurosci 8:733; Knusel et al. 1990, J. Neurosci. 10:558), NGF (50 ng/ml) had no effect on the number of TH+ cells (FIG. 33C).

As a further way of examining the effect of BDNF on the dopaminergic neurons in these cultures, the capacity of the TH+ cells to take up $^3$H-dopamine was studied. As shown in Table X, dopamine uptake capacity (normalized per TH+ neuron) increased markedly over the first 8 days in culture but dropped thereafter. It was found, however, that BDNF did not change the capacity of TH+ cells to take up dopamine, as the same time course and similar values were obtained in the presence or absence of BDNF (Table X). We hypothesized from this result that BDNF probably acts directly to promote survival of dopaminergic neurons in mesencephalic cultures as opposed to inducing the expression of a dopaminergic phenotype in neurons which do not necessarily require BDNF for survival. To examine this further, we carried out experiments in which the number of TH+ neurons was determined in culture in which BDNF addition was initially delayed for several days. We found that when BDNF addition was delayed until day 5, and the number of TH+ cells was subsequently determined at 6, 8 or 10 days, fewer dopaminergic cells were seen in these cultures when compared to parallel cultures in which BDNF had been present from day 2 onwards (FIG. 35). Although delayed addition of BDNF clearly increased the number of TH+ neurons compared to controls, when examined even at equivalent time points the effect of delayed addition was never found to rescue as many TH+ neurons as addition of BDNF on day 2.

Taken together, these results argue against the possibility that BDNF acts only to increase TH-gene expression within a fixed number of cells, and suggest that BDNF exerts its effect by increasing survival of dopaminergic neurons that are otherwise lost when this neurotrophic factor is not added to cultures at an early stage.

Several reports have documented the stimulation of maturation and enhancement of survival in vitro of mesencephalic dopaminergic neurons by either target-derived extracts or various growth factors (Dal Toso et al., 1988, J. Neurosci. 8:733; Knusel et al. 1990, J. Neurosci. 10:558; Prochiantz et al., 1979, Proc. Natl. Acad. Sci. USA 76:5387; DiPorzio et al., 1980, Nature 288:370; Prochiantz et al., 1981, Nature 293:570; Denis-Donini et al., 1983, J. Neurosci. 3:2292). So far, however, there has been no report of a fully purified molecule directly and selectively supporting the survival of TH+ neurons in the complete absence of glial cells or enhanced cell division (as observed, for example, with IGF-1 or FGF, Dal Toso et al., 1988, J. Neurosci 8:733). In agreement with previous reports using early embryonic mouse tissue (Dal Toso et al., 1988, J. Neurosci 8:733), E14 rat ventral mesencephalic cells cultured in serum-free, defined medium were found to be essentially free of astrocytes or fibroblasts. The relatively low cell plating density of 50,000 cells/cm$^2$ used in this study diminished the effects of any possible endogenous neurotrophic activity, and allowed for more accurate cell counting. In view of the results presented here, it appears that the neurotrophic factor, partially purified from bovine striatum by Del Toso et al. (Dal Toso et al., 1988, J. Neurosci 8:733), is likely to be BDNF. This suggests that BDNF is produced in the striatum and taken up by the terminals of the dopaminergic neurons projecting from the substantia nigra. As yet, however, mRNA for BNDF (or indeed mRNA for other members of the neurotrophin family) has not been found to be abundant in striatal tissue by Northern blot analyses.

It is clear that BDNF addition, even in the case of multiple additions, does not result in complete survival of nigral dopaminergic neurons during the culture periods analyzed. This phenomenon has already been observed under experimental conditions very similar to ours by Dal Toso et al. (Dal Toso et al., 1988, J. Neurosci 8:733) who showed that this loss might be related to the cell density used; at higher cell densities (4 times that used here) a larger number of catecholamine-fluorescent cells could be seen and the spontaneous disappearance of these cells was decreased. Possibly, cell-cell contact is needed for long term survival of these cells.

Further studies, particularly those directed at examining the effects of BDNF on the development and maintenance of dopaminergic neurons of the ventral mesencephalon in vivo, will be necessary to determine the physiological relevance of the effects of BDNF described here. In view of the specific loss of nigral dopaminergic neurons in Parkinson's disease, it is particularly desirable to find a neurotrophic factor which selectively affects these cells. Thus, the present finding that BDNF supports the survival of these neurons, cells which are refractory to NGF, provides rationale for animal experiments which will determine whether BDNF can protect dopaminergic neurons from the neurotoxic effects of either 6-hydroxydopamine or MPTP (1-methyl-4-phenyl-1,2,3,6-tetrahydropyridine). Such studies may lead to a novel therapeutic approach for Parkinsonism.

TABLE X

DOPAMINE UPTAKE IN VENTRAL MESENCEPHALIC CULTURES IS NOT INCREASED DIRECTLY BY BDNF

| Days In Culture | $^3$H-Dopamine Uptake (cpm/TH /(+) neuron/ 15 minutes) | |
| --- | --- | --- |
| | Control | BDNF-Treated |
| 3 | 0.51 ± 0.1 | 0.95 ± 0.2 |
| 6 | 4.5 ± 0.3 | 3.1 ± 0.6 |
| 8 | 13.5 ± 5.3 | 27.3 ± 1.2 |
| 10 | 3.37 ± 0.24 | 2.21 ± 0.18 |

19. EXAMPLE: BDNF PRODUCES A DOSE-DEPENDENT INHIBITION OF GAMMA-AMINOBUTYRIC ACID UPTAKE

19.1. Materials and Methods 19.1.1. Hippocampmal Cell Cultures

Hippocampi were dissected from E18-19 rat embryos of Sprague-Dawley rats, and collected in F10 medium. The tissues were minced, rinsed twice with F10 medium (Gibco) and trypsinized with 0.25% trypsin (Gibco) for 20 minutes at 37° C. Trypsin was inactivated by the addition of a serum-containing medium composed of minimum essential medium (MEM) supplemented with fetal calf serum (FCS, 10%), glutamine (2 mM), penicillin (25 U/ml) and streptomycin (25 ug/ml). Dissociated cells obtained by gentle trituration were collected and centrifuged at low speed (500 rpm) for 30 seconds. The centrifugation was repeated twice, and the cell pellets were then resuspended in serum-containing medium. The cells were then plated onto 6 mm wells or 35 mm dishes that were coated with polyornithine (10 ug/ml) and laminin (10 ug/ml). In most of the experiments, the cells were plated at a low density of approximately 71,000 cells/cm$^2$. Five to six hours following the plating of cells, medium was changed to a serum-free medium containing 1% N3 and penicillin-streptomycin (25 units/ml and 25 ug/ml, respectively), at which time BDNF was added. Medium was changed every three to four days, with re-addition of the factor.

19.1.2. Measurement of High Affinity Uptake for Gamma-Aminobutyric Acid (GABA)

High-affinity GABA uptake was measured using a modified procedure of Tomozawa and Appel (1986, Brain Res. 399:111-124). Cells were washed in the GABA uptake buffer containing 140 mM NaCl, 2.6 mM KCl, 1 mM KH$_2$PO$_4$, 1 mM Na$_2$HPO$_4$, 6 mg/ml glucose, 1 mM MgCl$_2$, 1 mM CaCl$_2$, 0.1% BSA. following washing, cells were incubated with the GABA uptake buffer for 5 minutes at 37° C. H-GABA (NEN, NET-191X, 111.4 Ci/mmol) was then added at a final concentration of 12 nM, and incubation was carried out at 37° C. for 10 minutes. Cells were then kept on ice, and washed three times with the uptake buffer. Cells were incubated with 0.14N NaOH for 2 hours at room temperature, and $^3$H-GABA in the extract was counted. $^3$H-GABA uptake was found to be linear for up to at least 30 minutes. Uptake of GABA into non-neuronal cells was inhibited by the addition of 2 mM B-alanine, whereas uptake specific for neurons is verified by inhibition with nipecotic acid at 1 mM.

19.2. Results and Discussion

We have recently detected abundant levels of message for BDNF in neuron-enriched hippocampal cultures, but not in hippocampal astrocytes. These data strongly suggest that BDNF is localized to hippocampal neurons. In order to examine the effect of BDNF on hippocampal neurons in culture, cells were treated with various concentrations of BDNF (rotorphor-purified from COS supernatants). At the end of the 8 days treatment period, high affinity GABA uptake into neurons was measured. As shown in FIG. 36, BDNF produced a dose-dependent inhibition of GABA uptake. Thus, BDNF may affect the survival and/or phenotypic expression of GABAergic neurons. BDNF did not have any effect on glutamate-containing neurons (as assessed by glutamate-uptake measurements), nor on the levels of neurofilament protein. Thus, the effect of BDNF on hippocampal cultures appears to be specific for Gabaergic neurons.

20. EXAMPLE: BDNF CONFERS A PROTECTIVE EFFECT AGAINST TOXIC EFFECTS OF MPP+

20.1. Materials and Methods 20.1.1. Measurement of the Effects of Neurotrophic Factors on MPP+-Treated SH-SY5Y Cells SH-SY5Y cells were seeded into 24 well plates at a density of $1 \times 10^5$ cells per well. Twenty four hours after seeding, the cells were treated with neurotrophic factors. Twenty four hours after neurotrophic factor treatment, the cells were treated with MPP+ (10 uM). Forty-eight hours after MPP+ addition, viable cells were quantitated by the trypan blue exclusion assay. Neurotrophic factors utilized were mNGF-COS (1:5 dilution), hBDNF-COS (1:5 dilution), purified rCNTF from E. coli (25 ng/ml), purified bovine brain bFGF (25 ng/ml), rNT3-COS (1:5 dilution), and purified hEGF (25 ng/ml).

Table XI shows data in which the uptake of 3H-MPP+ was measured in SH-SY5Y cells. Cells which were not treated with growth factors were used as controls and others were grown in the presence of BDNF for 48 hours. Specific uptake was determined by that uptake which was blocked by 100 $\mu$M nomifensine, a specific dopamine uptake blocker. Specific uptake accounted for more than 90% of total uptake. One half of the dishes were treated with 100 $\mu$M nomifensine for 15 minutes, then 10 $\mu$M MPP+ was added to all dishes. After the incubation period, the cells were washed several times with media and then 0.5N NaOH was added to each sample. The entire denatured sample is added to scintillation fluid and counted. The uptake was measured at 10, 20, 30, and 60 minutes. BDNF did not block the uptake of MPP+ into the cells. Based upon these data it is clear that the protection of BDNF against MPP+ toxicity does not occur by blocking its uptake into cells.

TABLE XI

BDNF DOES NOT BLOCK THE UPTAKE OF MMP+ INTO SH-SY5Y CELLS

| | Specific Uptake (CPM/DISH) | |
|---|---|---|
| | Control | BDNF |
| 10 minutes | 1999.3 ± 253.0 | 2272.4 ± 109.3 |
| 20 minutes | 5431.3 ± 611.7 | 4645.1 ± 92.9 |
| 30 minutes | 5262.2 ± 1405.9 | 5725.7 ± 463.3 |
| 60 minutes | 12973.5 ± 1808.2 | 11657.2 ± 832.5 |

20.1.2. Measurement of the Effects of Neurotrophic Factors on MPP+-Treated Ventral Mesencephalic Cultures Cultures of dissociated ventral mesencephalic neurons were established from E14 rat embryos according to established protocols (See Section 18, supra). Forty eight hours after these cultures were established, they were treated with the appropriate neurotrophic agents as indicated. Neurotrophic factors included hBDNF (rotophor-purified from CHO cells, ≦50 ng/ml), purified mNGF (50 ng/ml), rNT-3 (COS supernatants at 1:50 dilution), purified bovine brain bFGF (10 ng/ml), and purified rCNTF (25 ng/ml) from E. coli). Twenty four hours after neurotrophic factor addition, these cultures were treated with MPP+ (1 uM). Forty eight hours after MPP+ treatment, TH positive neurons were identified by immunohistochemistry and quantitated. Data represent the mean of three independent experiments done with triplicate samples per experiment. The number of TH-positive neurons following MPP+ treatment is represented by the cross-hatched bars. Open bars represent the number of TH-positive neurons without MPP+ treatment.

20.2. Results and Discussion

When BDNF, NGF, CNTF, NT-3, bFGF, and EGF were separately tested for the ability to protect SH-SY5Y cells from 1-methyl-4-phenyl pyridinium (MPP+) toxicity, as measured by trypan blue exclusion assay, only BDNF and NGF appeared to exhibit significant protective activity against MPP+ toxicity (Tables XIA and XII).

TABLE XIA

BDNF AND NGF PROTECTION OF SH-SY5Y CELLS FROM MPP+ TOXICITY

| Results: Treatment: | Number of Viable Cells (% Viable) |
|---|---|
| COS-Mock transfected (1:5) | $0.4 \times 10^4$ (5%) |
| BDNF-COS (1:5) | $1.2 \times 10^5$ (67%) |
| NGF-COS (1:5) | $1.7 \times 10^5$ (84%) |
| CNTF | $0.6 \times 10^4$ (14%) |
| NT-3 | $0.7 \times 10^4$ (20%) |
| bFGF | $0.4 \times 10^4$ (11%) |
| EGF | $0.1 \times 10^4$ (3%) |

TABLE XII

BDNF AND NGF CONCENTRATION CURVE FOR MPP+ TOXICITY EXPERIMENTS

| Treatment | % Viable Cells |
|---|---|
| COS-MOCK | |
| (1:2) | 13 |
| (1:5) | 5 |
| (1:10) | 3 |
| (1:20) | 6 |
| (1:50) | 7 |
| (1:100) | 2 |
| COS-BDNF | |
| (1:2) | 73 |
| (1:5) | 67 |
| (1:10) | 65 |
| (1:20) | 42 |
| (1:50) | 30 |
| (1:100) | 25 |
| COS-NGF | |
| (1:2) | 88 |
| (1:5) | 84 |
| (1:10) | 63 |
| (1:20) | 50 |
| (1:50) | 47 |
| (1:100) | 34 |

In ventral mesencephalic cultures, the data indicate that BDNF exhibited a significant protective effect against MPP+ toxicity, whereas bFGF exerted a lesser effect (FIG. 37). MPP+ treatment was found to reduce the number of tyrosine hydroxylase positive neurons by 85% in control cultures but only by 40% in cultures pretreated with BDNF prior to MPP+ exposure. MPP+ is the presumed active metabolite for the toxin MPTP, which has been observed to induce a Parkinson's disease-like syndrome in vivo, which is an accepted model system for Parkinson's disease. Thus, the protective effect of BDNF and NT-3 indicate that these compounds may prove useful in the treatment of Parkinson's disease or in the prevention of neurologic damage subsequent to toxic exposure.

21. EXAMPLE: PRETREATMENT OF CELLS WITH BDNF IS PROTECTIVE AGAINST 6-HYDROXYDOPAMINE TOXICITY

21.1. Materials and Methods 21.1.1. Cell Cultures

Primary dopaminergic neuron cell cultures were prepared from dissociated ventral mesencephalon tissue obtained from E14 rat embryos as set forth in Section 18.1.1., supra. SH-SY5Y cells, originally obtained from Dr. June Biedler, (Memorial Sloan-Kettering Institute, New York) were at passage 43, and maintained in RPMI 1640 medium with serum.

21.1.2. Pretreatment of Ventral Mesencephalon Cultures with BDNF Followed by Exposure to 6-Hydroxydopamine Primary ventral mesencephalon cultures were maintained in vitro in a serum-free, defined medium as described by Bottenstein and Sato (1979, Proc. Natl. Acad. Sci. U.S.A. 76:514) for three to five days, and then half the cultures were exposed to recombinant hBDNF ("BDNF-plus cultures") at a concentration of 50 ng/ml and the other half ("BDNF-minus cultures") were used as controls. Alternatively, cultures were exposed to BDNF at 50 ng/ml from the onset of the culture period. For the short term exposure experiments, sixteen hours later 6-hydroxydopamine (6-OHDA) treatment was carried out. 6-OHDA was prepared as a 100-fold concentrated stock solution either in 0.1N HCl or 0.1 mM ascorbate. Treatment was initiated by addition of stock such that the final 6-OHDA concentration was 100 μM in the case of the stock made up in 0.1N HCl, or 10 μM in the case of the stock made up in 0.1 mM ascorbate. Ascorbate serves to recycle oxidized 6-OHDA, thus potentiating the poisoning. It is for this reason that when ascorbate is used as vehicle, the final concentration chosen for 6-OHDA treatment is lower than in the case where 0.1N HCl is used as vehicle. The poisoning period for 100 μM 6-OHDA was 90 minutes; that for 10 μM 6-OHDA was 60 minutes.

21.1.3. Measurement of H-Dopamine Uptake

Both the viability and metabolic activity of the cultures were evaluated immediately after exposure to 6-OHDA; this was done by measurement of $^3$H-dopamine ($^3$H-DA) uptake activity as described in Section 18.1.2., supra. Each treatment group consisted of five culture dishes, two of which were treated with 5 μM benztropine mesylate (BZT) prior to the addition of $^3$H-DA in order to quantitate non-neuronal uptake of $^3$H-DA. Specific neuronal uptake of $^3$H-DA is defined as that uptake (cpm) observed in the absence of BZT less that observed in the presence of BZT.

Briefly, to measure $^3$H-DA uptake, all culture plates were preincubated in PBS for five minutes and $^3$H-DA (NEN #NET131) was then added to a final concentration of 50 nM. The cultures were incubated at 37° C. for 15 minutes and were placed in ice thereafter. The cultures were washed at 4° C. with PBS and then extracted in 0.5 ml 0.5N NaOH for two hours. The extracts were counted in the scintillation counter. As an alternative measure of cell viability, tyrosine hydroxylase immunocytochemistry (THICC) was carried out following poisoning with 6-OHDA. In these experiments, the treatment consisted of 100 μM 6-OHDA for 90 minutes using 0.1 mM ascorbate as carrier.

21.1.4. Measurement of Glutathione Disulfide

SH-SY5Y cells were plated into 100 mm plates. Two days after plating, BDNF (5 or 50 ng/ml) or basic fibroblast growth factor (bFGF, 10 ng/ml) were added to the appropriate plates. 24 hours later, 10 μM 6-OHDA was added. 24 hours after the addition of 6-OHDA, oxidized glutathione (glutathione disulfide, GSSG) levels were measured using the spectrophotometric-based assay of Tietze (1969, Anal. Bioch. 7:502–522). Protein levels were determined using the BioRad reagent.

21.2. Results and Discussion 21.2.1. BDNF Protects Primary Dopaminergic Cultures Against 6-Hydroxydopamine Toxicity As shown in TABLE XIII, treatment with BDNF prior to 6-OHDA exposure resulted in significantly less toxic effects, as measured by a smaller decrease in $^3$H-DA uptake, indicating a smaller loss in cell metabolic activity. After 6-OHDA exposure, cultures maintained in the presence of BDNF for the entire culture period (5 days) had lost 50 percent of $^3$H-DA uptake relative to sister cultures not exposed to 6-OHDA. In contrast, cultures maintained without BDNF and treated with 6-OHDA had lost 100 percent of uptake capability. In experiments in which a lower concentration of 6-OHDA was used for 60 minutes, cultures not exposed to BDNF had a 51% decline in $^3$H-DA uptake activity as a result of exposure to this neurotoxin, whereas cultures pre-exposed overnight to BDNF only had a loss of 11% of this activity.

The viability of cultures exposed to 6-OHDA was evaluated by THICC. Cultures maintained in the presence or absence of BDNF for 6 days were exposed to 6-OHDA and ascorbate or ascorbate alone for 90 minutes. Immediately after this period, cultures were processed for THICC to determine the viability of the dopaminergic neurons. In cultures maintained in the absence of BDNF, the toxic treatment led to a 77% decline in TH+ neurons whereas in cultures exposed to BDNF the corresponding decline was reduced to only 36% as shown in Table XIV.

TABLE XIII

% $^3$H-DA UPTAKE LOSS FOLLOWING EXPOSURE TO 6-OHDA*

| 6-OHDA Treatment | Control | +BDNF Treated Cultures Pre exposure (time) |
|---|---|---|
| 10 μM, 60 min. in 0.1 mM ascorbic acid | 51% | 11% (overnight) |
| 100 μM, 90 min. in 0.1 N HCL | 100% | 50% (5 days) |

*expressed as the percentage relative to cultures not treated with 6-OHDA

TABLE XIV

LOSS OF DOPAMINERGIC NEURONS FOLLOWING EXPOSURE TO 6-OHDA

| Culture Condition | % decline on TH(±) cells after 6-OHDA treatment |
|---|---|
| Control | 77% |
| +BDNF pre exposure | 36% |

21.2.2. BDNF Decreases the Oxidation of Glutathione in 6-Hydroxydopamine Treated Cultures Experiments which measured the amount of oxidation of glutathione in 6-OHDA treated BDNF-plus and BDNF-minus cultures (as well as basic fibroblast growth factor, bFGF, treated and untreated cultures) were performed in order to examine the mechanism of the protection conferred by BDNF against 6-OHDA toxicity. The dopaminergic neuroblastoma cell line SH-SY5Y was used in these experiments. 6-OHDA toxicity has been linked to the production of oxygen radicals. When 6-OHDA is oxidized, the superoxide radical is formed. Superoxide dismutase catalyzes the formation of hydrogen peroxide from superoxide. Hydrogen peroxide can be detoxified by two enzymatic systems, catalase and glutathione peroxidase. In the presence of hydrogen peroxide, reduced glutathione (GSH) will be oxidized to glutathione disulfide (GSSG). An increase in GSSG is used as an index of oxidative stress.

As shown in FIG. 38, 6-OHDA treatment caused about a 5-fold increase in the levels of GSSG. When cells were pretreated with 50 ng/ml BDNF, the rise in GSSG caused by 6-OHDA treatment was completely prevented. 5 ng/ml BDNF and bFGF did not prevent the rise in GSSG.

It therefore appears that BDNF may protect dopaminergic neurons from oxidative damage caused by agents such as 6-OHDA. Since oxidative mechanisms may be involved in the etiology or progression of neurological disorders, such as, for example, Parkinson's disease, BDNF may be useful in the prevention or treatment of such disorders.

FIG. 39 shows data in which SH-SY5Y cells were plated in 150 mm dishes and treated with the appropriate growth factors for 48 hours. Control cells were not treated with growth factors. A cytosol enriched fraction of the cells was prepared by centrifugation. The cellular pellet was homogenized in 0.25M sucrose and spun at 100,000×g for 1 hour. The supernatant was analyzed for GSSG reductase activity by the method of Carlberg and Mannervik, 1975, J. Biol. Chem. 205:5475–5480. The reductase activity was measured by following the oxidation of NADPH spectrophotometrically at 340 nm. Data are the mean±SEM. BDNF doubled the activity of GSSG reductase and bFGF had no effect. These data may explain a possible mechanism by which BDNF protects cells against 6-OHDA toxicity. The toxicity of 6-OHDA has been clearly linked to the production of oxygen radicals. An induction in the activity of a protective enzyme such as glutathione reductase by BDNF may explain its protective action. Studies are under way to investigate whether BDNF can increase the activity of other protective enzymes, such as catalase or superoxide dismutase.

22. EXAMPLE: RETROGRADE AXONAL TRANSPORT OF BDNF IN THE PERIPHERAL NERVOUS SYSTEM

Nerve growth factor (NGF), is a target-derived, retrogradely transported survival factor for peripheral sympathetic and sensory neurons (Thoenen and Barde, 1980, Physiolog. Rev. 60:1284). Quantitative retrograde transport studies of exogenous (Hendry et al., 1974, Brain Res. 6.8.:103 and endogenous (Korching and Thoenen, 1983, Neurosci. Lett. 39:1) NGF have shown that the transport is specific and saturable. The elucidation of transport mechanisms for BDNF and related neurotrophins will give insight to 1) routes of administration of BDNF, and 2) specific classes of neurons which may respond to BDNF in the course of regeneration or pathogenic degeneration.

22.1. Materials and Methods

22.1.1. Radioiodination of BDNF

Six μg of purified BDNF was iodinated by the lactoperoxidase method (Marchalonis, 1969, Biochem. J. 113:299). Incorporation of iodine was routinely 70–80% and specific activities ranged from 150–200 cpm/pg. The BDNF was brought up to 0.5% BSA containing 0.01% protamine sulfate in phosphate buffered saline.

22.1.2. Retrograde Transport of BDNF in Sensory Neurons

Sprague-Dawley rats of either sex were anesthetized with chloropentobarbital. The right sciatic nerve was exposed and a crush was made 0.3 cm distal to the tendon of the obturator internus muscle. $^{125}$I-BDNF was injected into the crush site with a hamilton syringe in a volume of 2 μl over a 2 minute time period. The wounds were sutured and the animals allowed to recover for 7.5 hours. At this time the rats were sacrificed and the fourth and fifth lumbar (L4 and L5) dorsal root ganglia (DRG) were removed from the right (ipsilateral) and left (contralateral) sides, immersed in 1% SDS, and counted for 1 minute in a gamma counter. For another group of animals the ganglia were excised and immersion fixed in 4% paraformaldehyde for processing of DRG's for autoradiography. Quantitative data are expressed as cpm in L4 plus L5 DRG and compared to L4, L5 cpm in the non-injected side.

22.2. Results

In two separate experiments $^{125}$I-BDNF was shown to be retrogradely transported from the crushed adult rat sciatic nerve to the L4, L5 DRG (see Table XV). The transport was specific in that an 80-fold excess of unlabeled BDNF was able to block 80–90% of the transport. Interestingly, the transport of BDNF was only partially inhibited by an 80-fold excess of NGF or a 16-fold excess of NT-3.

TABLE XV

RETROGRADE TRANSPORT OF $^{125}$I-BDNF IN ADULT RAT SCIATIC NERVE

| Injection | R<br>LR + L5 | L<br>L4 + L5 |
|---|---|---|
| Experiment I | | |
| $^{125}$I-BDNF + PBS | 1215[a] | 48 |
| $^{125}$I-BDNF + BDNF | 233 | 10 |
| $^{125}$I-BDNF + NGF | 1140 | 30 |
| $^{125}$I-BDNF + NT-3 | 958 | 32 |
| $^{125}$I-NGF + PBS | 10094 | 26 |
| $^{125}$I-PBS | 3090 | 73 |
| $^{125}$I-BDNF + $^{125}$I-NGF | 15803 | 37 |
| Experiment II | | |
| $^{125}$I-BDNF + PBS | 2474 | 35 |
| $^{125}$I-BDNF + BDNF | 211 | 27 |
| $^{125}$I-BDNF + NGF | 1179 | 56 |
| $^{125}$I-BDNF + NT-3 | 1270 | 45 |

[a]Counts per minute

23. EXAMPLE: RETROGRADE TRANSPORT OF [$^{125}$I]-BDNF IN THE CENTRAL NERVOUS SYSTEM

23.1. Materials and Methods

BDNF radioiodinated as described supra for the sciatic nerve transport studies. Male Sprague-Dawley rats were anesthetized with chloralhydrate-pentobarbital and fixed in a sterotaxic apparatus. Small volumes of [$^{125}$I]-labeled trophic factors (0.2–0.5 μl) were injected slowly into the hippocampus or neostriatum by way of a borosilicate glass micropipette. Equivalent amounts of [$^{125}$I]-NGF were injected in control animals to verify the specificity of the patterns of transport within the CNS. The wounds were closed and the animals allowed to recover. Approximately 24 hours later, the animals were sacrificed, the brains removed, and specific areas of the CNS excised and counted for 1 minute in a gamma counter. In other experiments, the animals were perfused, the brains removed, sectioned and processed for film and emulsion autoradiography. Hippocampal injections were centered in the Dentate Gyrus/CA4-Hilar region. Striatal injections were located centrally in the rostral caudate-putamen.

23.2. Results

Nerve growth factor (NGF), a neurotrophin related to BDNF, acts as a target derived survival factor for neurons of the basal forebrain cholinergic system (Swab et al., 1977, Brain Research, 168:473, Hefti, 1986, J. Neuroscience 6:2155). NGF uptake and retrograde transport in this system is specific, and thought to be causally related to the presence on these neurons of receptors specific for this trophic molecule. Following this logic, elucidation of the pattern of transport of BDNF in the central nervous system (CNS) should provide us with information regarding specific classes of central neurons which may respond to BDNF in a similar manner.

23.2.1. Transport of BDNF to the Cholinergic Nuclei of the Basal Forebrain

Experiments involving microdissections and counts (Table XVI) indicate that, as previously demonstrated for NGF, BDNF is retrogradely transported from the hippocampus to the cholinergic neurons of the medial septum/diagonal band albeit to a lesser degree. This was confirmed by both film and emulsion autoradiographic experiments (Table XVII), where labeling associated with both neurotrophic factors was well localized to the magnocellular neurons of the medial septum and diagonal band, cells which are known to provide the cholinergic input to hippocampus.

23.2.2. Transport of BDNF and NGF to the Substantia Nigra

Experiments involving microdissections and counts (Table I) indicate that both NGF and BDNF are transported from the striatum to the ventral mesencephalon, the region of the brain which contains the substantia nigra. This observation is novel with respect to both trophic factors. Examination of film autoradiograms support the above conclusion, clearly showing circumscribed areas of increased density overlying the substantia nigra. However, the pattern of distribution of NGF and BDNF associated label is clearly different within this structure. In experiments where NGF was injected, areas of increased film density were found to overly the pars reticulata of the substantia nigra, while in cases where BDNF was injected the areas of greatest densities in the film were found to be over the pars compacta.

23.2.3. Transport of BDNF and NGF to the Other CNS Cell Groups

Examination of film and emulsion autoradiograms clearly show that both NGF and BDNF are transported to regions of the brain not previously suspected to contain neurons sensitive to these trophic factors.

For NGF, these novel areas appear to be rather limited. At present, in addition to the areas noted above, we have found transport for NGF only to the dorsal thalamus and supramammillary nucleus of the hypothalamus (after striatal and hippocampal injections respectively).

On the other hand, BDNF is robustly transported to numerous cortical and subcortical sites in the rat forebrain. As is the case for NGF, we have demonstrated transport of radiolabeled BDNF to the supramamillary nucleus and the dorsal thalamus, but here the pattern of labeling is far more intense and widely distributed than is apparent for NGF. Additionally, BDNF is transported to a number of brain regions which do not appear to transport NGF at all. After injection into the dentate gyrus of the hippocampus, large numbers of labeled cells are observed within other areas of the hippocampal formation; including the pyramidal cell layers (CA1-3) on the side of the injection and bilaterally within the CA4/Hilus (Table XVII). Retrogradely labeled cells are also apparent within the nucleus reuniens of thalamus and the entorhinal cortex. After intrastriatal injections, film autoradiograms indicate that the following areas also accumulate radiolabeled BDNF; frontal and prefrontal cortex, substantia innominata and amygdala.

23.3. Discussion

Retrograde transport of radiolabeled NGF has been found to be restricted to a very limited number of types of neurons of the peripheral and central nervous system. Such transport of NGF has been found to be predicative of responsiveness to NGF both in developing and mature neurons. Thus the specific retrograde transport of BDNF in neurons within the adult brain can be predicted to indicate that these neurons will be found to be responsive to BDNF which may be required to sustain their survival of mature phenotype. The result of Tables XVI and XVII not only predict but support our tissue culture studies (supra) that BDNF is a required neurotrophic factor for cholinergic neurons of the basal forebrain (as shown by retrograde transport from the hippocampus to medial septum, vertical and horizontal diagonal bands—Table XVI; BDNF being found at high levels within the hippocampus) and dopaminergic neurons of the substantia nigra (as shown by transport of BDNF from the striatum to the ventral mesencephalon—Table XVI. In addition retrograde transport of BDNF with neurons of the hippocampal formation (all pyramidal cell layers, the hilar interneurons, the dentate gyrus, the subiculum) and from the hippocampus to the entorhinal cortex is predicative of novel effects of BDNF on these neurons. Many of these neurons are associated with neuronal loss in Alzheimer's disease, in addition to the loss of septal cholinergic neurons. Thus the potential therapeutic use of BDNF in Alzheimer's disease would appear to be greatly strengthened by these data. Similarly, the discovery of active retrograde transport of BDNF from the striatum to the ventral mesencephalon strongly supports a therapeutic potential of BDNF in Parkinson's disease, as already indicated by in vitro data on cultures of embryonic dopaminergic neurons (supra).

TABLE XVI

| COUNTS OF RADIOIODINATED BDNF AND NGF IN SPECIFIC REGIONS | | | | | |
|---|---|---|---|---|---|
| Trophic Factor | HPC (r) | HPC (l) | MS/DB (r) | MS/DB (l) | Cerebellum |
| HIPPOCAMPAL INJECTIONS | | | | | |
| NGF T-9 | 401721 | 1106 | 2381 | 1835 | 136 |
| BNDF T-12 | 1394204 | 1272 | 271 | 157 | 20 |
| Trophic Factor | Striatum (r) | Striatum (l) | V. Mes. (r) | V. Mes. (l) | Cerebellum |
| STRIATAL INJECTIONS | | | | | |
| NGF | | | | | |
| T-24 | 588004 | 269 | 2041 | 94 | 34 |
| T-25 | 652932 | 131 | 1868 | 137 | 35 |
| BDNF | | | | | |
| T-19 | 1458093 | 129 | 1953 | 73 | 28 |
| T-20 | 1454410 | 393 | 1747 | 115 | 53 |
| T-23 | 1880527 | 139 | 5710 | 78 | 33 |

HPC, dorsal hippocampus; MS/DB, medial septum/diagonal band of Broca; V. Mes., ventral mesencephalon; r, right side; l, left side. All injections (striatum and hippocampus) were made on the right side of the brain. Numbers with T prefix in the trophic factor column are animal code numbers. All other numbers represent cpm in the brain area indicated.

TABLE XVII

RETROGRADE NEURONL LABELING-HIPPOCAMPAL INJECTIONS OF RADIOIODINATED NGF AND BDNF

| Brain Area | NGF | BDNF |
|---|---|---|
| Basal Forebrain | | |
| Medial Septum | ++++ | ++ |
| Diagonal Band (v) | ++++ | ++ |
| Diagonal Band (h) | ++ | + |
| Basal Nuc. Meynert | + | − |
| Hippocampus | | |
| Hilus/CA4 | − | ++++ |
| CA 1 | − | ± |
| CA 2 | − | + |
| CA 3 | − | ++ |
| Dentate Gyrus | ? | ? |
| Subiculum | − | + |
| Hilus/CA 4 (contra) | − | +++ |
| Other | | |
| Supramam. Nucleus | ++ | +++ |
| N. Reuniens Thal. | − | + |
| Entorhinal Cortex | − | + |

Date reported above is derived from 6 emulsion autoradiographic experiments. Pluses represent relative numbers of cells labeled in a given area, from "++++" indicating many labeled cells to "+" indicating a few. Minus signs indicates that no labeled cells were observed. A question mark indicates areas that were difficult to evaluate given their proximity to the injection site.

24. DEPOSIT OF MICROORGANISMS

The following recombinant bacteriophage and recombinant plasmid DNA were deposited on Aug. 30, 1989, with the American Type Culture Collection, 12301 Parklawn Drive, Rockville, Md. 20852:

| ATCC | Accession No. |
|---|---|
| phBDNF-C-1 (containing human BDNF cDNA) | 40648 |
| λhBDNF-G-1 (containing human BDNF genomic DNA) | 40649 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An essentially purified, isolated and non-denatured protein having neurotrophic activity and an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg.

2. An essentially purified, isolated and non-denatured protein having neurotrophic activity and an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly.

3. An essentially purified, isolated and non-denatured protein having neurotrophic activity and an amino acid sequence as follows:

Met His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg.

4. An essentially purified, isolated and non-denatured protein having neurotrophic activity that is produced by and purified from a Chinese Hamster Ovary cell containing a nucleic acid that encodes a protein having an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg.

5. An essentially purified, isolated and non-denatured protein having neurotrophic activity that is produced by and purified from a bacterial cell containing a nucleic acid that encodes a protein having an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg.

6. A composition comprising an essentially purified, isolated and non-denatured protein having neurotrophic activity and an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys

Arg Gly Arg and a pharmaceutically acceptable carrier.

7. A composition comprising an essentially purified, isolated and non-denatured protein having neurotrophic activity and an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly and a pharmaceutically acceptable carrier.

8. A composition comprising an essentially purified, isolated and non-denatured protein having neurotrophic activity and an amino acid sequence as follows:

Met His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg and a pharmaceutically acceptable carrier.

9. A composition comprising an essentially purified, isolated and non-denatured protein having neurotrophic activity that is produced by and purified from a Chinese Hamster Ovary cell containing a nucleic acid that encodes a protein having an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg and a pharmaceutically acceptable carrier.

10. A composition comprising an essentially purified, isolated and non-denatured protein having neurotrophic activity that is produced by and purified from a bacterial cell containing a nucleic acid that encodes a protein having an amino acid sequence as follows:

His Ser Asp Pro Ala Arg Arg Gly Glu Leu Ser Val Cys Asp Ser Ile Ser Glu Trp Val Thr Ala Ala Asp Lys Lys Thr Ala Val Asp Met Ser Gly Gly Thr Val Thr Val Leu Glu Lys Val Pro Val Ser Lys Gly Gln Leu Lys Gln Tyr Phe Tyr Glu Thr Lys Cys Asn Pro Met Gly Tyr Thr Lys Glu Gly Cys Arg Gly Ile Asp Lys Arg His Trp Asn Ser Gln Cys Arg Thr Thr Gln Ser Tyr Val Arg Ala Leu Thr Met Asp Ser Lys Lys Arg Ile Gly Trp Arg Phe Ile Arg Ile Asp Thr Ser Cys Val Cys Thr Leu Thr Ile Lys Arg Gly Arg and a pharmaceutically acceptable carrier.

11. A composition of claim 6, 7, 8, 9, or 10 wherein the carrier is a slow release carrier.

* * * * *